US007985843B2

(12) United States Patent
Fanger et al.

(10) Patent No.: US 7,985,843 B2
(45) Date of Patent: Jul. 26, 2011

(54) COMPOSITIONS AND METHODS FOR THE THERAPY AND DIAGNOSIS OF OVARIAN CANCER

(75) Inventors: Gary R. Fanger, Mill Creek, WA (US); Steven P. Fling, Bainbridge Island, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 11/929,595

(22) Filed: Oct. 30, 2007

(65) Prior Publication Data

US 2008/0226633 A1 Sep. 18, 2008

Related U.S. Application Data

(63) Continuation of application No. 11/250,759, filed on Oct. 14, 2005, now Pat. No. 7,598,051, which is a continuation of application No. 10/369,186, filed on Feb. 14, 2003, now abandoned, which is a continuation-in-part of application No. 10/361,811, filed on Feb. 5, 2003, now abandoned, which is a continuation-in-part of application No. 10/212,677, filed on Aug. 2, 2002, now abandoned, which is a continuation-in-part of application No. 09/970,966, filed on Oct. 2, 2001, now Pat. No. 6,720,146, which is a continuation-in-part of application No. 09/825,294, filed on Apr. 3, 2001, now Pat. No. 6,710,170, which is a continuation-in-part of application No. 09/713,550, filed on Nov. 14, 2000, now Pat. No. 6,617,109, which is a continuation-in-part of application No. 09/656,668, filed on Sep. 7, 2000, now abandoned, which is a continuation-in-part of application No. 09/640,173, filed on Aug. 15, 2000, now Pat. No. 6,613,515, which is a continuation-in-part of application No. 09/561,778, filed on May 1, 2000, now abandoned, which is a continuation-in-part of application No. 09/394,374, filed on Sep. 10, 1999, now abandoned.

(51) Int. Cl.
*A61K 38/16* (2006.01)
*C12K 21/08* (2006.01)
*C07K 16/00* (2006.01)
*C07K 17/00* (2006.01)
*C07K 17/14* (2006.01)

(52) U.S. Cl. .............. 530/387.9; 530/380; 530/386; 530/387.1; 530/387.3; 530/387.7; 530/388.1; 530/391.1; 530/391.3; 530/391.5; 530/391.7; 530/391.9

(58) Field of Classification Search .................. None
See application file for complete search history.

(56) References Cited

U.S. PATENT DOCUMENTS

| 5,279,966 | A | 1/1994 | Jessell et al. ............... 435/320.1 |
| 5,585,232 | A | 12/1996 | Farr ................................ 435/6 |
| 5,589,337 | A | 12/1996 | Farr ................................ 435/6 |
| 5,849,480 | A | 12/1998 | Cros et al. ........................ 435/6 |
| 6,525,023 | B1 | 2/2003 | Yamasaki et al. ............... 514/12 |
| 6,617,109 | B1 | 9/2003 | Xu et al. ........................... 435/6 |
| 6,710,170 | B2 | 3/2004 | Xu et al. ....................... 536/23.1 |
| 7,598,051 | B2 | 10/2009 | Fanger et al. ................. 435/7.23 |
| 2002/0132237 | A1 | 9/2002 | Algate et al. ..................... 435/6 |

FOREIGN PATENT DOCUMENTS

| CA | 2370489 A1 | 10/2000 |
| DE | 20103510 U1 | 8/1998 |
| EP | 1067182 A2 | 1/2001 |
| JP | 6-303997 | 11/1994 |
| WO | WO 93/17715 | 9/1993 |
| WO | WO 94/12881 | 6/1994 |
| WO | WO 95/14772 | 6/1995 |
| WO | WO 98/37418 | 8/1998 |
| WO | WO 99/04265 | 1/1999 |
| WO | WO 00/52044 | 9/2000 |
| WO | WO 00/61629 | 10/2000 |
| WO | WO 00/77026 | 12/2000 |
| WO | WO 01/36685 | 5/2001 |
| WO | WO 01/47944 | 7/2001 |
| WO | WO 01/81634 | 11/2001 |
| WO | WO 01/92581 | 12/2001 |
| WO | WO 01/93983 | 12/2001 |
| WO | WO 02/08288 | 1/2002 |

OTHER PUBLICATIONS

Genbank Database, Accession No. AF034633, Dec. 1, 1997.
Chen, L. et al., "Increased expression of cerulopladmin in the retina following photic injury," *Molecular Vision* 9: 151-158, 2003.
Curti, B.D., "Physical barriers to drug delivery in tumors," *Critical Reviews in Oncology/Hematology* 14: 29-39, 1993.
Database EMBL Acccession No. AA536804, Jul. 31, 1997.
Database EMBL Accession No. AC016957, Dec. 14, 1999.
Database EMBL, Accession No. AF060226, May 6, 1998.
Database EMBL, Accession No. AX001326, Mar. 10, 2000.
Database EMBL, Accession No. X02662, May 7, 1999.
EMBL-EBI Database, Accession No. BE378674, Jul. 29, 2000.
EMBL-EBI Database, Accession No. BE385990, Jul. 29, 2000.
EMBL-EBI Database, Accession No. BE395581, Jul. 29, 2000.
EMBL-EBI Database, Accession No. BE395797, Jul. 29, 2000.
EMBL-EBI Database, Accession No. BE746601, Sep. 20, 2000.
EMBL-EBI Database, Accession No. BF125134, Oct. 26, 2000.
EMBL-EBI Database, Accession No. BF345141, Nov. 27, 2000.
GenBank Database, Accession No. AA173383, Sep. 30, 1997.

(Continued)

*Primary Examiner* — Alana M Harris
(74) *Attorney, Agent, or Firm* — Seed IP Law Group PLLC

(57) ABSTRACT

Compositions and methods for the therapy and diagnosis of cancer, particularly ovarian cancer, are disclosed. Illustrative compositions comprise one or more ovarian tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly ovarian cancer.

11 Claims, No Drawings

OTHER PUBLICATIONS

GenBank Database, Accession No. AA173739, Sep. 30, 1997.
GenBank Database, Accession No. AA223587, Feb. 19, 1997.
GenBank Database, Accession No. AA281245, Jan. 14, 1998.
GenBank Database, Accession No. AAH17318, Oct. 4, 2003.
GenBank Database, Accession No. AB041649, Jun. 30, 2000.
GenBank Database, Accession No. AF161511, Jun. 23, 1999.
GenBank Database, Accession No. AI023799, Aug. 28, 1998.
GenBank Database, Accession No. AI307373, Apr. 8, 1999.
GenBank Database, Accession No. AI360254, Feb. 16, 1999.
GenBank Database, Accession No. AI936826, Mar. 8, 2000.
GenBank Database, Accession No. AK012406, Sep. 2, 2005.
GenBank Database, Accession No. AW149665, Nov. 3, 1999.
GenBank Database, Accession No. AW150789, Nov. 3, 1999.
GenBank Database, Accession No. AW377176, Apr. 7, 1998.
GenBank Database, Accession No. AW406327, Oct. 30, 1998.
GenBank Database, Accession No. AX136281, May 30, 2001.
GenBank Database, Accession No. BAA95101, Jun. 30, 2000.
GenBank Database, Accession No. BC011449, Aug. 19, 2003.
GenBank Database, Accession No. BC017318, Oct. 4, 2003.
Genbank Database, Accession No. H06756, Jun. 21, 1995.
GenBank Database, Accession No. L19184, Oct. 13, 1994.
GenBank Database, Accession No. NM_001508, Dec. 15, 1997.
GenBank Database, Accession No. NP_001499, Dec. 15, 1997.
GenCore Database, Accession No. Q9JJ96, Oct. 1, 2000.
GenBank Database, Accession No. R60095, Apr. 14, 1993.
GenBank Database, Accession No. Z95125, Sep. 27, 1997.
Genseq (Derwent) Database, Accession No. AAK54063, Nov. 16, 2001.
Genseq (Derwent) Database, Accession No. AAL27277, Jan. 24, 2002.
Genseq (Derwent) Database, Accession No. AAL33984, Jan. 24, 2002.
Genseq (Derwent) Database, Accession No. AAL33985, Jan. 24, 2002.
Genseq (Derwent) Database, Accession No. AAL33986, Jan. 24, 2002.
Genseq (Derwent) Database, Accession No. AAU83599, May 8, 2002.
Gerhold, D. et al., "It's the genes! EST access to human genome content," BioEssays 18(12): 973-981, 1996.
Gibson et al., "Novel method for real time quantitative RT-PCR," Genome Research 6:995-1001, Oct. 1996.
Gura, T., "Systems for Identifying New Drugs Are Often Faulty," Science 278:1041-1042, Nov. 7, 1997.
Hartwell, L.H. et al., "Integrating Genetic Approaches into the Discovery of Anticancer Drugs," Science 278: 1064-1068, Nov. 7, 1997.
Haynes, P.A. et al., "Proteome analysis: Biological assay or data archive?," Electrophoresis 19: 1862-1871, 1998.
Heid et al., "Real time quantitative PCR," Genome Research 6:986-994, Oct. 1996.
Houghton, A.N. et al., "Monoclonal Antibodies: Potential Applications to the Treatment of Cancer," Seminars in Oncology 13(2): 166-179, Jun. 1986.
Hu, Y. et al., "Analysis of Genomic and Proteomic Data Using Advanced Literature Mining," Journal of Proteome Research 2: 405-412, 2003.
Jain, R.K., "Barriers to Drug Delivery in Solid Tumors," Scientific American 271: 58-65, Jul. 1994.
McKee, K.K. et al., "Cloning and characterization of two human G protein-coupled receptor genes (GPR38 and GPR39) related to the growth hormone secretagogue and neurotensin receptors," Genomics 46(3): 426-434, 1997.
Meden and Kuhn, "Overexpression of the oncogene c-crbB-2 (HER2/neu) in ovarian cancer: a new prognostic factor," European Journal of Obstetrics & Gynecology and Reproductive Biology 71:173-179, 1997.
Nagase et al, "Prediction of the coding sequences of unidentified human genes. XI. The complete sequences of 100 new cDNA clones from brain which code for large proteins in vitro," DNA Research 5(5): 277-286, 1998.
Novocastra Laboratories Ltd., Data Sheet, Mesothelin, NCL-L-MESO, Feb. 2004.
Prydz, K. et al., "Cholesterol depletion deduces apical transport capacity in epithelial Madin-Darby canine kidney cells," Biochemical Journal 357: 11-15, 2001.
Russell, R.B. et al., "Structural Features can be Unconserved in Proteins with Similar Folds," J. Mol. Biol. 244: 332-350, 1994.
Schena et al., "Quantitative monitoring of gene expression patterns with a complementary DNA microarray," Science 270:467-470, Oct. 20, 1995.
Tascilar, M. et al., "Role of tumor markers and mutations in cells and pancreatic juice in the diagnosis of pancreatic cancer," *Annals of Oncology 10*(Suppl. 4):S107-S110, 1999.
Tockman, M.S. et al., "Considerations in Bringing a Cancer Biomarker to Clinical Application," *Cancer Research 52*(Suppl):2711s-2718s, May 1, 1992.
Wells, T.N.C. et al., "The chemokine information source: identification and characterization of novel chemokines using the WorldWideWeb and Expressed Sequence Tag Databases," Journal of Leukocyte Biology 61(5): 545-550, May 1997.
Winter, G. et al., "Humanized antibodies," Trends in Protein Sciences 14: 139-143, May 1993.

COMPOSITIONS AND METHODS FOR THE THERAPY AND DIAGNOSIS OF OVARIAN CANCER

CROSS-REFERENCE TO RELATED APPLICATIONS

This application is a continuation of U.S. application Ser. No. 11/250,759, filed on Oct. 14, 2005, now pending; which is a continuation of U.S. application Ser. No. 10/369,186, filed on Feb. 14, 2003, now abandoned; which is a continuation-in-part of U.S. application Ser. No. 10/361,811, filed on Feb. 5, 2003, now abandoned; which is a continuation-in-part of U.S. application Ser. No. 10/212,677, filed on Aug. 2, 2002, now abandoned; which is a continuation-in-part of U.S. application Ser. No. 09/970,966, filed on Oct. 2, 2001, now U.S. Pat. No. 6,720,146; which is a continuation-in-part of U.S. application Ser. No. 09/825,294, filed on Apr. 3, 2001, now U.S. Pat. No. 6,710,170; which is a continuation-in-part of U.S. application Ser. No. 09/713,550, filed on Nov. 14, 2000, now U.S. Pat. No. 6,617,109; which is a continuation-in-part of U.S. application Ser. No. 09/656,668, filed on Sep. 7, 2000, now abandoned; which is a continuation-in-part of U.S. application Ser. No. 09/640,173, filed on Aug. 15, 2000, now U.S. Pat. No. 6,613,515; which is a continuation-in-part of U.S. application Ser. No. 09/561,778, filed on May 1, 2000, now abandoned; which is a continuation-in-part of U.S. application Ser. No. 09/394,374, filed on Sep. 10, 1999, now abandoned.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 210121_484C13_SEQUENCE_LISTING.txt. The text file is 400 KB, was created on Oct. 30, 2007, and is being submitted electronically via EFS-Web, concurrent with the filing of the specification.

BACKGROUND OF THE INVENTION

1. Field of the Invention

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

2. Description of Related Art

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

BRIEF SUMMARY OF THE INVENTION

Briefly stated, this invention provides compositions and methods for the therapy of cancer, such as ovarian cancer.

In one aspect, the present invention provides polynucleotide compositions comprising a sequence selected from the group consisting of:

(a) sequences provided in SEQ ID NO: 1-185, 187-199, 203-206, 208, 210-214, 216-246, 250-256, 262-268, 273-277, 283, 285, and 287-288;

(b) complements of the sequences provided in SEQ ID NO: 1-185, 187-199, 203-206, 208, 210-214, 216-246, 250-256, 262-268, 273-277, 283, 285, and 287-288;

(c) sequences consisting of at least 20 contiguous residues of a sequence provided in SEQ ID NO: 1-185, 187-199, 203-206, 208, 210-214, 216-246, 250-256, 262-268, 273-277, 283, 285, and 287-288;

(d) sequences that hybridize to a sequence provided in SEQ ID NO: 1-185, 187-199, 203-206, 208, 210-214, 216-246, 250-256, 262-268, 273-277, 283, 285, and 287-288, under moderately stringent conditions;

(e) sequences having at least 75% identity to a sequence provided in SEQ ID NO: 1-185, 187-199, 203-206, 208, 210-214, 216-246, 250-256, 262-268, 273-277, 283, 285, and 287-288;

(f) sequences having at least 90% identity to a sequence provided in SEQ ID NO: 1-185, 187-199, 203-206, 208, 210-214, 216-246, 250-256, 262-268, 273-277, 283, 285, and 287-288; and (g) degenerate variants of a sequence provided in SEQ ID NO: 1-185, 187-199, 203-206, 208, 210-214, 216-246, 250-256, 262-268, 273-277, 283, 285, and 287-288.

In one preferred embodiment, the polynucleotide compositions of the invention are expressed in at least about 20%, more preferably in at least about 30%, and most preferably in at least about 50% of ovarian tumors samples tested, at a level that is at least about 2-fold, preferably at least about 5-fold, and most preferably at least about 10-fold higher than that for normal tissues.

In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the ovarian carcinoma protein comprises a sequence that is encoded by a polynucleotide sequence selected from the group consisting of SEQ ID NO: 1-185, 187-199, 203-206, 208, 210-214, 216-246, 250-256, 262-268, 273-277, 283, 285, and 287-288, and complements of such polynucleotides.

The present invention further provides polynucleotides that encode a polypeptide as described above or a portion thereof, expression vectors comprising such polynucleotides and host cells transformed or transfected with such expression vectors.

The present invention further provides polypeptide compositions comprising an amino acid sequence selected from the group consisting of sequences recited in SEQ ID NO:186, 200-202, 207, 209, 215, 247-249, 257-261, 269-272, 278-282, 284, 286 and 289-293.

In certain preferred embodiments, the polypeptides of the present invention are immunogenic, i.e., they are capable of eliciting an immune response, particularly a humoral and/or cellular immune response, as further described herein.

The present invention further provides fragments, variants and/or derivatives of the disclosed polypeptide sequences, wherein the fragments, variants and/or derivatives preferably have a level of immunogenic activity of at least about 50%, preferably at least about 70% and more preferably at least about 90% of the level of immunogenic activity of the ovarian carcinoma protein comprises an amino acid sequence encoded by a polynucleotide that comprises a sequence recited in any one of SEQ ID NO: 1-185, 187-199, 203-206, 208, 210-214, 216-246, 250-256, 262-268, 273-277, 283, 285, and 287-288.

Within other aspects, the present invention provides pharmaceutical compositions comprising a polypeptide and/or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with ovarian cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with ovarian cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) an ovarian carcinoma polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4$^+$ and/or CD8$^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably an ovarian cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description. All references disclosed herein are hereby incorporated by reference in their entirety as if each was incorporated individually.

BRIEF DESCRIPTION OF THE SEQUENCE IDENTIFIERS

SEQ ID NO:1, 2, 5, 9, 10, 13, 16, 19, 23, 27, 28, 32, 33, 35, 38, 41-50, 52, 53, 56, 57, 63, 65, 69-72, 75, 78, 80-82, 84, 86, 89-93, 95, 97-100, 103, 107, 111, 114, 117, 120, 121, 125, 128, 132-134, 136, 137, 140, 143-146, 148-151, 156, 158, 160-162, 166-168, 171, 174-183, 185, and 193-199 are described in Tables III-VII below.

SEQ ID NO:200 is the amino acid sequence of a polypeptide encoded by the polynucleotide recited in SEQ ID NO:182;

SEQ ID NO:201 is the amino acid sequence of a polypeptide encoded by the polynucleotide recited in SEQ ID NO:182;

SEQ ID NO:202 is the amino acid sequence of a polypeptide encoded by the polynucleotide recited in SEQ ID NO:182.

SEQ ID NO:203 is the determined extended cDNA sequence for SEQ ID NO:197.

SEQ ID NO:204 is the determined extended cDNA sequence for SEQ ID NO:198.

SEQ ID NO:205 is the determined extended cDNA sequence for SEQ ID NO:199.

SEQ ID NO:206 is the determined cDNA sequence for the coding region of O568S fused to an N-terminal His tag.

SEQ ID NO:207 is the amino acid sequence of the polypeptide encoded by the polynucleotide recited in SEQ ID NO:206.

SEQ ID NO:208 is the determined cDNA sequence for the coding region of GPR39 as downloaded from the High Throughput Genomics Database.

SEQ ID NO:209 is the amino acid sequence encoded by the cDNA sequence recited in SEQ ID NO:208.

SEQ ID NO:210 is the nucleotide sequence of O1034C an ovary specific EST clone discovered using electronic subtraction.

SEQ ID NO:211 is the full length nucleotide sequence of O591S.

SEQ ID NO:212 is the sequence BF345141 which shows sequence homology with O1034C/O591S allowing for the extension of O591S.

SEQ ID NO:213 is the sequence BE336607 which shows sequence homology with O1034C/O591S allowing for the extension of O591S.

SEQ ID NO:214 is the consensus nucleotide sequence of O1034C/O591S containing 1897 base pairs.

SEQ ID NO:215 is the predicted translation of the open reading frame identified within SEQ ID NO:214 (nucleotides 260-682).

SEQ ID NO:216 is a determined 5' DNA sequence of clone number 91226.5.

SEQ ID NO:217 is a determined 5' DNA sequence of clone number 91227.2.

SEQ ID NO:218 is a determined 5' DNA sequence of clone number 91230.2.

SEQ ID NO:219 is a determined 5' DNA sequence of clone number 91231.2.

SEQ ID NO:220 is a determined 5' DNA sequence of clone number 91238.3.

SEQ ID NO:221 is a determined 5' DNA sequence of clone number 91239.6.

SEQ ID NO:222 is a determined 5' DNA sequence of clone number 91240.2.

SEQ ID NO:223 is a determined 5' DNA sequence of clone number 91241.2.

SEQ ID NO:224 is a determined 5' DNA sequence of clone number 91242.5.

SEQ ID NO:225 is a determined 5' DNA sequence of clone number 91243.6.

SEQ ID NO:226 is a determined 5' DNA sequence of clone number 91245.2.

SEQ ID NO:227 is a determined 5' DNA sequence of clone number 91246.4.

SEQ ID NO:228 is a determined 3' DNA sequence of clone number 91247.3.

SEQ ID NO:229 is a determined 5' DNA sequence of clone number 91247.4.

SEQ ID NO:230 is a determined 5' DNA sequence of clone number 91249.2.

SEQ ID NO:231 is a determined 5' DNA sequence of clone number 91253.2.

SEQ ID NO:232 is a determined 5' DNA sequence of clone number 91254.2.

SEQ ID NO:233 is a determined 5' DNA sequence of clone number 91259.2.

SEQ ID NO:234 is a determined 3' DNA sequence of clone number 91261.3.

SEQ ID NO:235 is a determined 5' DNA sequence of clone number 91261.4.

SEQ ID NO:236 is a determined 5' DNA sequence of clone number 91262.2.

SEQ ID NO:237 is a determined 5' DNA sequence of clone number 91263.2.

SEQ ID NO:238 is a determined 5' DNA sequence of clone number 91264.2.

SEQ ID NO:239 is a determined 5' DNA sequence of clone number 91268.2.

SEQ ID NO:240 is a determined 5' DNA sequence of clone number 91269.5.

SEQ ID NO:241 is a determined 5' DNA sequence of clone number 91271.5.

SEQ ID NO:242 is a determined 3' DNA sequence of clone number 91273.3.

SEQ ID NO:243 is a determined 5' DNA sequence of clone number 91274.6.

SEQ ID NO:244 is the DNA sequence of GenBank Accession Number 18549403, which shares homology to SEQ ID NO:246.

SEQ ID NO:245 is the DNA sequence of GenBank Accession Number 10436393_FLJ14035, which shares homology to SEQ ID NO:246.

SEQ ID NO:246, also referred to as O646SgenomicContig, is a DNA (contig) sequence assembled based on a search of the publicly available databases using SEQ ID NO:243 as a query.

SEQ ID NO:247 is a amino acid sequence corresponding to the DNA sequence of GenBank Accession Number 18549403, SEQ ID NO:244.

SEQ ID NO:248 is a amino acid sequence corresponding to the DNA sequence of GenBank Accession Number 10436393_FLJ14035, SEQ ID NO:245.

SEQ ID NO:249 is a amino acid sequence corresponding to a polypeptide encoded by SEQ ID NO:246, also referred to as O646GenomicContig_MajorORF.

SEQ ID NO:250 is the DNA sequence of GenBank Accession Number 3980529, which shares homology to SEQ ID NO:262.

SEQ ID NO:251 is the DNA sequence of GenBank Accession Number 13629915, which shares homology to SEQ ID NO:262.

SEQ ID NO:252 is the DNA sequence of GenBank Accession Number 9789986, which shares homology to SEQ ID NO:262.

SEQ ID NO:253 is the DNA sequence of GenBank Accession Number 6006516, which shares homology to SEQ ID NO:262.

SEQ ID NO:254 is the DNA sequence of GenBank Accession Number 5689424, which shares homology to SEQ ID NO:262.

SEQ ID NO:255 is the DNA sequence of GenBank Accession Number 15638833, which shares homology to SEQ ID NO:262.

SEQ ID NO:256, also referred to as O646SGenomicContig, is a DNA (contig) sequence assembled based on a search of the publicly available databases using SEQ ID NO:243 as a query.

SEQ ID NO:257 is an amino acid sequence corresponding to the DNA sequence of GenBank Accession Number 13629915, SEQ ID NO:251.

SEQ ID NO:258 is an amino acid sequence corresponding to the DNA sequence of GenBank Accession Number 9789986, SEQ ID NO:252.

SEQ ID NO:259 is an amino acid sequence corresponding to the DNA sequence of GenBank Accession Number 6006516, SEQ ID NO:253.

SEQ ID NO:260 is an amino acid sequence corresponding to the DNA sequence of GenBank Accession Number 5689424, SEQ ID NO:254.

SEQ ID NO:261, also referred to as O648S_GenomicContig_ORF, is a amino acid sequence corresponding to a polypeptide encoded by SEQ ID NO:262.

SEQ ID NO:262 is the DNA sequence of GenBank Accession Number 16933560, which shares homology to SEQ ID NO:268.

SEQ ID NO:263 is the DNA sequence of GenBank Accession Number 12053028, which shares homology to SEQ ID NO:268.

SEQ ID NO:264 is the DNA sequence of GenBank Accession Number 7638812, which shares homology to SEQ ID NO:268.

SEQ ID NO:265 is the DNA sequence of GenBank Accession Number 939922, which shares homology to SEQ ID NO:268.

SEQ ID NO:266 is the DNA sequence of GenBank Accession Number 6093230, which shares homology to SEQ ID NO:268.

SEQ ID NO:267 is the DNA sequence of GenBank Accession Number 11465000, which shares homology to SEQ ID NO:268.

SEQ ID NO:268 also referred to as O647SgenomicContig3, is a DNA (contig) sequence assembled based on a search of the publicly available databases using SEQ ID NO:234 as a query.

SEQ ID NO:269 is an amino acid sequence corresponding to the DNA sequence of GenBank Accession Number 16933560, SEQ ID NO:262.

SEQ ID NO:270 is an amino acid sequence corresponding to the DNA sequence of GenBank Accession Number 12053028, SEQ ID NO:263.

SEQ ID NO:271 is an amino acid sequence corresponding to the DNA sequence of GenBank Accession Number 7638812, SEQ ID NO:264.

SEQ ID NO:272 is an amino acid sequence corresponding to the DNA sequence of GenBank Accession Number 939922, SEQ ID NO:265.

SEQ ID NO:273 also referred to as O645SgenomicContig2, is a DNA (contig) sequence assembled based on a search of the publicly available databases using SEQ ID NO:238 as a query.

SEQ ID NO:274 is the DNA sequence of GenBank Accession Number NM006580, also referred to as Claudin16, which shares homology to SEQ ID NO:277.

SEQ ID NO:275 is the DNA sequence of GenBank Accession Number AF152101.1, also referred to as Paracellin-1, which shares homology to SEQ ID NO:277.

SEQ ID NO:276 is the DNA sequence of GenBank Accession Number 18425237, which shares homology to SEQ ID NO:277.

SEQ ID NO:277 also referred to as O644SgenomicContig2, is a DNA (contig) sequence assembled based on a search of the publicly available databases using SEQ ID NO:240 as a query.

SEQ ID NO:278 is an amino acid sequence corresponding to the DNA sequence of GenBank Accession Number NM006580, SEQ ID NO:277.

SEQ ID NO:279 is an amino acid sequence corresponding to the DNA sequence of GenBank Accession Number AF152101.1, SEQ ID NO:275.

SEQ ID NO:280 also referred to as O644S_GenomicContig2_ORF1, is a amino acid sequence corresponding to an open reading frame of SEQ ID NO:277.

SEQ ID NO:281 also referred to as O644S_GenomicContig2_ORF2, is a amino acid sequence corresponding to an open reading frame of SEQ ID NO:277.

SEQ ID NO:282 also referred to as O644S_GenomicContig2_ORF3, is a amino acid sequence corresponding to an open reading frame of SEQ ID NO:277.

SEQ ID NO:283 is a DNA sequence of a signal peptide minus O591S fusion protein containing a N-terminal histidine tag.

SEQ ID NO:284 is a corresponding amino acid sequence of a signal peptide minus O591S fusion protein containing a N-terminal histidine tag.

SEQ ID NO:285 is a 1740 bp DNA sequence identified by BlastN search of a LifeSeq Gold database using SEQ ID NO:198 as a query.

SEQ ID NO:286 is an amino acid sequence encode by the DNA sequence set forth in SEQ ID NO:285.

SEQ ID NO:287 is the sequence for the forward primer, CBH-005, used in the amplification of O591S-A.

SEQ ID NO:288 is the sequence for the reverse primer, CBH-003, used in the amplification of O591S-A.

SEQ ID NO:289 corresponds to the amino acid sequence corresponding to residue 1-114 of SEQ ID NO:215.

SEQ ID NO:290 corresponds to the amino acid sequence corresponding to residue 1-115 of SEQ ID NO:215 (O591S).

SEQ ID NO: 291 corresponds to amino acid residues 26-55 of SEQ ID NO:215 (O591S).

SEQ ID NO:292 corresponds to amino acid residues 53-78 of SEQ ID NO:215 (O591S).

SEQ ID NO:293 corresponds to amino acid residues 103-129 of SEQ ID NO:215 (O591S).

DETAILED DESCRIPTION OF THE INVENTION

U.S. patents, U.S. patent application publications, U.S. patent applications, foreign patents, foreign patent applications and non-patent publications referred to in this specification and/or listed in the Application Data Sheet, are incorporated herein by reference, in their entirety.

The present invention is directed generally to compositions and their use in the therapy and diagnosis of cancer, particularly ovarian cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NO: 1-185, 187-199, 203-206, 208, 210-214, 216-246, 250-256, 262-268, 273-277, 283, 285, and 287-288; or a sequence that hybridizes under moderately stringent conditions, or, alternatively, under highly stringent conditions, to a polynucleotide sequence identified above. Certain other illustrative polypeptides of the invention comprise amino acid sequences as set forth in any one of SEQ ID NO:186, 200-202, 207, 209, 215, 247-249, 257-261, 269-272, 278-282, 284, 286, and 289-293.

The polypeptides of the present invention are sometimes herein referred to as ovarian tumor proteins or ovarian tumor polypeptides, as an indication that their identification has been based at least in part upon their increased levels of expression in ovarian tumor samples. Thus, a "ovarian tumor polypeptide" or "ovarian tumor protein," refers generally to a polypeptide sequence of the present invention, or a polynucleotide sequence encoding such a polypeptide, that is expressed in a substantial proportion of ovarian tumor samples, for example preferably greater than about 20%, more preferably greater than about 30%, and most preferably greater than about 50% or more of ovarian tumor samples tested, at a level that is at least two fold, and preferably at least five fold, greater than the level of expression in normal tissues, as determined using a representative assay provided herein. An ovarian tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with ovarian cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide.

Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NO:186, 200-202, 207, 209, 215, 247-249, 257-261, 269-272, 278-282, 284, 286, and 289-293 or those encoded by a polynucleotide sequence set forth in any one of SEQ ID NO: 1-185, 187-199, 203-206, 208, 210-214, 216-246, 250-256, 262-268, 273-277, 283, 285, and 287-288.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1-30 amino acids, preferably 5-15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE I

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86-91, 1997).

In one preferred embodiment, the immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158, 585; see also, Skeiky et al., *Infection and Immun.* (1999) 67:3998-4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin).

Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NO:1-185, 187-199, 203-206, 208, 210-214, 216-246, 250-256, 262-268, 273-277, 283, 285, and 287-288, complements of a polynucleotide sequence set forth as described above, and degenerate variants of a polynucleotide sequence set forth as described above. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NO:1-185, 187-199, 203-206, 208, 210-214, 216-246, 250-256, 262-268, 273-277, 283, 285, and 287-288, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology vol.* 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al, 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10; 240(4858):1544-6; Vasanthakumar and Ahmed, Cancer Commun. 1989; 1(4): 225-32; Peris et al., Brain Res Mol Brain Res. 1998 Jun. 15; 57(2):310-20; U.S. Pat. No. 5,801,154; U.S. Pat. No. 5,789,573; U.S. Pat. No. 5,718,709 and U.S. Pat. No. 5,610,288). Antisense constructs have also been described that inhibit and can be used to treat a variety of abnormal cellular proliferations, e.g., cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15; 25(14):2730-6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol. Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. 1992 Aug. 15; 89(16): 7305-9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see, e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431-37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June; 15(6): 224-9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 Dec. 6; 254(5037):1497-500; Hanvey et al., Science. 1992 Nov. 27; 258(5087):1481-5; Hyrup and Nielsen, Bioorg Med Chem. 1996 January; 4(1):5-23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April; 3(4):437-45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April; 3(4):437-45; Petersen et al., J Pept Sci. 1995 May-June; 1(3):175-83; Orum et al., Biotechniques. 1995 September; 19(3):472-80; Footer et al., Biochemistry. 1996 Aug. 20; 35(33):10673-9; Griffith et al., Nucleic Acids Res. 1995 Aug. 11; 23(15):3003-8; Pardridge et al., Proc Natl Acad Sci USA. 1995 Jun. 6; 92(12):5592-6; Boffa et al., Proc Natl Acad Sci USA. 1995 Mar. 14; 92(6):1901-5; Gambacorti-Passerini et al., Blood. 1996 Aug. 15; 88(4):1411-7; Armitage et al., Proc Natl Acad Sci USA. 1997 Nov. 11; 94(23):12320-5; Seeger et al., Biotechniques. 1997 September; 23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15; 65(24):3545-9) and Jensen et al. (Biochemistry. 1997 Apr. 22; 36(16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then generally screened by hybridizing filters containing denatured bacterial colonies (or lawns containing phage plaques) with the labeled probe (see Sambrook et al.,

*Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1990) Cell 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides, neomycin and G-418 (Colbere-Garapin, F. et al (1981) J. Mol. Biol. 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors which contain fusion proteins is provided in Kroll, D. J. et al. (1993; DNA Cell Biol. 12:441-453).

In addition to recombinant production methods, polypeptides of the invention, and fragments thereof, may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as ovarian cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) J. Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered molecule.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671, 958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240, 856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml-100 µg/ml, preferably 200 ng/ml-25 µg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and therapeutic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, Crit. Rev. Therap. Drug Carrier Systems 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as Bacillus-Calmette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994)

Human Gene Therapy 5:793-801; Shelling and Smith (1994) Gene Therapy 1:165-169; and Zhou et al. (1994) J. Exp. Med. 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., Proc. Natl. Acad. Sci. USA 86:317-321, 1989; Flexner et al., Ann. N.Y. Acad. Sci. 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{-A-R,} \qquad (I)$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic antitumor immunity (see Timmerman and Levy, *Ann. Rev. Med.* 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456-460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit Rev Ther Drug Carrier Syst 1998; 15(3):243-84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2; 50(1-3):31-40; and U.S. Pat. No. 5,145,684.

Cancer Therapeutic Methods

In further aspects of the present invention, the pharmaceutical compositions described herein may be used for the treatment of cancer, particularly for the immunotherapy of ovarian cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more ovarian tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding an ovarian tumor protein, which is also indicative of the presence or absence of a cancer. In general, a ovarian tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10

μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising CD4$^+$ and/or CD8$^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with polypeptide (e.g., 5-25 µg/ml). It may be desirable to incubate another aliquot of a T cell sample in the absence of tumor polypeptide to serve as a control. For CD4$^+$ T cells, activation is preferably detected by evaluating proliferation of the T cells. For CD8$^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.,* 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLES

Example 1

Identification of Representative Ovarian Carcinoma cDNA Sequences

Primary ovarian tumor and metastatic ovarian tumor cDNA libraries were each constructed in kanamycin resistant pZErO™-2 vector (Invitrogen) from pools of three different ovarian tumor RNA samples. For the primary ovarian tumor library, the following RNA samples were used: (1) a moderately differentiated papillary serous carcinoma of a 41 year old, (2) a stage IIIC ovarian tumor and (3) a papillary serous adenocarcinoma for a 50 year old Caucasian. For the metastatic ovarian tumor library, the RNA samples used were omentum tissue from: (1) a metastatic poorly differentiated papillary adenocarcinoma with psammoma bodies in a 73 year old, (2) a metastatic poorly differentiated adenocarcinoma in a 74 year old and (3) a metastatic poorly differentiated papillary adenocarcinoma in a 68 year old.

The number of clones in each library was estimated by plating serial dilutions of unamplified libraries. Insert data were determined from 32 primary ovarian tumor clones and 32 metastatic ovarian tumor clones. The library characterization results are shown in Table II.

TABLE II

CHARACTERIZATION OF cDNA LIBRARIES

| Library | # Clones in Library | Clones with Insert (%) | Insert Size Range (bp) | Ave. Insert Size (bp) |
|---|---|---|---|---|
| Primary Ovarian Tumor | 1,258,000 | 97 | 175-8000 | 2356 |
| Metastatic Ovarian Tumor | 1,788,000 | 100 | 150-4300 | 1755 |

Four subtraction libraries were constructed in ampicillin resistant pcDNA3.1 vector (Invitrogen). Two of the libraries were from primary ovarian tumors and two were from metastatic ovarian tumors. In each case, the number of restriction enzyme cuts within inserts was minimized to generate full length subtraction libraries. The subtractions were each done with slightly different protocols, as described in more detail below.

A. POTS 2 Library: Primary Ovarian Tumor Subtraction Library

| | |
|---|---|
| Tracer: | 10 µg primary ovarian tumor library, digested with Not I |
| Driver: | 35 µg normal pancreas in pcDNA3.1(+) |
| | 20 µg normal PBMC in pcDNA3.1(+) |
| | 10 µg normal skin in pcDNA3.1(+) |
| | 35 µg normal bone marrow in pZErO ™-2 |
| | Digested with Bam HI/Xho I/Sca I |

Two hybridizations were performed, and Not I-cut pcDNA3.1(+) was the cloning vector for the subtracted library. Sequence results for previously unidentified clones that were randomly picked from the subtracted library are presented in Table III.

*TABLE III

OVARIAN CARCINOMA SEQUENCES

| Sequence | SEQ ID NO |
|---|---|
| 21907 | 1 |
| 21909 | 2 |
| 21911 | 5 |
| 21920 | 9 |
| 21921 | 10 |
| 25099 | 143 |
| 25101 | 144 |
| 25103 | 145 |
| 25107 | 146 |
| 25111 | 148 |
| 25113 | 149 |
| 25115 | 150 |
| 25116 | 151 |
| 25752 | 156 |
| 25757 | 158 |
| 25763 | 160 |
| 25769 | 161 |
| 25770 | 162 |

B. POTS 7 Library: Primary Ovarian Tumor Subtraction Library

| | |
|---|---|
| Tracer: | 10 µg primary ovarian tumor library, digested with Not I |
| Driver: | 35 µg normal pancreas in pcDNA3.1(+) |
| | 20 µg normal PBMC in pcDNA3.1(+) |
| | 10 µg normal skin in pcDNA3.1(+) |
| | 35 µg normal bone marrow in pZErO ™-2 |
| | Digested with Bam HI/Xho I/Sca I |
| | ~25 µg pZErO ™-2, digested with Bam HI and Xho I |

Two hybridizations were performed, and Not I-cut pcDNA3.1(+) was the cloning vector for the subtracted library. Sequence results for previously unidentified clones that were randomly picked from the subtracted library are presented in Table IV.

TABLE IV

OVARIAN CARCINOMA SEQUENCES

| Sequence | SEQ ID NO |
|---|---|
| 24937 | 125 |
| 24940 | 128 |
| 24946 | 132 |
| 24950 | 133 |
| 24951 | 134 |
| 24955 | 136 |
| 24956 | 137 |
| 25791 | 166 |
| 25796 | 167 |
| 25797 | 168 |
| 25804 | 171 |

C. OS1D Library: Metastatic Ovarian Tumor Subtraction Library

| | |
|---|---|
| Tracer: | 10 µg metastatic ovarian library in pZErO ™-2, digested with Not I |
| Driver: | 24.5 µg normal pancreas in pcDNA3.1 |
| | 14 µg normal PBMC in pcDNA3.1 |
| | 14 µg normal skin in pcDNA3.1 |
| | 24.5 µg normal bone marrow in pZErO ™-2 |
| | 50 µg pZErO ™-2, digested with Bam HI/Xho I/Sfu I |

Three hybridizations were performed, and the last two hybridizations were done with an additional 15 μg of biotinylated pZErO™-2 to remove contaminating pZErO™-2 vectors. The cloning vector for the subtracted library was pcDNA3.1/Not I cut. Sequence results for previously unidentified clones that were randomly picked from the subtracted library are presented in Table V.

TABLE V

| Ovarian Carcinoma Sequences | |
|---|---|
| Sequence | SEQ ID NO |
| 23645.1 | 13 |
| 23660.1 | 16 |
| 23666.1 | 19 |
| 23679.1 | 23 |
| 24635 | 57 |
| 24647 | 63 |
| 24651 | 65 |
| 24661 | 69 |
| 24663 | 70 |
| 24664 | 71 |
| 24670 | 72 |
| 24675 | 75 |
| 24683 | 78 |

D. OS1F Library: Metastatic Ovarian Tumor Subtraction Library

| | |
|---|---|
| Tracer: | 10 μg metastatic ovarian tumor library, digested with Not I |
| Driver: | 12.8 μg normal pancreas in pcDNA3.1 |
| | 7.3 μg normal PBMC in pcDNA3.1 |
| | 7.3 μg normal skin in pcDNA3.1 |
| | 12.8 μg normal bone marrow in pZErO ™-2 |
| | 25 μg pZErO ™-2, digested with Bam HI/Xho I/Sfu I |

One hybridization was performed. The cloning vector for the subtracted library was pcDNA3.1/Not I cut. Sequence results for previously unidentified clones that were randomly picked from the subtracted library are presented in Table VI.

TABLE VI

| OVARIAN CARCINOMA SEQUENCES | |
|---|---|
| Sequence | SEQ ID NO |
| 24336 (79% with *H. sapiens* mitochondrial genome (consensus sequence)) | 27 |
| 24337 | 28 |

TABLE VI-continued

| OVARIAN CARCINOMA SEQUENCES | |
|---|---|
| Sequence | SEQ ID NO |
| 24341 (91% *Homo sapiens* chromosome 5, BAC clone 249h5 (LBNL H149) | 32 |
| 24344 | 33 |
| 24348 | 35 |
| 24351 | 38 |
| 24355 (91% *Homo sapiens* chromosome 17, clone hCIT.91__J__4) | 41 |
| 24356 | 42 |
| 24357 (87% *S. scrofa* mRNA for UDP glucose pyrophosphorylase) | 43 |
| 24358 | 44 |
| 24359 (78% Human mRNA for KIAA0111 gene, complete cds) | 45 |
| 24360 | 46 |
| 24361 | 47 |
| 24362 (88% *Homo sapiens* Chromosome 16 BAC clone CIT987SK-A-233A7) | 48 |
| 24363 (87% *Homo sapiens* eukaryotic translation elongation factor 1 alpha 1 (EEF1A1) | 49 |
| 24364 (89% Human DNA sequence from PAC 27K14 on chromosome Xp11.3-Xp11.4) | 50 |
| 24367 (89% *Homo sapiens* 12p13.3 BAC RCPI11-935C2) | 52 |
| 24368 | 53 |
| 24690 | 81 |
| 24692 | 82 |
| 24694 | 84 |
| 24696 | 86 |
| 24699 | 89 |
| 24701 | 90 |
| 24703 | 91 |
| 24704 (88% *Homo sapiens* chromosome 9, clone hRPK.401__G__18) | 92 |
| 24705 | 93 |
| 24707 | 95 |
| 24709 | 97 |
| 24711 | 98 |
| 24713 | 99 |
| 24714 (91% Human DNA sequence from clone 125N5 on chromosome 6q26-27) | 100 |
| 24717 (89% *Homo sapiens* proliferation-associated gene A (natural killer-enhancing factor A) (PAGA) | 103 |
| 24727 | 107 |
| 24732 | 111 |
| 24737 (84% Human ADP/ATP translocase mRNA) | 114 |
| 24741 | 117 |
| 24745 | 120 |
| 24746 | 121 |

The sequences in Table VII, which correspond to known sequences, were also identified in the above libraries.

TABLE VII

| OVARIAN CARCINOMA SEQUENCES | | | |
|---|---|---|---|
| Identity | SEQ ID NO | Sequence | Library |
| *H. sapiens* DNA for muscle nicotinic acetylcholine receptor gene promotor, clone ICRFc105F02104 | 3 | 21910 | POTS2 |
| *Homo sapiens* complement component 3 (C3) gene, exons 1-30. | 4 | 21913 | POTS2 |
| *Homo sapiens* SWI/SNF related, matrix associated, actin dependent regulator of chromatin, subfamily a, member 4 (SMARCA4) | 6 | 21914 | POTS2 |
| Human ferritin Heavy subunit mRNA, complete cds. | 7 | 21915 | POTS2 |
| *Homo sapiens* CGI-151 protein mRNA, complete cds | 8 | 21916 | POTS2 |
| Human BAC clone GS055K18 from 7p15-p21 | 11 | 23636.1 | OS1D |

TABLE VII-continued

OVARIAN CARCINOMA SEQUENCES

| Identity | SEQ ID NO | Sequence | Library |
|---|---|---|---|
| HUMGFIBPA Human growth hormone-dependent insulin-like growth factor-binding protein | 12 | 23637.1 | OS1D |
| *Homo sapiens* ribosomal protein, large, P0 (RPLP0) mRNA | 14 | 23647.1 | OS1D |
| HUMTRPM2A Human TRPM-2 mRNA | 15 | 23657.1 | OS1D |
| HUMMTA *Homo sapiens* mitochondrial DNA | 17 | 23661.1 | OS1D |
| HSU78095 *Homo sapiens* placental bikunin mRNA | 18 | 23662.1 | OS1D |
| HUMTI227HC Human mRNA for TI-227H | 20 | 23669.1 | OS1D |
| HUMMTCG Human mitochondrion | 21 | 23673.1 | OS1D |
| *Homo sapiens* FK506-binding protein 1A (12 kD) (FKBP1A) mRNA | 22 | 23677.1 | OS1D |
| *Homo sapiens* mRNA for zinc-finger DNA-binding protein, complete cds | 24 | 24333 | OS1F |
| *Homo sapiens* mRNA; cDNA DKFZp564E1962 (from clone DKFZp564E1962) | 25 | 24334 | OS1F |
| *Homo sapiens* tumor protein, translationally-controlled 1 (TPT1) mRNA. | 26 | 24335 | OS1F |
| *Homo sapiens* interleukin 1 receptor accessory protein (IL1RAP) mRNA. | 29 | 24338 | OS1F |
| Human mRNA for KIAA0026 gene | 30 | 24339 | OS1F |
| *Homo sapiens* K—Cl cotransporter KCC4 mRNA, complete cds | 31 | 24340 | OS1F |
| *Homo sapiens* nuclear chloride ion channel protein (NCC27) mRNA | 34 | 24345 | OS1F |
| *Homo sapiens* mRNA for DEPP (decidual protein induced by progesterone) | 36 | 24349 | OS1F |
| *Homo sapiens* atrophin-1 interacting protein 4 (AIP4) mRNA | 37 | 24350 | OS1F |
| Human collagenase type IV mRNA, 3' end. | 39 | 24352 | OS1F |
| Human mRNA for T-cell cyclophilin | 40 | 24354 | OS1F |
| *Homo sapiens* tumor suppressing subtransferable candidate 1 (TSSC1) | 51 | 24366 | OS1F |
| *Homo sapiens* clone 24452 mRNA sequence | 54 | 24374 | OS1F |
| *Homo sapiens* eukaryotic translation elongation factor 1 alpha 1 (EEF1A1) | 55 | 24627 | OS1D |
| Genomic sequence from Human 9q34 | 56 | 24634 | OS1D |
| Human insulin-like growth factor-binding protein-3 gene | 58 | 24636 | OS1D |
| Human ribosomal protein L3 mRNA, 3' end | 59 | 24638 | OS1D |
| *Homo sapiens* annexin II (lipocortin II) (ANX2) mRNA | 60 | 24640 | OS1D |
| *Homo sapiens* tubulin, alpha, ubiquitous (K-ALPHA-1) | 61 | 24642 | OS1D |
| Human non-histone chromosomal protein HMG-14 mRNA | 62 | 24645 | OS1D |
| *Homo sapiens* ferritin, heavy polypeptide 1 (FTH1) | 64 | 24648 | OS1D |
| *Homo sapiens* 12p13.3 PAC RPCI1-96H9 (Roswell Park Cancer Institute Human PACLibrary) | 66 | 24653 | OS1D |
| *Homo sapiens* T cell-specific tyrosine kinase mRNA | 67 | 24655 | OS1D |
| *Homo sapiens* keratin 18 (KRT18) mRNA | 68 | 24657 | OS1D |
| *Homo sapiens* growth arrest specific transcript 5 gene | 73 | 24671 | OS1D |
| *Homo sapiens* ribosomal protein S7 (RPS7) | 74 | 24673 | OS1D |
| *Homo sapiens* mRNA; cDNA DKFZp564H182 | 76 | 24677 | OS1D |
| Human TSC-22 protein mRNA | 77 | 24679 | OS1D |
| Human mRNA for ribosomal protein | 79 | 24687 | OS1D |
| Genomic sequence from Human 13 | 80 | 24689 | OS1F |
| *Homo sapiens* clone IMAGE 286356 | 83 | 24693 | OS1F |
| *Homo sapiens* v-fos FBJ murine osteosarcoma viral oncogene homolog(FOS) mRNA | 85 | 24695 | OS1F |
| *Homo sapiens* hypothetical 43.2 Kd protein mRNA | 87 | 24697 | OS1F |
| Human heat shock protein 27 (HSPB1) gene exons 1-3 | 88 | 24698 | OS1F |
| *Homo sapiens* senescence-associated epithelial membrane protein (SEMP1) | 94 | 24706 | OS1F |
| Human ferritin H chain mRNA | 96 | 24708 | OS1F |
| *Homo sapiens* mRNA for KIAA0287 gene | 101 | 24715 | OS1F |
| *Homo sapiens* CGI-08 protein mRNA | 102 | 24716 | OS1F |
| *H. sapiens* CpG island DNA genomic Mse1 fragment, clone 84a5 | 104 | 24719 | OS1F |

TABLE VII-continued

OVARIAN CARCINOMA SEQUENCES

| Identity | SEQ ID NO | Sequence | Library |
|---|---|---|---|
| Human clone 23722 mRNA | 105 | 24721 | OS1F |
| *Homo sapiens* zinc finger protein slug (SLUG) gene | 106 | 24722 | OS1F |
| *Homo sapiens* (clone L6) E-cadherin (CDH1) gene | 108 | 24728 | OS1F |
| *Homo sapiens* ribosomal protein L13 (RPL13) | 109 | 24729 | OS1F |
| *H. sapiens* RNA for snRNP protein B | 110 | 24730 | OS1F |
| *Homo sapiens* mRNA; cDNA DKFZp434K114 | 112 | 24734 | OS1F |
| *Homo sapiens* cornichon protein mRNA | 113 | 24735 | OS1F |
| *Homo sapiens* keratin 8 (KRT8) mRNA | 115 | 24739 | OS1F |
| Human DNA sequence from PAC 29K1 on chromosome 6p21.3-22.2. | 116 | 24740 | OS1F |
| *Homo sapiens* mRNA for KIAA0762 protein | 118 | 24742 | OS1F |
| Human clones 23667 and 23775 zinc finger protein mRNA | 119 | 24744 | OS1F |
| Human H19 RNA gene, complete cds. | 122 | 24933 | POTS7 |
| Human triosephosphate isomerase mRNA, complete cds. | 123 | 24934 | POTS7 |
| Human cyclooxygenase-1 (PTSG1) mRNA, partial cds | 124 | 24935 | POTS7 |
| *Homo sapiens* megakaryocyte potentiating factor (MPF) mRNA. | 126 | 24938 | POTS7 |
| Human mRNA for Apo1_Human (MER5(Aop1-Mouse)-like protein), complete cds | 127 | 24939 | POTS7 |
| *Homo sapiens* arylacetamide deacetylase (esterase) (AADAC) mRNA. | 129 | 24942 | POTS7 |
| *Homo sapiens* echinoderm microtubule-associated protein-like EMAP2 mRNA, complete cds | 130 | 24943 | POTS7 |
| *Homo sapiens* podocalyxin-like (PODXL) mRNA. | 131 | 24944 | POTS7 |
| *Homo sapiens* synaptogyrin 2 (SYNGR2) mRNA. | 135 | 24952 | POTS7 |
| *Homo sapiens* amyloid beta precursor protein-binding protein 1, 59 kD (APPBP1) mRNA. | 138 | 24959 | POTS7 |
| Human aldose reductase mRNA, complete cds. | 139 | 24969 | POTS7 |
| Genomic sequence from Human 9q34, complete sequence [*Homo sapiens*] | 140 | 25092 | POTS2 |
| Human glyceraldehyde-3-phosphate dehydrogenase (GAPDH) mRNA, complete cds. | 141 | 25093 | POTS2 |
| *Homo sapiens* breast cancer suppressor candidate 1 (bcsc-1) mRNA, complete cds | 142 | 25098 | POTS2 |
| *Homo sapiens* SKB1 (*S. cerevisiae*) homolog (SKB1) mRNA. | 147 | 25110 | POTS2 |
| *Homo sapiens* prepro dipeptidyl peptidase I (DPP-I) gene, complete cds | 152 | 25117 | POTS2 |
| *Homo sapiens* preferentially expressed antigen of melanoma (PRAME) mRNA | 153 | 25745 | POTS2 |
| Human translocated t(8; 14) c-myc (MYC) oncogene, exon 3 and complete cds | 154 | 25746 | POTS2 |
| Human 12S RNA induced by poly(rI), poly(rC) and Newcastle disease virus | 155 | 25749 | POTS2 |
| Human mRNA for fibronectin (FN precursor) | 157 | 25755 | POTS2 |
| *Homo sapiens* mRNA for hepatocyte growth factor activator inhibitor type 2, complete cds | 159 | 25758 | POTS2 |
| *Homo sapiens* mRNA for KIAA0552 protein, complete cds | 163 | 25771 | POTS7 |
| *Homo sapiens* IMP (inosine monophosphate) dehydrogenase 2 (IMPDH2) mRNA | 164 | 25775 | POTS7 |
| *Homo sapiens* clone 23942 alpha enolase mRNA, partial cds | 165 | 25787 | POTS7 |
| *H. sapiens* vegf gene, 3'UTR | 169 | 25799 | POTS7 |
| *Homo sapiens* 30S ribosomal protein S7 homolog mRNA, complete cds | 170 | 25802 | POTS7 |
| *Homo sapiens* acetyl-Coenzyme A acetyltransferase 2 (acetoacetyl Coenzyme A thiolase) (ACAT) mRNA | 172 | 25808 | POTS7 |
| *Homo sapiens* Norrie disease protein (NDP) mRNA | 173 | 25809 | POTS7 |

Still further ovarian carcinoma polynucleotide and/or polypeptide sequences identified from the above libraries are provided below in Table VIII. Sequences O574S (SEQ ID NO:183 & 185), O584S (SEQ ID NO:193) and O585S (SEQ ID NO:194) represent novel sequences. The remaining sequences exhibited at least some homology with known genomic and/or EST sequences.

TABLE VIII

| SEQ ID: | Sequence | Library |
|---|---|---|
| 174: | O565S_CRABP | OS1D |
| 175: | O566S_Ceruloplasmin | POTS2 |
| 176: | O567S_41191.SEQ(1 > 487) | POTS2 |
| 177: | O568S_KIAA0762.seq(1 > 3999) | POTS7 |
| 178: | O569S_41220.seq(1 > 1069) | POTS7 |
| 179: | O570S_41215.seq(1 > 1817) | POTS2 |
| 180: | O571S_41213.seq(1 > 2382) | POTS2 |
| 181: | O572S_41208.seq(1 > 2377) | POTS2 |
| 182: | O573S_41177.seq(1 > 1370) | OS1F |
| 183: | O574S_47807.seq(1 > 2060) | n/a |
| 184: | O568S/VSGF DNA seq | n/a |
| 185: | O574S_47807.seq(1 > 3000) | n/a |
| 186: | O568S/VSGF protein seq | n/a |
| 187: | 449H1(57581) | OS1D |
| 188: | 451E12(57582) | OS1D |
| 189: | 453C7_3'(57583.1)Osteonectin | OS1D |
| 190: | 453C7_5'(57583.2) | OS1D |
| 191: | 456G1_3'(57584.1)Neurotensin | OS1F |
| 192: | 456G1_5'(57584.2) | OS1F |
| 193: | O584S_465G5(57585) | OS1F |
| 194: | O585S_469B12(57586) | POTS2 |
| 195: | O569S_474C3(57587) | POTS7 |
| 196: | 483B1_3'(24934.1)Triosephosphate | POTS7 |
| 197: | 57885 Human preferentially expressed antigen of melanoma | POTS2 |
| 198: | 57886 Chromosome 22q12.1 clone CTA-723E4 | POTS2 |
| 199: | 57887 Homologous to mouse brain cDNA clone MNCb-0671 | POTS2 |

Further studies on the clone of SEQ ID NO:182 (also referred to as O573S) led to the identification of multiple open reading frames that encode the amino acid sequences of SEQ ID NO:200-202.

Example 2

Analysis of cDNA Expression Using Microarray Technology

In additional studies, sequences disclosed herein were found to be overexpressed in specific tumor tissues as determined by microarray analysis. Using this approach, cDNA sequences are PCR amplified and their mRNA expression profiles in tumor and normal tissues are examined using cDNA microarray technology essentially as described (Shena et al., 1995). In brief, the clones are arrayed onto glass slides as multiple replicas, with each location corresponding to a unique cDNA clone (as many as 5500 clones can be arrayed on a single slide or chip). Each chip is hybridized with a pair of cDNA probes that are fluorescence-labeled with Cy3 and Cy5 respectively. Typically, 1 µg of polyA+ RNA is used to generate each cDNA probe. After hybridization, the chips are scanned and the fluorescence intensity recorded for both Cy3 and Cy5 channels. There are multiple built-in quality control steps. First, the probe quality is monitored using a panel of ubiquitously expressed genes. Secondly, the control plate also can include yeast DNA fragments of which complementary RNA may be spiked into the probe synthesis for measuring the quality of the probe and the sensitivity of the analysis. Currently, the technology offers a sensitivity of 1 in 100,000 copies of mRNA. Finally, the reproducitility of this technology can be ensured by including duplicated control cDNA elements at different locations.

The microarray results for clones 57885 (SEQ ID NO:197), 57886 (SEQ ID NO:198) and 57887 (SEQ ID NO:199) are as follows.

Clone 57885: 16/38 (42%) of ovarian tumors showed an expression signal value of >0.4. The mean value for all ovary tumors was 0.662 with a mean value of 0.187 for all normal tissues, which yields a 3.64 fold overexpression level in ovary tumor relative to essential normal tissues. Normal tissue expression was elevated (>0.4) in peritoneum, skin and thymus.

Clone 57886: 16/38 (42%) of ovarian tumors showed an expression signal value of >0.4. The mean value for all ovary tumors was 0.574 with a mean value of 0.166 for all normal tissues which yields a 3.46 fold overexpression level in ovary tumor relative to essential normal tissues. Normal tissue expression was elevated (>0.4) in heart, pancreas and small intestive.

Clone 57887: 17/38 (44%) of ovarian tumors showed an expression signal value of >0.4. The mean value for all ovary tumors is 0.744 with a mean value of 0.184 for all normal tissues which yields a 4.04 fold overexpression level in ovary tumor relative to essential normal tissues. Normal tissue expression was elevated (>0.4) in esophagus.

Example 3

Expression of Recombinant Antigen O568S in *E. coli*

This example describes the expression of recombinant antigen O568S (SEQ ID NO:177) in *E. coli*. This sequence was identified in Example 1 from the POTS 7 subtraction library using primary ovarian tumor cDNA as the tracer. PCR primers specific for the open reading frame of O568S were designed and used in the specific amplification of O568S. The PCR product was enzymatically digested with EcoRI and ligated into pPDM, a modified pET28 vector which had been cut with the restriction enzymes EcoRI and Eco72I. The construct sequence and orientation was confirmed through sequence analysis, the sequence of which is shown in SEQ ID NO:206. The vector was then transformed into the expression hosts, BLR (DE3) and HMS174 (DE3) pLys S. Protein expression was confirmed, the sequence of which is provided in SEQ ID NO:207.

Example 4

Additional Sequence Obtained for Clone O591S

The sequence of O591S (clone identifier 57887) was used to search public sequence databases. It was found that the reverse strand showed some degree of identity to the C-terminal end of GPR39. The cDNA for the coding region of GPR39 is disclosed in SEQ ID NO:208 and the corresponding amino acid sequence in SEQ ID NO:209. The GPR39 coding region contains two exons. Both O591S and GPR39, encoded by the complementary strand of O591S, are located on chromosome 2.

Example 5

Further Characterization of O591S and Identification of Extended Sequence

O1034C is an ovary specific gene identified by electronic subtraction. Briefly, electronic subtraction involves an analysis of EST database sequences to identify ovarian-specific genes. In the electronic subtraction method used to identify O1034C, sequences of EST clones derived from ovary libraries (normal and tumor) were obtained from the GenBank public human EST database. Each ovary sequence was used as a "seed" query in a BLASTN search of the total human EST database to identify other EST clones that share sequence with the seed sequence (clones that potentially originated from the same mRNA). EST clones with shared sequence were grouped into clusters, and clusters that shared sequence with other clusters were grouped into superclusters. The tissue source of each EST within each supercluster was noted, and superclusters were ranked based on the distribution of the tissues from which the ESTs originated. Superclusters that comprise primarily, or solely, EST clones from ovary libraries were considered to represent genes that were differentially expressed in ovary tissue, relative to all other normal adult tissue.

This clone was identified from the public EST databases as Integrated Molecular Analysis of Genomics and their Expression (IMAGE) clone number 595449 (the IMAGE consortium is a repository of EST clones and cDNA clones) and is disclosed as SEQ ID NO:210. Accession numbers AA173739 and AA173383 represents the sequence of the identified EST in Genebank. This clone is part of Unigene cluster HS.85339 (Unigene is an experimental system for automatically partitioning Genbank sequences into a non-redundant set of gene-orientated clusters) and was annotated as encoding a neurotensin-like G protein coupled receptor (GRP39). However, the inventors have discovered that IMAGE#595449 encodes a novel protein derived from the complementary strand to that which encodes the potential GPR39.

Microarray analysis of the clone using a series of ovary tumor specific probes indicated that this clone was over expressed 4.95-fold in a group of ovary tumor and normal ovary samples as compared to a group of essential normal tissue samples.

IMAGE#59449 was subjected to a Blast A search of the EST database and Genbank and an electronic full length clone contig (O1034C) was generated by extending IMAGE#595449 and its resulting contigs to completion. This process was repeated to completion when no further EST sequences were identified to extend the consensus sequence. This electronically derived clone was identified as coding a previously described clone, O591S, the sequence of which is disclosed in SEQ ID NO:211. The discovery of this ovary specific candidate is described in more detail in Example 4.

The consensus sequence for O1034C extended further 5' than O591S due to the additional sequences derived from two EST clones, accession numbers BF345141 and BE336607, the sequences for which are disclosed in SEQ ID NO:212 and 213 respectively. Although BF345141 diverges from the O1034C/O591S consensus at its 3'-end (possibly representing a different splice form), and from BE336607 at several bases at its 5'-end, the two ESTs were compared to the available matching chromosome sequence. They were found on human chromosome 2, clone RP11-159N20:htgs database accession number AC010974. These sequences were used to extend O1034C/O591S to form a final consensus sequence for O1034C/O591S of 1897 base pairs, disclosed in SEQ ID NO:214.

An open reading frame (ORF) was identified within the O1034C/O591S consensus sequence (nucleotides 260-682), the predicted translation of which is disclosed in SEQ ID NO:215. A BLASTx database search against the Genbank database indicated that this ORF had no identity (E value <1e-25) with any known human protein. The only match was with the G protein-coupled receptors, including GPR39, which the inventors have shown to be encoded at the 3'-end of O1034C/O591S on the complementary strand. However, the ORF did encode a protein that had 93% similarity (131/141 amino acids) and 91% identity (129/141 amino acids) with an un-named murine product (Accession #BAA95101), suggesting that this is a real translation product that represents a novel human ovary-specific antigen.

The novelty of O1034C/O591S was confirmed by Northern Blot analysis using single stranded probes that complement either GRP39 or O1034C/O591S. The strand-specific O1034C/O591S probe specifically hybridized to the ovary tumor samples probed on the Northern blot, whilst all samples were negative when probed with GPR39. In addition real-time PCR was performed using primers specific for either GPR39 or O1034C/O591S. These results further demonstrated the differential expression profiles of the two sequences. This protein is a putative membrane protein as determined from Corixa's Tmpred protein prediction algorithm.

Example 6

Expression Analysis and Further Characterization of Ovarian Sequence O568S

The ovarian sequence O568S was originally identified as cDNA clone 24742 (SEQ ID NO:118). Using clone 24742 as a query sequence to search public sequence databases, the sequence was found to have a high degree of homology with KIAA0762 (SEQ ID NO:177) and with VSGF. The DNA sequence for VSGF is provided in SEQ ID 184 and the VSGF protein sequence is provided in SEQ ID NO:186.

Real-time PCR (see Gibson et al., *Genome Research* 6:995-1001, 1996; Heid et al., *Genome Research* 6:986-994, 1996) is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR is performed, for example, using a Perkin Elmer/Applied Biosystems (Foster City, Calif.) 7700 Prism instrument. Matching primers and fluorescent probes are designed for genes of interest using, for example, the primer express program provided by Perkin Elmer/Applied Biosystems (Foster City, Calif.). Optimal concentrations of primers and probes are initially determined by those of ordinary skill in the art, and control (e.g., β-actin) primers and probes are obtained commercially from, for example, Perkin Elmer/Applied Biosystems (Foster City, Calif.). To quantitate the amount of specific RNA in a sample, a standard curve is generated using a plasmid containing the gene of interest. Standard curves are generated using the Ct values determined in the real-time PCR, which are related to the initial cDNA concentration used in the assay. Standard dilutions ranging from $10-10^6$ copies of the gene of interest are generally sufficient. In addition, a standard curve is generated for the control sequence. This permits standardization of initial RNA content of a tissue sample to the amount of control for comparison purposes.

By RealTime PCR analysis, O568 was highly overexpressed in the majority of ovary tumors and ovary tumor metastases tested relative to normal ovary tissue and relative to an extensive normal tissue panel. Little or no expression was observed in normal esophagus, spinal cord, bladder, colon, liver, PBMC (activated or resting), lung, skin, small intestine, stomach, skeletal muscle, pancreas, dendritic cells, heart, spleen bone marrow, thyroid, trachea, thymus, bronchia, cerebellum, ureter, uterus and peritoneum epithelium. Some low level expression was observed in normal breast, brain, bone, kidney, adrenal gland and salivary gland, but the expression levels in these normal tissues were generally at least several fold less than the levels observed in ovary tumors overexpressing O568S.

Moreover, a series of Northern blots was performed which also demonstrated that the ORF region of O568S is specifically overexpressed in ovary tumors. The initial blot contained RNA from a series of normal tissues as well as from ovary tumors. This blot was probed using, as a labeled probe, DNA from O568S that corresponded to the 3'UTR of the VSGF sequence disclosed in SEQ ID NO:184. This blot revealed an ovary tumor-specific 5.0 Kb message as well as a potential 3.5 Kb brain specific message and a ubiquitously expressed 1.35 Kb message.

Another Northern blot was performed with RNAs from a number of different brain tissues and probed with the 3'UTR region as above. Five of eleven brain samples showed overexpression of the 3.5 Kb message. In order to determine whether the ORF region of O568S was specifically overexpressed in ovary tumors, a series of three blots was carried out using three separate probes designed from within the VSGF ORF of O568S. Results from these experiments clearly indicated that only the 5.0 Kb message is expressed in ovary tumor.

Example 7

Synthesis of Polypeptides

Polypeptides are synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence is attached to the amino terminus of the peptide to provide a method of conjugation, binding to an immobilized surface, or labeling of the peptide. Cleavage of the peptides from the solid support is carried out using the following cleavage mixture: trifluoroacetic acid:ethanedithiol: thioanisole:water:phenol (40:1:2:2:3). After cleaving for 2 hours, the peptides are precipitated in cold methyl-t-butyl-ether. The peptide pellets are then dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) is used to elute the peptides. Following lyophilization of the pure fractions, the peptides are characterized using electrospray or other types of mass spectrometry and by amino acid analysis.

Example 8

O568S Northern Blot Analysis

As described in Example 6, Northern blot analysis demonstrated that the ORF region of O568S was specifically over expressed in ovarian tumors. The original probe used corresponded to the 3'UTR of the VSGF sequence disclosed in SEQ ID NO:184. The results from these Northern blots revealed an ovarian tumor-specific 5.0 Kb message as well as a potential 3.5 Kb brain specific message. To confirm that the entire region covered by the ORF yields a single 5.0 Kb ovarian tumor-specific message, two additional probes were designed. The probes were located at the 5' and 3' regions of the ORF. Northern blot analysis using these two probes demonstrated that both probes hybridized to a 5.0 Kb product present only in ovarian tumor samples. Both probes failed to hybridize with RNA derived from multiple brain samples.

Example 9

Real Time PCR and Northern Blot Analysis of O590S

Real time PCR analysis of ovarian tumor antigen O590S was performed essentially as described in Example 6. O590S specific primers and probe were designed and quantitative Real Time PCR was performed on a panel of cDNAs prepared from a variety of tissues including ovarian tumor samples and a panel of normal tissues. This analysis revealed that O590S-specific mRNA was over expressed in approximately 65% of ovarian tumor samples tested, 100% tumor samples derived from SCID mice, and 100% ovarian tumor cell lines tested, when compared to normal ovarian tissue. No detectable expression was observed in normal tissues.

In addition to Real Time PCR, Northern blot analysis was performed to determine to transcript size of O590S. The Northern blot was probed with a 537 bp PCR product specific for O590S, which was designed to avoid regions of repeat sequences. This probe revealed a smeared band that was approximately 9.0 Kb in size, which was present in the majority of ovarian tumor samples tested.

Example 10

Analysis of cDNA Expression Using Microarray Technology

This example describes microarray expression analysis of ovary tumor- and tissue-specific cDNAs identified from OTCLS4, POTS2 and POTS7 (Subtraction libraries described in Example 1). Microarray analysis was performed essentially as described in Example 2. Sequence expression was determined by probing with a number of ovarian tumor samples, including papillary serous cystic carcinoma, papillary serous adenocarcinoma, papillary serous neoplasm, papillary serous carcinoma, papillary serous cytstadenocarcinoma, and a panel of normal tissues including adrenal gland, pituitary gland, thymus, bronchus, stomach, pancreas, skin, spinal cord, kidney, spleen, brain, breast, small intestine, thyroid, trachea, colon, PBMC resting, PBMC activated, lung, aorta, bone marrow, mammary epithelial tissue, esophagus, heart, and liver.

Clones showing an ovarian tumor mean or median value that was at least two fold greater than the normal tissue value were selected for further analysis. Further selection criteria was imposed on mean and median values as follows:

Mean tumor value $\geq 0.2$ and mean normal value of <0.4

Median tumor value $\geq 0.2$ and median normal value of <0.3.

Based on the selection criteria above, 26 clones were selected from the OTCLS4, POTS2 and POTS7 for sequencing. These sequences are disclosed herein in SEQ ID NOs: 216-243. See Table IX for details.

TABLE IX

| SEQ ID NO | Clone ID | GenBank ID NO | GenBank Description | Ratio | Ratio 1/2 | Group 1 | Group 2 |
|---|---|---|---|---|---|---|---|
| 216 | 91226.5 | 15779016 | *Homo sapiens*, clone IMAGE: 4047062, mRNA | Mean | 2.09 | 0.722 | 0.346 |
| 217 | 91227.2 | 14760620 | *Homo sapiens* bHLH protein DEC2 (DEC2), mRNA | Mean | 2.45 | 0.62 | 0.153 |
| 218 | 91230.2 | 13543043 | *Homo sapiens*, hypothetical protein dJ473B4, clone MGC: 4987 IMAGE: 3450155, mRNA, complete cds | Mean | 2.17 | 0.434 | 0.2 |
| 219 | 91231 | 13277551 | *Homo sapiens*, coxsackie virus and adenovirus receptor, clone MGC: 5086 IMAGE: 3463613, mRNA, complete cds | Mean | 2.16 | 0.545 | 0.253 |
| 220 | 91238.3 | 12804424 | *Homo sapiens*, similar to phosphoserine aminotransferase, clone MGC: 1460 IMAGE: 3544564, mRNA, complete cds | Mean | 2.18 | 0.229 | 0.105 |
| 221 | 91239.6 | 14589888 | *Homo sapiens* cadherin 2, type 1, N-cadherin (neuronal) (CDH2), mRNA | Median | 2.22 | 0.581 | 0.262 |
| 222 | 91240.2 | 5729900 | *Homo sapiens* IGF-II mRNA-binding protein 3 (KOC1), mRNA | Mean | 2.08 | 0.236 | 0.114 |
| 223 | 91241.2 | 12653176 | *Homo sapiens*, MAD2 (mitotic arrest deficient, yeast, homolog)-like 1, clone MGC: 8662 IMAGE: 2964388, mRNA, complete cds | Median | 2.13 | 0.316 | 0.148 |
| 224 | 91242.5 | 12653176 | *Homo sapiens*, MAD2 (mitotic arrest deficient, yeast, homolog)-like 1, clone MGC: 8662 IMAGE: 2964388, mRNA, complete cds | Mean | 2.36 | 0.458 | 0.194 |
| 225 | 91243.6 | 15297244 | *Homo sapiens* laminin, gamma 2 (nicein (100 kD), kalinin (105 kD), BM600 (100 kD), Herlitz junctional epidermolysis bullosa)) (LAMC2), mRNA | Mean | 2.91 | 0.755 | 0.26 |
| 226 | 91245.2 | 7022574 | *Homo sapiens* cDNA FLJ10500 fis, clone NT2RP2000369 | Mean | 2.1 | 0.571 | 0.272 |
| 227 | 91246.4 | 1575533 | Human MAD2 (hsMAD2) mRNA, complete cds | Median | 2.51 | 0.292 | 0.116 |
| 228 | 91247.3 | 5912166 | *Homo sapiens* mRNA; cDNA DKFZp564H1663 (from clone DKFZp564H1663) | Mean | 2.03 | 0.369 | 0.182 |
| 229 | 91247.4 | 5912166 | *Homo sapiens* mRNA; cDNA DKFZp564H1663 (from clone DKFZp564H1663) | Mean | 2.03 | 0.369 | 0.182 |
| 230 | 91249.2 | 14711935 | *Homo sapiens*, hypothetical protein FLJ10461, clone IMAGE: 4102110, mRNA | Mean | 2.26 | 0.271 | 0.12 |
| 231 | 91253.2 | 14756011 | *Homo sapiens* similar to coxsackie virus and adenovirus receptor; 46 kD coxsackie and adenovirus receptor (CAR) protein (*H. sapiens*) (LOC93529), mRNA | Mean | 2.4 | 0.411 | 0.172 |
| 232 | 91254.2 | 11493240 | Human DNA sequence from clone RP11-124N19 on chromosome 13, complete sequence [*Homo sapiens*] | Mean | 5.15 | 1.396 | 0.271 |
| 233 | 91259.2 | 14771329 | *Homo sapiens* Wilms tumor (WT1), mRNA | Mean | 3.87 | 0.406 | 0.105 |
| 234 | 91261.3 | 11465000 | *Homo sapiens* 12 BAC RP11-283G6 (Roswell Park Cancer Institute Human BAC library) complete sequence | Mean | 2.57 | 0.34 | 0.132 |
| 235 | 91261.4 | 11465000 | *Homo sapiens* 12 BAC RP11-283G6 (Roswell Park Cancer Institute Human BAC library) complete sequence | Mean | 2.57 | 0.34 | 0.132 |
| 236 | 91262.2 | 4506070 | *Homo sapiens* protein kinase C, iota (PRKC1), mRNA | Mean | 2.46 | 0.695 | 0.282 |
| 237 | 91263.2 | 13647850 | *Homo sapiens* matrix metalloproteinase 11 (stromolysin 3) (MMP11), mRNA | Mean | 2.63 | 0.254 | 0.097 |
| 238 | 91264.2 | NA | NOVEL (no GENSEQ) | Mean | 15.6 | 2.058 | 0.132 |
| 239 | 91268.2 | 3980529 | *Homo sapiens* PAC clone RP4-797C5 from 7q31, complete sequence | Mean | 2.41 | 0.232 | 0.096 |
| 240 | 91269.5 | NA | NOVEL (no GENSEQ) | Mean | 3.04 | 0.226 | 0.074 |
| 241 | 91271.5 | 339440 | *Homo sapiens* transcriptional enhancer factor (TEF1) DNA, complete cds | Mean | 2.1 | 0.407 | 0.194 |
| 242 | 91273.3 | 15297244 | *Homo sapiens* laminin, gamma 2 (nicein (100 kD), kalinin (105 kD), BM600 (100 kD), Herlitz junctional epidermolysis bullosa)) (LAMC2), mRNA | Mean | 2.5 | 0.625 | 0.25 |
| 243 | 91274.6 | NA | NOVEL (GENSEQ"AAQ60336) | Mean | 2.58 | 0.204 | 0.079 |

Example 11

Expression Analysis and Further Characterization of Ovarian Sequence O646S

Ovarian tumor antigen O646S was originally described in Example 10 as clone 91274.6 (SEQ ID NO:243). Using SEQ ID NO:243 to search publicly available databases, a contig was generated, the DNA sequence of which is disclosed in SEQ ID NO:246, with a corresponding protein sequence disclosed in SEQ ID NO:249. This sequence was shown to share homology with Genbank Accession Number 18549403, the DNA and protein sequences of which are disclosed in SEQ ID NOs:244 and 247, respectively, and Genbank Accession Number FLJ14035, the DNA and protein sequences for which are disclosed in SEQ ID NOs:245 and 248, respectively.

Example 12

Further Characterization of Ovarian Sequence O648S

Ovarian tumor antigen O648S was originally described in Example 10 as clone 91268.2 (SEQ ID NO:239). Using SEQ ID NO:239 to search publicly available databases, a contig was generated, the DNA sequence of which is disclosed in SEQ ID NO:256, with a corresponding protein sequence disclosed in SEQ ID NO:261. This sequence was shown to share homology with several sequences including, Genbank Accession Number 3980529, the DNA sequence of which is disclosed in SEQ ID NOs:250, Genbank Accession Number 13629915, the DNA and protein sequences for which are disclosed in SEQ ID NOs:251 and 257, Genbank Accession Number 9789986, the DNA and protein sequences of which are disclosed in SEQ ID NOs:252 and 258, respectively, Genbank Accession Number 6006516, the DNA and protein sequences of which are disclosed in SEQ ID NOs:253 and 259, Genbank Accession Number 5689424, the DNA and protein sequences of which are disclosed in SEQ ID NOs:254 and 260, and Genbank Accession Number 15638833, the DNA sequence of which is disclosed in SEQ ID NO:255.

Example 13

Further Characterization of Ovarian Sequence O647S

Ovarian tumor antigen O647S was originally described in Example 10 as clone 91261.3 (SEQ ID NO:234). Using SEQ ID NO:234 to search publicly available databases, a contig was generated, the DNA sequence of which is disclosed in SEQ ID NO:268. This sequence was shown to share homology with several sequences, including Genbank Accession Number 16933560, the DNA and protein sequences of which are disclosed in SEQ ID NOs:262 and 269, Genbank Accession Number 12053028, the DNA and protein sequences for which are disclosed in SEQ ID NOs:263 and 270, Genbank Accession Number 7638812, the DNA and protein sequences of which are disclosed in SEQ ID NOs:264 and 271, Genbank Accession Number 939922, the DNA and protein sequences of which are disclosed in SEQ ID NOs:265 and 272, Genbank Accession Number 6093230, the DNA sequence of which are disclosed in SEQ ID NO:266 and Genbank Accession Number 11465000, the DNA sequence of which is disclosed in SEQ ID NO:267.

Example 14

Further Characterization of Ovarian Sequence O648S

Ovarian tumor antigen O645S was originally described in Example 10 as clone 91264.2 (SEQ ID NO:238). Using SEQ ID NO:238 to search publicly available databases, a contig was generated, the DNA sequence of which is disclosed in SEQ ID NO:273.

Example 15

Further Characterization of Ovarian Sequence O644S

Ovarian tumor antigen O644S was originally described in Example 10 as clone 91269.5 (SEQ ID NO:240). Using SEQ ID NO:240 to search publicly available databases, a contig was generated, the DNA sequence of which is disclosed in SEQ ID NO:277. This sequence was found to contain three open reading frames, the sequences of which are disclosed in SEQ ID NOs:280-282. These sequences were shown to share homology with Genbank Accession Number NM006580, the DNA and protein sequences of which are disclosed in SEQ ID NOs:274 and 278, Genbank Accession Number AF152101.1, the DNA and protein sequences for which are disclosed in SEQ ID NOs:275 and 279, and Genbank Accession Number 18425237, the DNA sequence of which is disclosed in SEQ ID NOs:276.

Example 16

O591S Expression in *E. coli*

The identification and characterization of O591S (SEQ ID NO: 214, encoding the protein of SEQ ID NO: 215) was described above (Example 1 and 4). For production and purification of O591S protein used for antibody generation, a truncated form of O591S, lacking the signal peptide sequence, was expressed in *E. coli* using a modified pET 28 vector with an N-terminal histidine tag.

The truncated coding region of O591S-A was PCR amplified minus the signal sequence (amino acids 24-141) with the following primer pairs:

```
                                          (SEQ ID NO:287)
CBH-005   5' cacttcttgcttccaggctttgcgctgcaaat 3'

(SEQ ID NO:288)
CBH-003   5' actagctcgagtcagcagtgtgccgagaa 3'
```

PCR amplification was performed under the following reaction conditions:
  10 µl 10×Pfu buffer
  1 µl 10 mM dNTPs
  2 µl 10 µM of each primer
  83 µl of sterile water
  1.5 µl Pfu DNA polymerase (Stratagene, La Jolla, Calif.)
  50 ηg DNA The reaction was amplified under the following conditions: 96° C. 2 minutes, followed by 40 cycles of 96° C. 20 seconds, 64° C. 15 seconds, and 72° C. 1 minute, With a final extension step of 72° C. for 4 minutes.

The PCR product was digested with Xho I and cloned into pPDM His (a modified pET28 vector with a histidine tag in frame on the 5' end) that has been digested with Eco72I and XhoI. Constructs were confirmed through nucleic acid sequence analysis, the corresponding DNA and protein sequence for which are disclosed in SEQ ID NOs:283 and 284, respectively. Following sequence analysis, the construct was then transformed into BLR (DE3) pLys S and HMS174 (DE3) pLys S cells.

Example 17

The Generation of Rabbit Anti-O568S Polyclonal Antibodies and Expression Determination in Ovarian Tumors The over-expression of O568S in ovarian tumor samples and normal ovary was verified using affinity purified rabbit polyclonal antibodies to O568S in the immunohistorchemical (IHC) analysis of ovarian tumors and normal tissues.

Rabbits were immunized with purified recombinant O568S protein and polyclonal antibodies prepared. Briefly, production and purification of the O568S antigen used for antibody generation was as follows:

The ovarian tumor protein antigen O568S (amino acids 29-808) was expressed in an E. coli recombinant expression system and grown overnight at 37° C. in LB Broth with the appropriate antibiotics in a shaking incubator. The next morning, 10 ml of the overnight culture was added to 500 ml of 2×YT plus the appropriate antibiotics in a 2 L-baffled Erlenmeyer flask. When the Optical Density (at 560 nanometers) of the culture reached 0.4-0.6 the cells were induced with IPTG (1 mM) for 4 hours, and then harvested by centrifugation, washed with phosphate buffered saline and centrifuged again. The supernatant was discarded and the cells were either processed immediately or frozen for future use. When processed immediately, in order to break open the E. coli cells, twenty milliliters of lysis buffer was added to the cell pellets, followed by vortex mixing and French Press disruption at a pressure of 16,000 psi. This lysed cell suspension was then centrifuged, the resulting supernatant and pellet fractions of which were examined by SDS-PAGE for the presence of recombinant protein.

The pellet prepared as described above was resuspended in 10 mM Tris pH 8.0, 1% CHAPS, washed and centrifuged again. This step was repeated an additional two times. The washed pellet containing inclusion bodies was then solubilized with either 8 M urea or 6 M guanidine HCl containing 10 mM Tris pH 8.0 plus 10 mM imidazole (solubilization buffer). The solubilized protein was added to 5 ml of nickel-chelate resin (Qiagen Inc.) and incubated for 45 min to 1 hour at room temperature with continuous agitation. After incubation, the resin and protein mixture was added to a disposable column and the flow through containing unbound proteins was collected. The column containing resin with bound protein was then washed with 10-20 column volumes of solubilization buffer, and eluted using an elution buffer solution containing 8M urea, 10 mM tris pH 8.0 and 300 mM imidazole. Column fractions (amounting to 3 ml of elution buffer each) were collected and examined by SDS-PAGE for the presence of O568S protein. Fractions containing the desired protein were pooled for further characterization. As an additional purification step, a strong anion exchange resin such as Hi-Prep Q (Biorad) was equilibrated with the appropriate buffer and the pooled fractions containing O568S protein were loaded onto this column and eluted using an increasing salt gradient. Fractions were collected and again evaluated by SDS-PAGE for the presence of O568S protein. The appropriate fractions were identified, combined and dialyzed against 10 mM Tris pH 8.0. Purity was determined by SDS-PAGE or HPLC, the concentration of purified protein was determined by Lowry assay or Amino Acid Analysis, the amino terminal protein sequence was determined to confirm authenticity, and the level of endotoxin was determined using a standard Limulus (LAL) assay. Fractions containing purified O568S were pooled, sterilized by filtration using a 0.22 micron filter, aliquoted and frozen until needed.

For the generation of polyclonal antiserum, rabbits were immunized with 400 micrograms of purified O568S protein combined with 100 micrograms of muramyldipeptide (MDP) and an equal volume of Incomplete Freund's Adjuvant (IFA). Every four weeks thereafter, animals were boosted with 100 micrograms of O568S antigen mixed with an equal volume of IFA. Seven days following each boost a blood sample from each immunized animal was taken and a serum fraction therefrom prepared by incubating the blood sample at 4° C. for 12-24 hours, clarified by centrifugation.

In order to characterize the above-mentioned rabbit polyclonal anti-O568S antiserum, 96 well plates were coated with the appropriate antigen in 50 μl (typically 1 μg of protein), incubated at 4 C for 20 hours, after which 250 μl of BSA blocking buffer was added followed by an additional 2 hours of incubation at room temperature (RT). Each well was then washed 6 times with PBS/0.01% tween. The rabbit anti-O568S antiserum to be tested was diluted in PBS, 50 μl of which was added to each well and incubated at RT for 30 minutes. Plates were washed as described above and then 50 μl of a 1:10000 dilution of goat anti-rabbit horse radish peroxidase (HRP) conjugated antibody was added and incubated at RT for 30 minutes. Next, plates were washed as described above and 100 μl of TMB containing microwell Peroxidase was added. Substrate was added to each well, incubated for 15 minutes in the dark at RT, the colorimetric reaction stopped with the addition of 100 μl of 1N H2SO4 and signal determined immediately at 450 nm.

For IHC analysis, paraffin embedded formalin-fixed tissue was sliced into 4 micron sections. Steam heat induced epitope retrieval (SHIER) in 0.1M sodium citrate buffer (pH 6.0) was used for optimal staining conditions. Sections were incubated with 10% serum/PBS for 5 minutes. Primary antibody (0.5 μg/ml rabbit affinity purified anti-O568S polyclonal antibody) was added to each section for 25 minutes at varying concentrations, followed by a 25 minute incubation with an anti-rabbit biotinylated antibody. Rabbit IgG was also tested on all tissues and served as a negative control. Endogenous peroxidase activity was blocked by three 1.5 minute incubations with hydrogen peroxidase. The avidin biotin complex/horse radish peroxidase (ABC/HRP) system was used along with DAB chromogen to visualize antigen expression. Slides were counterstained with hematoxylin.

The tissues tested and their expression profiles are described in detail in Table X. Of the ovarian cancer metastases tested, six were adenocarcinomas, five of which tested positive and one was marginal. The majority of the tumor samples stained positive with a strong membrane localized signal, demonstrating that O568S is expressed on the surface of the tumor cells.

TABLE X

Tissue Expression of O568S

| TISSUE | O568S EXPRESSION |
|---|---|
| Ovarian cancer | 3/5 |
| Ovarian cancer metastases | 8/12 |
| Normal ovary | 3/4 |
| Normal lung (alveolar epithelium) | 0/1 |
| Normal lung (bronchiole epithelium) | 0/1 |
| Brain (cortex) | 6/6 (marginal staining of selected neuronal populations) |
| Brain (spinal cord) | 6/6 (marginal staining of purkinje cells) |
| Stomach | 5/5 (marginal staining of selected neuronal populations) |
| Skin | 0/1 |
| Heart | 0/1 |
| Kidney | 0/1 |
| Liver | 0/1 |
| Colon | 0/1 |
| Tonsil | 0/1 |
| Vagina | 1/1 (squamous epithelium) |

Example 18

Real-Time PCR Analysis of Ovarian Tumor Antigens Identified from the OTCLS4, POTS2 and POTS7 Libraries Clones identified as having a good expression profile by microarray analysis (as described in Example 10), were further analyzed by real-time PCR on an extended panel of ovarian tumor and normal tissue samples (including ovary, aorta, adrenal gland, bladder, bone, bronchus, brain, breast, CD34+ cells, dendritic cells, esophagus, heart, kidney, large intestine, liver, lung, lymph nodes, pancreas, peritoneum, bane marrow, skin, small intestine, spinal cord, spleen, stomach, thymus, thyroid, tonsil, trachea, ureter, uterus). Real time PCR was performed as described above in Example 6.

The first-strand cDNA used in the quantitative real-time PCR was synthesized from 20 µg of total RNA that was treated with DNase I (Amplification Grade, Gibco BRL Life Technology, Gaithersburg, Md.), using Superscript Reverse Transcriptase (RT) (Gibco BRL). Real-time PCR was performed with an ABIPRISM 7900 sequence detection system (PE Biosystems, Foster City, Calif.). The 7900 system uses SYBR™ green, a fluorescent dye that only intercalates into double stranded DNA, and a set of gene-specific forward and reverse primers. The increase in fluorescence was monitored during the whole amplification process. The optimal concentration of primers was determined using a checkerboard approach, and a pool of cDNAs from tumors was used in this process. The PCR reaction was performed in 12.5 µl volumes that included 2.5 µl of SYBR green buffer, 2 µl of cDNA template and 2.5 µl each of the forward and reverse primers for the gene of interest. The cDNAs used for RT reactions were diluted 1:10 for each gene of interest and 1:100 for the β-actin control. The expression of the gene of interest in various tissue samples was represented by comparative $C_T$ (threshold cycle) method. $C_T$ indicates the fractional cycle number at which the amount of amplified target reaches a fixed threshold. The $C_T$ value of normal aorta, skin, peritoneum, thyroid gland, dendritic cells, or CD34+ cells was used as a comparative reference in order to evaluate the overexpression levels seen with each of the genes.

The following clones have been evaluated on the extended ovarian real-time panel. In some cases where expression was fairly ubiquitous, mean real-time expression values were determined for ovarian tumor (not including ovarian tumor cell line and SCID samples), normal ovarian, and other normal tissues (not including normal ovary). All clones were found to be over-expressed in ovarian tumor to some degree, demonstrating their use as tumor immunotherapeutics and/or diagnostic targets.

Ovarian tumor antigen O644S (SEQ ID NO:240) was shown to be over-expressed in ovarian tumor tissue samples compared to normal tissues. Expression of O644S was similar in ovarian tumor samples compared to normal ovary. Mean expression ratios for O644S were as follows: ovarian tumor/normal ovary was 0.6 and ovarian tumor/other normal tissues was 5.8. These results indicate that O644S may be used in developing tumor immunotherapeutic and/or diagnostic agents.

Ovarian tumor antigen O645S (SEQ ID NO:238) was found to be over-expressed in over 70% of the ovarian tumors tested, and 100% of ovarian tumor SCID samples. No expression was detected in the normal tissues tested. This finding further supports the use of ovarian tumor antigen O645S in the diagnosis and treatment of ovarian cancer. Based on the excellent expression profile of this ovarian candidate, SEQ ID NO:238 was also run on an the Ovarian Metastatic Extended Panel, which included 14 primary ovarian tumors and 13 metastatic ovarian tumors. O645S was determined to be elevated in 10/14 (71%) of primary tumors and 11/13 (85%) metastatic tumors.

Ovarian tumor antigen O646S (SEQ ID NO:243) was found to be over-expressed in 100% of the ovarian tumors tested, 1/1 ovarian tumor cell lines (SKOV3-HTB77) and 100% of ovarian tumor SCID samples. Low-level expression was observed in 2/2 normal ovary samples tested, but no expression was detected in any other normal tissues tested. This finding further supports the use of ovarian tumor antigen O646S in the diagnosis and treatment of ovarian cancer, especially metastatic ovarian cancer. Based on the excellent expression profile of this ovarian candidate, SEQ ID NO:243 was also run on an the Ovarian Metastatic Extended Panel, which included 14 primary ovarian tumors and 13 metastatic ovarian tumors. O646S was determined to be elevated in 14/14 (100%) of primary tumors and 13/13 (100%) metastatic tumors.

Ovarian tumor antigen O647S (SEQ ID NO:234 and 235) was found to be over-expressed in over 80% of the ovarian tumors tested, and 100% of ovarian tumor SCID samples. O647S was also found to have low level expression in normal ovary, bronchus, brain/cerebellum, and heart. No expression was detected in any other normal tissues tested. This finding further supports the use of ovarian tumor antigen O647S in the diagnosis and treatment of ovarian cancer.

Ovarian tumor antigen O648S (SEQ ID NO:239) was found to be over-expressed in over 50% of the ovarian tumors tested. O648S was not expressed in normal ovary. Very low-level expression was seen in normal liver and pancreas. This finding further supports the use of ovarian tumor antigen O648S in the diagnosis and treatment of ovarian cancer.

Ovarian tumor antigen O651S (SEQ ID NO:232) was found to be over-expressed in over 60% of the ovarian tumors tested, 1/1 ovarian tumor cell lines (SKOV3-HTB77) and 100% of ovarian tumor SCID samples. No expression was detected in the normal tissues tested. This finding further supports the use of ovarian tumor antigen O651S in the diagnosis and treatment of ovarian cancer.

Ovarian tumor antigen O645S (SEQ ID NO:238) was found to be over-expressed in over 70% of the ovarian tumors tested, and 100% of ovarian tumor SCID samples. No expression was detected in the normal tissues tested. This finding further supports the use of ovarian tumor antigen O645S in the diagnosis and treatment of ovarian cancer.

Example 19

LifeSeq Analysis of Ovarian Tumor Antigen O590S

In Example 1 (Table VII) the DNA insert of clone 57886 was identified, and disclosed in SEQ ID NO:198 (606 bps in length), also referred to as O590S. Characterization of SEQ ID NO:198 by microarray analysis (Examples 2 and 9) indicated that corresponding mRNA was overexpressed in ovarian tumor tissue relative to normal tissues. Additional characterization by Northern blot analysis detected an mRNA transcript approximately 9.0 kb in size (Example 9). In this example, the DNA sequence for the ovarian tumor antigen O590S (SEQ ID NO:198) disclosed in Example 1 was used as a query to perform a BlastN search of the Incyte Genomics LifeSeq Gold database (LGtemplatesJan2001). This analysis identified an identical sequence match on template number 93744.1, corresponding to a 1740 base pair sequence, as is disclosed in SEQ ID NO:285. The gene bin, 93744, from which this match was identified contained 21 clones from various tumor libraries. Further analysis of the template 93744.1 sequence (SEQ ID NO:285), identified a −2 open reading frame that would translate a polypeptide with a predicted amino acid sequence disclosed in SEQ ID NO:286. In addition, this analysis confirmed that the open reading frame identified by SEQ ID NO:286 overlaps with and is contained within the nucleotide sequence of SEQ ID NO:198 corresponding to the ovarian tumor antigen O590S.

Example 20

Analysis of Ovarian Tumor Antigen O664S

O644S (initially described in example 10 as SEQ ID NO:240, with extended open reading frames disclosed in SEQ ID NOs:280-282) was previously identified as having a good expression profile by microarray (see Example 18 for details) and was further analyzed by real-time PCR.

The first strand cDNA used in the quantitative real-time PCR was synthesized from 20 µg of total RNA that was treated with DNase I (Amplification Grade, Gibco BRLLife Technology, Gaithersburg, MD0, using Superscript Reverse Transcriptase (RT) (Gibco BRL). Real-time PCR was performed with an ABIPRISM 7900 sequence detection system (PE Biosystems, Foster City, Calif.). The 7900 system uses SYBR™ green, a fluorescent dye that only intercalates into double stranded DNA, and a set of O644S specific forward and reverse primers. The increase in fluorescence was monitored during the whole amplification process. The optimal concentration of primers was determined using a checkerboard approach, and a pool of cDNAs from tumors was used in this process. The PCR was performed in 12.5 µl volumes that included 2.5 µl of SYBR green buffer, 2 µl of cDNA template and 2.5 µl each of the forward and reverse primer. The cDNAs used for the RT reactions were diluted 1:10 for O644S and 1:100 for the β-actin control. The expression of O644S in each of the tissue samples was represented by the comparative $C_T$ (threshold cycle) method. $C_T$ indicates the fractional cycle number at which the amount of amplified target reaches a fixed threshold. The $C_T$ value of normal skin was used as a comparative reference in order to evaluate the over-expression levels seen with O644S.

O644S did not show over-expression in ovarian tumor tissue compared to normal tissue, however it did show higher expression in ovarian tumor tissue than in other normal tissue. As O644S is over-expressed in ovarian tumor tissue compared to normal tissues, it is a useful ovarian tumor antigen for the development of immunotherapeutic and/or diagnostic reagents. The high expression of O644S in both ovary tumor and normal ovary demonstrates that it would be a useful marker in the detection of metastatic cancer.

Example 21

O591S is Over-Expressed in Ovarian Cancer

This example describes how the ovarian antigen O591S, and antibodies specific for O591S, represent important therapeutic and diagnostic reagents useful in the detection of various types of carcinomas. The identification and characterization of O591S (SEQ ID NO: 214, encoding the protein of SEQ ID NO: 215) was described above (Example 1 and 4). In order to further characterize O591S, antibodies were generated against amino acid 14-141 of SEQ ID NO:215.

To generate these antibodies, amino acids 14-141 of SEQ ID NO:215 were expressed in an *E. Coli* recombinant expression system and the cultures grown over-night in LB Broth, supplemented with the appropriate antibiotics, at 37° C. in a shaking incubator. Following the incubation, 10 mls of the over-night culture was added to 500 ml of 2×YT, supplemented with the appropriate antibiotics, in a two-liter baffled Erlenmeyer flask. When the optical density (at 560 nm) of the cultures reached 0.4-0.6, the cells were induced with IPTG (1 mM). Fours hours post-induction with IPTG, the cells were harvested by centrifugation, followed by washing with phosphate buffered saline (PBS). The supernatant was then discarded and the cells either frozen for future use, or immediately processed.

To process the cells, 20 µl of lysis buffer was added to the cell pellet and the mixture vortexed. To break open the *E. coli* cells, the mixture was run through a French Press at a pressure of 16,000 psi. The mixture was then centrifuged again and the supernatant and cell pellet checked by SDS-PAGE for the partitioning of the O591S-specific recombinant protein.

To isolate the O591S proteins localized to the cell pellet, the pellet was resuspended in 10 mM Tris pH 8.0, 1% CHAPS and the inclusion body pellet was washed and centrifuged. This procedure was repeated twice more. The washed inclusion body pellet was solubilized with either 8 M urea or 6 M guanidine HCl containing 10 mM Tris, pH 8.0 plus 10 mM imidazole. The solubilized protein was added to 5 ml of nickel-chelate resin (Qiagen) and incubated for 45 minutes to 1 hour at room temperature with continuous agitation. After incubation, the resin and protein mixture were poured through a disposable column and the flow through collected. The column was then washed with 10-20 column volumes of the solubilized buffer. The antigen was then eluted from the column using 8 M urea, 10 mM Tris, pH 8.0, and 300 mM imidazole and collected in 3 ml fractions.

A SDS-PAGE gel was run to determine which fractions to pool for further purification. As a final purification step, a strong anion resin, such as Hi-Prep Q (Biorad) was equilibrated with the appropriate buffer and the pooled fractions from above were loaded onto the column. Each antigen was eluted off the column with an increasing salt gradient. Fractions were collected as the column was run and second SDS-PAGE gel was run to determine which fractions from the column to pool. The pooled fractions were dialyzed against 10 mM Tris, pH 8.0.

In order to generate polyclonal anti-sera against O591S, 400 µg of O591S protein was combined with 100 µg of muramydipeptide (MDP). An equal volume of Incomplete Freund's Adjuvant (IFA) was added and the resulting solution mixed. Every four weeks, animals were boosted with 100 µg of antigen mixed with an equal volume of IFA. Seven days following each boost, the animal was bleed, and the sera isolated by incubating the blood at 4° C. for 12-24 hours followed by centrifugation.

In order to characterize the rabbit polyclonal anti-sera, 96 well plates were coated with antigen by incubating with 50 µl (typically 1 µg) at 4° C. for 20 hours. Following the incubation, 250 µl of BSA blocking buffer was added to the wells and incubated at room temperature for 2 hours. The plates were then washed 6 times with PBS/0.01% Tween.

Fifty microliters of the diluted sera was added to each well and incubated at room temperature for 30 minutes. Plates were washed as described above, before 50 µl of goat-anti-rabbit horse radish peroxidase (HRP) at a 1:10,000 dilution was added and incubated for 30 minutes. Plates were washed as described above and 100 µl of TMB microwell Peroxidase Substrate was added to each well. Following a 15-minute incubation in the dark at room temperature, the colorimatric reaction was stopped with 100 µl of $H_2SO_4$ and immediately read at 450 nm. All polyclonal antibodies tested demonstrated specific immunoreactivity to the appropriate antigen.

Immunohistochemical analysis (IHC) of O591S expression was then performed to determine the tissue specificity of O591S. For IHC, paraffin-embedded formalin fixed tissues were slice into 8-micron sections. Steam heat induced epitope retrieval (SHIER) in 0.1 M sodium citrate buffer (ph 6.0) was used for optimal staining conditions. Sections were incubated with 10% serum/PBS for 5 minutes. Primary antibody was added to each section for 25 minutes at a range of concentrations, followed by a 25-minute incubation with an anti-rabbit biotinylated antibody. Endogenous peroxidase activity was blocked by three 1.5-minute incubations with hydrogen peroxidase. The avidin biotin complex/horse radish peroxidase (ABC/HRP) system was used along with DAB chromogen to visualize antigen expression. The slides were then counterstained with hematoxylin.

Of the tissues tested, 4/5 primary ovarian cancers and 3/5 metastatic ovarian samples tested positive for O591S immunoreactivity. Of the normal tissue samples tested, 2/5 normal ovary samples were positive, and 1/1 normal bronchial epithelium was positive. Normal alveolar epithelium, kidney, colon, liver, and heart were all negative for O591S immunoreactivity.

These findings further validate the use of O591S in any of a variety of illustrative diagnostic and therapeutic embodiments described herein.

Example 22

Cell Surface Expression of the Ovarian Tumor Antigen, O591S

The identification and characterization of O591S (SEQ ID NO: 214, encoding the protein of SEQ ID NO: 215) was described above (Example 1 and 4). To characterize the cell surface expression of O591S, cell lines were either transfected with full-length O591S cDNA or infected with an adenoviral expression construct expressing O591S cDNAs. These cell lines were then stained using purified rabbit polyclonal anti-O591S antibodies raised against synthetic O591S peptides, and surface expression analyzed by FACS. The O591S polyclonal antibodies were raised against the following peptides; peptide 1 (SEQ ID NO:291) corresponding to amino acid positions 26-55 of the O591S protein sequence (SEQ ID NO:215), peptide 2 (SEQ ID NO:292) corresponding to amino acid positions 53-78 of the O591S protein sequence (SEQ ID NO:215), and peptide 3 (SEQ ID NO:293) corresponding to amino acid positions 103-129 of O591S protein sequence (SEQ ID NO:215). Polyclonal antibodies were generated essentially as described in Examples 17 and 21 of the present application.

Cell surface expression of O591S was determined as follows:

1. oNXA cells were transfected by CaPO$_4$ precipitation with (a) a negative control cDNA cloned into the expression vector pBIB, or (b) O591S cDNA cloned into the expression vector pBIB. Seventy-two hours post-transfection, the cells were harvested and stained with either (i) control rabbit polyclonal antibody, (ii) rabbit polyclonal anti-O591S antibody, or (iii) secondary antibody (anti-rabbit-FITC) alone. All cells transfected with an expression vector containing O591S stained using the O591S specific polyclonal antibodies, demonstrating surface expression of O591S.

2. oNXA cells were transfected by CaPO$_4$ precipitation with either; pBIB/O591S (O591S cDNA cloned into the expression vectors pBIB), pcDNA/O591S (O591S cDNA cloned into the expression vector, pcDNA3), or pCEP/O591S (O591S cDNA cloned into the expression vector pCEP4). Seventy-two hours post-transfection, cells were harvested and stained with either (i) control rabbit polyclonal antibody or (ii) rabbit polyclonal anti-O591S antibody. O591S was detected on the surface of all cells transfected with O591S specific sequences. O591S expression levels were shown to be highest with the episomal replicating vector pcDNA4.

3. oNXA and 293 cells were transfected by CaPO$_4$ precipitation with pcDNA/O591S (O591S cDNA cloned into the expression vector pc DNA3). Seventy-two hours post-transfection, the cells were harvested and stained with either (i) control rabbit polyclonal antibodies, or (ii) rabbit polyclonal anti-O519S antibody. The cells were than analyzed using FACS analysis. Both oNXA and 293 cells transfected with O591S demonstrated cell surface expression of O591S.

4. VA13 cells and oNXA cells were infected (MOI of 10:1) with O591S/adenovirus (O591S cDNA cloned into the adenoviral expression vector). Seventy-two hours post-infection, the cells were harvested and stained with either, (i) control rabbit polyclonal antibody, or (ii) rabbit polyclonal anti-O591S antibody. The cells were then analyzed using FACS. Cells infected with O591S/adenovirus demonstrated cell surface staining specific for O591S.

To further characterize that O591S was a surface expressed protein, oNXA cells were transfected by CaPO$_4$ precipitation with pBIB/O591S (O591S cDNA cloned into the expression vector pBIB). Seventy-two hours post-transfection the cells were harvested and incubated for an additional one hour in either the presence or absence of phoshatidylinositol phospholipae C (PI-PLC), an enzyme known to cleave glycosyl-phosphatidylinositol (GPI)-linked proteins. GPI-linked proteins are known to be surface expressed proteins. Following incubation with PI-PLC, the cells were washed and either stained with (i) rabbit polyclonal anti-O591S antibody, or (ii) secondary antibody (anti-rabbit-FITC) alone, and analyzed by FACS for O591S cell surface expression. Analysis demonstrated that cells treated with PI-PLC were negative for the cell surface expression of O591S, further demonstrating that this protein is a surface expressed protein. Analysis of the O591S protein sequence (SEQ ID NO:215) revealed that the enzyme PI-PLC cleaved at either the Arg at position 114 of SEQ ID NO:215, resulting in the generation of a liberated 114 amino acid fragment, the sequence of which is disclosed in SEQ ID NO:289, and theoretically a 27 amino acid cell associated fragment (residues 115-141 of SEQ ID NO:215) or at the Gly at position 115 of SEQ ID NO:215, resulting in the generation of a 115 amino acid fragment, the sequence of which is disclosed in SEQ ID NO:290 and theoretically a 26 amino acid cell associated fragment (residues 116-141 of SEQ ID NO:215).

These data demonstrate that O591S is a surface expressed, GPI-linked protein, making the sequence a target for therapeutic antibodies.

From the foregoing it will be appreciated that, although specific embodiments of the invention have been described herein for purposes of illustration, various modifications may be made without deviating from the spirit and scope of the invention. Accordingly, the invention is not limited except as by the appended claims.

All of the above U.S. patents, U.S. patent application publications, U.S. patent applications, foreign patents, foreign patent applications and non-patent publications referred to in this specification and listed in the Application Data Sheet are incorporated herein by reference in their entirety.

What is claimed:

1. An isolated antibody, or antigen-binding fragment thereof, that specifically binds to a polypeptide having an amino acid sequence set forth in SEQ ID NO: 215.

2. A composition comprising a first component selected from the group consisting of physiologically acceptable carriers and immunostimulants, and a second component selected from the group consisting of an antibody or antigen-binding fragment according to claim 1.

3. A diagnostic kit comprising at least one antibody or antigen binding fragment according to claim 1 and a detection reagent, wherein the detection reagent comprises a reporter group.

4. The isolated antibody or antigen-binding fragment of claim 1, wherein the antibody or antigen-binding fragment binds an amino acid sequence set forth in residues 14-141 of SEQ ID NO: 215.

5. The isolated antibody or antigen-binding fragment of claim 1, wherein the antibody or antigen-binding fragment binds an amino acid sequence selected from the group consisting of residues 14-141, 1-114, 1-115, 115-141, 116-141, 26-55, 53-78 and 103-129 of SEQ ID NO: 215.

6. The isolated antibody or antigen-binding fragment of claim 1, wherein the antibody is a polyclonal antibody or an antigen-binding fragment thereof.

7. The isolated antibody or antigen-binding fragment of claim 1, wherein the antibody is a monoclonal antibody or an antigen-binding fragment thereof.

8. The isolated antibody or antigen-binding fragment of claim 1, wherein the antibody or antigen-binding fragment is conjugated to a toxin.

9. The isolated antibody or antigen-binding fragment of claim 8, wherein the toxin is selected from the group consisting of a ricin toxin, abrin toxin, diptheria toxin, cholera toxin, gelonin toxin, *Pseudomonas* exotoxin, *Shigella* toxin, and pokeweed antiviral protein.

10. The isolated antibody or antigen-binding fragment of claim 1, wherein the antibody or antigen-binding fragment is conjugated to a radionuclide.

11. The isolated antibody or antigen-binding fragment of claim 10, wherein the radionuclide is selected from the group consisting of $^{90}$Y, $^{123}$I, $^{125}$I, $^{131}$I, $^{186}$Re, $^{188}$Re, $^{211}$At and $^{212}$Bi.

* * * * *

UNITED STATES PATENT AND TRADEMARK OFFICE
CERTIFICATE OF CORRECTION

| | | |
|---|---|---|
| PATENT NO. | : 7,985,843 B2 | Page 1 of 1 |
| APPLICATION NO. | : 11/929595 | |
| DATED | : July 26, 2011 | |
| INVENTOR(S) | : Gary R. Fanger et al. | |

It is certified that error appears in the above-identified patent and that said Letters Patent is hereby corrected as shown below:

Item (73):
"Corixa Corporation, Seattle, WA (US)" should read,
--Corixa Corporation, Hamilton, MT (US)--.

Signed and Sealed this
Twenty-fourth Day of July, 2012

David J. Kappos
*Director of the United States Patent and Trademark Office*

SEQUENCE LISTING

<160> NUMBER OF SEQ ID NOS: 293

<210> SEQ ID NO 1
<211> LENGTH: 396
<212> TYPE: DNA
<213> ORGANISM: Homo sapiens
<220> FEATURE:
<221> NAME/KEY: misc_feature
<222> LOCATION: 303, 370, 377, 382
<223> OTHER INFORMATION: n = A,T,C or G

<400> SEQUENCE: 1
caacctcact agtaaatgaa agaaatattg taatttgtat ttgatctgct gggtctttgg      60
agtcagaact ggttttatca gcagtttgat cttctgaggt ctggtatgta gtttgctggc     120
ccacagaacc ttcacgtgta ttcacagcct caatgccata aggaaactct tttagaagtt     180
ctgacagctg gtcatgtagg tataagacag gtgccttatc actgtggatt tcatttcttg     240
caggatcttg gggagtatag ttgctggatg catctatttc ctgagggtaa atatcctcct     300
ggncgacgcg gccgctcgag tctagagggc ccgtttaaac ccgctgatca gcctcgactg     360
tgccttctan ttgccancca tntgttgttt gccoct                               396

<210> SEQ ID NO 2
<211> LENGTH: 396
<212> TYPE: DNA
<213> ORGANISM: Homo sapiens

<400> SEQUENCE: 2
cgaccaaaaa gtaaactcca agtgaacatc aaatcaaatc taatccttt ggccacatga       60 ctggttgttc tttatctcat agttacaatg aatcatataa actgtagact gccactacca     120
cgatacttct gtgacacaga aggaatgtcc tatttgccta tctatctgag gaatgttaaa     180
tagagaaaaa tagattataa acaacctgg aggtcacagg attctgagat aatccctctg      240
ttaaaaaaca tctgaacagc aaatgtccaa tctgtaataa aatagttaaa ggtccaagtc     300
aagtccactt ctacttggct ggcccagcac aagaaatcta acagcacttt gtaatcattt     360
tgcttttcta atttteccgg aggacatggg ccattg                               396

<210> SEQ ID NO 3
<211> LENGTH: 396
<212> TYPE: DNA
<213> ORGANISM: Homo sapiens
<220> FEATURE:
<221> NAME/KEY: misc_feature
<222> LOCATION: 22, 28, 29, 30, 33, 36, 41, 43, 45, 46, 53, 56, 58, 61,
      64, 69, 70, 74, 75, 78, 83, 84, 85, 102, 143, 335
<223> OTHER INFORMATION: n = A,T,C or G

<400> SEQUENCE: 3 cgccctttt tttttttttt tnattggnnnn aantcncttt nantnnaaaa acntgnangg       60
naancccann cccnnggnac cannnccagg agttgggtgg anactgagtg gggtttgtgt     120
gggtgagggg gcatctactc ctnttgcaac aagccaaaag tagaacagcc taaggaaaag     180
tgacctgcct tggagcctta gtccctccct tagggccccc tcagcctacc ctatccaagt     240
ctgaggctat ggaagtctcc ctcctagttc actagcaggt tccccatctt ttccaggctg     300 ccctagcac tccacgtttt tctgaaaaaa tctanacagg cccttttgg gtacctaaaa       360 cccagctgag gttgtgagct tgtaaggtaa agcaag                               396

```
<210> SEQ ID NO 4
<211> LENGTH: 396
<212> TYPE: DNA
<213> ORGANISM: Homo sapiens
<220> FEATURE:
<221> NAME/KEY: misc_feature
<222> LOCATION: 13, 15, 21, 27, 34, 37, 41, 57, 58, 59, 63, 64, 71, 72,
      77, 78, 83, 87, 93, 170, 207, 210, 308, 379, 382, 389, 391,
      392, 393, 395
<223> OTHER INFORMATION: n = A,T,C or G

<400> SEQUENCE: 4
gaccaatcct tgncncacta ncaaaangac cccnctnacc nccaggaact gaacctnnnt      60
gtnnacctcc nnctgcnnag ccntatntcc aanatcaccc accgtatcca ctgggaatct    120
gccagcctcc tgcgatcaga agagaccaat cgaaaatgag ggtttcacan tcacagctga    180
aggaaaaggc caaggcacct tgtcggnggn gacaatgtac catgctaagg ccaaagatca    240
actcacctgt aataaattcg acctcaaggt caccataaaa ccagcaccgg aacagaaaaa    300
gaggcctnag gatgcccaag aaacactttt gatcctttga aaactgtacc aaggtaccgg    360
ggggagaccc aggaaaggnc cnttatgtnt nnntnt                              396

<210> SEQ ID NO 5
<211> LENGTH: 396
<212> TYPE: DNA
<213> ORGANISM: Homo sapiens
<220> FEATURE:
<221> NAME/KEY: misc_feature
<222> LOCATION: 135, 172, 343, 348, 354, 395
<223> OTHER INFORMATION: n = A,T,C or G

<400> SEQUENCE: 5
gacgccggag ctgccgcgcc agtcgcctag caggtcctct accggcttat tcctgtgccg      60
gatcttcatc ggcacagggg ccactgagac gtttctgcct ccctctttct tcctccgctc    120
tttctcttcc ctctngttta gtttgcctgg gagcttgaaa ggagaaagca cnggggtcgc    180
cccaaaccct ttctgcttct gcccatcaca agtgccacta ccgccatggg cctcactatc    240
tcctccctct tctcccgact atttggcaag aagcagatgc gcattttgat ggttggattg    300
gatgctgctg gcaagacaac cattcttgat aaactgaaag tanggganat aagnaccacc    360
atttctacca ttgggtttaa tgggggaaac agtana                              396

<210> SEQ ID NO 6
<211> LENGTH: 396
<212> TYPE: DNA
<213> ORGANISM: Homo sapiens
<220> FEATURE:
<221> NAME/KEY: misc_feature
<222> LOCATION: 212
<223> OTHER INFORMATION: n = A,T,C or G

<400> SEQUENCE: 6
acgggaggcg ccgggaagtc gacggcgccg gcggctcctg caggaggcca ctgtctgcag      60
ctcccgtgaa gatgtccact ccagacccac ccctgggcgg aactcctcgg ccaggtcctt    120 cccgggccc tgcccttccc ctggagccat gctgggccct agcccgggtc cctcgccggg    180
ctccgcccac agcatgatgg ggcccagccc angggccgcc ctcagcagga caccccatcc    240
ccacccaggg gcctggaggg taccctcagg acaacatgca ccagatgcac aagcccatgg    300
agtccatgca tgagaagggc atgtcggacg acccgcgcta caaccagatg aaaggaatgg    360
ggatgcggtc aggggccat gctgggatgg ggcccc                               396
```

```
<210> SEQ ID NO 7
<211> LENGTH: 396
<212> TYPE: DNA
<213> ORGANISM: Homo sapiens

<400> SEQUENCE: 7
acccgagagt cgtcggggtt tcctgcttca acagtgcttg gacggaaccc ggcgctcgtt      60
ccccaccccg gccggccgcc catagccagc cctccgtcac ctcttcaccg cacccctcgga   120 ctgccccaag gccccgccg ccgctccagc gccgcgcagc caccgccgcc gccgccgcct      180
ctccttagtc gccgccatga cgaccgcgtc cacctcgcag gtgcgccaga actaccacca    240
ggactcagag gccgccatca accgccagat caacctggag ctctacgcct cctacgttta    300
cctgtccatg tcttactact ttgaccgcga tgatgtggct ttgaagaact ttgccaaata   360
ctttcttcac caatctcatg aggagaggga acatgc                              396

<210> SEQ ID NO 8
<211> LENGTH: 396
<212> TYPE: DNA
<213> ORGANISM: Homo sapiens

<400> SEQUENCE: 8
cgacaacaag gttaatacct tagttcttaa cattttttt ctttatgtgt agtgttttca      60
tgctaccttg gtaggaaact tatttacaaa ccatattaaa aggctaattt aaatataaat   120
aatataaagt gctctgaata aagcagaaat atattacagt tcattccaca gaaagcatcc    180
aaaccaccca aatgaccaag gcatatatag tatttggagg aatcaggggt ttggaaggag    240
tagggaggag aatgaaggaa aatgcaacca gcatgattat agtgtgttca tttagataaa    300
agtagaaggc acaggagagg tagcaaaggc caggcttttc tttggttttc ttcaaacata    360
ggtgaaaaaa acactgccat tcacaagtca aggaac                              396

<210> SEQ ID NO 9
<211> LENGTH: 396
<212> TYPE: DNA
<213> ORGANISM: Homo sapiens
<220> FEATURE:
<221> NAME/KEY: misc_feature
<222> LOCATION: 321, 344
<223> OTHER INFORMATION: n = A,T,C or G

<400> SEQUENCE: 9
tcgacatcgc ggcaactttt tgcggattgt tcttgcttcc aggctttgcg ctgcaaatcc      60
agtgctacca gtgtgaagaa ttccagctga acaacgactg ctcctccccc gagttcattg    120
tgaattgcac ggtgaacgtt caagacatgt gtcagaaaga agtgatggag caaagtgccg    180
ggatcatgta ccgcaagtcc tgtgcatcat cagcggcctg tctcatcgcc tctgccgggt    240
accagtcctt ctgctcccca gggaaactga actcagtttg catcagctgc tgcaacaccc    300
ctctttgtaa cgggccaagg nccaaaaaaa ggggaaagtt ctgncctcgg ccctcaggcc    360
agggctccgc accaccatcc tgttcctcaa attagc                              396

<210> SEQ ID NO 10
<211> LENGTH: 396
<212> TYPE: DNA
<213> ORGANISM: Homo sapiens
<220> FEATURE:
<221> NAME/KEY: misc_feature
<222> LOCATION: 115, 116, 117, 130, 138, 142, 143, 144, 145, 146, 153,
       157, 158, 159, 160, 164, 175, 176, 177, 178, 179, 183, 187, 197,
       198, 202, 203, 204, 205, 206, 211, 212, 213, 215, 216, 217,
       220, 221, 222, 226, 231, 234, 236, 237, 245, 246, 247
```

<223> OTHER INFORMATION: n = A,T,C or G
<220> FEATURE:
<221> NAME/KEY: misc_feature
<222> LOCATION: 250, 255, 264, 266, 267, 268, 269, 270, 271, 272, 279,
      284, 297, 303, 304, 305, 308, 315, 317, 318, 319, 320, 321, 322,
      323, 333, 334, 337, 338, 342, 343, 368, 372, 374, 380, 381,
      391, 395
<223> OTHER INFORMATION: n = A,T,C or G

<400> SEQUENCE: 10

```
ccttttttt tttttttttt tttttttttt tttttttttt tttttttttt tttttttttt      60
tttttttttt tttttttttt tttttttttt tttttttttt ttttaaaaaa aaaanntttt    120
tttttttttn aaaaaaangg gnnnntttt ttnccnnnn gggngggggg gggnnnnnt       180 ttnaaanaaa aaaccnnaa annnnngggg nnnannnaan nncccncccc naancnntaa     240
aaaannnggn aaaanagggg gggnannnnn nnggggggna aaanttttt tttttnaag      300 ggnnnggnaa aaaantnnnn nnntttttt ttnnaanngg gnnaaaaaaa aaaaaaaaaa    360
attttttngg gntnaggggn ngggggaaaa ncccna                              396
```

<210> SEQ ID NO 11
<211> LENGTH: 396
<212> TYPE: DNA
<213> ORGANISM: Homo sapiens

<400> SEQUENCE: 11

```
agaacacagg tgtcgtgaaa actacccta aaagccaaaa tgggaaagga aaagactcat    60
atcaacattg tcgtcattgg acacgtagat tcgggcaagt ccaccactac tggccatctg   120
atctataaat gcggtggcat cgacaaaaga accattgaaa aatttgagaa ggaggctgct   180
gagatgggaa agggctcctt caagtatgcc tgggtcttgg ataaactgaa agctgagcgt   240
gaacgtggta tcaccattga tatctccttg tggaaatttg agaccagcaa gtactatgtg   300
actatcattg atgccccagg acacagagac tttatcaaaa acatgattac agggacatct   360
caggctgact gtgctgtcct gattgttgct gctggt                             396
```

<210> SEQ ID NO 12
<211> LENGTH: 396
<212> TYPE: DNA
<213> ORGANISM: Homo sapiens

<400> SEQUENCE: 12

```
cgaaaacctt taaccccgg tcatccggac atcccaacgc atgctcctgg agctcacagc     60
cttctgtggt gtcatttctg aaacaagggc gtggatccct caaccaagaa gaatgtttat   120
gtcttcaagt gacctgtact gcttggggac tattggagaa aataaggtgg agtcctactt   180
gtttaaaaaa tatgtatcta agaatgttct agggcactct gggaacctat aaaggcaggt   240
atttcgggcc ctcctcttca ggaatcttcc tgaagacatg gcccagtcga aggcccagga   300
tggcttttgc tgcggccccg tggggtagga gggacagaga gacagggaga gtcagcctcc   360
acattcagag gcatcacaag taatggcaca attctt                             396
```

<210> SEQ ID NO 13
<211> LENGTH: 396
<212> TYPE: DNA
<213> ORGANISM: Homo sapiens

<400> SEQUENCE: 13

```
accacaggct ggcccacaaga agcgctggag tgtgctggcg gctgcaggcc tacggggcct    60
ggtccggctg ctgcacgtgc gtgccggctt ctgctgcggg gtcatccgag cccacaagaa   120
```

```
ggccatcgcc accctgtgct tcagccccgc ccacgagacc catctcttca cggcctccta      180
tgacaagcgg atcatcctct gggacatcgg ggtgcccaac caggactacg aattccaggc      240
cagccagctg ctcacactgg acaccacctc tatcccctg cgcctctgcc ctgtcgcctc       300
ctgcccggac gcccgcctgc tggccggctg cgagggcggc tgctgctgct gggacgtgcg      360
gctggaccag ccccaaaaga ggagggtgtg tgaagt                                396
```

```
<210> SEQ ID NO 14
<211> LENGTH: 396
<212> TYPE: DNA
<213> ORGANISM: Homo sapiens

<400> SEQUENCE: 14
acggcgtcct cgtggaagtg acatcgtctt taaaccctgc gtggcaatcc ctgacgcacc      60
gccgtgatgc ccagggaaga cagggcgacc tggaagtcca actacttcct taagatcatc     120
caactattgg atgattatcc gaaatgtttc attgtgggag cagacaatgt gggctccaag     180
cagatgcagc agatccgcat gtcccttcgc gggaaggctg tggtgctgat gggcaagaac     240
accatgatgc gcaaggccat ccgagggcac ctggaaaaca cccagctct ggagaaactg      300 ctgcctcata tccgggggaa tgtgggcttt gtgttcacca aggaggacct cactgagatc     360
agggacatgt tgctggccaa taaggtgcca gctgct                               396
```

```
<210> SEQ ID NO 15
<211> LENGTH: 396
<212> TYPE: DNA
<213> ORGANISM: Homo sapiens
<220> FEATURE:
<221> NAME/KEY: misc_feature
<222> LOCATION: 333
<223> OTHER INFORMATION: n = A,T,C or G

<400> SEQUENCE: 15
accgcgcggg cacagggtgc cgctgaccga ggcgtgcaaa gactccagaa ttggaggcat     60
gatgaagact ctgctgctgt ttgtggggct gctgctgacc tgggagagtg ggcaggtcct    120
gggggaccag acggtctcag acaatgagct ccaggaaatg tccaatcagg gaagtaagta    180
cgtcaataag gaaattcaaa atgcttgtca acggggtgaa acagataaag actctcatag    240
aaaaaacaaa cgaagagcgc aagacactgc tcagcaacct agaagaagcc aagaagaaga    300
aagaggatgc cctaaatgag accagggaat canagacaaa gctgaaggag ctcccaggag    360
tgtgcaatga gaccatgatg gccctctggg aagagt                              396
```

```
<210> SEQ ID NO 16
<211> LENGTH: 396
<212> TYPE: DNA
<213> ORGANISM: Homo sapiens
<220> FEATURE:
<221> NAME/KEY: misc_feature
<222> LOCATION: 114, 121, 122, 123, 127, 134, 136, 138, 140, 141, 142,
      143, 144, 148, 163, 166, 172, 173, 174, 176, 177, 183, 184, 185,
      187, 195, 196, 198, 199, 202, 203, 206, 213, 214, 215, 216,
      217, 218, 219, 223, 225, 226, 227, 229, 230, 236, 238
<223> OTHER INFORMATION: n = A,T,C or G
<220> FEATURE:
<221> NAME/KEY: misc_feature
<222> LOCATION: 239, 252, 256, 257, 261, 262, 268, 269, 273, 278, 280,
      288, 289, 290, 292, 293, 303, 312, 325, 327, 333, 335, 336, 341,
      342, 347, 354, 359, 365, 371, 383, 384, 386, 388, 391
<223> OTHER INFORMATION: n = A,T,C or G

<400> SEQUENCE: 16
```

```
tttttttttt tttttttttt tttttttttt tttttttttt tttttttttt tttttttttt    60
tttttttttt tttttttttt tttttttttt tttttttttt tttttttttt tttnggggg    120 nnnaaantt tttntnanan nnnngggnaa aaaaaaaaa aanaanggg gnnntnnggc      180 ccnnanaaa aaaanngnna annaancccc ccnnnnnnnc ccncnnntnn ggaaananna    240
aaaccccccc cngggnnggg nnaaaaannc ccngggggnan ttttatnnn anncccccc   300 ccnggggggg gnggaaaaaa aaaantnccc ccnannaaaa nngggncccc cccnttttnc   360 aaaangggg nccgggcccc ccnnantntt nggggg                              396

<210> SEQ ID NO 17
<211> LENGTH: 396
<212> TYPE: DNA
<213> ORGANISM: Homo sapiens

<400> SEQUENCE: 17
accacactaa ccatatacca atgatggcgc gatgtaacac gagaaagcac ataccaaggc    60
caccacacac cacctgtcca aaaaggcctt cgatacggga taatcctatt tattacctca   120
gaagtttttt tcttcgcagg attttttctga gcctttacc actccagcct agcccctacc   180
ccccaactag gagggcactg gccccccaaca ggcatcaccc cgctaaatcc cctagaagtc   240
ccactcctaa acacatccgt attactgcca tcaggagtat caatcacctg agctcaccat    300
agtctaatag aaaacaaccg aaaccaaata attcaagcac tgcttattac aattttactg    360
ggtctctatt ttaccctcct acaagcctca gagtac                              396

<210> SEQ ID NO 18
<211> LENGTH: 396
<212> TYPE: DNA
<213> ORGANISM: Homo sapiens
<220> FEATURE:
<221> NAME/KEY: misc_feature
<222> LOCATION: 51, 54, 66, 81, 86, 98, 106, 111, 117, 124, 129, 133,
      135, 150, 151, 154, 159, 161, 172, 179, 181, 183, 185, 220, 223,
      229, 238, 258, 259, 264, 282, 289, 292, 294, 299, 303, 311,
      315, 329, 343, 349, 351, 353, 361, 369, 370, 389, 392
<223> OTHER INFORMATION: n = A,T,C or G
<220> FEATURE:
<221> NAME/KEY: misc_feature
<222> LOCATION: 396
<223> OTHER INFORMATION: n = A,T,C or G

<400> SEQUENCE: 18
tttttttttt tttttttttt tttttttttt tttttttttt tttttttta ntcnaaaggg    60 gaaggnccct ttttattaaa nttggncatt ttactttnct tttttnaaaa ngctaanaaa   120 aaantttttnt ttntncttaa aaaaaccctn natntcacna ncaaaaaaaa cnattcccnc   180
ntncnttttg tgataaaaaa aaaggcaatg gaattcaacn tanccctaana aaactttncc   240 tgggaggaaa aaaaattnnt ccgngggaaa cacttgggc tntccaaant gnanccatc    300 tangaggacc ntctntaaga tttccaaang aaacccttc ctnccaaang nantaccccg    360
ntgcctacnn cccataaaaa aaacctcanc cntaan                              396

<210> SEQ ID NO 19
<211> LENGTH: 396
<212> TYPE: DNA
<213> ORGANISM: Homo sapiens
<220> FEATURE:
<221> NAME/KEY: misc_feature
<222> LOCATION: 47, 69, 75, 80, 83, 87, 88, 90, 92, 102, 104, 108, 116,
      121, 130, 138, 139, 142, 153, 156, 158, 162, 165, 166, 180, 192,
      193, 195, 201, 224, 226, 232, 235, 237, 241, 248, 251, 253,
      256, 269, 272, 274, 277, 284, 287, 290, 292, 297
```

```
<223> OTHER INFORMATION: n = A,T,C or G
<220> FEATURE:
<221> NAME/KEY: misc_feature
<222> LOCATION: 299, 305, 306, 315, 323, 324, 326, 332, 351, 368, 377,
      380, 383, 387, 392
<223> OTHER INFORMATION: n = A,T,C or G

<400> SEQUENCE: 19
tttttttttt tttttttttt tttttttttt tttttttttt tttttttntgg tctgggcttt    60 tattttacna aaaanctaan ggnaaanntn cnttaaacta antngaaanac aaagtnttaa   120 ngaaaaaggn ctgggggnnt cntttacaaa aanggncngg gncannttg gcttaaaan     180 ttcaaaaagg gnncntcaaa ngggtttgca tttgcatgtt tcancnctaa ancgnangaa   240
naaacccngg ngccnctgg gaaaagttnt tnanctncca aaanatnaan tntttgnanc    300
agggnntttt tgggnaaaaa aannanttcc anaaactttc catccctgg ntttgggttc    360 ggccttgngt tttcggnatn atntccntta angggg                             396

<210> SEQ ID NO 20
<211> LENGTH: 396
<212> TYPE: DNA
<213> ORGANISM: Homo sapiens
<220> FEATURE:
<221> NAME/KEY: misc_feature
<222> LOCATION: 29, 43, 49, 53, 55, 75, 81, 100, 110, 111, 125, 129,
      160, 162, 168, 246, 277
<223> OTHER INFORMATION: n = A,T,C or G

<400> SEQUENCE: 20
tttttttttt tttttttttt tttttctna acaaaccctg ttnttgggng ggngnggta     60 taatactaag ttganatgat ntcatttacg ggggaaggcn ctttgtgaan naggccttat   120
ttctnttgnc ctttcgtaca gggaggaatt tgaagtaaan anaaaccnac ctggattact   180
ccggtctgaa ctcaaatcac gtaggacttt aatcgttgaa caaacaaacc tttaatagcg   240
gctgcnccat tgggatgtcc tgatccaaca tcgaggncgt aaaccctatt gttgatatgg   300
actctaaaaa taggattgcg ctgttatccc tagggtaact tgttcccgtg gtcaaagtta   360
ttggatcaat tgagtataag tagttcgctt tgactg                             396

<210> SEQ ID NO 21
<211> LENGTH: 396
<212> TYPE: DNA
<213> ORGANISM: Homo sapiens
<220> FEATURE:
<221> NAME/KEY: misc_feature
<222> LOCATION: 6, 9, 18, 23, 37, 43, 48, 55, 65, 73, 75, 103, 110, 117,
      123, 125, 134, 153, 182, 195, 202, 205, 213, 216, 223, 239,
      249, 276, 293, 294, 302, 307, 344, 356, 359, 369, 374, 381,
      392
<223> OTHER INFORMATION: n = A,T,C or G

<400> SEQUENCE: 21
acatanatnt tatactanca ttnaccatct cacttgnagg aanactanta tatcnctcac    60
acctnatatc ctncntacta tgcctagaag gaataatact atngctgttn attatancta   120
ctntnataac cctnaacacc cactccctct tanccaatat tgtgcctatt gccatactag   180
tntttgccgc ctgcnaagca gnggngggcc tanccntact agnctcaatc tccaacacnt   240
atggcctana ctacgtacat aacctaaacc tactcnaatg ctaaaactaa tcnnccccaac   300 anttatntta ctaccactga catgactttc caaaaacac atantttgaa tcaacncanc    360
cacccacanc ctanttatta ncatcatccc cntact                             396
```

```
<210> SEQ ID NO 22
<211> LENGTH: 396
<212> TYPE: DNA
<213> ORGANISM: Homo sapiens
<220> FEATURE:
<221> NAME/KEY: misc_feature
<222> LOCATION: 17, 244
<223> OTHER INFORMATION: n = A,T,C or G

<400> SEQUENCE: 22
tttttttttt ttttganaaa agccggcata aagcactttt attgcaataa taaaacttga      60
gactcataaa tggtgctggg ggaagggtgc agcaacgatt tctcaccaaa tcactacaca     120
ggacagcaaa ggggtgagaa ggggctgagg gaggaaaagc caggaaactg agatcagcag     180
agggagccaa gcatcaaaaa acaggagatg ctgaagctgc gatgaccagc atcattttct     240
taanagaaca ttcaaggatt tgtcatgatg gctgggcttt cactgggtgt taagtctaca     300
aacagcacct tcaattgaaa ctgtcaatta aagttcttaa gatttaggaa gtggtggagc     360
ttggaaagtt atgagattac aaaattcctg aaagtc                              396

<210> SEQ ID NO 23
<211> LENGTH: 396
<212> TYPE: DNA
<213> ORGANISM: Homo sapiens

<400> SEQUENCE: 23
acaaaggcgg ttccaagcta aggaattcca tcagtgcttt tttcgcagcc accaaattta      60
gcaggcctgt gaggttttca tatcctgaag agatgtattt taaagctttt ttttttttaat   120 gaaaaaatgt cagacacaca caaaagtaga atagtaccat ggagtcccca cgtacccagc    180
ctgcagcttc aacagttacc acatttgcca accggagaga ctgccaaggc aggaaaaagc    240
cctggaaagc ccacggcccc ttttcccctt gggtcagagg ccttagagct ggctgccaaa    300
gcagccaacc aaaggggcag ctcagctcct tcgtggcacc agcagtgttc ctgatgcagt    360
tgaagagttg atgtctttga caacatacgg acactg                             396

<210> SEQ ID NO 24
<211> LENGTH: 396
<212> TYPE: DNA
<213> ORGANISM: Homo sapiens
<220> FEATURE:
<221> NAME/KEY: misc_feature
<222> LOCATION: 313, 337, 340, 350, 351, 352, 353, 354, 355, 356, 366,
      376, 377, 378, 382, 384, 385, 387, 389, 390, 392, 393, 396
<223> OTHER INFORMATION: n = A,T,C or G

<400> SEQUENCE: 24
cgactatcct ctcagattct tatctggcac taatttataa ctattatatt atcagagact      60
atgtagcaat atatcagtgc acaggcgcat cccaggcctg tacagatgta tgtctacacg    120
taagtataaa tgaatttgca taccaggttt tacacttgca tctctaatag agattaaaaa    180
caacaaattg gcctcttcct aagtatatta atatcattta tccttacatt ttatgcctcc    240
ccctaaatta atgactgagt tggtggaaag cggctaggtt ttattcatac tgttttttgt    300
tctcaacttc aanagtaatc tacctctgaa aaatttntan tttaatattn nnnnnnagga    360
atttgngcca ctttannnct tncnntntnn tnnccn                             396

<210> SEQ ID NO 25
<211> LENGTH: 396
<212> TYPE: DNA
<213> ORGANISM: Homo sapiens
<220> FEATURE:
```

```
<221> NAME/KEY: misc_feature
<222> LOCATION: 90, 125, 136, 278, 299, 301, 305, 344, 347, 353, 355,
      356, 357, 359, 360, 361, 365, 369, 378, 380, 381, 382, 383, 384,
      385, 386, 391, 392, 393, 395, 396
<223> OTHER INFORMATION: n = A,T,C or G

<400> SEQUENCE: 25
tttttttttt ttttttttt gtcttttaaa aatataaaa gtgttattat tttaaaacat      60
caagcattac agactgtaaa atcaattaan aactttctgt atatgaggac aaaaatacat   120
ttaanacata tacaanaaga tgcttttttcc tgagtagaat gcaaactttt atattaagct   180
tctttgaatt ttcaaaatgt aaaataccaa ggcttttttca catcagacaa aaatcaggaa   240 tgttcaccttt cacatccaaa agaaaaaaa aaaaaaancc aattttcaag ttgaagttna   300
ncaanaatga tgtaaaatct gaaaaaagtg gccaaaattt taanttncaa canannngnn   360
ncagntttna tggatctntn nnnnnncttc nnntnn                            396

<210> SEQ ID NO 26
<211> LENGTH: 396
<212> TYPE: DNA
<213> ORGANISM: Homo sapiens
<220> FEATURE:
<221> NAME/KEY: misc_feature
<222> LOCATION: 313, 314, 316, 318, 321, 343, 344, 352, 353, 356, 363,
      366, 370, 372, 373, 374, 375, 377, 378, 379, 383, 384, 385, 386,
      387, 391, 393, 394, 395, 396
<223> OTHER INFORMATION: n = A,T,C or G

<400> SEQUENCE: 26
gacgctcccc cctccccccg agcgccgctc cggctgcacc gcgctcgctc cgagtttcag    60
gctcgtgcta agctagcgcc gtcgtcgtct cccttcagtc gccatcatga ttatctaccg   120
ggacctcatc agccacgatg agatgttctc cgacatctac aagatccggg agatcgcgga   180
cgggttgtgc ctggaggtgg agggaagat ggtcagtagg acagaaggta acattgatga   240
ctcgctcatt ggtggaaatg cctccgctga aggccccgag ggcgaaggta cccgaaagca   300
cagtaatcac tgnngncnat nttgtcatga accatcacct gcnngaaaca annttnacaa   360
aanaancctn cnnnnannnc ctnnnnnatt ncnnnn                             396

<210> SEQ ID NO 27
<211> LENGTH: 396
<212> TYPE: DNA
<213> ORGANISM: Homo sapiens
<220> FEATURE:
<221> NAME/KEY: misc_feature
<222> LOCATION: 49, 61, 66, 73, 75, 99, 102, 103, 105, 107, 120, 124,
      126, 129, 138, 139, 141, 147, 155, 157, 162, 165, 175, 187, 191,
      193, 198, 207, 217, 218, 220, 221, 223, 226, 231, 232, 245,
      257, 259, 260, 263, 266, 271, 287, 305, 306, 307, 308
<223> OTHER INFORMATION: n = A,T,C or G
<220> FEATURE:
<221> NAME/KEY: misc_feature
<222> LOCATION: 321, 330, 332, 335, 342, 343, 344, 345, 349, 350, 351,
      352, 354, 355, 356, 357, 365, 366, 367, 370, 371, 372, 373, 374,
      375, 376, 377, 378, 379, 380, 381, 382, 383, 386, 387, 388,
      389, 391, 392, 393, 394, 395, 396
<223> OTHER INFORMATION: n = A,T,C or G

<400> SEQUENCE: 27
tttttttttt tttttttttt tttttttttt tttttttttt tggctaaant ttatgtatac    60
nggttnttca aangngggg aggggggggg gcatccatnt anncncncca ggtttatggn   120
gggntnttnt actattanna nttttcncttt caaancnaag gnttntcaaa tcatnaaaat  180
tattaanatt ncngctgnta aaaaaangaa tgaaccnncn nanganagga nntttcatgg   240
```

-continued

```
ggggnatgca tcggggnann ccnaanaacc ncggggccat tcccganagg cccaaaaaat    300
gtttnnnnaa aaagggtaaa nttaccccccn tnaantttat annnnaaann nnannnnagc    360
ccaannnttn nnnnnnnnnn nnnccnnnna nnnnnn                              396
```

<210> SEQ ID NO 28
<211> LENGTH: 396
<212> TYPE: DNA
<213> ORGANISM: Homo sapiens
<220> FEATURE:
<221> NAME/KEY: misc_feature
<222> LOCATION: 278, 283, 298, 309, 326, 331, 338, 351, 355, 356, 357,
      358, 360, 371, 377, 378, 383, 386, 387, 391, 393, 394, 395
<223> OTHER INFORMATION: n = A,T,C or G

<400> SEQUENCE: 28

```
cgaccttttt tttttttttt atagatgaaa gagggtttat ttattaatat atgatagcct     60
tggctcaaaa aagacaaatg agggctcaaa aaggaattac agtaacttta aaaaatatat    120
taaacatatc caagatccta atatattat tctccccaaa agctagctgc ttccaaactt     180
gatttgatat tttgcatgtt ttccctacgt tgcttggtaa atatatttgc ttctcctttc    240
tgcaatcgac gtctgacagc tgattttgc tgttttgnca acntgacgtt tcaccttntg     300
tttcaccant tctggaggaa ttgttnaaca ncttacanca ctgccttgaa naaannnnan    360
gcctcaaaag ntcttgnnct atnctnnttc ntnnnt                              396
```

<210> SEQ ID NO 29
<211> LENGTH: 396
<212> TYPE: DNA
<213> ORGANISM: Homo sapiens
<220> FEATURE:
<221> NAME/KEY: misc_feature
<222> LOCATION: 329, 334, 361, 386, 390
<223> OTHER INFORMATION: n = A,T,C or G

<400> SEQUENCE: 29

```
gacttgctca tttagagttt gcaggaggct ccatactagg ttcagtctga aagaaatctc     60
ctaatggtgc tatagagagg gaggtaacag aaagactctt ttagggcatt tttctgactc    120
atgaaaagag cacagaaaag gatgtttggc aatttgtctt ttaagtctta accttgctaa    180
tgtgaatact gggaaagtga ttttttttctc actcgttttt gttgctccat tgtaaagggc    240
ggaggtcagt cttagtggcc ttgagagttg cttttggcat ttaaatattc taagagaatt    300
aactgtattt cctgtcacct attcactant gcangaaata tacttgctcc aaataagtca    360
ntatgagaag tcactgtcaa tgaaanttgn tttgtt                              396
```

<210> SEQ ID NO 30
<211> LENGTH: 396
<212> TYPE: DNA
<213> ORGANISM: Homo sapiens
<220> FEATURE:
<221> NAME/KEY: misc_feature
<222> LOCATION: 28, 83, 126, 138, 254, 275, 298, 310, 311, 353, 363,
      374, 379, 393
<223> OTHER INFORMATION: n = A,T,C or G

<400> SEQUENCE: 30

```
tttttttttt tttttttttg aaatttanaa acaaatttta tttaagatct gaaatacaat     60
tcctaaaata tcaactttc canaaaaccg tggctacaca ataatgcatt gcctctatca    120
tgttanaacg tgcattanac tcaaatacaa aaaccatgaa acaaatcacc atccttcaac    180
aatttgagca aagatagaat gcctaagaac aacatagatg gacttgcaga ggatgggctg    240
```

```
ttttacttca agcnccataa aaaaaaaaaa gagcncaaat gcattgggtt ttcaggtnta      300
tacattaagn ngaacctttg gcactaggaa tcagggcgtt ttgtcacata gcnttaacac      360
atnttaaaaa attntgtant gtcaagggga tangaa                               396
```

<210> SEQ ID NO 31
<211> LENGTH: 396
<212> TYPE: DNA
<213> ORGANISM: Homo sapiens
<220> FEATURE:
<221> NAME/KEY: misc_feature
<222> LOCATION: 285, 287, 350, 362, 365, 377, 378, 382, 388, 390, 393
<223> OTHER INFORMATION: n = A,T,C or G

<400> SEQUENCE: 31

```
gacgggccag ggccatctgg aaagggaact cggcttttcc agaacgtggt ggatcatctg      60
tcgggtgtgt ggtgaacacg ttcagttcat cagggcctac gctccgggaa ggggccccca     120
gctgtggctc tgccatgccg ggctgtgttt gcagctgtcc gagtctccat ccgcctttag     180
aaaaccagcc acttcttttc ataagcactg acagggccca gcccacagcc acaggtgcga     240
tcagtgcctc acgcaggcaa atgcactgaa acccaggggc acacncncgc agagtgaaca     300
gtgagttccc ccgacagccc acgacagcca ggactgccct ccccaccccn ccccgacccc     360
angancacgg cacacanntc ancctctnan ctngct                               396
```

<210> SEQ ID NO 32
<211> LENGTH: 396
<212> TYPE: DNA
<213> ORGANISM: Homo sapiens
<220> FEATURE:
<221> NAME/KEY: misc_feature
<222> LOCATION: 341
<223> OTHER INFORMATION: n = A,T,C or G

<400> SEQUENCE: 32

```
cgactggcct catacccttgt ctacacagtc cctgcacagg gttcctaacc tgtggttagt     60
aaagaatgtc actttctaac aggtctggaa gctccgagtt tatccttggga actcaagagg    120 agaggatcac ccagttcaca ggtatttgag gatacaaacc cattgctggg ctcggcttta    180
aaagtcttat ctgaaattcc ttgtgaaaca gagtttcatc aaagccaatc caaaaggcct    240
atgtaaaaat aaccattctt gctgcacttt atgcaaataa tcaggccaaa tataagacta    300
cagtttattt acaatttgtt tttaccaaaa atgaggacta nagagaaaaa tggtgctcca    360
aagcttatca tacatttgtc attaagtcct agtctc                               396
```

<210> SEQ ID NO 33
<211> LENGTH: 396
<212> TYPE: DNA
<213> ORGANISM: Homo sapiens
<220> FEATURE:
<221> NAME/KEY: misc_feature
<222> LOCATION: 121, 122, 124, 125, 126, 128, 130, 131, 132, 133, 134,
      136, 137, 153, 154, 155, 156, 157, 158, 159, 168, 169, 170, 171,
      172, 173, 174, 175, 176, 177, 178, 179, 184, 185, 192, 197,
      199, 200, 202, 204, 205, 208, 209, 210, 211, 214, 215
<223> OTHER INFORMATION: n = A,T,C or G
<220> FEATURE:
<221> NAME/KEY: misc_feature
<222> LOCATION: 216, 217, 218, 222, 227, 228, 229, 233, 234, 241, 242,
      244, 245, 246, 247, 248, 249, 252, 260, 261, 262, 263, 264, 265,
      270, 272, 273, 274, 275, 279, 282, 284, 288, 290, 291, 292,
      293, 294, 299, 300, 301, 302, 303, 306, 313, 314, 319
<223> OTHER INFORMATION: n = A,T,C or G
<220> FEATURE:
<221> NAME/KEY: misc_feature
<222> LOCATION: 327, 328, 330, 331, 332, 333, 334, 335, 343, 349, 350, 351, 352, 355, 360, 369, 370, 371, 375, 379, 387, 388, 390, 391,
392, 393, 394, 395, 396
<223> OTHER INFORMATION: n = A,T,C or G

<400> SEQUENCE: 33
cctttttttt tttttttttt tttttttttt tttttttttt tttttttttt tttttttttt     60
tttttttttt tttttttttt tttttttttt tttttttttt tttttttttt tttttttttt    120
nngnnntntn nnnnannaaa aaaaaaaaaa aannnnnnna aaaaaaannn nnnnnnnnnt    180
tttnnggggg gnttttnann gnannttnnn nttnnnnnaa ancccnnng ggnngggggg    240 nntnnnnnng gnaaaaaaan nnnnnggggn cnnnngggnc cncnccnan nnnnaaaann    300 nnnggntttt ttnnttttna aaaaaanngn nnnnnaacaa aantttttnn nnaantttt n   360 ggggaaann ncccntttnt tttttnnan nnnnnn                                396

<210> SEQ ID NO 34
<211> LENGTH: 396
<212> TYPE: DNA
<213> ORGANISM: Homo sapiens
<220> FEATURE:
<221> NAME/KEY: misc_feature
<222> LOCATION: 8, 60, 72, 123, 128, 155, 172, 198, 207, 246, 305, 325,
348, 349, 369, 371, 380, 393, 394
<223> OTHER INFORMATION: n = A,T,C or G

<400> SEQUENCE: 34
acggaccnag ctggaggagc tgggtgtggg gtgcgttggg ctggtgggga ggcctagttn     60
gggtgcaagt angtctgatt gagcttgtgt tgtgctgaag ggacagccct gggtctaggg    120
ganagagncc ctgagtgtga gacccacctt ccccngtccc agccctccc anttccccca    180 gggacggcca cttcctgntc cccgacncaa ccatggctga agaacaaccg caggtcgaat    240
tgttcntgaa ggctggcagt gatggggcca agattgggaa ctgcccattc tcccacagac    300
tgttnatggt actgtggctc aaggnagtca ccttcaatgt taccaccnnt gacaccaaaa    360
ggcggaccna nacagtgcan aagctgtgcc canngg                              396

<210> SEQ ID NO 35
<211> LENGTH: 396
<212> TYPE: DNA
<213> ORGANISM: Homo sapiens

<400> SEQUENCE: 35
tcgaccaaaa tcaaatctgg cactcacaag ccctggccga ccccaatgg gttttaccac      60 tccccctcta gaccctgtct tgcaaaatcc tctccctagc cagctagtat tttctgggct    120
aaagactgta caaccagttc ctccatttta tagaagttta ctcactccag gggaaatggt    180
gagtcctcca acctcccttt caaccagtcc catcattcca accagtggta ccatagagca    240
gcaccccccg ccaccctctg agccagtagt gccagcagtg atgatggcca cccatgagcc    300
cagtgctgac ctggcaccca agaaaaagcc caggaagtca agcatgcctg tgaagattga    360
gaaggaaatt attgataccg ccgatgagtt tgatga                              396

<210> SEQ ID NO 36
<211> LENGTH: 396
<212> TYPE: DNA
<213> ORGANISM: Homo sapiens

<400> SEQUENCE: 36
tcgacgggaa gagcctgcta cggtggactg tgagactcag tgcactgtcc tcctcccagc     60
gaccccacgc tggacccct gccggaccct ccaccttcg gccccaagc ttcccagggg       120

| | |
|---|---|
| cttcctttgg actggactgt ccctgctcat ccattctcct gccaccccca gacctcctca | 180 |
| gctccaggtt gccacctcct ctcgccagag tgatgaggtc ccggcttctg ctctccgtgg | 240 |
| cccatctgcc cacaattcgg gagaccacgg aggagatgct gcttggggt cctggacagg | 300 |
| agcccccacc ctctcctagc ctggatgact acgtgaggtc tatatctcga ctggcacagc | 360 |
| ccacctctgt gctggacaag gccacggccc agggcc | 396 |

<210> SEQ ID NO 37
<211> LENGTH: 396
<212> TYPE: DNA
<213> ORGANISM: Homo sapiens
<220> FEATURE:
<221> NAME/KEY: misc_feature
<222> LOCATION: 376
<223> OTHER INFORMATION: n = A,T,C or G

<400> SEQUENCE: 37

| | |
|---|---|
| cgacggtgtc agcaactggc catgccacag cacataaaga ttacagtgac aagaaaaaca | 60 |
| ttgtttgagg attcctttca acagataatg agcttcagtc cccaagatct gcgaagacgt | 120 |
| ttgtgggtga ttttttccagg agaagaaggt ttagattatg gaggtgtagc aagagaatgg | 180 |
| ttctttcttt tgtcacatga agtgttgaac ccaatgtatt gcctgtttga atatgcaggg | 240 |
| aaggataact actgcttgca gataaacccc gcttcttaca tcaatccaga tcacctgaaa | 300 |
| tattttcgtt ttattggcag atttattgcc atggctctgt tccatgggaa aattcataga | 360 |
| cacgggtttt tctttnccat tctataagcg tatctt | 396 |

<210> SEQ ID NO 38
<211> LENGTH: 396
<212> TYPE: DNA
<213> ORGANISM: Homo sapiens

<400> SEQUENCE: 38

| | |
|---|---|
| cgaccaaaat gataaatagc tttaagaatg tgctaatgat aaatgattac atgtcaattt | 60 |
| aatgtactta atgtttaata ccttatttga ataattacct gaagaatata tttttttagta | 120 |
| ctgcatttca ttgattctaa gttgcacttt ttaccccccat actgttaaca tatctgaaat | 180 |
| cagaatgtgt cttacaatca gtgatcgttt aacattgtga caaagtttaa tggacagttt | 240 |
| tttcccatat gtatatataa aataatgtgt tttacaatca gtggcttaga ttcagtgaaa | 300 |
| tacagtaatt cattcaatta tgatagtatc tttacagaca tttaaaaat aagttatttt | 360 |
| tatatgctaa tattctatgt tcaagtggaa tttgga | 396 |

<210> SEQ ID NO 39
<211> LENGTH: 396
<212> TYPE: DNA
<213> ORGANISM: Homo sapiens

<400> SEQUENCE: 39

| | |
|---|---|
| tcgaccaaga atagatgctg actgtactcc tcccaggcgc cccttccccc tccaatccca | 60 |
| ccaaccctca gagccacccc taaagagata ctttgatatt ttcaacgcag ccctgctttg | 120 |
| ggctgccctg gtgctgccac acttcaggct cttctccttt cacaaccttc tgtggctcac | 180 |
| agaacccttg gagccaatgg agactgtctc aagagggcac tggtgcccg acagcctggc | 240 |
| acagggcaag tgggacaggg catggccagg tggccactcc agacccctgg cttttcactg | 300 |
| ctggctgcct tagaaccttt cttacattag cagtttgctt tgtatgcact tgtttttttt | 360 |
| ctttgggtct tgtttttttt ttccacttag aaattg | 396 |

```
<210> SEQ ID NO 40
<211> LENGTH: 396
<212> TYPE: DNA
<213> ORGANISM: Homo sapiens
<220> FEATURE:
<221> NAME/KEY: misc_feature
<222> LOCATION: 200, 375
<223> OTHER INFORMATION: n = A,T,C or G

<400> SEQUENCE: 40
tttttttttt ttttgttatt tagtttttat ttcataatca taaacttaac tctgcaatcc      60
agctaggcat gggagggaac aaggaaaaca tggaacccaa agggaactgc agcgagagca     120
caaagattct aggatactgc gagcaaatgg ggtggagggg tgctctcctg agctacagaa     180
ggaatgatct ggtggttaan ataaaacaca agtcaaactt attcgagttg tccacagtca     240
gcaatggtga tcttcttgct ggtcttgcca ttcctggacc caaagcgctc catggcctcc     300
acaatattca tgccttcttt cactttgcca acaccacat gcttgccatc caaccactca     360
gtcttggcag tgcanatgaa aaactgggaa ccattt                               396

<210> SEQ ID NO 41
<211> LENGTH: 396
<212> TYPE: DNA
<213> ORGANISM: Homo sapiens
<220> FEATURE:
<221> NAME/KEY: misc_feature
<222> LOCATION: 288
<223> OTHER INFORMATION: n = A,T,C or G

<400> SEQUENCE: 41
tcgacctctt gtgtagtcac ttctgattct gacaatcaat caatcaatgg cctagagcac      60
tgactgttaa cacaaacgtc actagcaaag tagcaacagc tttaagtcta aatacaaagc     120
tgttctgtgt gagaattttt taaaaggcta cttgtataat aacccttgtc atttttaatg     180
tacaaaacgc tattaagtgg cttagaattt gaacatttgt ggtctttatt tactttgctt     240
cgtgtgtggg caaagcaaca tcttccctaa atatatatta cccaaagnaa agcaagaag     300 ccagattagg ttttgacaa acaaacagg ccaaaagggg gctgacctgg agcagagcat     360
ggtgagaggc aaggcatgag agggcaagtt tgttgt                               396

<210> SEQ ID NO 42
<211> LENGTH: 396
<212> TYPE: DNA
<213> ORGANISM: Homo sapiens
<220> FEATURE:
<221> NAME/KEY: misc_feature
<222> LOCATION: 65, 68, 69, 71, 72, 75, 77, 79, 82, 85, 86, 87, 89, 90,
      97, 98, 105, 107, 109, 112, 117, 121, 122, 124, 126, 149, 152,
      153, 155, 157, 161, 163, 167, 168, 169, 174, 177, 178, 179,
      180, 186, 188, 192, 201, 202, 207, 208, 215, 217, 220
<223> OTHER INFORMATION: n = A,T,C or G
<220> FEATURE:
<221> NAME/KEY: misc_feature
<222> LOCATION: 225, 230, 242, 243, 247, 250, 259, 263, 271, 272, 279,
      284, 295, 298, 299, 308, 309, 312, 323, 342, 348, 351, 363, 366,
      370, 386, 390, 392
<223> OTHER INFORMATION: n = A,T,C or G

<400> SEQUENCE: 42
cttttttttt tttttttttt tttttttttt tttttttttt tttttttttt tttttttttt      60
aaaanccnna nnaananang gnaannnann aaaaaannca aaccncntnt anaaaangcc     120
nntntnaggg gggggggttca aaaccaaaang gnngntngga ngnaaannna aaanttnnnn    180
```

```
gggggnanaa anaaaaaggg nngaaanntg acccnanaan gaccngaaan cccgggaaac    240
cnngggntan aaaaaaagnt ganccctaaa nnccccgna aaanggggga agggnaannc     300
caaatccnnt gngggttggg ggngggaaa aaaaaaccc cnaaaaantg naaaaaaccg     360
ggnttnaaan atttgggttc gggggntttn tnttaa                             396

<210> SEQ ID NO 43
<211> LENGTH: 396
<212> TYPE: DNA
<213> ORGANISM: Homo sapiens
<220> FEATURE:
<221> NAME/KEY: misc_feature
<222> LOCATION: 108, 195, 213, 279, 287, 349
<223> OTHER INFORMATION: n = A,T,C or G

<400> SEQUENCE: 43
tttttttttt ttttgcttca ctgctttatt tttgaaatca caagcaattc aaagtgatca    60
tcattgaggc ttctgttaaa agttcttcca aagttgccca gttttaanat taaacaatat   120
tgcactttaa gatgaactaa cttttgggat tctcttcaaa gaaggaaagt attgctccat   180
ctgtgctttt cttanactaa aagcatactg canaaaactc tattttaaaa atcaacactg   240
cagggtacag taacatagta aagtacctgc ctattttana atcctanaga acatttcatt   300
gtaagaaact agcccattat ttaagtgtcc acagtatttt tcatttcant ggtccaagat   360
gccaaggttt ccaaacacaa tcttgttctc taatac                             396

<210> SEQ ID NO 44
<211> LENGTH: 396
<212> TYPE: DNA
<213> ORGANISM: Homo sapiens

<400> SEQUENCE: 44
gacctagttt tacctcttaa atatctctgt tcccttctaa gttgtttgct gtgttttctt    60
cagagcaaga aggttatatt ttttaaaatt tacttagtaa tgcacattca aaacacacat   120
caagtcttca ggataaagtt caaaaccgct gtcatggccc catgtgatct ctccctcccc   180 taccccctcta tcatttagtt tcttctgcgc aagccactct ggcttccttt cagttttgtg   240
gttcccgttt ttagctagtt cagtggtttt caatgggcat ttcttgcctt ttttttttcta   300 aacgacaaat agaaatacat cttctttatt atcctccaaa tccaattcag aggtaatatg   360
ctccacctac acacaatttt agaaataaat taaaaa                             396

<210> SEQ ID NO 45
<211> LENGTH: 396
<212> TYPE: DNA
<213> ORGANISM: Homo sapiens
<220> FEATURE:
<221> NAME/KEY: misc_feature
<222> LOCATION: 18, 19, 22, 39, 40, 43, 62, 84, 90, 99, 103, 104, 105,
      117, 120, 123, 128, 134, 139, 141, 142, 143, 144, 145, 182, 187,
      207, 218, 219, 242, 247, 257, 260, 263, 272, 276, 277, 279,
      284, 288, 294, 296, 297, 305, 310, 314, 319, 320, 322
<223> OTHER INFORMATION: n = A,T,C or G
<220> FEATURE:
<221> NAME/KEY: misc_feature
<222> LOCATION: 364, 366, 376, 378, 381, 387, 388, 396
<223> OTHER INFORMATION: n = A,T,C or G

<400> SEQUENCE: 45
tttttttttt ttttaaannt tntaaattt taatgaaann ganttagaac aatgtattat    60
tnacatgtaa ataaaaaaag aganncataan ccccatatnc tcnnnaaagg aagggganacn  120 gcnggccntt tatnagaana nnnnncatat aagaccccat taagaagaat ctggatctaa   180
```

```
anacttncaa acaggagttc acagtangtg aacagcannc cctaatccca ctgatgtgat    240
gnttcanata aaatcancan cgntgatcgg gnatcnnanc aatntgancg gaanannact    300
gctcnatatn tttnaggann cngatgtggt cattttttac aaagataatg gccacaccct    360
tccngnccga atcgancnga nctcccnntt ctgtgn                              396
```

<210> SEQ ID NO 46
<211> LENGTH: 396
<212> TYPE: DNA
<213> ORGANISM: Homo sapiens
<220> FEATURE:
<221> NAME/KEY: misc_feature
<222> LOCATION: 24, 105, 144, 188, 190, 214, 317, 369, 371, 378
<223> OTHER INFORMATION: n = A,T,C or G

<400> SEQUENCE: 46

```
tttttttttt tttttttttc tganacagag tctcattctg ttgcctaggc tggattgcag    60
tggtgccatc tcggctcact gcaacctccg cctcctgggt tccanaaatt ctcctgcctc   120
agcctcccgg gtagctggga ctanaggcac acgccaccac gccaggctaa tttttatatt   180
tttagtanan atggcgtttc accatgttga ccanactgat ctcgaactcc cgacctcgtg   240
atccacccac ctcggcctcc caaagtgctg ggattacagg cgtgaaacca ccaggcccgg   300
cctgaaatat ctatttnttt tcagattatt tttaaaattc catttgatga atcttttaaa   360
gtgagctana naaagtgngt gtgtacatgc acacac                              396
```

<210> SEQ ID NO 47
<211> LENGTH: 396
<212> TYPE: DNA
<213> ORGANISM: Homo sapiens
<220> FEATURE:
<221> NAME/KEY: misc_feature
<222> LOCATION: 290
<223> OTHER INFORMATION: n = A,T,C or G

<400> SEQUENCE: 47

```
tttttttttt tttttttgct gttgccaact gtttattcag ggccctgaac gggtggtgcg    60
tggacatgca acacactcgg gcccacagca gcgtgaccgg ccgctcccaa gccccgggcg   120
cacaaccaca gccaggagca gcccctgcca ccactgggcc accgtccagg gccccacagg   180
accagccgaa ggtgccccgg gccgaggcca gctgggtcag gtgtaccccT agcctggggt   240
tgagtgagga gcggcacccc cagtatcctg tgtacccccaa gttgcccagn aggccgaggg   300
ggccttgggc tccatctgca ctggccaccc cgtgccaagc atcacagctg cgtgagcagg   360
tttgtgtgtg agcgtgtggc ggggcctggt tgtccc                              396
```

<210> SEQ ID NO 48
<211> LENGTH: 396
<212> TYPE: DNA
<213> ORGANISM: Homo sapiens
<220> FEATURE:
<221> NAME/KEY: misc_feature
<222> LOCATION: 393, 396
<223> OTHER INFORMATION: n = A,T,C or G

<400> SEQUENCE: 48

```
ctgggcctgt gccgaagggt ctgggcagat cttccaaaga tgtacaaaat gtagaaattg    60
ccctcaagca aatgcaaaga tgctcaacac ccttagtcat caagaaaatg caaatggaat   120
ccacagagag atactgcaca ctgacaaaga tggtcgtatt actaaaggtg aataaccagc   180
gcggggggca cgtggagtca ctggaacatt tgtgcaatgc tggtgggaat gtcaacccgt   240
```

```
gcggccctct ggaataagcc tggcagctcc tccaagagtt acccgtgtga cccagcaatt    300
ccactcctag ctccacccac aggaattgaa agcaaagacg caaacagatg cctgtgcacc    360
aaagttcacg gcagcatcct tcgccatagt ggnaan                              396
```

<210> SEQ ID NO 49
<211> LENGTH: 396
<212> TYPE: DNA
<213> ORGANISM: Homo sapiens
<220> FEATURE:
<221> NAME/KEY: misc_feature
<222> LOCATION: 32, 40, 44, 64, 70, 83, 87, 92, 104, 115, 118, 125, 127,
      130, 137, 155, 168, 171, 173, 175, 192, 201, 206, 208, 218,
      219, 235, 247, 249, 256, 259, 260, 269, 297, 306, 310, 320,
      321, 328, 331, 345, 356, 381, 389, 395
<223> OTHER INFORMATION: n = A,T,C or G

<400> SEQUENCE: 49

```
accccaaaat gggaaaggaa aagactcata tnaacattgn cgtnattgga cacgtacatt    60
cggncaagtn caccactact ggncatntga tntataaatg cggnggcatc gacanaanaa    120
ccatngnaan atttganaag gaggctgctg atatnggaaa gggctccntc nantntgcct    180
gggtcttgga tnaactgaaa nctgancntg aacgtggnnt caccattgat atctncttgt    240
ggaaatntna gaccancann tactatgtna ctatcattga tgccccagga cacaganact    300
ttatcnaaan catgattacn nggacatnta nagctgactg tgctngcctg attgtngctg    360
ctggtgttgg tgaatttgaa nctggtatnt ccaana                              396
```

<210> SEQ ID NO 50
<211> LENGTH: 396
<212> TYPE: DNA
<213> ORGANISM: Homo sapiens

<400> SEQUENCE: 50

```
cgacttcttg ctggtgggtg gggcagtttg gtttagtgtt atactttggt ctaagtattt    60
gagttaaact gctttttttgc taatgagtgg gctggttgtt agcaggtttg ttttttcctgc   120 tgttgattgt tactagtggc attaactttt agaatttggg ctggtgagat taattttttt    180
taatatccca gctagagata tggcctttaa ctgacctaaa gaggtgtgtt gtgatttaat    240
tttttcccgt tcctttttct tcagtaaacc caacaatagt ctaaccttaa aaattgagtt    300
gatgtcctta taggtcacta cccctaaata aacctgaagc aggtgttttc tcttggacat    360
actaaaaaat acctaaaagg aagcttagat gggctg                              396
```

<210> SEQ ID NO 51
<211> LENGTH: 396
<212> TYPE: DNA
<213> ORGANISM: Homo sapiens
<220> FEATURE:
<221> NAME/KEY: misc_feature
<222> LOCATION: 18, 52, 59, 148, 267, 321, 332
<223> OTHER INFORMATION: n = A,T,C or G

<400> SEQUENCE: 51

```
ttttttttttt ttcagcgngg atttatttta tttcattttt tactctcaag anaaagaana    60
gttactattg caggaacaga cattttttta aaaagcgaaa ctcctgacac ccttaaaaca    120
gaaaacattg ttattcacat aataatgngg ggctctgtct ctgccgacag gggctgggtt    180
cgggcattag ctgtgccgtc gacaatagcc ccattcaccc cattcataaa tgctgctgct    240
acaggaaggg aacagcggct ctcccanaga gggatccacc ctggaacacg agtcacctcc    300
```

| aaagagctgc gactgtttga naatctgcca anaggaaaac cactcaatgg gacctggata | 360 |
| acccaggccc gggagtcata gcaggatgtg gtactt | 396 |

<210> SEQ ID NO 52
<211> LENGTH: 396
<212> TYPE: DNA
<213> ORGANISM: Homo sapiens
<220> FEATURE:
<221> NAME/KEY: misc_feature
<222> LOCATION: 81, 189
<223> OTHER INFORMATION: n = A,T,C or G

<400> SEQUENCE: 52

| acctcgctaa gtgttcgcta cgcggggcta ccggatcggt cggaaatggc agaggtggag | 60 |
| gagacactga agcgactgca nagccagaag ggagtgcagg gaatcatcgt cgtgaacaca | 120 |
| gaaggcattc ccatcaagag caccatggac aaccccacca ccacccagta tgccagcctc | 180 |
| atgcacagnt tcatcctgaa ggcacggagc ccgtgcgtg acatcgaccc ccagaacgat | 240 |
| ctcaccttcc ttcgaattcg ctccaagaaa aatgaaatta tggttgcacc agataaagac | 300 |
| tatttcctga ttgtgattca gaatccaacc gaataagcca ctctcttggc tccctgtgtc | 360 |
| attccttaat ttaatgcccc ccaagaatgt taatgt | 396 |

<210> SEQ ID NO 53
<211> LENGTH: 396
<212> TYPE: DNA
<213> ORGANISM: Homo sapiens
<220> FEATURE:
<221> NAME/KEY: misc_feature
<222> LOCATION: 224, 225, 228, 235, 240, 246, 257, 266, 274, 279, 281,
      282, 283, 285, 287, 288, 290, 291, 292, 293, 294, 295, 296, 297,
      300, 301, 303, 307, 311, 313, 314, 317, 318, 319, 320, 321,
      323, 324, 328, 329, 330, 336, 337, 338, 339, 340, 341
<223> OTHER INFORMATION: n = A,T,C or G
<220> FEATURE:
<221> NAME/KEY: misc_feature
<222> LOCATION: 342, 343, 344, 345, 346, 347, 348, 349, 350, 351, 352,
      356, 357, 358, 359, 362, 363, 364, 365, 366, 367, 373, 380, 381,
      382, 385, 387, 388, 389, 390, 392
<223> OTHER INFORMATION: n = A,T,C or G

<400> SEQUENCE: 53

| tttttttttt tttttttttt tttttttttt tttttttttt tttttttttt tttttttttt | 60 |
| tttttttttt tttttttttt tttttttttt tttttttttt tttttttttt tttttttttt | 120 |
| tttttttttt tttttttttt tttttttttt tttttttttt tttttttttt tttttttttt | 180 |
| tttttttttt tttttttttt tttttttttt tttttttttt ttannttntt ttttnttttn | 240 |
| cctttntttt aattcanaaa aagaanaaga aaanataana nnnancnnan nnnnnnnatn | 300 |
| ntncttnata ntnnttnnnn nannggannn gcgagnnnnn nnnnnnnnnn nntctnnnnt | 360 |
| tnnnnnnctt gcnccccttn nnttngnnnn angcaa | 396 |

<210> SEQ ID NO 54
<211> LENGTH: 396
<212> TYPE: DNA
<213> ORGANISM: Homo sapiens
<220> FEATURE:
<221> NAME/KEY: misc_feature
<222> LOCATION: 367
<223> OTHER INFORMATION: n = A,T,C or G

<400> SEQUENCE: 54

| ctcttggggc tgctgggact cgcgtcggtt ggcgactccc ggacgtaggt agtttgttgg | 60 |
| gccgggttct gaggccttgc ttctctttac ttttccactc taggccacga tgccgcagta | 120 |

```
ccagacctgg gaggagttca gccgcgctgc cgagaagctt tacctcgctg accctatgaa    180
ggcacgtgtg gttctcaaat ataggcattc tgatgggaac ttgtgtgtta aagtaacaga    240
tgatttagtt tgtttggtgt ataaaacaga ccaagctcaa gatgtaaaga agattgagaa    300
attccacagt caactaatgc gacttatggt agccaaggaa gcccgcaatg ttaccatgga    360
aactgantga atggtttgaa atgaagactt tgtcgt                              396
```

```
<210> SEQ ID NO 55
<211> LENGTH: 396
<212> TYPE: DNA
<213> ORGANISM: Homo sapiens

<400> SEQUENCE: 55
cgacggtttg ccgccagaac acaggtgtcg tgaaaactac ccctaaaagc caaaatggga    60
aaggaaaaga ctcatatcaa cattgtcgtc attggacacg tagattcggg caagtccacc    120
actactggcc atctgatcta taatgcggt ggcatcgaca aaagaaccat tgaaaaattt     180
gagaaggagg ctgctgagat gggaaagggc tccttcaagt atgcctgggt cttggataaa    240
ctgaaagctg agcgtgaacg tggtatcacc attgatatct ccttgtggaa atttgagacc    300
agcaagtact atgtgactat cattgatgcc ccaggacaca gagactttat caaaaacatg    360
attacaggga catctcaggc tgactgtgct gtcctg                              396
```

```
<210> SEQ ID NO 56
<211> LENGTH: 396
<212> TYPE: DNA
<213> ORGANISM: Homo sapiens
<220> FEATURE:
<221> NAME/KEY: misc_feature
<222> LOCATION: 134, 145, 255, 279, 337, 344, 369
<223> OTHER INFORMATION: n = A,T,C or G

<400> SEQUENCE: 56
tttttttttt tttttctca tttaactttt ttaatgggtc tcaaaattct gtgacaaatt     60
tttggtcaag ttgtttccat taaaaagtac tgattttaaa aactaataac ttaaaactgc    120
cacacgcaaa aaanaaaacc aaagnggtcc acaaaacatt ctcctttcct tctgaaggtt   180
ttacgatgca ttgttatcat taaccagtct tttactacta aacttaaatg gccaattgaa    240
acaaacagtt ctganaccgt tcttccacca ctgattaana gtggggtggc aggtattagg    300
gataatattc atttagcctt ctgagctttc tgggcanact tggngacctt gccagctcca    360
gcagccttnt tgtccactgc tttgatgaca cccacc                              396
```

```
<210> SEQ ID NO 57
<211> LENGTH: 396
<212> TYPE: DNA
<213> ORGANISM: Homo sapiens
<220> FEATURE:
<221> NAME/KEY: misc_feature
<222> LOCATION: 52, 57, 58, 61, 72, 75, 77, 84, 87, 88, 93, 100, 101,
      111, 117, 119, 121, 131, 132, 133, 134, 142, 143, 154, 156, 159,
      167, 168, 170, 175, 176, 182, 183, 185, 186, 190, 192, 194,
      198, 199, 200, 209, 212, 217, 218, 220, 232, 235, 253
<223> OTHER INFORMATION: n = A,T,C or G
<220> FEATURE:
<221> NAME/KEY: misc_feature
<222> LOCATION: 255, 257, 258, 260, 262, 263, 270, 271, 273, 277, 280,
      281, 284, 285, 289, 296, 297, 298, 303, 305, 307, 309, 310, 317,
      322, 324, 337, 338, 342, 344, 346, 347, 349, 351, 356, 358,
      366, 368, 371, 377, 380, 388, 389, 393, 396
<223> OTHER INFORMATION: n = A,T,C or G

<400> SEQUENCE: 57
```

```
cctttttttt tttttttttt tttttttttt tttttttttt tttttttttt tnaaaannttt    60 nttttttgcaa anccnancaa aaanggnngg aangaaaaan nggaaaaatt nttttttncnt    120 ntttgggaac nnnnagccct tnnttttgaaa aaangnggnc ttaaaanngn tgaannaaag    180
gnnanncccn gntncttnnn tttaaaaana angggggnngn tttttttttaa anaanatttt    240 tttttttccct aanancnncn anntgaaacn ngncccnacn nctnncttna aagggnnnaa    300
atnanangnn aaaaaancc tnancccccc cccttanntt tncnannana naaagncntt    360
ttgggncntg naaaaanaan ccttttttnnt gcnttn                              396

<210> SEQ ID NO 58
<211> LENGTH: 396
<212> TYPE: DNA
<213> ORGANISM: Homo sapiens

<400> SEQUENCE: 58
cgacctcaaa tatgccttat tttgcacaaa agactgccaa ggacatgacc agcagctggc    60
tacagcctcg atttatattt ctgtttgtgg tgaactgatt ttttttaaac caaagtttag    120
aaagaggttt ttgaaatgcc tatggtttct ttgaatggta aacttgagca tcttttcact    180
ttccagtagt cagcaaagag cagtttgaat tttcttgtcg cttcctatca aaatattcag    240
agactcgagc acagcaccca gacttcatgc gcccgtggaa tgctcaccac atgttggtcg    300
aagcggccga ccactgactt tgtgacttag gcggctgtgt tgcctatgta gagaacacgc    360
ttcaccccca ctccccgtac agtgcgcaca ggcttt                              396

<210> SEQ ID NO 59
<211> LENGTH: 396
<212> TYPE: DNA
<213> ORGANISM: Homo sapiens
<220> FEATURE:
<221> NAME/KEY: misc_feature
<222> LOCATION: 25, 45, 116, 178, 198, 211, 225, 235, 253, 266, 281,
      324, 367, 377, 389
<223> OTHER INFORMATION: n = A,T,C or G

<400> SEQUENCE: 59
cttttttttt tttttttttt tcagnggaaa ataacttta ttganacccc accaactgca    60
aaatctgttc ctggcattaa gctccttctt cctttgcaat tcggtctttc ttcagnggtc    120
ccatgaatgc tttcttctcc tccatggtct ggaagcggcc atggccaaac ttggaggngg    180
tgtcaatgaa cttaaggnca atcttctcca nagcccgccg cttcntctgc accancaagg    240
acttgcggag ggngagcacc cgcttnttgg ttcccaccac ncagcctttc agcatgacaa    300
agtcattggt cacttcacca tagnggacaa agccacccaa agggttgatg ctccttggca    360
aataggncat agtcacngga ggcattgtnc ttgatc                              396

<210> SEQ ID NO 60
<211> LENGTH: 396
<212> TYPE: DNA
<213> ORGANISM: Homo sapiens

<400> SEQUENCE: 60
acctcagctc tcggcgcacg gcccagcttc cttcaaaatg tctactgttc acgaaatcct    60
gtgcaagctc agcttggagg gtgatcactc tacaccccca agtgcatatg ggtctgtcaa    120
agcctatact aactttgatg ctgagcggga tgctttgaac attgaaacag ccatcaagac    180
caaaggtgtg gatgaggtca ccattgtcaa cattttgacc aaccgcagca atgcacagag    240
```

```
acaggatatt gccttcgcct accagagaag gaccaaaaag gaacttgcat cagcactgaa      300
gtcagcctta tctggccacc tggagacggt gattttgggc ctattgaaga cacctgctca      360
gtatgacgct tctgagctaa aagcttccat gaaggg                                396
```

<210> SEQ ID NO 61
<211> LENGTH: 396
<212> TYPE: DNA
<213> ORGANISM: Homo sapiens

<400> SEQUENCE: 61

```
tagcttgtcg gggacggtaa ccgggacccg gtgtctgctc ctgtcgcctt cgcctcctaa       60
tccctagcca ctatgcgtga gtgcatctcc atccacgttg gccaggctgg tgtccagatt      120
ggcaatgcct gctgggagct ctactgcctg gaacacggca tccagcccga tggccagatg      180
ccaagtgaca agaccattgg gggaggagat gactccttca acaccttctt cagtgagacg      240
ggcgctggca agcacgtgcc ccgggctgtg tttgtagact ggaacccac agtcattgat       300 gaagttcgca ctggcaccta ccgccagctc ttccaccctg agcagctcat cacaggcaag      360
gaagatgctg ccaataacta tgcccgaggg cactac                                396
```

<210> SEQ ID NO 62
<211> LENGTH: 396
<212> TYPE: DNA
<213> ORGANISM: Homo sapiens
<220> FEATURE:
<221> NAME/KEY: misc_feature
<222> LOCATION: 261, 269, 313, 333, 346, 354, 359, 390, 394, 395, 396
<223> OTHER INFORMATION: n = A,T,C or G

<400> SEQUENCE: 62

```
tcgacgtttc ctaaagaaaa ccactctttg atcatggctc tctctgccag aattgtgtgc       60
actctgtaac atctttgtgg tagtcctgtt ttcctaataa ctttgttact gtgctgtgaa      120
agattacaga tttgaacatg tagtgtacgt gctgttgagt tgtgaactgg tgggccgtat      180
gtaacagctg accaacgtga agatactggt acttgatagc ctcttaagga aaatttgctt      240 ccaaattta agctggaaag ncactggant aactttaaaa aagaattaca atacatggct      300
ttttagaatt tcnttacgta tgttaagatt tgngtacaaa ttgaantgtc tgtnctganc      360
ctcaaccaat aaaatctcag tttatgaaan aaannn                                396
```

<210> SEQ ID NO 63
<211> LENGTH: 396
<212> TYPE: DNA
<213> ORGANISM: Homo sapiens
<220> FEATURE:
<221> NAME/KEY: misc_feature
<222> LOCATION: 3, 11, 16, 18, 23, 26, 30, 34, 37, 50, 51, 60, 61, 62,
       63, 64, 75, 82, 83, 84, 85, 87, 89, 93, 94, 97, 98, 99, 118,
       119, 120, 122, 134, 136, 138, 139, 141, 144, 145, 147, 152,
       156, 187, 188, 193, 195, 204, 211, 214, 216, 222, 226
<223> OTHER INFORMATION: n = A,T,C or G
<220> FEATURE:
<221> NAME/KEY: misc_feature
<222> LOCATION: 228, 235, 242, 258, 264, 265, 269, 275, 294, 298, 301,
       307, 316, 326, 334, 335, 339, 340, 343, 350, 351, 355, 373, 378,
       390
<223> OTHER INFORMATION: n = A,T,C or G

<400> SEQUENCE: 63

```
ttnttttttt ntttttntntt ttntcnttgn ttgnacngaa cccggcgctn nttccccacn       60
nnnnacggcc gccntattc annnntncnt canntannna ccgcaccctc ggactgcnnn       120
tngggccccg ccgncnannc nccnncnccc anttcnccgc cgccgccgcc gcctttttt       180
```

```
attggcnncc atnanaaccg gggncacctc ncangngcgc cnaaantngg ggcangactc    240
anagggggcc atcaaccncc aagnncaanc tgganctcta caaacggcct acgntttntg    300
nccatgnggg tagggnttta cccgcnatga tgannatgnn aanaactttn ncaanccctt    360
tattaaccaa tgnggtgngg agacggaacn tggtta                              396

<210> SEQ ID NO 64
<211> LENGTH: 396
<212> TYPE: DNA
<213> ORGANISM: Homo sapiens
<220> FEATURE:
<221> NAME/KEY: misc_feature
<222> LOCATION: 175, 177, 340, 393
<223> OTHER INFORMATION: n = A,T,C or G

<400> SEQUENCE: 64
tcgacgtcgg ggtttcctgc ttcaacagtg cttggacgga acccggcgct cgttccccac    60
cccggccggc cgcccatagc cagccctccg tcacctcttc accgcaccct cggactgccc    120
caaggccccc ccgccgcctc cagcgccgcg cagccaccgc cgccgccgcc gcctntnctt    180
agtcgccgcc atgacgaccg cgtccacctc gcaggtgcgc cagaactacc accaggactc    240
agaggccgcc atcaaccgcc agatcaacct ggagctctac gcctcctacg tttacctgtc    300
catgtcttac tactttgacc gcgatgatgt ggctttgaan aactttgcca aatactttct    360
tcccaatctc atgaggagaa ggaacatgct ganaaa                              396

<210> SEQ ID NO 65
<211> LENGTH: 396
<212> TYPE: DNA
<213> ORGANISM: Homo sapiens
<220> FEATURE:
<221> NAME/KEY: misc_feature
<222> LOCATION: 26, 56, 103, 122, 145, 151, 154, 187, 189, 203, 224,
      256, 273, 305, 344
<223> OTHER INFORMATION: n = A,T,C or G

<400> SEQUENCE: 65
tttttttttt tttttttttt tttttnacca ataatgcttt tattttccac atcaanatta    60
atttatatgt tagttttagt acaagtacta aaatgtatac ttnttgccct aatagctaag    120
gnatacataa gcttcaccat acatnttgca nccncctgtc tgtcctatgt cattgttata    180
aatgtanana ttttaggaaa ctnttttatt caacctggga catntatact gtaggagtta    240
gcactgacct gatgtnttat ttaaaagtaa tgnatattac ctttacatat attccttata    300
tattnaaacg tatttccatg ttatccagct taaaatcaca tggnggttaa aagcatgagt    360
tctgagtcaa atctggactg aaatcctgat gctccc                              396

<210> SEQ ID NO 66
<211> LENGTH: 396
<212> TYPE: DNA
<213> ORGANISM: Homo sapiens

<400> SEQUENCE: 66
tcgacttttt tttttccagg acattgtcat aatttttat tatgtatcaa attgtcttca     60
atataagtta caacttgatt aaagttgata gacatttgta tctatttaaa gacaaaaaaa    120
ttcttttatg tacaatatct tgtctagagt ctagcaaata tagtaccttt cattgcagga    180
tttctgctta ataacaag caaaacaaa caactgaaaa aatataaacc aaagcaaacc       240
aaaccccccg ctcaactaca aatgtcaata ttgaatgaag cattaaaaga caaacataaa    300
```

```
gtaacttcag cttttatcta gcaatgcaga atgaatacta aaattagtgg caaaaaaaca    360
aacaacaaac aacaaacaaa acaaaacaaa caaaca                               396
```

<210> SEQ ID NO 67
<211> LENGTH: 396
<212> TYPE: DNA
<213> ORGANISM: Homo sapiens

<400> SEQUENCE: 67

```
acgcttttgt ccttcatttt aactgttatg tcatactgtt atgttgacat atttctttat    60
aagagaatag aggcaaaagt atagaactga ggatcatttg tattttttgag ttggaaatta   120 tgaaacttca ccatattatg atcatacata ttttgaagaa cagactgacc aaagctcacc   180
tgttttttgt gttaggtgct ttggctgaac ttgattccag ccccctttc cctttggtgt    240 tgtgtatgtc tctttcatttc ctctcaaatc ttcaactctt gccccatgtc tccttggcag   300
caggatgctg gcatctgtgt agtcctcata ctgtttactg ataacccaca aattcatttt    360
catggcagac ctaagctcag accctgcctt gtcctg                              396
```

<210> SEQ ID NO 68
<211> LENGTH: 396
<212> TYPE: DNA
<213> ORGANISM: Homo sapiens

<400> SEQUENCE: 68

```
acctgagtcc tgtcctttct ctctccccgg acagcatgag cttcaccact cgctccacct    60
tctccaccaa ctaccggtcc ctgggctctg tccaggcgcc cagctacggc gcccggccgg   120
tcagcagcgc ggccagcgtc tatgcaggcg ctggggggctc tggttcccgg atctccgtgt   180
cccgctccac cagcttcagg ggcggcatgg ggtccggggg cctggccacc gggatagccg   240
ggggtctggc aggaatggga ggcatccaga acgagaagga gaccatgcaa agcctgaacg   300
accgcctggc ctcttacctg gacagagtga ggagcctgga gaccgagaac cggaggctgg   360
agagcaaaat ccgggagcac ttggagaaga agggac                              396
```

<210> SEQ ID NO 69
<211> LENGTH: 396
<212> TYPE: DNA
<213> ORGANISM: Homo sapiens
<220> FEATURE:
<221> NAME/KEY: misc_feature
<222> LOCATION: 1, 4, 6, 8, 9, 11, 18, 19, 36, 53, 60, 64, 79, 84, 92,
      94, 97, 105, 114, 120, 123, 127, 129, 134, 137, 138, 139, 142,
      143, 147, 149, 151, 152, 156, 158, 167, 170, 172, 180, 182,
      184, 187, 188, 189, 194, 197, 201, 209, 212, 218, 219
<223> OTHER INFORMATION: n = A,T,C or G
<220> FEATURE:
<221> NAME/KEY: misc_feature
<222> LOCATION: 220, 222, 223, 225, 228, 229, 230, 232, 233, 236, 242,
      244, 247, 250, 251, 253, 256, 257, 259, 261, 270, 271, 274, 277,
      278, 279, 282, 284, 288, 289, 296, 298, 300, 310, 315, 316,
      320, 321, 324, 328, 330, 331, 334, 336, 340, 347, 350
<223> OTHER INFORMATION: n = A,T,C or G
<220> FEATURE:
<221> NAME/KEY: misc_feature
<222> LOCATION: 352, 353, 355, 359, 361, 362, 364, 367, 370, 372, 374,
      376, 382, 388, 390, 394, 396
<223> OTHER INFORMATION: n = A,T,C or G

<400> SEQUENCE: 69

```
ntcncngnng ntgtggtnnt ttttttaatt tttatntttt cttttttttt ctngctagcn    60
cttncttttt ttgaattnc ggtnccttt tntntcnatt ttttngacaa aaanaacctn    120
ttntttnana ccanagnnng gnncacncnt nnaatntncc ccttttncgn tngggagctn    180
```

```
cncttnnnc gccnacntca ntcgagacng tncttttnnn tnnancannn tnngtncgtt    240
gncngcnttn ntncannant nttccctatn nacntgnnnt cncncatnnt tggacnancn    300
cctagccttn ccatnntttn nttntttntn natnancctn gaaaacntcn gnntnttcnc    360
nncnttnccn cncncncctt cntatgtncn atgncn                              396

<210> SEQ ID NO 70
<211> LENGTH: 396
<212> TYPE: DNA
<213> ORGANISM: Homo sapiens
<220> FEATURE:
<221> NAME/KEY: misc_feature
<222> LOCATION: 15, 38, 57, 59, 63, 64, 65, 66, 68, 78, 79, 84, 87, 90,
      97, 114, 115, 127, 128, 141, 143, 145, 151, 159, 168, 169, 172,
      173, 176, 178, 197, 198, 207, 209, 211, 215, 220, 221, 223,
      225, 228, 240, 248, 249, 260, 262, 263, 273, 283, 287
<223> OTHER INFORMATION: n = A,T,C or G
<220> FEATURE:
<221> NAME/KEY: misc_feature
<222> LOCATION: 294, 304, 314, 334, 339, 340, 348, 362, 367, 376, 382,
      384, 386, 395
<223> OTHER INFORMATION: n = A,T,C or G

<400> SEQUENCE: 70
tttttttttt tttntttttt tttttttttt tttttttntt tttttttttt tttttntntc    60
aannnntnaa cttttaanng gccnccngcn ccccaanggg gaccctgctt tgnnggcta     120 aatgccnnaa aactttgggg nantnggtat naaacccncn tttgccnnc annttncngg    180 gggggggggg ttttgnngg ggaacangna naacnttttn ncnanggnat caccaaaaan    240
aaagcccnnc cctttttccn annggggggg ggnggggga aantcanccc ccanattgac    300
cttnatttca aaangggct tataatcctg ggcntggann cttccctnta cccggggtt    360 gnccacnttt tattanaggg gnangnggat ccccnt                              396

<210> SEQ ID NO 71
<211> LENGTH: 396
<212> TYPE: DNA
<213> ORGANISM: Homo sapiens
<220> FEATURE:
<221> NAME/KEY: misc_feature
<222> LOCATION: 15, 21, 30, 33, 35, 36, 42, 43, 44, 45, 46, 51, 56, 58,
      59, 63, 70, 77, 81, 88, 94, 95, 96, 97, 101, 102, 109, 114,
      118, 119, 120, 124, 131, 132, 133, 134, 135, 141, 142, 143,
      144, 145, 146, 148, 149, 154, 158, 162, 164, 166, 172
<223> OTHER INFORMATION: n = A,T,C or G
<220> FEATURE:
<221> NAME/KEY: misc_feature
<222> LOCATION: 177, 179, 181, 184, 185, 213, 216, 218, 219, 222, 223,
      224, 230, 231, 240, 241, 242, 245, 247, 251, 252, 255, 258, 259,
      261, 264, 268, 269, 272, 276, 285, 288, 289, 291, 292, 293,
      297, 299, 300, 307, 312, 315, 316, 317, 325, 329, 334
<223> OTHER INFORMATION: n = A,T,C or G
<220> FEATURE:
<221> NAME/KEY: misc_feature
<222> LOCATION: 340, 341, 347, 350, 354, 355, 357, 360, 361, 367, 368,
      370, 371, 376, 377, 378, 387, 393, 394
<223> OTHER INFORMATION: n = A,T,C or G

<400> SEQUENCE: 71
gcatctagag ggccngttta ntctagaggn ccngnntaaa cnnnnncatc nacctncnnt    60
gcncctgctn gttgccnccc ntctgtgnct tgcnnnnccc nngagcgtnc cttnaccnnn    120
gaangtgcct nnnnnactga nnnnnncnna taanatgngg anantncgtc gncattntnt    180 natnggggt gatgctattc tggggggtgg ggnggngnna tnnnatactn ngggacgtn     240 nnatnangag nnatntcnng nttntctnnt gntttntggg gggcnatnng nnntctntnn    300
```

-continued

```
ggactcntcg cncannnatc aatancttna ttcngtgtan ngtccgnccn tagnncngcn      360
ngtactnnan ngttgnnntc attactnttc gtnngg                                396
```

<210> SEQ ID NO 72
<211> LENGTH: 396
<212> TYPE: DNA
<213> ORGANISM: Homo sapiens
<220> FEATURE:
<221> NAME/KEY: misc_feature
<222> LOCATION: 2, 23, 27, 34, 35, 36, 37, 39, 41, 45, 55, 56, 59, 61,
      88, 92, 96, 97, 98, 101, 103, 104, 106, 108, 111, 114, 115,
      121, 128, 129, 131, 159, 170, 191, 202, 227, 233, 235, 240,
      262, 268, 271, 272, 280, 281, 303, 304, 305, 311, 316, 317
<223> OTHER INFORMATION: n = A,T,C or G
<220> FEATURE:
<221> NAME/KEY: misc_feature
<222> LOCATION: 321, 324, 336, 344, 345, 353, 360, 362, 363, 364, 365,
      366, 370, 373, 389, 391, 392, 394, 395
<223> OTHER INFORMATION: n = A,T,C or G

<400> SEQUENCE: 72

```
tntttttttt tttctaaaac atnactnttt attnnnnang ntttntgaac ctctnngcnt      60
natggtgaga gtttgtctga ttaataanaa tnggannntt nannanangc ntgnncgcaa     120
ngatggcnnc nctgtatatc ccaccatccc attacactnt gaacctttn tttgattaat     180 aaaaggaagg natgcgggga angggggaaag agaatgcttg aacattncca tgngnccttn    240
gacaaacttt ccaatggagg cnggaacnaa nnaccaccan ncaactcccc tttttgtaat    300
ttnnnaactt ncaacnncta nctntttatt ttggcntccc tggnngaaac agnctgtatn    360
annnnnaagn ccntgagaac atccctggnt nncnna                               396
```

<210> SEQ ID NO 73
<211> LENGTH: 396
<212> TYPE: DNA
<213> ORGANISM: Homo sapiens
<220> FEATURE:
<221> NAME/KEY: misc_feature
<222> LOCATION: 1, 7, 9, 14, 23, 35, 38, 44, 48, 50, 61, 74, 76, 79, 80,
      85, 86, 91, 95, 101, 109, 112, 113, 117, 118, 121, 122,
      127, 129, 132, 137, 141, 146, 214, 234, 243, 251, 266, 296,
      305, 306, 336
<223> OTHER INFORMATION: n = A,T,C or G

<400> SEQUENCE: 73

```
ntcaacntng actnctgtga ggnatggtgc tgggngcnta tgcngtgngn ttttggatac     60
naccttatgg acantngcnn tcccnnggaa ngatnataat ncttactgna gnnactnnaa    120
nnttccntnt cnaaaangtt naaaancatt ggatgtgcca caatgatgac agtttatttg    180
ctactcttga gtgctataat gatgaagatc ttanccacca ttatcttaac tgangcaccc    240
aanatggtga nttggggaac atatanagta cacctaagtt cacatgaagt tgtttnttcc    300
caggnnctaa agagcaagcc taactcaagc cattgncaca caggtgagac acctctattt    360
tgtacttctc acttttaagg gattagaaaa tagcca                               396
```

<210> SEQ ID NO 74
<211> LENGTH: 396
<212> TYPE: DNA
<213> ORGANISM: Homo sapiens
<220> FEATURE:
<221> NAME/KEY: misc_feature
<222> LOCATION: 22, 118
<223> OTHER INFORMATION: n = A,T,C or G

<400> SEQUENCE: 74

```
ccttttttt tttttttact gngaatatat acttttatt tagtcatttt tgtttacaat       60
```

```
tgaaactctg ggaattcaaa attaacatcc ttgcccgtga gcttcttata gacaccanaa     120
aaagtttcaa ccttgtgttc cacattgttc tgctgtgctt tgtccaaatg aacctttatg     180
agccggctgc catctagttt gacgcggatt ctcttgccca caatttcgct tgggaagacc     240
aagtcctcaa ggatggcatc gtgcacagct gtcagagtac ggctcctggg acgcttttgc     300
ttattttttg tacggctttt tcgagttggc ttaggcagaa ttctcctctg agcgataaag     360
acgacatgct tcccactgaa cttttttctcc aattcg                              396
```

<210> SEQ ID NO 75
<211> LENGTH: 396
<212> TYPE: DNA
<213> ORGANISM: Homo sapiens
<220> FEATURE:
<221> NAME/KEY: misc_feature
<222> LOCATION: 14, 38, 41, 43, 47, 53, 73, 75, 78, 83, 96, 112, 113,
      117, 124, 127, 146, 160, 167, 169, 176, 177, 178, 179, 194, 197,
      198, 209, 210, 220, 222, 226, 227, 231, 238, 241, 244, 258,
      259, 260, 270, 271, 274, 288, 301, 302, 305, 307, 316
<223> OTHER INFORMATION: n = A,T,C or G
<220> FEATURE:
<221> NAME/KEY: misc_feature
<222> LOCATION: 319, 328, 339, 344, 347, 354, 359, 364, 367, 369, 370,
      371, 373, 374, 381, 384, 387, 388
<223> OTHER INFORMATION: n = A,T,C or G

<400> SEQUENCE: 75

```
ttttttttt tttnttttt tttttttttt ttttttnaa ntntaanggg ganggcccct     60
tttttttaaa ctngnccntt ttncttccct tttttnaaaa ggaaaaaaaa anntttnttt    120
ttcnttnaaa aaccctttt cccacnaaca aaaaaaaccn ttcccntnc cttttnnnna     180 aaaaaaaggg gctnggnntt tcccttann caaaaaaccn tntccnnggg naaaaaantt    240
ntcnccgggg gggaaacnnn tggggggtgtn nccnaaattt ggggggccntc ggaaggggg     300 nnccncncct aaagangtnt ttcaaaanaa aaaccccccnt cctnttntaa aaanaaaana    360
aaanaangnn ngnnttttttt ntcnttnncc ccccaa                              396
```

<210> SEQ ID NO 76
<211> LENGTH: 396
<212> TYPE: DNA
<213> ORGANISM: Homo sapiens
<220> FEATURE:
<221> NAME/KEY: misc_feature
<222> LOCATION: 87, 94, 102, 108, 138, 139, 143, 144, 145, 146, 151,
      152, 158, 168, 170, 171, 187, 204, 206, 224, 261, 262, 267, 268,
      270, 287, 305, 306, 313, 315, 319, 320, 330, 331, 333, 342,
      344, 348, 349, 356, 358, 360, 362, 368, 374, 376, 381
<223> OTHER INFORMATION: n = A,T,C or G
<220> FEATURE:
<221> NAME/KEY: misc_feature
<222> LOCATION: 390
<223> OTHER INFORMATION: n = A,T,C or G

<400> SEQUENCE: 76

```
acattcttca gaaatacagt gatgaaaatt cattttgaaa ctcaaatatt ttcattttgg     60
atattctcct gttttatta aaccagngat tacncctgc cntccctnta aatgttctag     120
gaaggcatgt ctgttgtnnt ttnnnnaaaa nnaaattntt ttttttttngn naaacccccaa  180 atcccanttt atcaggaagt tagncnaatg aaatggaaat tggntaatgg acaaaagcta    240
gcttgtaaaa aggaccaccc nnccacnngn ctttaccccc ttggttngtt ggggaaaaa    300 ccatnnttaa ccntntggnn aaaattgggn ncntaaagtt tncntggnna acagtncntn    360
cngtattnaa ttgncnttat nggaaaatcn gggatt                              396
```

<210> SEQ ID NO 77
<211> LENGTH: 396
<212> TYPE: DNA
<213> ORGANISM: Homo sapiens
<220> FEATURE:
<221> NAME/KEY: misc_feature
<222> LOCATION: 63, 66, 81, 83, 89, 107, 115, 118, 147, 151, 190, 232,
     275, 288, 294, 304, 323, 332, 369, 392
<223> OTHER INFORMATION: n = A,T,C or G

<400> SEQUENCE: 77
tttttttttt tttttttttt tttttttttt tatcaacatt tatatgcttt attgaaagtt      60
ganaanggca acagttaaat ncngggacnc cttacaattg tgtaaanaac atgcncanaa     120
acatatgcat ataactacta tacaggngat ntgcaaaaac ccctactggg aaatccattt     180
cattagttan aactgagcat ttttcaaagt attcaaccag ctcaattgaa anacttcagt     240
gaacaaggat ttacttcagc gtattcagca gctanatttc aaattacnca aagngagtaa     300
ctgngccaaa ttcttaaaat ttntttaggg gnggttttg gcatgtacca gttttatgt      360 aaatctatnt ataaaagtcc acacctcctc anacag                              396

<210> SEQ ID NO 78
<211> LENGTH: 396
<212> TYPE: DNA
<213> ORGANISM: Homo sapiens
<220> FEATURE:
<221> NAME/KEY: misc_feature
<222> LOCATION: 8, 14, 16, 20, 26, 28, 36, 38, 39, 40, 51, 52, 55, 57,
     58, 67, 71, 114, 120, 132, 138, 142, 159, 165, 169, 172, 174,
     175, 183, 187, 195, 197, 198, 200, 202, 206, 209, 243, 259,
     260, 267, 283, 292, 305, 311, 315, 317, 319, 323, 324
<223> OTHER INFORMATION: n = A,T,C or G
<220> FEATURE:
<221> NAME/KEY: misc_feature
<222> LOCATION: 331, 333, 334, 338, 343, 348, 353, 355, 357, 366, 376,
     388
<223> OTHER INFORMATION: n = A,T,C or G

<400> SEQUENCE: 78
agctggcnaa aggngnatgn gctgcnangc gattangnnn ggtaacgtca nnggntnncc      60
agtgcangac nttgtaaaac gacggccaca tgaattgtaa tacgactcac tatngggcgn    120
attgggccgt gnaggatngt gntcacactc gaatgtatnc tggcngatnc ananngcttt    180
atngctnttg acggngnntn anccanctng ggctttaggg ggtatcccct cgcccctgct    240
tcnttgattt gcacgggcnn ctccganttc cttcataata ccngacgctt cnatccccta    300
gctcngacct ntcantntnt tcnntgggtt ntnnccgntc acngcttncc cgnangntat    360
aatctnggct cctttnggga tccattantc tttact                              396

<210> SEQ ID NO 79
<211> LENGTH: 396
<212> TYPE: DNA
<213> ORGANISM: Homo sapiens
<220> FEATURE:
<221> NAME/KEY: misc_feature
<222> LOCATION: 116, 153, 189, 194, 210, 218, 241, 270, 272, 288, 291,
     304, 324, 325, 329, 333, 334, 338, 340, 342, 366, 372, 377, 384,
     396
<223> OTHER INFORMATION: n = A,T,C or G

<400> SEQUENCE: 79
caccaaccaa aacctggcgc cgttggcatc gtagagtgaa cacaacccaa aaacgatacg     60
ccatctgttc tgccctggct gcctcagccc taccagcact ggtcatgtct aaaggncatc    120
gtattgagga agttcctgaa cttcctttgg tangttgaag ataaagctga aggctacaag    180

| | |
|---|---|
| aagaccaang aagntgtttt gctccttaan aaacttanac gcctggaatg atatcaaaaa | 240 |
| ngctatgcct ctcagcgaat gagactggan angcaaaatg agaaaccntc nccgcatcca | 300 |
| gcgnaggggc cgtgcatctc tatnntgang atnntggnan cnttcaaggc cttcagaacc | 360 |
| tccctngaaa tnctctnctt taangaacca aactgn | 396 |

<210> SEQ ID NO 80
<211> LENGTH: 396
<212> TYPE: DNA
<213> ORGANISM: Homo sapiens
<220> FEATURE:
<221> NAME/KEY: misc_feature
<222> LOCATION: 312, 319, 353, 383
<223> OTHER INFORMATION: n = A,T,C or G

<400> SEQUENCE: 80

| | |
|---|---|
| tgtacatagg catcttattc actgcaccct gtcacaccca gcaccccccg ccccgcacat | 60 |
| tatttgaaag actgggaatt taatggttag ggacagtaaa tctacttctt tttccaggga | 120 |
| cgactgtccc ctctaaagtt aaagtcaata caagaaaact gtctattttt agcctaaagt | 180 |
| aaaggctgtg aagaaaattc attttacatt gggtagacag taaaaaacaa gtaaaataac | 240 |
| ttgacatgag cacctttaga tccttccctt catggggctt tgggcccaga atgacctttg | 300 |
| aggcctgtaa anggattgna atttcctata agctgtatag tggagggatt ggnggggtcat | 360 |
| ttgagtaagc cctccaagat acnttcaata cctggg | 396 |

<210> SEQ ID NO 81
<211> LENGTH: 396
<212> TYPE: DNA
<213> ORGANISM: Homo sapiens
<220> FEATURE:
<221> NAME/KEY: misc_feature
<222> LOCATION: 240, 286, 361, 364, 374, 375, 379, 380, 381, 387
<223> OTHER INFORMATION: n = A,T,C or G

<400> SEQUENCE: 81

| | |
|---|---|
| gcagctgaag ttcagcaggt gctgaatcga ttctcctcgg ccctctcat tccacttcca | 60 |
| accctccca ttattccagt actacctcag caatttgtgc ccctacaaa tgttagagac | 120 |
| tgtatacgcc ttcgaggtct tccctatgca gccacaattg aggacatcct gcatttcctg | 180 |
| ggggagttcg ccacagatat tcgtactcat ggggttcaca tggttttgaa tcaccagggn | 240 |
| ccgccatcag gagatgcctt tatccagatg aagtctgcgg acagancatt tatggctgca | 300 |
| cagaagtggc ataaaaaaaa catgaaggac agatatgttg aagttttcag tgtcagctga | 360 |
| nganagaaca ttgnngtann nggggnact ttaaat | 396 |

<210> SEQ ID NO 82
<211> LENGTH: 396
<212> TYPE: DNA
<213> ORGANISM: Homo sapiens
<220> FEATURE:
<221> NAME/KEY: misc_feature
<222> LOCATION: 220, 251, 297, 301, 309, 349, 395
<223> OTHER INFORMATION: n = A,T,C or G

<400> SEQUENCE: 82

| | |
|---|---|
| gactcagaaa tgtcagtctc atgaagttca aaagatcgag aatgtttgct atcttggtgg | 60 |
| agcagccgca gccaagcaag taacttgtaa aatgaggaat gccatcaccc ctcgagtgtc | 120 |
| catcccacat aacttgggt tagagcacaa gcgttcccag gaactactca ccttaccatc | 180 |
| ttggccgttt catttgcttc caccagttct ggaaagagan ggcctagaag ttcaaaaaaa | 240 | aagtaggaaa ngtgcttttg gagaaaatca cctgctcctc agaactgggc ttacaanctg    300 ngaagtacnc tatgtgccac ctaatcctca tatatgacct caagagacnc caataagcat    360 atttccacca cggaatgacc agtgctttgg gtaana                              396

<210> SEQ ID NO 83
<211> LENGTH: 396
<212> TYPE: DNA
<213> ORGANISM: Homo sapiens
<220> FEATURE:
<221> NAME/KEY: misc_feature
<222> LOCATION: 13, 372, 379, 393
<223> OTHER INFORMATION: n = A,T,C or G

<400> SEQUENCE: 83
tttgatttaa ganatttatt attttttttaa aaaaagcaac ttccagggtt gtcattgtac    60
aggttttgcc cagtctccta tagcatggta tagtgataac tgattttta taacaatgac    120 tcagaggcat tgaagatcca taactatctt ctgaattatc acagaaagaa gaaagttaga    180
agagtttaat gttaagtgta ttaaaaatca tattctaatt cttttaattt ggttatctga    240
gtatgataat ataggagagc tcagataaca aggaaaaggc attggggtaa gaacactcct    300
tcccacagga tggcattaac agactttttc tgcatatgct ttatatagtt gccaactaat    360 tcaccttttta cncagcttna tttttttttta ctnggg                            396

<210> SEQ ID NO 84
<211> LENGTH: 396
<212> TYPE: DNA
<213> ORGANISM: Homo sapiens
<220> FEATURE:
<221> NAME/KEY: misc_feature
<222> LOCATION: 61, 232, 254, 270, 271, 286, 354, 356, 368, 374, 389,
      394
<223> OTHER INFORMATION: n = A,T,C or G

<400> SEQUENCE: 84
tttttacagc aattttttttt tattgatgtt taacctgtat acaaccatac ccatttttaag   60 ngtacagaca aatgaatttt gacaaattca ttcactcatc taatcatcac tataaccatg    120
atacagattt ttatcactcc aaaagtccat cctgtgctct tttcaagtcc atcctcctca    180
tctgataccc caagccacca ttgttttgct ttctggaact acagttttgg gnttttagaa    240
tttcatatat ggtngaatca taccatttgn natttggggc tgacgncttt cctccaataa    300
tggatttgag aattatctac attttgcatg gatcctgggt tatttatacc aacnangggt    360
tattatgnaa aatnggacca caatttggng gcanta                              396

<210> SEQ ID NO 85
<211> LENGTH: 396
<212> TYPE: DNA
<213> ORGANISM: Homo sapiens
<220> FEATURE:
<221> NAME/KEY: misc_feature
<222> LOCATION: 293, 305, 306, 317, 347, 357, 372, 377, 386, 391
<223> OTHER INFORMATION: n = A,T,C or G

<400> SEQUENCE: 85
cagtgaccgt gctcctaccc agctctgctc cacagcgccc acctgtctcc gccctcggc     60 ccctcgcccg gctttgccta accgccacga tgatgttctc gggcttcaac gcagactacg   120
aggcgtcatc ctcccgctgc agcagcgcgt cccggccgg ggatagcctc tcttactacc    180
actcacccgc agactccttc tccagcatgg gctcgcctgc aacgcgcagg acttctgcac   240

```
ggacctggcc gctccagtgc caacttcatt ccacggcact gcatctcgac canccggact    300
tgcannggtt ggggaanccg cccttgtttc tccgtggccc atctaanacc aaacccntca    360 cctttcgga gnccccnccc ctccgntggg nttact                               396
```

<210> SEQ ID NO 86
<211> LENGTH: 396
<212> TYPE: DNA
<213> ORGANISM: Homo sapiens
<220> FEATURE:
<221> NAME/KEY: misc_feature
<222> LOCATION: 5, 6, 28, 50, 58, 90, 108, 110, 118, 145, 154, 194, 244,
      285, 292, 300, 312, 315, 342, 344, 346, 359, 374, 378, 380,
      396
<223> OTHER INFORMATION: n = A,T,C or G

<400> SEQUENCE: 86

```
ttttnnactg aatgtttaat acatttgnag gaacagaaga aatgcagtan ggattaanat    60
tttataatta gacattaatg taacagatgn ttcatttttc aaagaagntn ccccttntc    120 cctatctttt tttaatcttc cttanagcaa taantagtaa ttactatatt tgtggacaag   180
ctgctccact gtgntggaca gtaattatta aatctttatg tttcacatca ttattacctt   240
ccanaattct accttcattt ccctgcacag gttcactgga ctggntcaca ancaaattgn   300
actccactca antanaagag cccaaagaaa ttagagtaac gncnantcct atgaattana   360
gacccaaaga tttnaggngn tgattagaaa cataan                             396
```

<210> SEQ ID NO 87
<211> LENGTH: 396
<212> TYPE: DNA
<213> ORGANISM: Homo sapiens
<220> FEATURE:
<221> NAME/KEY: misc_feature
<222> LOCATION: 231, 277, 285, 296, 341, 351, 372, 377, 380
<223> OTHER INFORMATION: n = A,T,C or G

<400> SEQUENCE: 87

```
atggaggcgc tggggaagct gaagcagttc gatgcctacc ccaagacttt ggaggacttc    60
cgggtcaaga cctgcggggg cgccaccgtg accattgtca gtggccttct catgctgcta   120
ctgttcctgt ccgagctgca gtattacctc accacggagg tgcatcctga gctctacgtg   180
gacaagtcgc ggggagataa actgaagatc aacatcgatg tacttttttcc ncacatgcct   240 tgtgcctatc tgagtattga tgccatggat gtggccngag aacancagct ggatgnggaa   300
cacaacctgt ttaagccacc actagataaa gatgcatccc ngtgagctca nagctgagcg   360
gcatgagctt gngaaantcn aggtgaccgg gtttga                             396
```

<210> SEQ ID NO 88
<211> LENGTH: 396
<212> TYPE: DNA
<213> ORGANISM: Homo sapiens
<220> FEATURE:
<221> NAME/KEY: misc_feature
<222> LOCATION: 246, 266, 301, 328, 347, 349, 368, 370, 371, 374, 379,
      387, 391
<223> OTHER INFORMATION: n = A,T,C or G

<400> SEQUENCE: 88

```
tccagagcag agtcagccag catgaccgag cgccgcgtcc ccttctcgct cctgcggggc    60
cccagctggg acccctccg cgactggtac ccgcatagcc gctcttcgac caggccttcg   120
ggctgccccg gctgccggag gagtggtcgc agtggttagg cggcagcagc tggccaggct   180
acgtgcgccc cctgccccccc gccgcatcga gagcccccgca gtggccgcgc ccgctacagc   240
```

```
cgcgcngctc agccggcaac tcacancggg gctcggagat ccgggacact gcggaccgct      300
ngcgcgtgcc ctggatgtca ccactttngc ccggacaact gacggtnana caaggatggg      360
gggtgganan nccngtaanc caagaanggg naggac                                396
```

<210> SEQ ID NO 89
<211> LENGTH: 396
<212> TYPE: DNA
<213> ORGANISM: Homo sapiens
<220> FEATURE:
<221> NAME/KEY: misc_feature
<222> LOCATION: 37, 76, 230, 295, 306, 333, 346, 370, 376, 377, 395
<223> OTHER INFORMATION: n = A,T,C or G

<400> SEQUENCE: 89

```
gagagaacag taaacatcca gccttagcat ctctcangag tactgcagat cttcattagc      60
tatattcaca tggagnaatg ctattcaacc tatttctctt atcaaaacta attttgtatt     120
ctttgaccaa tgttcctaaa ttcactctgc ttctctatct caatcttttt cccctttctc     180
atctttcctc cttttttcag tttctaactt tcactggttc tttggaatgn tttttctttc     240
atctcttttc tttacatttt tggggtgtcc cctctctttt cttaccctct ttctncatcc     300
ttcttnttct tttgaattgg ctgcccttta tcntctcatc tgctgncatc ttcatttctc     360
ctccctcctn tttccnntca ttctactctc tcccnt                               396
```

<210> SEQ ID NO 90
<211> LENGTH: 396
<212> TYPE: DNA
<213> ORGANISM: Homo sapiens
<220> FEATURE:
<221> NAME/KEY: misc_feature
<222> LOCATION: 82, 110, 115, 120, 121, 125, 126, 129, 131, 140, 141,
      144, 145, 146, 148, 149, 150, 153, 154, 157, 158, 160, 161, 163,
      164, 166, 170, 172, 173, 174, 175, 179, 182, 184, 189, 193,
      194, 195, 200, 206, 213, 215, 217, 218, 219, 220, 227
<223> OTHER INFORMATION: n = A,T,C or G
<220> FEATURE:
<221> NAME/KEY: misc_feature
<222> LOCATION: 228, 231, 233, 236, 241, 247, 248, 249, 250, 254, 259,
      262, 269, 273, 274, 275, 280, 281, 282, 286, 287, 289, 293, 294,
      301, 302, 304, 309, 311, 318, 319, 324, 325, 330, 331, 333,
      334, 336, 337, 341, 342, 343, 344, 349, 352, 353, 358
<223> OTHER INFORMATION: n = A,T,C or G
<220> FEATURE:
<221> NAME/KEY: misc_feature
<222> LOCATION: 361, 365, 367, 373, 377, 381, 385, 386, 387, 392
<223> OTHER INFORMATION: n = A,T,C or G

<400> SEQUENCE: 90

```
gggcgccggc gcgccccccc acccccgccc cacgtctcgt cgcgcgcgcg tccgctgggg      60
gcggggagcg gtcgggccgg cngcggtcgg ccggcggcag ggtggtgcgn tttcntttn      120 nattnnccnc nttcttcttn nttnnncnnn ctnntanncn ntnncnttcn cnnnntttnc     180
tntntcttna ccnnntttn taatcntctt ctncntnnnn tctcttnnat ntnttnctta     240
nttcctnnnn tttnttctnt cntttctcnc ctnnntctcn nnctcnncnc tcnncatttt     300
nntnttttnt nccttctnnt cttnnttctn ntnntnnttt nnnnttctnt tnntcatntt     360
ncctntntta ctntcanctt ntatnnncct cntttt                               396
```

<210> SEQ ID NO 91
<211> LENGTH: 396
<212> TYPE: DNA
<213> ORGANISM: Homo sapiens
<220> FEATURE:
<221> NAME/KEY: misc_feature
<222> LOCATION: 1, 3, 8, 9, 16, 17, 18, 21, 22, 32, 33, 45, 50, 63, 64,
      68, 75, 82, 92, 95, 98, 102, 106, 108, 110, 111, 116, 121, 135,
      151, 154, 158, 162, 167, 170, 176, 181, 185, 187, 209, 212,
      215, 225, 231, 245, 257, 278, 283, 288, 290, 292, 293
<223> OTHER INFORMATION: n = A,T,C or G
<220> FEATURE:
<221> NAME/KEY: misc_feature
<222> LOCATION: 312, 324, 326, 330, 331, 333, 334, 344, 345, 349, 351,
      352, 357, 358, 382, 384, 390, 392
<223> OTHER INFORMATION: n = A,T,C or G

<400> SEQUENCE: 91

```
ntntcctnna ttttnnntc nncttttttt tnnaatttttt ctttnttttn tttataaaaa    60
tcnncacnta aaacngcgga anaggggatt tnttnttngg gngtancncn nggccncaaa   120
naacccaaa aatancccaa aatgcacagg nccngggnaa angaccnacn tgggtntttt   180
ntttntnaac aaggggggtt ttaaagggna tnggnatcaa agggnataaa ntttaaacct   240
ttganaaatt ttttaanagg cttgcccccc actttggncc ccnccccncn gnngggatcc   300
aattttttttt cnttgggggct cccngncccn nannttccgg gttnntggnc nntcctnntt   360
tttttttttt tgccttcacc cntnccattn cntttt                              396
```

<210> SEQ ID NO 92
<211> LENGTH: 396
<212> TYPE: DNA
<213> ORGANISM: Homo sapiens
<220> FEATURE:
<221> NAME/KEY: misc_feature
<222> LOCATION: 3, 7, 8, 9, 11, 31, 149, 152, 221, 233, 259, 263, 264,
      265, 266, 274, 278, 279, 283, 286, 294, 302, 307, 309, 310, 311,
      314, 316, 320, 343, 351, 363, 372, 377, 386, 393
<223> OTHER INFORMATION: n = A,T,C or G

<400> SEQUENCE: 92

```
ctntttnnnt nttttttttcc ccatcatcca naaatgggtt ttattctcag ccgagggaca    60
gcaggactgg taaaaactgt caggccacac ggttgcctgc acagcacccc catgcttggt   120
aggggggtggg agggatggcg ggggctggnt gnccacaggc cgggcatgac aaggaggctc   180
actggaggtg gcacactttg gagtgggatg tcgggggaca ncttctttgg tanttgggcc   240
acaagattcc caaggatanc acnnnnactg attnccannc tanagncaag cggntggcca   300
tntgtangnn nttntntatn tgactattta tagattttta tanaacaggg naagggcata   360
ccncaaaagg gnccaantttt ttaccnccgg gcncc                              396
```

<210> SEQ ID NO 93
<211> LENGTH: 396
<212> TYPE: DNA
<213> ORGANISM: Homo sapiens
<220> FEATURE:
<221> NAME/KEY: misc_feature
<222> LOCATION: 290, 304, 313, 320, 325, 333, 337, 348, 351
<223> OTHER INFORMATION: n = A,T,C or G

<400> SEQUENCE: 93

```
gctgccacag atctgttcct tgtccgtttt tgggatcca caggccctat gtatttgaag    60
ggaaatgtgt atggctcaga tccttttga aacatatcat acaggttgca gtcctgaccc   120
aagaacagtt ttaatggacc actatgagcc cagttacata agaaaaagg agtgctaccc   180
atgttctcat ccttcagaag aatcctgcga acggagcttc agtaatatat cgtggcttca   240
catgtgagga agctacttaa cactagttac tctcacaatg aaggacctgn aatgaaaaat   300
ctgnttctaa ccnagtcctn tttanatttt agngcanatc cagaccancg ncggtgctcg   360
agtaattctt tcatgggacc tttggaaaac tttcag                              396
```

<210> SEQ ID NO 94
<211> LENGTH: 396
<212> TYPE: DNA
<213> ORGANISM: Homo sapiens
<220> FEATURE:
<221> NAME/KEY: misc_feature
<222> LOCATION: 115, 204, 205, 243, 266, 276, 316, 319, 355, 357, 364
<223> OTHER INFORMATION: n = A,T,C or G

<400> SEQUENCE: 94
tgccttaacc agtctctcaa gtgatgagac agtgaagtaa aattgagtgc actaaacgaa     60
taagattctg aggaagtctt atcttctgca gtgagtatgg cccaatgctt tctgnggcta    120
aacagatgta atgggaagaa ataaaagcct acgtgttggt aaatccaaca gcaagggaga    180
tttttgaatc ataataactc atanngtgct atctgtcagt gatgccctca gagctcttgc    240
tgntagctgg cagctgacgc ttctangata gttagnttgg aaatggtctt cataataact    300
acacaaggaa agtcanccnc cgggcttatg aggaattgga cttaataaat ttagngngct    360
tccnacctaa aatatatctt ttggaagtaa aattta                              396

<210> SEQ ID NO 95
<211> LENGTH: 396
<212> TYPE: DNA
<213> ORGANISM: Homo sapiens
<220> FEATURE:
<221> NAME/KEY: misc_feature
<222> LOCATION: 11, 16, 31, 36, 42, 49, 53, 56, 57, 60, 67, 70, 84, 89,
      91, 92, 99, 105, 106, 112, 120, 121, 125, 127, 128, 133, 137,
      141, 151, 152, 153, 154, 155, 162, 166, 167, 168, 174, 177,
      179, 186, 188, 194, 195, 199, 203, 205, 213, 217, 221
<223> OTHER INFORMATION: n = A,T,C or G
<220> FEATURE:
<221> NAME/KEY: misc_feature
<222> LOCATION: 227, 232, 235, 236, 240, 242, 260, 261, 265, 266, 291,
      297, 318, 325, 330, 339, 348, 351, 352, 354, 356, 362, 364, 372,
      380, 392, 395, 396
<223> OTHER INFORMATION: n = A,T,C or G

<400> SEQUENCE: 95
cctcccaccc ncttanttca tgagattcga naatgncact tntgtgctnt ttnctnnttn     60
tattctnacn atttctttct tggngcggna nnaatcccnt ttttnnggge gnctctcccn    120 ncttntnntt tcntggngct ntcccttttc nnnnnaaact tntacnnngt ttanaantnt    180
ttctgnangg gggnntccna aananttttt ccncctncct nattccnctc tnaannctcn    240
cnaattgttt cccccccccn ntagnntatt ttttctaaaa aattaactcc nacgganaaa    300
attttcccta aaatttcncc tccanatttn gaaaaaacnc gcccggannct nntntncgaa    360 tntnaatttt tnaaaaaaan ttattttcat cnggnn                              396

<210> SEQ ID NO 96
<211> LENGTH: 396
<212> TYPE: DNA
<213> ORGANISM: Homo sapiens
<220> FEATURE:
<221> NAME/KEY: misc_feature
<222> LOCATION: 161, 193, 253, 259, 281, 288, 299, 309, 318, 319, 335,
      340, 344, 352, 355, 356, 387, 396
<223> OTHER INFORMATION: n = A,T,C or G

<400> SEQUENCE: 96
cctgggtacc aaatttcttt atttgaagga atggtacaaa tcaaagaact taagtggatg     60
ttttggacaa cttatagaaa aggtaaagga aaccccaaca tgcatgcact gccttggcga    120
ccagggaagt caccccacgg ctatggggaa attagcccga ngcttaactt tcattatcac    180

```
tgcttccaag ggngtgcttg gcaaaaaaat attccgccaa ccaaatcggg cgctccatct      240
tgcccagttg gtnccgggnc cccaattctt ggatgctttc ncctcttntt ccggaatgng      300
ctcatgaant cccccaanng gggcattttg ccagnggccn tttngccatt cnagnnggcc      360
tgatccattt tttccaatgt aatgccnctt cattgn                                396
```

<210> SEQ ID NO 97
<211> LENGTH: 396
<212> TYPE: DNA
<213> ORGANISM: Homo sapiens
<220> FEATURE:
<221> NAME/KEY: misc_feature
<222> LOCATION: 13, 15, 16, 19, 23, 31, 38, 39, 41, 45, 68, 94, 95, 100,
      119, 131, 133, 141, 144, 164, 171, 182, 186, 190, 191, 195,
      196, 198, 213, 229, 231, 235, 239, 247, 257, 265, 269, 272,
      278, 279, 286, 289, 291, 306, 309, 310, 312, 317, 320
<223> OTHER INFORMATION: n = A,T,C or G
<220> FEATURE:
<221> NAME/KEY: misc_feature
<222> LOCATION: 321, 327, 328, 337, 340, 343, 351, 360, 361, 368, 375,
      381, 385, 386, 387, 388
<223> OTHER INFORMATION: n = A,T,C or G

<400> SEQUENCE: 97

```
ctcaccctcc tcntnnttnt canaatattg ngaacttnnt nctgntcgaa tcactggcat      60
taaagganca ctagctaatg gcactaaatt tacnnactan ggaaactttt ttataatant     120
gcaaaaacat ntnaaaaaga ntgnagttcg cccatttctg cttnggaaga nctcttcact     180
tntaancccn natgnngncc tttgggtcaa aanctccgcg attattacng ngttncccnc     240
tatttgncct tcctttntcc ccaangccnc anatttcnna actttnccnt naaatgcctt     300
tatttnatnn cntttcnacn ncttaannt ccctttnaan aangatccct ncttcaaatn     360
ntttcccngt tcctngcatt ncccnnnnat ttctct                               396
```

<210> SEQ ID NO 98
<211> LENGTH: 396
<212> TYPE: DNA
<213> ORGANISM: Homo sapiens
<220> FEATURE:
<221> NAME/KEY: misc_feature
<222> LOCATION: 130, 202, 285, 296, 299, 308, 314, 321, 322, 336, 373
<223> OTHER INFORMATION: n = A,T,C or G

<400> SEQUENCE: 98

```
acagggacaa tgaagccttt gaagtgccag tctatgaaga ggccgtggtg ggactagaat      60
cccagtgccg cccccaagag ttggaccaac caccccctac agcactgttg tgatacccc     120 agcacctgan gaggaacaac ctaccatcca gaggggccag gaaaagccaa actggaacag    180
aggcgaatgg ctcagagggg tncatggcca agaaggaagc cctggaagaa cttcaatcac    240
cttcggtttc gggaccaccg gcttgtgtcc ctgttctgac tgcanaactt ggcgcngtnc    300
cccattanaa cctntgactc nncccttgct ataagnctgt tttggcccct gatgatgata    360 gggttttat gangacactt gggcacccc ttaatg                                 396
```

<210> SEQ ID NO 99
<211> LENGTH: 396
<212> TYPE: DNA
<213> ORGANISM: Homo sapiens
<220> FEATURE:
<221> NAME/KEY: misc_feature
<222> LOCATION: 1, 4, 13, 15, 26, 31, 43, 46, 48, 52, 54, 55, 60, 62,
      68, 72, 93, 112, 118, 119, 122, 131, 132, 133, 134, 145, 147,
      152, 157, 163, 164, 186, 190, 225, 231, 239, 246, 247, 250,
      255, 262, 285, 314, 316, 319, 325, 332, 339, 343, 345

<223> OTHER INFORMATION: n = A,T,C or G
<220> FEATURE:
<221> NAME/KEY: misc_feature
<222> LOCATION: 348, 351, 352, 355, 357, 361, 370, 387
<223> OTHER INFORMATION: n = A,T,C or G

<400> SEQUENCE: 99 nttnttttc cgncnaaagg gcaagngttt ncatctttcc tgnccncnca ananngggtn     60
tntgtgcntt tnttttttcc caaaacccgg gtngggaca cctttgagg anccactnnt   120 cntccgggc nnnnttttag aaggngncta anaagcntct tgnngggga aaaacatctt    180 tttgcnccn acataccccc aaggggggg ggtgtctgg agganactaa ngacttttnt    240 tttttnncn caaanaactg anggccccca ttgctccccc cccantcttt aaaaaacccc   300
ttcaatttcc ttgncnggna aaaanggttg gnaaaaaang agngngcntc nnttncnttt   360
natggaaggn aaaaggtttt tggttgnaaa accccg                            396

<210> SEQ ID NO 100
<211> LENGTH: 396
<212> TYPE: DNA
<213> ORGANISM: Homo sapiens
<220> FEATURE:
<221> NAME/KEY: misc_feature
<222> LOCATION: 229, 286, 303, 312, 334, 335, 348, 350, 357, 364, 371, 395
<223> OTHER INFORMATION: n = A,T,C or G

<400> SEQUENCE: 100
ctaacacggt gaaaccctgt ctctactaaa aatacaaaaa aattagccag gcgtggtggc     60
gggcacctgt agtcccagct gctcaggaag ctgaggcagg agaatggcgt gaacccagaa   120
ggcggagctt gcagtgagct gagatcgtgt cagtgcactc cagcctgggc gacagagcga   180
gactcccgct caaaaaaaaa aaaaaaaga gaaagaaaa agctgcagng agctgggaat    240
gggccctatc ccctccttgg ggatcaatga gaccccttt caaanaaaa aaaaaaataa   300 tgngattttg gnaacatatg gcactggtgc ttcnnggaat tctgttttntn ggcatgnccc   360 cctntgactg nggaaaaatc cagcaggagg cccana                            396

<210> SEQ ID NO 101
<211> LENGTH: 396
<212> TYPE: DNA
<213> ORGANISM: Homo sapiens
<220> FEATURE:
<221> NAME/KEY: misc_feature
<222> LOCATION: 93, 99, 100, 111, 168, 172, 174, 199, 209, 216, 218, 219, 227, 242, 243, 269, 272, 297, 300, 301, 308, 315, 317, 323, 331, 341, 344, 348, 357, 359, 363, 364, 366, 376, 379, 386, 389, 392
<223> OTHER INFORMATION: n = A,T,C or G

<400> SEQUENCE: 101
agttataact caacagttca tttatatgct gttcatttaa cagttcattt aaacagttca     60
ttataactgt ttaaaatat atatgcttat agncaaaann tgttgtggcg nagttgttgc   120
cgcttatagc tgagcattat ttcttaaatt cttgaatgtt cttttggngg gntnctaaaa   180
ccgtatatga tccattttna tgggaaacng aattcntnnc attatcncac cttggaaata   240
cnnaacgtgg gggaaaaaaa tcattcccnc cntccaaaac tatacttctt ttatctngan   300
nttcttgntc ctgcncnggt ttngaatata nctgggcaaa nggntttncc aaatccntnt   360
acnntncttt gggaantanc ggcaantcnt cncttt                            396

<210> SEQ ID NO 102

```
<211> LENGTH: 396
<212> TYPE: DNA
<213> ORGANISM: Homo sapiens
<220> FEATURE:
<221> NAME/KEY: misc_feature
<222> LOCATION: 17, 93, 136, 183, 317
<223> OTHER INFORMATION: n = A,T,C or G

<400> SEQUENCE: 102
actatacata agaacangct cacatgggag gctggaggtg ggtacccagc tgctgtggaa      60
cgggtatgga caggtcataa acctagagtc agngtcctgt tggcctagcc catttcagca     120
ccctgccact tggagnggac ccctctactc ttcttagcgc ctaccctcat acctatctcc     180
ctnctcccat ctcctacgga ctggcgccaa atggctttcc tgccaatttt gggatcttct     240
ctggctctcc agcctgctta ctcctctatt tttaaagggc caaacaaatc ccttctcttt     300
ctcaaacaca gtaatgnggc actgaccota ccacacctca tgaaggggc ttgttgcttt      360 tatttgggcc cgatctgggg ggggcaaaat attttg                              396

<210> SEQ ID NO 103
<211> LENGTH: 396
<212> TYPE: DNA
<213> ORGANISM: Homo sapiens
<220> FEATURE:
<221> NAME/KEY: misc_feature
<222> LOCATION: 91, 174, 176, 188, 201, 214, 254, 277, 299, 325, 349,
      355, 365, 372, 390
<223> OTHER INFORMATION: n = A,T,C or G

<400> SEQUENCE: 103
ttgtgttggg actgctgata ggaagatgtc ttcaggaaat gctaaaattg ggcaccctgc      60
cccaacttca aagccacagc tggtatgcca natggtcagg ttaaagatat caacctgctg     120
actacaaagg aaaatatggt ggggtcttct tttaccctct tgacttccct ttgngngccc     180
cccgaganca ttgctttccg ngatagggca aaanaaatta aaaaacttaa ctggccagtg     240
aatgggcttt ctgnggatct ccttctggca ttacatnggc aatccctaaa aaacaagang     300
actgggaccc ataacattct tttgnatcaa ccgaagcccc cattgttang atatngggct     360
taaangctga tnaagcatct cgtccgggcn ttttat                              396

<210> SEQ ID NO 104
<211> LENGTH: 396
<212> TYPE: DNA
<213> ORGANISM: Homo sapiens
<220> FEATURE:
<221> NAME/KEY: misc_feature
<222> LOCATION: 32, 53, 86, 141, 154, 156, 181, 182, 197, 204, 219, 224,
      226, 229, 232, 245, 253, 260, 262, 271, 273, 276, 292, 301,
      303, 305, 321, 325, 332, 343, 352, 382, 392
<223> OTHER INFORMATION: n = A,T,C or G

<400> SEQUENCE: 104
aagggagggc gcgccaagac cttcccactc gngcacactg ggggcgccga cangacgcaa      60
cccagtccaa cttggatacc cttggnttta gttctcggac acttcttta tctctccgtc     120 gcaacttgtc aagttctcaa nactgtctct ctgngntatc tttttttcttc gctgctcttc   180 nnccccogac gtatttntca aaangtctgc aattgttgna tacntngana tncaccactg    240
ttacnaggtc atnaatttcn cntcaactct ntnccncttg ttccctgata tntcggccgg    300
ngncnccaat tctgtatttt nctcntcaac gntctcactt ttnccctcctc cnggccactt    360 tctcccttc cttattccgg cnttgttgc cnccat                                396
```

<210> SEQ ID NO 105
<211> LENGTH: 396
<212> TYPE: DNA
<213> ORGANISM: Homo sapiens
<220> FEATURE:
<221> NAME/KEY: misc_feature
<222> LOCATION: 57, 306, 356, 388, 391
<223> OTHER INFORMATION: n = A,T,C or G

<400> SEQUENCE: 105
tcaatagcca gccagtgttc attttatcc ttgagctttt agtaaaaact tcctggnttt      60
atttttagtc attgggtcat acagcactaa agtctgctat ttatggaaac taactttttt     120
gtttttaatc caggccaaca tgtatgtaaa ttaaattttt agataattga ttatctcttt     180
gtactacttg agatttgatt atgagatgtg catattgctt tgggaagagc tcgaggaagg     240
aaataattct ctcctttggt ttgaacctca actagataaa ccctaggaat tgttaactgc     300
acaagnattt tcattccaca aaacctgagg cagctctttt gccagagcgt tcctgnaccc     360
ccccacccca cttgccttgg gtctttanaa ngagcc                              396

<210> SEQ ID NO 106
<211> LENGTH: 396
<212> TYPE: DNA
<213> ORGANISM: Homo sapiens

<400> SEQUENCE: 106
gctgtgtagc acactgagtg acgcaatcaa tgtttactcg aacagaatgc atttcttcac      60
tccgaagcca aatgacaaat aaagtccaaa ggcattttct cctgtgctga ccaaccaaat     120
aatatgtata gacacacaca catatgcaca cacacacaca cacacccaca gagagagagc     180
tgcaagagca tggaattcat gtgtttaaag ataatccttt ccatgtgaag tttaaaatta     240
ctatatattt gctgatggct agattgagag aataaaagac agtaaccttt ctcttcaaag     300
ataaaatgaa aagcaattgc tcttttcttc ctaaaaaatg caaagatttt acattgctgc     360
caaatcattt caactgaaaa gaacagtatt gctttg                              396

<210> SEQ ID NO 107
<211> LENGTH: 396
<212> TYPE: DNA
<213> ORGANISM: Homo sapiens
<220> FEATURE:
<221> NAME/KEY: misc_feature
<222> LOCATION: 12, 210, 257, 261, 271, 302, 311, 314, 318, 368, 374,
       385, 389, 396
<223> OTHER INFORMATION: n = A,T,C or G

<400> SEQUENCE: 107
ttcacagaac anggtggttt attatttcaa tagcaaagag ctgaaaaatg tcgggtccca      60
taaaggagca gaacctgacc cagagcctgc agtacatttc caccccacag gggtgcaggc     120
tgggccaggc agggccaaag gcagcagaaa tgggagtaag agactgtgcc cactgagaag     180
ctctgctggg tgtgggcagg tgggcatgan atgatgatga tgtagtgtaa ggaccaggta     240
ggcaaaacct gtcaggnttg ntgaatgtca nagtggatcc aaaaggctga ggggtcgtc     300 anaaggccgg nggncccncc cttgcccgta tgggccttca aaaagtatgc ttgctcatcc     360
gttgtttncc ccanggagct gccanggana aggctn                              396

<210> SEQ ID NO 108
<211> LENGTH: 396
<212> TYPE: DNA
<213> ORGANISM: Homo sapiens
<220> FEATURE:

```
<221> NAME/KEY: misc_feature
<222> LOCATION: 280, 281, 286, 305, 311, 313, 323, 326, 327, 340, 352,
      356, 363, 369, 378, 388, 392
<223> OTHER INFORMATION: n = A,T,C or G

<400> SEQUENCE: 108
gcctgctttt gatgatgtct acagaaaatg ctggctgagc tgaacacatt tgcccaattc      60
caggtgtgca cagaaaaccg agaatattca aaattccaaa ttttttttctt aggagcaaga    120 agaaaatgtg gccctaaagg gggttagttg aggggtaggg ggtagtgagg atcttgattt    180
ggatctcttt ttatttaaat gtgaatttca acttttgaca atcaaagaaa agactttttgt   240 tgaaatagct ttactgcttc tcacgtgttt tggagaaaan natcanccct gcaatcactt    300
tttgnaactg ncnttgattt tcngcnncca agctatatcn aatatcgtct gngtanaaaa    360
tgncctggnc ttttgaanga atacatgngt gntgct                              396

<210> SEQ ID NO 109
<211> LENGTH: 396
<212> TYPE: DNA
<213> ORGANISM: Homo sapiens
<220> FEATURE:
<221> NAME/KEY: misc_feature
<222> LOCATION: 237, 279, 284, 291, 305, 307, 308, 313, 326, 343, 351,
      366, 376, 392, 394, 395
<223> OTHER INFORMATION: n = A,T,C or G

<400> SEQUENCE: 109
ggccgtaggc agccatggcg cccagcccgg aatggcatgg tcttgaagcc ccacttccac      60
aaggactggc agcggcgcgt ggccacgtgg ttcaaccagc cggcccggaa gatccgcaga    120
cgtaaggccc ggcaagccaa ggcgcgccgc atcgctccgc gccccgcgtc gggtcccatc    180
cggcccatcg tgcgctgccc acggttcggt accacacgaa gggcgcgccg gcgcggnttc    240
agcctggagg agctcaggt ggccggattt acaagaagng gccngacatc ngtattcttg    300
ggatncnnga agnggaacaa gtcacngagt ccttgcagcc acntcagcgg ntgatgacac    360
cgttcnaact catctnttcc caagaaacct cngnnc                              396

<210> SEQ ID NO 110
<211> LENGTH: 396
<212> TYPE: DNA
<213> ORGANISM: Homo sapiens
<220> FEATURE:
<221> NAME/KEY: misc_feature
<222> LOCATION: 1, 2, 12, 13, 16, 18, 29, 39, 60, 66, 70, 86, 90, 104,
      121, 122, 127, 128, 146, 165, 171, 172, 173, 176, 188, 189, 193,
      195, 205, 210, 211, 224, 226, 227, 231, 233, 240, 243, 244,
      248, 249, 255, 257, 258, 260, 266, 268, 272, 273, 275
<223> OTHER INFORMATION: n = A,T,C or G
<220> FEATURE:
<221> NAME/KEY: misc_feature
<222> LOCATION: 278, 280, 287, 292, 294, 303, 308, 312, 315, 320, 322,
      332, 333, 334, 335, 345, 347, 351, 363, 364, 369, 371, 372, 379,
      381, 382, 386, 391, 393
<223> OTHER INFORMATION: n = A,T,C or G

<400> SEQUENCE: 110
nntgggctcc tnncantnat aataaaccng actcatacnc cacaaggaga tgaacaggan      60
tatgtncatn ctgacgcgga aacagngcan ggagctgagg aggngccaag atgagaccta    120
nnggccnngg tgggcgcatt cccggnggag ggggccacta aggantacga nnntcnagcg    180
gctcttgnng gcngncctcc tcacncctgn ntattcgatt gtcncnnatg ncntcctatn    240
atnntcanna ttctntnntn atctcntnta cnncntcncn ttcatgntta cngntccctc    300
tcnttctnac cnttntctgn anctcctttc tnnnncttc atctntntttc ngctttctttt    360
```
ctnnaatcnt nntttaacnt nntctncttt ntnatt                              396

<210> SEQ ID NO 111
<211> LENGTH: 396
<212> TYPE: DNA
<213> ORGANISM: Homo sapiens
<220> FEATURE:
<221> NAME/KEY: misc_feature
<222> LOCATION: 4, 7, 11, 16, 19, 25, 26, 30, 33, 39, 54, 60, 69, 75,
      81, 99, 102, 130, 132, 143, 154, 156, 166, 180, 182, 188, 190,
      192, 194, 198, 201, 226, 242, 253, 261, 264, 295, 305, 313,
      315, 320, 323, 325, 330, 334, 337, 340, 344, 348, 349
<223> OTHER INFORMATION: n = A,T,C or G
<220> FEATURE:
<221> NAME/KEY: misc_feature
<222> LOCATION: 351, 352, 357, 358, 359, 361, 362, 381, 387, 388, 389,
      394
<223> OTHER INFORMATION: n = A,T,C or G

<400> SEQUENCE: 111
taangancat nctggnttnt gcctnnccgn ctnattgant gttaaaggca attntgtggn    60
tgtcccagng aatgncggct nattttcttt ccacattgng cncattcact cctcccactc   120
ttggcatgtn gngacataag canggtacat aatngnaaaa atctgnattt ctgatgccan   180
angggtanan cntnttgnat ntcattccat tgatatacag ccactntttt atttttgatc   240
ancggccttc ggntcactgc ncanggtact tgacctcagt gtcactatta tgggntttgg   300
tttcnctctt ttncnggccn tttntttcn cacnttncan cttncttnnt nnaaaannna   360
nncactctct cttgctctct ngatacnnng tctnaa                             396

<210> SEQ ID NO 112
<211> LENGTH: 396
<212> TYPE: DNA
<213> ORGANISM: Homo sapiens
<220> FEATURE:
<221> NAME/KEY: misc_feature
<222> LOCATION: 172, 186, 378, 380, 382, 388
<223> OTHER INFORMATION: n = A,T,C or G

<400> SEQUENCE: 112
tcaacgtcac caattactgc catttagccc acgagctgcg tctcagctgc atggagagga    60
aaaaggtcca gattcgaagc atggatccct ccgccttggc aagcgaccga tttaacctca   120
tactggcaga taccaacagt gaccggctct tcacagtgaa cgatgttaaa gntgnaggct   180
ccaagnatgg tatcatcaac ctgcaaagtc tgaagacccc tacgctcaag gtgttcatgc   240
acgaaaacct ctacttcacc aaccggaagg tgaattcggg gggctgggcc tcgctgaatc   300
acttggattc cacattctgc tatgcctcat gggactcgca gaacttcagg ctggccaccc   360
tgctcccacc atcactgntn gncaatantc acccag                             396

<210> SEQ ID NO 113
<211> LENGTH: 396
<212> TYPE: DNA
<213> ORGANISM: Homo sapiens
<220> FEATURE:
<221> NAME/KEY: misc_feature
<222> LOCATION: 1, 2, 3, 4, 7, 8, 9, 10, 11, 65, 273, 279, 280, 289,
      321, 338, 380
<223> OTHER INFORMATION: n = A,T,C or G

<400> SEQUENCE: 113
nnnnttnnnn nggagcctta atttcagagt tttattgtat tgcactaaag gaacagcagg    60
atggntatac aatttctctc cattcagttt tgaaaatctg tagtacctgc aaattcttaa   120

```
gaataccttt accaccagat tagaacagta agcataataa ccaatttctt aataagtaat      180
gtcttacaaa taaaaacaca tttaaaatag ctttaaatgc attcttcaca agtaattcag      240
catatatttt atatcatggt tacttatgct tangaattnn agcaggatnt ttattctttt      300
gatggaaata tgggaaaact ntattcatgc atatacangg ataatattca gcgaagggaa      360
aatcccgttt ttattttggn aatgattcat atataa                               396
```

<210> SEQ ID NO 114  
<211> LENGTH: 396  
<212> TYPE: DNA  
<213> ORGANISM: Homo sapiens  
<220> FEATURE:  
<221> NAME/KEY: misc_feature  
<222> LOCATION: 40, 82, 114, 116, 146, 164, 166, 174, 185, 212, 215, 219, 224, 236, 242, 254, 258, 263, 270, 286, 299, 308, 327, 328, 329, 345, 363, 378, 382, 385  
<223> OTHER INFORMATION: n = A,T,C or G

<400> SEQUENCE: 114

```
aaatgggaca acgtgattct tttgttttaa ataaatactn agaacacgga cttggctcct      60
acaagcattt ggactctaag gnttagaact ggagagtctt acccatgggc cccncncagg      120
gacgccacgg ttccctccca ccccgngatc aagacacgga atcngntggc gatngttgga      180
tcgcnatgtg cccttatct atagccttcc cnggncatnt acangcagga tgcggntggg      240
anaactacaa ctgnaatntc tcnaacggtn atggtcccca ccgatnaaga ttctacctng      300
tcttttcntc ccctggagtg tgagtgnnng aggaagaagc ccttnccta catcacctttt     360 tgnacttctg aacaaganca anacnatggc cccccc                               396
```

<210> SEQ ID NO 115  
<211> LENGTH: 396  
<212> TYPE: DNA  
<213> ORGANISM: Homo sapiens  
<220> FEATURE:  
<221> NAME/KEY: misc_feature  
<222> LOCATION: 277, 297, 321, 341, 381, 391  
<223> OTHER INFORMATION: n = A,T,C or G

<400> SEQUENCE: 115

```
ccgcctggtt cggcccgcct gcctccactc ctgcctctac catgtccatc agggtgaccc      60
agaagtccta caaggtgtcc acctctggcc cccgggcctt cagcagccgc tcctacacga      120
gtgggcccgg ttcccgcatc agctcctcga gcttctcccg agtgggcagc agcaactttc      180
gcggtggcct ggcggcggct atggtgggc cagcggcatg ggaggcatca cccgcagtta      240
cggcaaccag agcctgctga gccccttgcc tggaggngga ccccaacatc aagccgngcg      300
cacccaggaa aaggagcaga ncaagaccct caacaacaag nttgcttctt catagacaag      360
ggaccggtcc ttgaacagca naacaagatg ntggag                               396
```

<210> SEQ ID NO 116  
<211> LENGTH: 396  
<212> TYPE: DNA  
<213> ORGANISM: Homo sapiens  
<220> FEATURE:  
<221> NAME/KEY: misc_feature  
<222> LOCATION: 267, 290, 343, 351, 376  
<223> OTHER INFORMATION: n = A,T,C or G

<400> SEQUENCE: 116

```
atctcagttt actagctaag tgactttggg caagggattt aacctctcgt ccctcagttt      60
cctcctatgt aaaatgacaa ggataatagt accaacccaa tgtagattaa atgagtttac     120
```

-continued

| | |
|---|---|
| gaagtgttag aatagtgctt ggcacattag tgctttacaa ctgctatttt gattgttgtt | 180 |
| gtgggctctc tcaaatgcat tgtctctaga tgccagtgac ccaggtcaaa atttaccttt | 240 |
| aaccaagctg catgtttccc agactgntgc acagtcctct accctgagan aaagcttcca | 300 |
| cccaaggata cttttacttt ctgctggaaa actgatgagc aanggcaaca ngggacactt | 360 |
| atcgccaact ggaaangaga aattcttcct tttgct | 396 |

<210> SEQ ID NO 117
<211> LENGTH: 396
<212> TYPE: DNA
<213> ORGANISM: Homo sapiens
<220> FEATURE:
<221> NAME/KEY: misc_feature
<222> LOCATION: 228, 267, 318, 331, 357, 368, 376
<223> OTHER INFORMATION: n = A,T,C or G

<400> SEQUENCE: 117

| | |
|---|---|
| aaacattttt taataaaatt cctatagaaa gctcagtcat agggcaaata ctcagttctc | 60 |
| tttcccatat caccgaggat tgagagctcc caatattctt tggagaataa gcagtagttt | 120 |
| tgctggatgt tgccaggact cagagagatc acccatttac acattcaaac cagtagttcc | 180 |
| tattgcacat attaacatta cttgcccta gcaccctaaa tatatggnac ctcaacaaat | 240 |
| aacttaaaga tttccgtggg gcgcganacc atttcaattt gaactaatat ccttgaaaaa | 300 |
| aatcacatta ttacaagntt taataaatac nggaagaaga gctggcattt ttctaanatc | 360 |
| tgaattcnga cttggntta ttccataaat acggtt | 396 |

<210> SEQ ID NO 118
<211> LENGTH: 396
<212> TYPE: DNA
<213> ORGANISM: Homo sapiens
<220> FEATURE:
<221> NAME/KEY: misc_feature
<222> LOCATION: 4, 5, 12, 14, 15, 16, 24, 59, 80, 87, 225, 280, 286, 287, 295, 297, 298, 337, 349, 362, 375, 387, 394
<223> OTHER INFORMATION: n = A,T,C or G

<400> SEQUENCE: 118

| | |
|---|---|
| accnncacct gntnnntttt aacnattaca acttctttat atggcagttt ttactgggng | 60 |
| cctaacactc tctttactgn ctcaagngga agtccaaaca aatttcattt ttgtagtaaa | 120 |
| aaatctttat ttccaaaatg atttgttagc caaaagaact ataaaccacc taacaagact | 180 |
| ttggaagaaa gagacttgat gcttcttata aattccccat tgcanacaaa aaataacaat | 240 |
| ccaacaagag catggtaccc attcttacca ttaacctggn tttaannctc caaancnnga | 300 |
| tttaaaaatg accccactgg gcccaatcca acatganacc tagggggggnt tgccttgatt | 360 |
| angaatcccc cttanggact ttatctnggc tganaa | 396 |

<210> SEQ ID NO 119
<211> LENGTH: 396
<212> TYPE: DNA
<213> ORGANISM: Homo sapiens
<220> FEATURE:
<221> NAME/KEY: misc_feature
<222> LOCATION: 251, 281, 298, 301, 308, 326, 332, 337, 351, 358, 362, 388, 394
<223> OTHER INFORMATION: n = A,T,C or G

<400> SEQUENCE: 119

| | |
|---|---|
| atggccagct cactttaaat accacctcaa gactcatcga aatgaccgct ccttcatctg | 60 |
| tcctgcagaa ggttgtggga aaagcttcta tgtgctgcag aggctgaagg tgcacatgag | 120 |

```
gacccacaat ggagagaagc cctttatgtg ccatgagtct ggctgtggta agcagtttac      180
tacagctgga aacctgaaga accaccggcg catccacaca ggagagaaac ctttcctttg      240
tgaagcccaa ngatgtggcc gtcctttgct gagtattcta ncttcgaaaa catctggngg      300
ntactcanga gagaaagcct cattantgcc antctgnggg aaaaccttct ntcagagngg      360
angcaggaat gtgcatatta aaaagctncc ttgnac                                396
```

<210> SEQ ID NO 120
<211> LENGTH: 396
<212> TYPE: DNA
<213> ORGANISM: Homo sapiens
<220> FEATURE:
<221> NAME/KEY: misc_feature
<222> LOCATION: 261, 263, 265, 272, 273, 288, 308, 310, 330, 379
<223> OTHER INFORMATION: n = A,T,C or G

<400> SEQUENCE: 120

```
catgggtcag tcggtcctga gagttcgaag agggcacatt cccaaagaca ttcccagtca      60
tgaaatgtag aagactggaa aattaagaca ttatgtaaag gtagatatgg cttttagagt     120
tacattatgc ttggcatgaa taaggtgcca ggaaaacagt ttaaaattat acatcagcat     180
acagactgct gttagaaggt atgggatcat attaagataa tctgcagctc tactacgcat     240
ttattgttaa ttgagttaca nangncattc annactgagt ttatagancc atattgctct     300
atctctgngn agaacatttg attccattgn gaagaatgca gtttaaaata tctgaatgcc     360
atctagatgt attgtaccna aaggggaaaa ataaca                                396
```

<210> SEQ ID NO 121
<211> LENGTH: 396
<212> TYPE: DNA
<213> ORGANISM: Homo sapiens
<220> FEATURE:
<221> NAME/KEY: misc_feature
<222> LOCATION: 77, 125, 130, 142, 155, 162, 166, 176, 204, 227, 242,
      243, 245, 246, 249, 251, 252, 265, 279, 306, 310, 314, 336, 341,
      354, 367, 382, 385, 390, 395
<223> OTHER INFORMATION: n = A,T,C or G

<400> SEQUENCE: 121

```
tttttttttt tttttttaa aatcaagtta tgtttaataa acattaataa atgtttactt       60
aaaagggtta ataaacnttt actacatggc aaattatttt agctagaatg cttttggctt     120
caagncatan aaaccagatt cnaatgccct taaanaattt tnaaanatcc attgangggg     180
ataactgtaa tccccaaggg gaanagggtt gggtatgaca ggtacanggg gccagcccag     240
tnntnncana nncagactct taccntcttt ctgctgtgnc accctcaggc attggctcca     300
ttctcngggn tgcncatggg aagatggctt tggacntaac nacacccttt tgtncacgta     360
aaggccngat gcagggtcaa anagnttccn ccatnt                                396
```

<210> SEQ ID NO 122
<211> LENGTH: 396
<212> TYPE: DNA
<213> ORGANISM: Homo sapiens

<400> SEQUENCE: 122

```
gtcgacatgg ctgccctctg ggctcccaga acccacaaca tgaaagaaat ggtgctaccc       60
agctcaagcc tgggcctttg aatccggaca caaaaccctc tagcttggaa atgaatatgc     120
tgcactttac aaaccactgca ctacctgact caggaatcgg ctctggaagg tgaagctaga     180
ggaaccagac ctcatcagcc caacatcaaa gacaccatcg gaacagcagc gcccgcagca     240
```

```
cccaccccgc accggcgact ccatcttcat ggccacccce tgcggtggac ggttgaccac    300
cagccaccac atcatcccag agctgagctc ctccagcggg atgacgccgt ccccaccacc    360
tccctcttct tcttttttcat ccttctgtct ctttgt                             396
```

<210> SEQ ID NO 123
<211> LENGTH: 396
<212> TYPE: DNA
<213> ORGANISM: Homo sapiens
<220> FEATURE:
<221> NAME/KEY: misc_feature
<222> LOCATION: 74, 94, 142, 149, 194, 219, 233, 279, 316, 335, 368
<223> OTHER INFORMATION: n = A,T,C or G

<400> SEQUENCE: 123

```
gcccttttt tttttttttt tttcctagtg ccaggtttat tccctcacat gggtggttca     60
catacacagc acanaggcac gggcaccatg gganagggca gcactcctgc cttctgaggg    120
gatcttggcc tcacggtgta anaagggana ggatggttc tcttctgccc tcactagggc    180
ctagggaacc cagnagcaaa tcccaccacg ccttccatnt ctcagccaag ganaagccac    240
cttggtgacg tttagttcca accattatag taagtggana agggattggc ctggtcccaa    300
ccattacagg gtgaanatat aaacagtaaa ggaanataca gtttggatga ggccacagga    360
aggagcanat gacaccatca aaagcatatg caggga                              396
```

<210> SEQ ID NO 124
<211> LENGTH: 396
<212> TYPE: DNA
<213> ORGANISM: Homo sapiens

<400> SEQUENCE: 124

```
gaccattgcc ccagacctgg aagatataac attcagttcc caccatctga ttaaaacaac    60
ttcctccctt acagagcata caacagaggg ggcacccggg gaggagagca catactgtgt    120
tccaatttca cgcttttaat tctcattgt tctcacacca acagtgtgaa gtgcgtggta     180
taatctccat ttcaaaacca aggaagcagc ctcagagtgg tcgagtgaca cacctcacgc    240
aggctgagtc cagagcttgt gctcctcttg attcctggtt tgactcagtt ccaggcctga    300
tcttgcctgt ctggctcagg gtcaaagaca gaatggtgga gtgtagcctc cacctgatat    360
tcaggctact cattcagtcc caaatatgta ttttcc                              396
```

<210> SEQ ID NO 125
<211> LENGTH: 396
<212> TYPE: DNA
<213> ORGANISM: Homo sapiens
<220> FEATURE:
<221> NAME/KEY: misc_feature
<222> LOCATION: 43, 88, 91, 94, 139, 141, 150, 163, 193, 202, 212, 215,
      222, 238, 253, 256, 286, 297, 331, 343, 350, 360, 376, 385, 396
<223> OTHER INFORMATION: n = A,T,C or G

<400> SEQUENCE: 125

```
cccttttttt tttttttttt tttttttttt tttttactt tgnaacaaaa atttattagg     60
attaagtcaa attaaaaaac ttcatgcncc nccncttgtc atatttacct gaatgacaa    120 agttatactt agcttgagng naaaacttgn gccccaaaaa ttntgtttgg aaagcaaaaa    180
aataattgat gcncatagca gngggcctga tnccnccaca gngaatgttg tttaaggnct    240
aacaaacagg ggncancaaa gcatacatta cttttaagct tgggnccaa ggaaaangtc    300 attccctacc tccttcaaaa gcaaactcat natagcctgg gcnectaggn ctggagcctn    360 tttttcgag tctaanatga acatntggat ttcaan                               396
```

<210> SEQ ID NO 126
<211> LENGTH: 396
<212> TYPE: DNA
<213> ORGANISM: Homo sapiens

<400> SEQUENCE: 126

| | | | | | | |
|---|---|---|---|---|---|---|
| cgcgtcgact | cgcaagtgga | atgtgacgtc | cctggagacc | ctgaaggctt | tgcttgaagt | 60 |
| caacaaaggg | cacgaaatga | gtcctcaggt | ggccaccctg | atcgaccgct | tgtgaaggg | 120 |
| aaggggccag | ctagacaaag | acaccctaga | caccctgacc | gccttctacc | ctgggtacct | 180 |
| gtgctccctc | agccccgagg | agctgagctc | cgtgccccc | agcagcatct | gggcggtcag | 240 |
| gccccacgac | ctggacacgc | tggggctacg | gctacagggc | ggcatcccca | acggctacct | 300 |
| ggtcctagac | ctcagcatgc | aagaggccct | ctcggggacg | ccctgcctcc | taggacctgg | 360 |
| acctgttctc | accgtcctgg | cactgctcct | agcctc | | | 396 |

<210> SEQ ID NO 127
<211> LENGTH: 396
<212> TYPE: DNA
<213> ORGANISM: Homo sapiens
<220> FEATURE:
<221> NAME/KEY: misc_feature
<222> LOCATION: 15
<223> OTHER INFORMATION: n = A,T,C or G

<400> SEQUENCE: 127

| | | | | | | |
|---|---|---|---|---|---|---|
| tttttttttt | ttggnggtaa | aatgcaaatg | ttttaaaata | tgtttatttt | gtatgtttta | 60 |
| caatgaatac | ttcagcaaag | aaaataatta | taatttcaaa | atgcaatccc | tggatttgat | 120 |
| aaatatcctt | tataatcgat | tacactaatc | aatatctaga | aatatacata | gacaaagtta | 180 |
| gctaatgaat | aaaataagta | aaatgactac | ataaactcaa | tttcagggat | gagggatcat | 240 |
| gcatgatcag | ttaagtcact | ctgccacttt | ttaaaataat | acgattcaca | tttgcttcaa | 300 |
| tcacataaac | attcattgca | ggagttacac | ggctaatcat | tgaaaattat | gatctttgtt | 360 |
| agcttaaaag | aaaattcagt | ttaatacaaa | gacatt | | | 396 |

<210> SEQ ID NO 128
<211> LENGTH: 396
<212> TYPE: DNA
<213> ORGANISM: Homo sapiens
<220> FEATURE:
<221> NAME/KEY: misc_feature
<222> LOCATION: 220, 244, 351, 384
<223> OTHER INFORMATION: n = A,T,C or G

<400> SEQUENCE: 128

| | | | | | | |
|---|---|---|---|---|---|---|
| gcccttttt | tttttttta | aaggcaaata | aataagttt | attgggatgt | aaccccatca | 60 |
| taaattgagg | agcatccata | caggcaagct | ataaaatctg | gaaaatttaa | atcaaattaa | 120 |
| attctgcttt | taaaaggtg | ccttaagtta | accaagcatt | ttgataacac | attcaaattt | 180 |
| aatatataaa | aatagatgta | tcctggaaga | tataatgaan | aacatgccat | gtgtataaat | 240 |
| tcanaatacg | cttttacac | aaagaactac | aaaaagttac | aaagacagcc | ttcaggaacc | 300 |
| acacttagga | aaagtgagcc | gagcagcctt | cacgcaaagc | ctccttcaaa | naagtctcac | 360 |
| aaagactcca | gaaccagccg | agtntgtgaa | aaagga | | | 396 |

<210> SEQ ID NO 129
<211> LENGTH: 396
<212> TYPE: DNA
<213> ORGANISM: Homo sapiens

```
<220> FEATURE:
<221> NAME/KEY: misc_feature
<222> LOCATION: 104, 164, 177, 204, 217, 234, 273, 312, 350, 353, 370
<223> OTHER INFORMATION: n = A,T,C or G

<400> SEQUENCE: 129 gcccttttt   tttttttttt   ttttactcag   acaggcaata   tttgctcaca   tttattctct       60
tgcatcgtaa  atagtagcca   actcacaaaa   ataaagtata   caanaatgta   atatttttta      120
aaataagatt  aacagtgtaa   gaaggaaaat   ctcaaaaaaa   gcanatagac   aatgtanaaa      180
attgaaatga  aatcccacag   taanaaaaaa   aaaacanaaa   agtgcctatt   taanaattat      240
gctacatgtg  gaacttaact   agaccatttt   aanaaagacc   aatttctaat   gcaaattttc      300
tgaggttttc  anatttat    tttaaaatat   gttatagcta   catgttgtcn   acncggccgc      360
tcgagtctan  agggcccgtt   taaacccgct   gatcag                                   396

<210> SEQ ID NO 130
<211> LENGTH: 396
<212> TYPE: DNA
<213> ORGANISM: Homo sapiens
<220> FEATURE:
<221> NAME/KEY: misc_feature
<222> LOCATION: 23, 24, 26, 32, 56, 191, 286, 355
<223> OTHER INFORMATION: n = A,T,C or G

<400> SEQUENCE: 130
cgcccttttt  tttttttttt   tanngnacgt   gnctttattt   ctggatgata   taaanaaaa       60 aacttaaaaa  acaccccaaa   ccaaacacca   atggatcccc   aaagcgatgt   gactccctct     120
tcccacccgg  ataaatagag   acttctgtat   gtcagtctac   cctcccgccc   ccataacccc     180
ctctgctata  nacatactct   gggtatatat   tactctactc   ggcaatagac   atctcccgaa     240
aatagaattc  ctgccctgac   acctgactct   tccctggccg   catcanacca   cccgccactg     300
tagcacactg  gtgtccttgc   cccctgtggt   cagggccatg   ctgtcatccc   acaanaaggc     360
cacatttgtc  acatggctgc   tgtgtccacc   gtactt                                   396

<210> SEQ ID NO 131
<211> LENGTH: 396
<212> TYPE: DNA
<213> ORGANISM: Homo sapiens
<220> FEATURE:
<221> NAME/KEY: misc_feature
<222> LOCATION: 49, 68, 69, 83, 88, 93, 136, 140, 154, 158, 166, 167,
      168, 170, 172, 173, 187, 226, 239, 241, 247, 257, 259, 271, 293,
      301, 318, 334, 336, 342, 344, 357, 377, 384
<223> OTHER INFORMATION: n = A,T,C or G

<400> SEQUENCE: 131 gcccttttt   tttttttttt   tttttttttt   ttcagtttac   acaaaaacnc   tttaattgac      60
agtatacnnt  tttccaaaat   atnttttngt   aanaaaatgc   aataattatt   aactatagtt     120
tttacaaaca  agtttntcan   taaattccag   tgtncttnaa   acccnnncn    annaaaacat     180 atatganccc  ccagttcctg   ggcaaactgt   tgaacattca   ctgcanacaa   aaagaccanc     240
nccaaanagt  catctgngnc   ctccatgctg   ngtttgcacc   aaacctgagg   gancagctag     300
ngaccgtgac  aaaagctntg   ctacagtttt   actntngccc   tntntgcctc   ccccatnatg     360
tttccttggt  ccctcantcc   tgtnggagta   agttcc                                   396

<210> SEQ ID NO 132
<211> LENGTH: 396
<212> TYPE: DNA
<213> ORGANISM: Homo sapiens
```

```
<220> FEATURE:
<221> NAME/KEY: misc_feature
<222> LOCATION: 69
<223> OTHER INFORMATION: n = A,T,C or G

<400> SEQUENCE: 132
cgcgtcgacc gcggccgtag cagccgggct ggtcctgctg cgagccggcg gcccggagtg      60
gggcggcgnt atgtaccttc cacattgagt attcagaaag aagtgatctg aactctgacc     120
attctttatg gatacattaa gtcaaatata agagtctgac tacttgacac actggctcgg    180
tgagttctgc ttttcttt taatataaat ttattatgtt ggtaaattta gcttttggct     240
tttcactttg ctctcatgat ataagaaaat gtaggttttc tctttcagtt tgaattttcc     300
tattcagtaa aacaacatgc tagaaaacaa acttttggaa aggcattgta actatttttt    360
caaatagaac cataataaca agtcttgtct taccct                              396

<210> SEQ ID NO 133
<211> LENGTH: 396
<212> TYPE: DNA
<213> ORGANISM: Homo sapiens
<220> FEATURE:
<221> NAME/KEY: misc_feature
<222> LOCATION: 1, 17, 18, 20, 21, 25, 26, 30, 31, 40, 44, 45, 46, 51,
      52, 66, 67, 68, 74, 89, 109, 122, 166, 193, 214, 218, 266, 269,
      291, 307, 315, 348, 375, 378, 379, 386, 393
<223> OTHER INFORMATION: n = A,T,C or G

<400> SEQUENCE: 133
ntattacccc tcctggnnan ntggnnatan nctgcaaggn gatnnnccg nngaacttca      60 ctgatnnncc aatnaaaact gctttaaanc tgactgcaca tatgaattnt aatacttact   120
tngcgggagg ggtggggcag ggacagcaag ggggaggatt gggaanacaa tagacaggca    180
tgctggggat gcngcgggct ctatggcttc tgangcgnaa agaaccagct ggggctctag   240
ggggtatccc cacgcgccct gtagcngcnc attaaacgcg gcgggtgtgg nggttacttc   300
gcaaagngac cgatncactt gccagcgccc tagctgcccg ctcctttngc tttcttccct   360
tcctttctcg ccacnttnnc cggctntccc cgncaa                             396

<210> SEQ ID NO 134
<211> LENGTH: 396
<212> TYPE: DNA
<213> ORGANISM: Homo sapiens
<220> FEATURE:
<221> NAME/KEY: misc_feature
<222> LOCATION: 133, 144, 221, 229, 302, 358
<223> OTHER INFORMATION: n = A,T,C or G

<400> SEQUENCE: 134
tttttttttt ttctgctttt tatatgttta aaaatctctc attctattgc tgctttattt      60
aaagaaagat tactttcttc cctacaagat ctttattaat tgtaaaggga aaatgaataa    120
ctttacaatg ganacacctg gcanacacca tcttaaccaa agcttgaagt taacataacc    180
agtaatagaa ctgatcaata tcttgtgcct cctgatatgg ngtactaana aaaacacaac    240
atcatgccat gatagtcttg ccaaaagtgc ataacctaaa tctaatcata aggaaacatt     300
anacaaactc aaattgaagg acattctaca aagtgccctg tattaaggaa ttattcanag   360
taaaggagac ttaaaagaca tggcaacaat gcagta                             396

<210> SEQ ID NO 135
<211> LENGTH: 396
<212> TYPE: DNA
<213> ORGANISM: Homo sapiens
```

<400> SEQUENCE: 135

```
gcgtcgacgc tggcagagcc acaccccaag tgcctgtgcc cagagggctt cagtcagctg    60
ctcactcctc cagggcactt ttaggaaagg gtttttagct agtgttttc ctcgcttta    120 atgacctcag ccccgcctgc agtggctaga agccagcagg tgcccatgtg ctactgacaa   180
gtgcctcagc ttccccccgg cccgggtcag gccgtgggag ccgctattat ctgcgttctc   240
tgccaaagac tcgtgggggc catcacacct gccctgtgca gcggagccgg accaggctct   300
tgtgtcctca ctcaggtttg cttcccctgt gcccactgct gtatgatctg ggggccacca   360
ccctgtgccg gtggcctctg ggctgcctcc cgtggt                             396
```

<210> SEQ ID NO 136
<211> LENGTH: 396
<212> TYPE: DNA
<213> ORGANISM: Homo sapiens
<220> FEATURE:
<221> NAME/KEY: misc_feature
<222> LOCATION: 18, 185, 188, 191, 193, 396
<223> OTHER INFORMATION: n = A,T,C or G

<400> SEQUENCE: 136

```
ttatgcttcc ggctcgtntg ttgtgtggaa ttgtgagcgg ataacaattt cacacaggaa    60
acagctatga ccatgattac gccaagctat taggtgaca ctatagaata ctcaagctat   120
gcatcaagct tggtaccgag ctcggatcca ctagtaacgg ccgccagtgt gctggaattc   180
gcggncgntc nantctagag ggcccgttta aacccgctga tcagcctcga ctgtgccttc   240
tagttgccag ccatctgttg tttgcccctc ccccgtgcct tccttgaccc tggaaggtgc   300
cactcccact gtcctttcct aataaaatga ggaaattgca tcgcattgtc tgagtaggtg   360
tcattctatt ctgggggggtg gggtggggca ggacan                            396
```

<210> SEQ ID NO 137
<211> LENGTH: 396
<212> TYPE: DNA
<213> ORGANISM: Homo sapiens
<220> FEATURE:
<221> NAME/KEY: misc_feature
<222> LOCATION: 156, 216
<223> OTHER INFORMATION: n = A,T,C or G

<400> SEQUENCE: 137

```
ttttttttt ttctgctttg tacttgagtt tatttcacaa aaccacggag aaagatactg     60
aaatggagct ctttccagcc tccaagcaag gaggccccag cagccagtct ccagccccttt   120 gagccctttt tgttaggccc acacccaaaa gagganaacc agtgtgtgcg cgaaggtaca   180
tggcaaggca cttttgaaaa catcccagtt taccgnggtg aaattgaact tactctgaaa   240
cagatgaaaa gggacatgca aaattgctga gcacatggag gtgtttgtta gtaggtgaaa   300
atcatgtcct gggtataacc cagcttctcc aggttagggt gagccgccgt ctggatcagt   360
ggtggcgggc cacacaccag gatgagcgtg gacttc                             396
```

<210> SEQ ID NO 138
<211> LENGTH: 396
<212> TYPE: DNA
<213> ORGANISM: Homo sapiens
<220> FEATURE:
<221> NAME/KEY: misc_feature
<222> LOCATION: 69, 136, 265, 272
<223> OTHER INFORMATION: n = A,T,C or G

<400> SEQUENCE: 138

```
cccttttttt ttttttttac aaatgagaaa aatgtttatt aagaaaacaa tttagcagct    60
ctcctttana attttacaga ctaaagcaca acccgaaggc aattacagtt tcaatcatta   120
acacactact taaggngctt gcttactcta caactggaaa gttgctgaag tttgtgacat   180
gccactgtaa atgtaagtat tattaaaaat tacaaattgt ttggtgatta ttttgatgac   240
ctcttgagca gcagctcccc ccaanaatgc ancaatggta tgtggctcac cagctccata   300
tcggcaaaat tcgtggacat aatcatcttt caccattaca gataaaccat attcctgaag   360
gaagccagtg agacaagact tcaactttcc tatatc                             396
```

<210> SEQ ID NO 139
<211> LENGTH: 396
<212> TYPE: DNA
<213> ORGANISM: Homo sapiens
<220> FEATURE:
<221> NAME/KEY: misc_feature
<222> LOCATION: 51, 105, 126, 147, 210, 212, 236, 241, 258, 263, 348
<223> OTHER INFORMATION: n = A,T,C or G

<400> SEQUENCE: 139

```
ccgccctttt ttttttttt ttcacaaaag cacttttat ttgaggcaaa nagaagtctt     60
gctgaaagga ttccagttcc aagcagtcaa aactcaaccg ttagnggcac tattttgacc   120
tggtanattt tgcttctctt tggtcanaaa agggtattca ggttgtactt tccccagcag   180
ggtaaaaaga agggcaaagc aaactggaan anacttctac tctactgaca gggctnttga   240
natccaacat caagctanac acnccctcgc tggccactct acaggttgct gtcccactgc   300
tgagtgacac aggccatact acatttgcaa ggaaaaaaat gaggcaanaa acacaggtat   360
aggtcacttg gggacgagca ggcaaccaca gcttca                             396
```

<210> SEQ ID NO 140
<211> LENGTH: 396
<212> TYPE: DNA
<213> ORGANISM: Homo sapiens
<220> FEATURE:
<221> NAME/KEY: misc_feature
<222> LOCATION: 50, 60, 63, 100, 133, 135, 172, 183, 190, 196, 220, 240,
      262, 266, 273, 278, 293, 327, 332, 341, 348, 355, 380, 391
<223> OTHER INFORMATION: n = A,T,C or G

<400> SEQUENCE: 140

```
tttttttttt tttttttttt ttttttctc atttaactt ttaatgggn ctcaaaattn      60 tgngacaaat tttggtcaa gttgtttcca ttaaaaagtn ctgattttaa aaactaataa   120
cttaaaactg ccncnccaa aaaaaaaaac caagggggtc cacaaaacat tntccttttcc  180 ttntgaaggn tttacnatgc attgttatca ttaaccagtn ttttactact aaacttaaan  240
ggccaattga acaaacagt tntganaccg ttnttccncc actgattaaa agnggggggg   300
caggtattag ggataatatt catttancct tntgagcttt ntgggcanac ttggngacct  360
tgccagctcc agcagccttn ttgtccactg ntttga                            396
```

<210> SEQ ID NO 141
<211> LENGTH: 396
<212> TYPE: DNA
<213> ORGANISM: Homo sapiens

<400> SEQUENCE: 141

```
acgccgagcc acatcgctca gacaccatgg ggaaggtgaa ggtcggagtc aacggatttg    60
gtcgtattgg gcgcctggtc accagggctg cttttaactc tggtaaagtg gatattgttg   120
```

```
ccatcaatga cccottcatt gacctcaact acatggttta catgttccaa tatgattcca      180
cccatggcaa attccatggc accgtcaagg ctgagaacgg gaagcttgtc atcaatggaa      240
atcccatcac catcttccag gagcgagatc cctccaaaat caagtggggc gatgctggcg      300
ctgagtacgt cgtggagtcc actggcgtct tcaccaccat ggagaaggct ggggctcatt      360
tgcagggggg agccaaaagg gtcatcatct ctgccc                                396
```

<210> SEQ ID NO 142
<211> LENGTH: 396
<212> TYPE: DNA
<213> ORGANISM: Homo sapiens

<400> SEQUENCE: 142

```
acgcaggaga ggaagcccag cctgttctac cagagaactt gcccaggtca gaggtctgcg      60 tagaagcect tttctgagca tcctctcctc tcctcacacc tgccactgtc ctctgcgttg      120
ctgtcgaatt aaatcttgca tcaccatggt gcacttctgt ggcctactca ccctccaccg      180
ggagccagtg ccgctgaaga gtatctctgt gagcgtgaac atttacgagt tgtggctgg       240 tgtgtctgca actttgaact acgagaatga ggagaaagtt cctttggagg ccttctttgt      300
gttccccatg gatgaagact ctgctgttta cagctttgag gccttggtgg atgggaagaa      360
aattgtagca gaattacaag acaagatgaa ggcccg                                396
```

<210> SEQ ID NO 143
<211> LENGTH: 396
<212> TYPE: DNA
<213> ORGANISM: Homo sapiens
<220> FEATURE:
<221> NAME/KEY: misc_feature
<222> LOCATION: 19, 48, 69, 122, 183, 227, 332, 390
<223> OTHER INFORMATION: n = A,T,C or G

<400> SEQUENCE: 143

```
tttttttttt tttccatana aataggatt tattttcaca tttaaggnga acacaaatcc       60
atgttccana aatgttttat gcataacaca tcatgagtag attgaatttc tttaacacac      120
anaaaaatca aagcctacca ggaaatgctt ccctccggag cacaggagct tacaggccac      180
ttntgttagc aacacaggaa ttcacattgt ctaggcacag ctcaagngag gtttgttccc      240
aggttcaact gctcctaccc ccatgggccc tcctcaaaaa cgacagcagc aaaccaacag      300
gcttcacagt aaccaggagg aaagatctca gnggggaac cttcacaaaa gccctgagtt      360
gtgtttcaaa agccaagctc tggggtctgn ggcctg                                396
```

<210> SEQ ID NO 144
<211> LENGTH: 396
<212> TYPE: DNA
<213> ORGANISM: Homo sapiens
<220> FEATURE:
<221> NAME/KEY: misc_feature
<222> LOCATION: 221, 331
<223> OTHER INFORMATION: n = A,T,C or G

<400> SEQUENCE: 144

```
tttttttttt tttcgctctt tggtctgaca agaaaagagt tttaggtgtg tgaagtaggg      60
tgggaaaaaa ggtcagtttc aaattcagta acatatggta acactaagtt aggctgctgc      120
attcttttct ttgggtactt aagccagctg gcacttccac tttgtaacca attatattat      180
gatcaacaac taatcagtta gttcctcagc ttcaactgaa nagttcctga ttacctgatg      240
aaggacatac ttgctctggc ttcaattagc atgctgtcaa gcatccctct ccatgcttaa      300
```

```
catggcaaca caaaacccaa gagtccttct nttttttttca ttagccatga ataaacactc    360
acaaagggga agagtagaca ctgcttttag taaacg                               396
```

<210> SEQ ID NO 145
<211> LENGTH: 396
<212> TYPE: DNA
<213> ORGANISM: Homo sapiens
<220> FEATURE:
<221> NAME/KEY: misc_feature
<222> LOCATION: 45, 56, 61, 63, 120, 122, 147, 151, 158, 259, 262, 274,
      339, 345, 353
<223> OTHER INFORMATION: n = A,T,C or G

<400> SEQUENCE: 145

```
tttttttttt tttttttcaa tggatccgtt agctttacta ctaanatctt gctganatca     60
nanaagggct tctgggcagg ctgagcactg ggggtgtgca acatggtaac tctgaataan    120 anaaacctg agttttactg ggcaaanaaa naacaagngg taggtatgat ttctgaacct     180
ggaaatagcg aaaatgaagg aaattccaaa agcgcgtatt tccaaataat gacaggccag    240
caagaggaca ccaaacctnt anaaagaggt attntttctt ccagctactg atggctttgg    300
catcccacag gcacattcct ttggccttca ggatcttana tgcanatgtg ganagtcaag    360
aggtaggctg actctgagtc ttcagctaaa ttcttt                              396
```

<210> SEQ ID NO 146
<211> LENGTH: 396
<212> TYPE: DNA
<213> ORGANISM: Homo sapiens
<220> FEATURE:
<221> NAME/KEY: misc_feature
<222> LOCATION: 120, 130, 176, 180, 185, 208, 238, 254, 259, 261, 275,
      285, 296, 347
<223> OTHER INFORMATION: n = A,T,C or G

<400> SEQUENCE: 146

```
tttttttttt tttttcattag caaggaagga tttattttt cttttgaggg gagggcggaa     60
cagccgggat ttttggaaca ctacctttgt ctttcacttt gttgtttgtg tgttaacacn    120
aataaatcan aagcgactt aaatctccct tcgcaggact gtcttcacgt atcagngcan    180
acaanaaaac agtggctta caaaaaaanat gttcaagtag gctgcacttt gcctctgngg    240
gtgaggcaca ctgngggana nacaaggtcc cctgnaacca gaggngggaa ggacanagct    300
ggctgactcc ctgctctccc gcattctctc ctccatgtgt tttgaanagg gaagcaacat    360
gttgaggtct gatcatttct acccagggaa cctgtt                              396
```

<210> SEQ ID NO 147
<211> LENGTH: 396
<212> TYPE: DNA
<213> ORGANISM: Homo sapiens

<400> SEQUENCE: 147

```
acggggaagc caagtgaccg tagtctcatc agacatgagg gaatgggtgg ctccagagaa     60
agcagacatc attgtcagtg agcttctggg ctcatttgct gacaatgaat tgtcgcctga    120
gtgcctggat ggagcccagc acttcctaaa agatgatggt gtgagcatcc ccggggagta    180
cacttccttt ctggctccca tctcttcctc caagctgtac aatgaggtcc gagcctgtag    240
ggagaaggac cgtgaccctg aggcccagtt tgagatgcct tatgtggtac ggctgcacaa    300
cttccaccag ctctctgcac cccagccctg tttcaccttc agccatccca acagagatcc    360
tatgattgac aacaaccgct attgcacctt ggaatt                              396
```

```
<210> SEQ ID NO 148
<211> LENGTH: 396
<212> TYPE: DNA
<213> ORGANISM: Homo sapiens

<400> SEQUENCE: 148
acgtcccatg attgttccag accatgactc ttcctggttg tgggtttgtt acagagcagg      60
agaagcagag gttatgacag ttatgcagac tttccccctc cttttttctct tttctcttcc    120 ccttgctttt ccactgtttc ttcctgctgc cacctgggcc ttgaattcct gggctgtgaa     180
gacatgtagc agctgcaggg tttaccacac gtgggagggc agcccagtac tgtccctctg     240
ccttccccac tttgagaata tggcagcccc tttcattcct ggcttggggt aggggagacc     300
attgaagtag aagcctcaaa gcagactttt ccctttactg tgtgtactcc aggacgaaga     360
aggaagatca tgcttgatac ttagattggt tttccc                               396

<210> SEQ ID NO 149
<211> LENGTH: 396
<212> TYPE: DNA
<213> ORGANISM: Homo sapiens
<220> FEATURE:
<221> NAME/KEY: misc_feature
<222> LOCATION: 214, 295
<223> OTHER INFORMATION: n = A,T,C or G

<400> SEQUENCE: 149
tttttttttt tttaaagagt cacattttat tcaatgccta tttgtacatg ttactagcaa      60
taaactcttt tatctttaat tttgagaagt tttacaaata cagcaaagca gaatgactaa     120
tagagccggt aaccaggaca cagatttgga aaaataggtc taattggttg ttacactgtg     180
tttatgtcat acatttcgct tatttttatc aaanaaaaat cagaatttat aaaatgttaa     240
ttaaaaggaa aacattctga gtaaatttag tcccgtgttt cttcctccaa atctnttttgt    300 tctacactaa caggtcagga taagtatgga tggggaggct ggaaaaaggg catccttccc     360
catgcggtcc ccagagccac cctctccaag caggac                               396

<210> SEQ ID NO 150
<211> LENGTH: 396
<212> TYPE: DNA
<213> ORGANISM: Homo sapiens

<400> SEQUENCE: 150
acgcctctct tcagttggca cccaaacatc tggattggca aatcagtggc aagaagttcc      60
agcatctgga cttttcagaa ttgatcttaa gtctactgtc atttccagat gcattatttt     120
acaactgtat ccttggaaat atatttctag ggagaatatt attgaagaaa atgttaatag     180
cctgagtcaa atttcagcag acttaccagc atttgtatca gtggtagcaa atgaagccaa     240
actgtatctt gaaaaacctg ttgttccttt aaatatgatg ttgccacaag ctgcattgga     300
gactcattgc agtaatattt ccaatgtgcc acctacaaga gagatacttc aagtctttct     360
tactgatgta cacatgaagg aagtaattca gcagtt                               396

<210> SEQ ID NO 151
<211> LENGTH: 396
<212> TYPE: DNA
<213> ORGANISM: Homo sapiens
<220> FEATURE:
<221> NAME/KEY: misc_feature
<222> LOCATION: 146, 299, 332
<223> OTHER INFORMATION: n = A,T,C or G
```

<400> SEQUENCE: 151

```
acaaaatgcc cagcctacag agtctgagaa ggaaatttat aatcaggtga atgtagtatt      60
aaaagatgca gaaggcatct tggaggactt gcagtcatac agaggagctg ccacgaaat     120
acgagaggca atccagcatc cagcanatga aagttgcaa gagaaggcat ggggtgcagt     180
tgttccacta gtaggcaaat taaagaaatt ttacgaattt tctcagaggt tagaagcagc    240
attaagaggt cttctgggag ccttaacaag taccccatat tctcccaccc agcatctana   300
gcgagagcag gctcttgcta aacagtttgc anaaattctt catttcacac tccggtttga   360
tgaactcaag atgacaaatc ctgccataca gaatga                              396
```

<210> SEQ ID NO 152
<211> LENGTH: 396
<212> TYPE: DNA
<213> ORGANISM: Homo sapiens
<220> FEATURE:
<221> NAME/KEY: misc_feature
<222> LOCATION: 249
<223> OTHER INFORMATION: n = A,T,C or G

<400> SEQUENCE: 152

```
acgcagcgct cggcttcctg gtaattcttc acctcttttc tcagctccct gcagcatggg     60
tgctgggccc tccttgctgc tcgccgccct cctgctgctt ctctccggcg acggcgccgt    120
gcgctgcgac acacctgcca actgcaccta tcttgacctg ctgggcacct gggtcttcca    180
ggtgggctcc agcggttccc agcgcgatgt caactgctcg gttatgggac acaagaaaa    240
aaaagtagng gtgtaccttc agaagctgga tacagcatat gatgaccttg gcaattctgg    300
ccatttcacc atcatttaca accaaggctt tgagattgtg ttgaatgact acaagtggtt    360
tgccttttt aagtataaag aagagggcag caaggt                                396
```

<210> SEQ ID NO 153
<211> LENGTH: 396
<212> TYPE: DNA
<213> ORGANISM: Homo sapiens

<400> SEQUENCE: 153

```
ccagagacaa cttcgcggtg tggtgaactc tctgaggaaa aacacgtgcg tggcaacaag     60
tgactgagac ctagaaatcc aagcgttgga ggtcctgagg ccagcctaag tcgcttcaaa    120
atggaacgaa ggcgtttgcg gggttccatt cagagccgat acatcagcat gagtgtgtgg    180
acaagcccac ggagacttgt ggagctggca gggcagagcc tgctgaagga tgaggccctg   240
gccattgccg ccctggagtt gctgcccagg gagctcttcc cgccactctt catggcagcc   300
tttgacggga gacacagcca gaccctgaag gcaatggtgc aggcctggcc cttcacctgc   360
ctccctctgg gagtgctgat gaagggacaa catctt                              396
```

<210> SEQ ID NO 154
<211> LENGTH: 396
<212> TYPE: DNA
<213> ORGANISM: Homo sapiens
<220> FEATURE:
<221> NAME/KEY: misc_feature
<222> LOCATION: 42, 45, 59, 82
<223> OTHER INFORMATION: n = A,T,C or G

<400> SEQUENCE: 154

```
acagcaaacc tcctcacagc ccactggtcc tcaagagggg cnacntcttc acacatcanc     60
acaactacgc attgcctccc tncactcgga aggactatcc tgctgccaag agggtcaagt   120
```

```
tggacagtgt cagagtcctg agacagatca gcaacaaccg aaaatgcacc agccccaggt    180
cctcggacac cgaggagaat gtcaagaggc gaacacacaa cgtcttggag cgccagagga    240
ggaacgagct aaaacggagc ttttttgccc tgcgtgacca gatcccggag ttggaaaaca    300
atgaaaaggc ccccaaggta gttatcctta aaaaagccac agcatacatc ctgtccgtcc    360
aagcagagga gcaaaagctc atttctgaag aggact                              396
```

<210> SEQ ID NO 155
<211> LENGTH: 396
<212> TYPE: DNA
<213> ORGANISM: Homo sapiens
<220> FEATURE:
<221> NAME/KEY: misc_feature
<222> LOCATION: 15, 17, 202, 280, 339
<223> OTHER INFORMATION: n = A,T,C or G

<400> SEQUENCE: 155

```
tttttttttt tgaananaca ggtctttaat gtacggagtc tcacaaggca caaacaccct    60
caccaggacc aaataaataa ctccacggtt gcaggaaggc gcggtctggg gaggatgcgg   120
catctgagct ctcccagggc tggtgggcga gccggggtc tgcagtctgt gaggggcctc    180
ctgggtgtgt ccgggcctct anagcgggtc cagtctccag gatgggatc gctcactcac    240 tctccgagtc ggagtagtcc gccacgaggg aggagccgan actgcagggg tgccgcgtgt   300 cggggggtgtc agctgcctcc tgggaggagc ctgctggcna caggggcttg tcctgacggc    360
tcccttcctg cccctcggg ctgctgcact tggggg                              396
```

<210> SEQ ID NO 156
<211> LENGTH: 396
<212> TYPE: DNA
<213> ORGANISM: Homo sapiens
<220> FEATURE:
<221> NAME/KEY: misc_feature
<222> LOCATION: 11, 30, 32, 37, 309, 332
<223> OTHER INFORMATION: n = A,T,C or G

<400> SEQUENCE: 156

```
gaagggggggc ngggcagggg cggaatgtan anattantgc catgattgaa gatttaagaa    60
acgtgagatt caggatttc accacatccc catttagtta gcttgctcgt ttggctggtg   120
caaatgccag atggattatg aacaatgaca gtaaattaat gcaacataat caggtaatga    180
tgccaagcgt atctggtgtt ccaggtattg tacctttacc ggaacaaatc agtaaatcca    240
caatccctgg cacctgttag gcagctatta acctagtaaa tgctccccca tcccatctca    300
atcagcaang acaatcaaaa acatttgctt tnagtggcag gaacactggt acattttac    360 ttgctccaag ggctgtgcca acgctccctc tctctg                              396
```

<210> SEQ ID NO 157
<211> LENGTH: 396
<212> TYPE: DNA
<213> ORGANISM: Homo sapiens
<220> FEATURE:
<221> NAME/KEY: misc_feature
<222> LOCATION: 121, 202, 204, 255, 314, 332, 368
<223> OTHER INFORMATION: n = A,T,C or G

<400> SEQUENCE: 157

```
tttttttttt ttttggggga atgtaaatct tttattaaaa cagttgtctt tccacagtag    60
taaagctttg gcacatacag tataaaaaat aatcacccac cataattata ccaaattcct   120
nttatcaact gcatactaag tgttttcaat acaatttttt ccgtataaaa atactgggaa    180
```
aaattgataa ataacaggta ananaaagat atttctaggc aattactagg atcatttgga    240
aaaagtgagt actgnggata tttaaaatat cacagtaaca agatcatgct tgttcctaca    300
gtattgcggg ccanacactt aagtgaaagc anaagtgttt gggtgacttt cctacttaaa    360
attttggnca tatcatttca aaacatttgc atcttg    396

<210> SEQ ID NO 158
<211> LENGTH: 396
<212> TYPE: DNA
<213> ORGANISM: Homo sapiens

<400> SEQUENCE: 158
tttccgaaga cgggcagctt cagagaagag gattattcgg gagattgctg gtgtggccca    60
tagactcttt ggcatagact cttcgcagg cagccactct gagtgtggcc agttctataa    120
ccatccccaa actagctgga gcctgatgga taggaacggg tagtctgtcc tcttccccat    180
aaaaatgttc caaaaagtta tctccagaga gagtcccttta tgaagacagt tgccaagctg    240
tattctcatt ctttaaacca atacccaggt cagggctagt tcacactagc actgttaggg    300
acatggtgtg gctagaaatg aattgagtgt gacttctccc tacaaccca ggcccaggga    360 taggaggagg cagaggggtg cctggagttt ctgcac    396

<210> SEQ ID NO 159
<211> LENGTH: 396
<212> TYPE: DNA
<213> ORGANISM: Homo sapiens

<400> SEQUENCE: 159
tccgcgcgtt gggaggtgta gcgcggctct gaacgcgctg agggccgttg agtgtcgcag    60
gcggcgaggg cgcgagtgag gagcagaccc aggcatcgcg cgccgagaag gccgggcgtc    120
cccacactga aggtccggaa aggcgacttc cggggctttt ggcacctggc ggaccctccc    180
ggagcgtcgg cacctgaacg cgaggcgctc cattgcgcgt gcgcgttgag gggcttcccg    240
cacctgatcg cgagacccca acggctggtg gcgtcgcctg cgcgtctcgg ctgagctggc    300
catggcgcag ctgtgcgggc tgaggcggag ccgggcgttt ctcgccctgc tgggatcgct    360
gctcctctct ggggtcctgg cggccgaccg agaacg    396

<210> SEQ ID NO 160
<211> LENGTH: 396
<212> TYPE: DNA
<213> ORGANISM: Homo sapiens
<220> FEATURE:
<221> NAME/KEY: misc_feature
<222> LOCATION: 96, 102, 122, 124, 129, 146, 148, 184, 189, 196, 205,
      208, 229, 246, 259, 261, 269, 272, 281, 297, 305, 308, 327, 331,
      337, 338, 339, 343, 346, 354, 366, 367, 369, 378, 379, 380,
      381, 391, 395
<223> OTHER INFORMATION: n = A,T,C or G

<400> SEQUENCE: 160
ggaaaccttc tcaactaaga gaacatcatt tctggcaaac tattttttgtt agctcacaat    60 atatgtcgta cactctacaa tgtaaatagc actganccac ancttacaga aggtaaaaag    120
angnataana acttcctttta caaaananntt cctgttgttc ttaatactcc ccattgctta    180
tganaattnt ctatangtct ctcangantg ttcgcaccca tttctttttnt aacttctact    240 aaaaanccat ttacattgna nagtgtacna cntatatttg ngagctaaca aaaaatngtt    300
ttccngaant gatgttctttt tagttttnaga nggttcnnnc aanttnctac tccngcccgc    360
cactgnncnc cacatttnnn naattacacc ncacng    396

<210> SEQ ID NO 161
<211> LENGTH: 396
<212> TYPE: DNA
<213> ORGANISM: Homo sapiens
<220> FEATURE:
<221> NAME/KEY: misc_feature
<222> LOCATION: 271, 273, 325, 364
<223> OTHER INFORMATION: n = A,T,C or G

<400> SEQUENCE: 161
tttttgtttg attattttta ttataatgaa attaaactta tgactattac agtatgctca      60
gcttaaaaca tttatgagta ctgcaaggac taacagaaac aggaaaaatc ctactaaaaa     120
tatttgttga tgggaaatca ttgtgaaagc aaacctccaa atattcattt gtaagccata     180
agaggataag cacaaccata tgggaggaga taaccagtct ctcccttcat atatattctt     240
ttttatttct tggtatacct tcccaaaaca nanacattca acagtagtta gaatggccat     300
ctcccaacat tttaaaaaaa ctgcnccccc caatgggtga acaaagtaaa gagtagtaac     360
ctanagttca gctgagtaag ccactgtgga gcctta                               396

<210> SEQ ID NO 162
<211> LENGTH: 396
<212> TYPE: DNA
<213> ORGANISM: Homo sapiens
<220> FEATURE:
<221> NAME/KEY: misc_feature
<222> LOCATION: 33, 38, 51, 62, 71, 72, 88, 97, 98, 100, 106, 142, 155,
      160, 161, 163, 168, 170, 174, 183, 190, 194, 203, 214, 216, 231,
      232, 241, 242, 252, 258, 260, 264, 265, 267, 276, 278, 282,
      287, 289, 292, 295, 297, 301, 311, 319, 322, 325
<223> OTHER INFORMATION: n = A,T,C or G
<220> FEATURE:
<221> NAME/KEY: misc_feature
<222> LOCATION: 330, 337, 341, 342, 347, 348, 354, 356, 361, 367, 368,
      375, 379, 385, 391, 394, 395
<223> OTHER INFORMATION: n = A,T,C or G

<400> SEQUENCE: 162
tttttttttt tttttttttt tttttttttt ttngggnncc aaattttttt ntttgaagga      60
angggacaaa nnaaaaaact taagggggntg ttttggnncn acttanaaaa aagggaaagg    120 aaacccaac atgcatgccc tnccttgggg accanggaan ncnccccncn ggtntggga      180 aantaacccn aggnttaact ttnattatca ctgncnccca gggggggctt nnaaaaaaaa    240
nnttccccca anccaaantn gggnncnccc attttncnca anttggncnc cnggncnccc    300 natttttga ngggtttcnc cngcncattn agggaanggg nntcaannaa accncncaaa    360 nggggnnat tttntcang ggccnatttg ngcnnt                                 396

<210> SEQ ID NO 163
<211> LENGTH: 396
<212> TYPE: DNA
<213> ORGANISM: Homo sapiens

<400> SEQUENCE: 163
cactgtccgg ctctaacaca gctattaagt gctacctgcc tctcaggcac tctcctcgcc      60
cagtttctga ggtcagacga gtgtctgcga tgtcttcccg cactctattc ccccagcctc     120
tttctgcttt catgctcagc acatcatctt cctaggcagt ctcttcccca aagtctcacc     180
ttttcttcca atagaaaatt ccgcttgacc tttggtgcac tgcccacttc ccagctccac     240
tggcccaagt ctgagccgga ggccttgtt ttggggcgg gggagagtt ggatgtgatt      300 gcccttgaag aacaaggctg acctgagagg ttcctggcgc cctgaggtgg ctcagcacct     360

```
gcccagggta ggcctggcat gaggggttag gtcagc                                   396

<210> SEQ ID NO 164
<211> LENGTH: 396
<212> TYPE: DNA
<213> ORGANISM: Homo sapiens

<400> SEQUENCE: 164
gacacgcggc ggtgtcctgt gttggccatg ccgactacc tgattagtgg gggcacgtcc          60
tacgtgccag acgacggact cacagcacag cagctcttca actgcggaga cggcctcacc        120
tacaatgact ttctcattct ccctgggtac atcgacttca ctgcagacca ggtggacctg        180
acttctgctc tgaccaagaa aatcactctt aagaccccac tggtttcctc tcccatggac       240
acagtcacag aggctgggat ggccatagca atggcgctta caggcggtat tggcttcatc        300
caccacaact gtacacctga attccaggcc aatgaagttc ggaaagtgaa gaaatatgaa        360
cagggattca tcacagaccc tgtggtcctc agcccc                                  396

<210> SEQ ID NO 165
<211> LENGTH: 396
<212> TYPE: DNA
<213> ORGANISM: Homo sapiens
<220> FEATURE:
<221> NAME/KEY: misc_feature
<222> LOCATION: 29, 33, 55, 57, 65, 77, 82, 87, 98, 101, 103, 114, 118,
      124, 169, 171, 173, 183, 186, 188, 216, 219, 227, 230, 242, 243,
      245, 252, 265, 273, 290, 296, 321, 324, 332, 338, 340, 342,
      345, 359, 372, 380
<223> OTHER INFORMATION: n = A,T,C or G

<400> SEQUENCE: 165
tttttttttt ttttttttt ttttttcang ggncactgag ctttttatt ttgancncaa          60 aaccnccggg gatctancct gnggccnccc cggaaatnac ncnaggctca catnactnta        120
aacncttggg ggaaagggag gcaaaaaaaa caatgacttg ggccaattnc ncnactgcaa        180
agntananct gccaacaggg ctccaggag cttggnttnt gtaaaanttn taaggaagcg         240
gnncnaactc cncgggggg gggcnctaac tancaggac ccctgcaagn gttggncggg          300
ggcctcaacc tgcctgagct nacncaaggg gngggtntn tntanccaac aggggaccna        360
agggcttgcc tncccacagn ttacttggcc aagggg                                  396

<210> SEQ ID NO 166
<211> LENGTH: 396
<212> TYPE: DNA
<213> ORGANISM: Homo sapiens
<220> FEATURE:
<221> NAME/KEY: misc_feature
<222> LOCATION: 151, 255
<223> OTHER INFORMATION: n = A,T,C or G

<400> SEQUENCE: 166 tttttttcaaa ttcagagcat ttttattaaa agaacaaaat attaaggcac aaaatacatc       60 aattttcaa atgaaaaccc ttcaaacggt tatgtcctac attcaacgaa acttcttcca        120
aattacggaa taatttaact ttttaaaata naaaaataca agttcttaaa tgcctaaaat       180
ttctccccaa ataaatgttt tcttagtttt aatgaagtct cttcatgcag tactgagctc       240
caatattata atgtncactt ccttaaaaat ctagttttgc cacttatata cattcaatat       300
gtttaaccag tatattaacc agtatattaa ccaatatgtt aaacttcttt taagtataag      360
gcttggtatt ttgtattgct tattgcatgc tttgat                                  396
```

```
<210> SEQ ID NO 167
<211> LENGTH: 396
<212> TYPE: DNA
<213> ORGANISM: Homo sapiens

<400> SEQUENCE: 167
tggcggcagc ggcggtggcg gtggctgagc agaggacccg gcgggcggcc tcgcgggtca      60
ggacacaatg tttgcacgag gactgaagag gaaatgtgtt ggccacgagg aagacgtgga     120
gggagccctg gccggcttga agacagtgtc ctcatacagc ctgcagcggc agtcgctcct     180
ggacatgtct ctggtgaagt tgcagctttg ccacatgctt gtggagccca atctgtgccg     240
ctcagtcctc attgccaaca cggtccggca gatccaagag gagatgacgc aggatgggac     300
gtggcgcaca gtggcacccc aggctgcaga gcgggcgccg ctcgaccgct tggtctccac     360
ggagatcctg tgccgtgcag cgtgggggca agaggg                              396

<210> SEQ ID NO 168
<211> LENGTH: 396
<212> TYPE: DNA
<213> ORGANISM: Homo sapiens

<400> SEQUENCE: 168
taggatggta agagtattat aaggattggt acaaggcatg atgagtcctt ttgcttttag      60
gcttttgact tctggtttta dactttcttt agcttctgtt gttagacaac attgtgcaag     120
cttggttttt ataagtttgc atggattaaa ctgaacttaa tgaaattgtc cctccccca     180 aattctcagc acaattttta ggcccacaag gagtcaagca cctcaaggag atcttcagtt     240
tgaacttggt gtagacacag ggatactgat gaatcaatat tcaaattagc tgttacctac     300
ttaagaaaga gaggagacct tggggatttc gaggaagggt tcataaggga gattttagct     360
gagaaatacc atttgcacag tcaatcactt ctgacc                              396

<210> SEQ ID NO 169
<211> LENGTH: 396
<212> TYPE: DNA
<213> ORGANISM: Homo sapiens
<220> FEATURE:
<221> NAME/KEY: misc_feature
<222> LOCATION: 16, 58, 76, 84, 99, 111, 114, 124, 136, 140, 161, 167,
      184, 189, 204, 206, 210, 228, 230, 232, 243, 275, 277, 289, 301,
      303, 312, 319, 321, 323, 325, 333, 345, 349, 355, 359, 364,
      365, 372, 375, 377, 379, 383, 387, 389, 394, 396
<223> OTHER INFORMATION: n = A,T,C or G

<400> SEQUENCE: 169
tttttttttt tttcanaatt aaattctttta atacaaaatg cttttttttt tttaaaanat      60
atctgtattt ctttgncgtt gttnaaaaat aaatatgtnc tacggaatat ntcnaaaaac     120
tgcnctaaaa acaaanacgn gatgttaata tcttttcccc ncaattntta cggataaaca     180 gtancccna taaataaatg atancnaatn ttaaaattaa aaaaggananan anatttagta     240 tgnaaaattc tctattttttt cttggtttgg ttttncntat aaaaaacana atagcaatgt     300
ntnttttatc anaatcccnt ntntncctaa acnttttttt ttttntttnc ccccnaatnc     360
aagnngccaa anatntntnt agnatgnana tgtntn                              396

<210> SEQ ID NO 170
<211> LENGTH: 396
<212> TYPE: DNA
<213> ORGANISM: Homo sapiens

<400> SEQUENCE: 170
```

```
tgagaagtac catgccgctt ctgcagagga acaggcaacc atcgaacgca acccctacac    60
catcttccat caagcactga aaaactgtga gcctatgatt gggctggtac ccatcctcaa   120
gggaggccgt ttctaccagg tccctgtacc cctacccgac cggcgtcgcc gcttcctagc   180
catgaagtgg atgatcactg agtgccggga taaaaagcac cagcggacac tgatgccgga   240
gaagctgtca cacaagctgc tggaggcttt ccataaccag gccccgtga tcaagaggaa    300 gcatgacttg cacaagatgg cagaggccaa ccgtgccctg gcccactacc gctggtggta   360
gagtctccag gaggagccca gggccctctg cgcaag                             396
```

<210> SEQ ID NO 171
<211> LENGTH: 396
<212> TYPE: DNA
<213> ORGANISM: Homo sapiens
<220> FEATURE:
<221> NAME/KEY: misc_feature
<222> LOCATION: 133, 224, 260, 264, 268, 279, 283, 317, 322, 338, 360,
      370, 371, 378
<223> OTHER INFORMATION: n = A,T,C or G

<400> SEQUENCE: 171

```
ggtcctcgtc gtggtgagcg cagccactca ggctggtcct gggggtgggg ctgtagggga    60
aagtgctaaa gccgctgagt gaagtaagaa ctctgctaga gaggaaaatg ggcttgcttt   120
catcatcatc ctnctcagct ggtggggtca agtgggaagt tctgtcactg ggatctggtt   180
cagtgtctca agaccttgcc ccaccacgga aagccttttt cacntacccc aaaggacttg   240
gagagatgtt agaagatggn tctnaaaanat tcctctgcna atntgttttt agctatcaag   300
tggcttcccc ccttaancag gnaaaacatg atcagcangt tgctcggatg gaaaaactan   360
cttggtttgn naaaaaanct ggaggcttga caatgg                             396
```

<210> SEQ ID NO 172
<211> LENGTH: 396
<212> TYPE: DNA
<213> ORGANISM: Homo sapiens
<220> FEATURE:
<221> NAME/KEY: misc_feature
<222> LOCATION: 239, 242, 244, 246, 249, 257, 260, 314, 329, 355, 372,
      378, 385, 387, 388, 395
<223> OTHER INFORMATION: n = A,T,C or G

<400> SEQUENCE: 172

```
agccttgggc caccctcttg gagcatctgg ctgtcgaatt cttgtgaccc tgttacacac    60
actggagaga atgggcagaa gtcgtggtgt tgcagccctg tgcattgggg gtgggatggg   120
aatagcaatg tgtgttcaga gagaatgaat tgcttaaact ttgaacaacc tcaatttctt   180
tttaaactaa taaagtacta ggttgcaata tgtgaaaaaa aaaaaaaaag ggcggccgnt   240
cnantntana gggcccnttn aaacccgttg atcaacctcg actgtgcctt ctagttgcca   300
gccatctgtt gttngccccct ccccgtgnc tttcttgacc ttgaaagggg cccncccct    360 gtctttccta anaaaaanga agaantnncc ttccnt                             396
```

<210> SEQ ID NO 173
<211> LENGTH: 396
<212> TYPE: DNA
<213> ORGANISM: Homo sapiens
<220> FEATURE:
<221> NAME/KEY: misc_feature
<222> LOCATION: 209, 210, 232, 244, 270, 275, 284, 341, 343, 349, 359,
      364, 368, 376, 380, 382, 388, 389, 390, 392
<223> OTHER INFORMATION: n = A,T,C or G

<400> SEQUENCE: 173

```
aagcatgtgg atatgtttag ctacgtttac tcacagccag cgaactgaca ttaaaataac      60
taacaaacag attcttttat gtgatgctgg aactcttgac agctataatt attattcaga     120
aatgactttt tgaaagtaaa agcagcataa agaatttgtc acaggaaggc tgtctcagat     180
aaattatggt aaaattttgc aggggacann ctttttaaga cttgcacaat tnccggatcc     240
tgcnctgact ttggaaaagg catatatgtn ctagnggcat gganaatgcc ccatactcat     300
gcatgcaaat taaacaacca agtttgaatc ttttttggggg ngngctatnc tttaaccnng    360
tacnggcntt attatntaan gnccctgnnn cntgtg                               396
```

<210> SEQ ID NO 174
<211> LENGTH: 924
<212> TYPE: DNA
<213> ORGANISM: Homo sapiens

<400> SEQUENCE: 174

```
cctgacgacc cggcgacggc gacgtctctt ttgactaaaa gacagtgtcc agtgctccag      60
cctaggagtc tacggggacc gcctcccgcg ccgccaccat gcccaacttc tctggcaact     120
ggaaaatcat ccgatcggaa aacttcgagg aattgctcaa agtgctgggg gtgaatgtga     180
tgctgaggaa gattgctgtg gctgcagcgt ccaagccagc agtggagatc aaacaggagg     240
gagacacttt ctacatcaaa acctccacca ccgtgcgcac cacagagatt aacttcaagg     300
ttggggagga gtttgaggag cagactgtgg atgggaggcc ctgtaagagc ctggtgaaat     360
gggagagtga gaataaaatg gtctgtgagc agaagctcct gaagggagag ggccccaaga     420
cctcgtggac cagagaactg accaacgatg gggaactgat cctgaccatg acggcggatg     480
acgttgtgtg caccagggtc tacgtccgag agtgagtggc cacaggtaga accgcggccg     540
aagcccacca ctggccatgc tcaccgccct gcttcactgc ccctccgtc  ccacccctc     600
cttctaggat agcgctcccc ttaccccagt cacttctggg ggtcactggg atgcctcttg     660
cagggtcttg ctttctttga cctcttctct cctcccctac accaacaaag aggaatggct     720
gcaagagccc agatcaccca ttccgggttc actcccccgcc tccccaagtc agcagtccta     780
gccccaaacc agcccagagc agggtctctc taaaggggac ttgagggcct gagcaggaaa     840
gactggcccct ctagcttcta cccctttgtcc ctgtagccta tacagtttag aatatttatt    900
tgttaatttt attaaaatgc ttta                                             924
```

<210> SEQ ID NO 175
<211> LENGTH: 3321
<212> TYPE: DNA
<213> ORGANISM: Homo sapiens

<400> SEQUENCE: 175

```
atgaagattt tgatacttgg tatttttctg tttttatgta gtaccccagc ctgggcgaaa      60
gaaaagcatt attacattgg aattattgaa acgacttggg attatgcctc tgaccatggg     120
gaaaagaaac ttatttctgt tgacacggaa cattccaata tctatcttca aaatggccca     180
gatagaattg ggagactata taagaaggcc ctttatcttc agtacacaga tgaaaccttt     240
aggacaacta tagaaaaacc ggtctggctt gggttttttag gccctattat caaagctgaa     300
actggagata agtttatgt acacttaaaa aaccttgcct ctaggcccta cacctttcat     360
tcacatggaa taacttacta taggaacat gagggggcca tctaccctga taacaccaca     420
gattttcaaa gagcagatga caaagtatat ccaggagagc agtatacata catgttgctt    480
```

```
gccactgaag aacaaagtcc tggggaagga gatggcaatt gtgtgactag gatttaccat    540
tcccacattg atgctccaaa agatattgcc tcaggactca tcggacccttt aataatctgt    600 aaaaaagatt ctctagataa agaaaaagaa aaacatattg accgagaatt tgtggtgatg    660
ttttctgtgg tggatgaaaa tttcagctgg tacctagaag acaacattaa aacctactgc    720
tcagaaccag agaaagttga caaagacaac gaagacttcc aggagagtaa cagaatgtat    780
tctgtgaatg gatacacttt tggaagtctc ccaggactct ccatgtgtgc tgaagacaga    840
gtaaaatggt accttttttgg tatgggtaat gaagttgatg tgcacgcagc tttctttcac    900
gggcaagcac tgactaacaa gaactaccgt attgacacaa tcaacctctt tcctgctacc    960
ctgtttgatg cttatatggt ggcccagaac cctggagaat ggatgctcag ctgtcagaat    1020
ctaaaccatc tgaaagccgg tttgcaagcc ttttttccagg tccaggagtg taacaagtct    1080
tcatcaaagg ataatatccg tgggaagcat gttagacact actacattgc cgctgaggaa    1140
atcatctgga actatgctcc ctctggtata gacatcttca ctaaagaaaa cttaacagca    1200
cctggaagtg actcagcggt gttttttgaa caaggtacca caagaattgg aggctcttat    1260
aaaaagctgg tttatcgtga gtacacagat gcctccttca caaatcgaaa ggagagaggc    1320
cctgaagaag agcatcttgg catcctgggt cctgtcattt gggcagaggt gggagacacc    1380
atcagagtaa ccttccataa caaaggagca tatccccctca gtattgagcc gattggggtg    1440
agattcaata agaacaacga gggcacatac tattccccaa attacaaccc ccagagcaga    1500
agtgtgcctc cttcagcctc ccatgtggca cccacagaaa cattcaccta tgaatggact    1560
gtccccaaag aagtaggacc cactaatgca gatcctgtgt gtctagctaa gatgtattat    1620
tctgctgtgg atcccactaa agatatattc actgggctta ttgggccaat gaaaatatgc    1680
aagaaaggaa gtttacatgc aaatgggaga cagaaagatg tagacaagga attctatttg    1740
tttcctacag tatttgatga gaatgagagt ttactcctgg aagataatat tagaatgttt    1800
acaactgcac ctgatcaggt ggataaggaa gatgaagact tcaggaatc taataaaatg    1860 cactccatga atggattcat gtatgggaat cagccgggtc tcactatgtg caaaggagat    1920
tcggtcgtgt ggtacttatt cagcgccgga aatgaggccg atgtacatgg aatatacttt    1980
tcaggaaaca catatctgtg gagaggagaa cggagagaca cagcaaacct cttccctcaa    2040
acaagtctta cgctccacat gtggcctgac acagaggcga ctttttaatgt tgaatgcctt    2100 acaactgatc attacacagg cggcatgaag caaaaatata ctgtgaacca atgcaggcgg    2160
cagtctgagg attccacctt ctacctggga gagaggacta ctatatcgc agcagtggag    2220 gtggaatggg attattcccc acaaagggag tgggaaaagg agctgcatca tttacaagag    2280
cagaatgttt caaatgcatt tttagataag ggagagtttt acataggctc aaagtacaag    2340
aaagttgtgt atcggcagta tactgatagc acattccgtg ttccagtgga gagaaaagct    2400
gaagaagaac atctgggaat tctaggtcca caacttcatg cagatgttgg agacaaagtc    2460
aaaattatct ttaaaaacat ggccacaagg ccctactcaa tacatgccca tggggtacaa    2520
acagagagtt ctacagttac tccaacatta ccaggtgaaa ctctcactta cgtatggaaa    2580
atcccagaaa gatctggagc tggaacagag gattctgctt gtattccatg ggcttattat    2640
tcaactgtgg atcaagttaa ggacctctac agtggattaa ttggccccct gattgtttgt    2700
cgaagacctt acttgaaagt attcaatccc agaaggaagc tggaatttgc ccttctgttt    2760
ctagtttttg atgagaatga atcttggtac ttagatgaca acatcaaaac atactctgat    2820 cacccccgaga aagtaaacaa agatgatgag gaattcatag aaagcaataa aatgcatgct    2880
```

| | |
|---|---|
| attaatggaa gaatgtttgg aaacctacaa ggcctcacaa tgcacgtggg agatgaagtc | 2940 |
| aactggtatc tgatgggaat gggcaatgaa atagacttac acactgtaca ttttcacggc | 3000 |
| catagcttcc aatacaagca caggggagtt tatagttctg atgtctttga catttttccct | 3060 |
| ggaacatacc aaaccctaga aatgtttcca agaacacctg gaatttggtt actccactgc | 3120 |
| catgtgaccg accacattca tgctggaatg gaaaccactt acaccgttct acaaaatgaa | 3180 |
| gacaccaaat ctggctgaat gaaataaatt ggtgataagt ggaaaaaaga gaaaaaccaa | 3240 |
| tgattcataa caatgtatgt gaaagtgtaa aatagaatgt tactttggaa tgactataaa | 3300 |
| cattaaaaga gactggagca t | 3321 |

<210> SEQ ID NO 176
<211> LENGTH: 487
<212> TYPE: DNA
<213> ORGANISM: Homo sapiens

<400> SEQUENCE: 176

| | |
|---|---|
| gaaatacttt ctgtcttatt aaaattaata aattattggt ctttacaaga cttggataca | 60 |
| ttacagcaga catggaaata taattttaaa aaatttctct ccaacctcct tcaaattcag | 120 |
| tcaccactgt tatattacct tctccaggaa ccctccagtg gggaaggctg cgatattaga | 180 |
| tttccttgta tgcaaagttt ttgttgaaag ctgtgctcag aggaggtgag aggagaggaa | 240 |
| ggagaaaact gcatcataac tttacagaat tgaatctaga gtcttccccg aaaagcccag | 300 |
| aaacttctct gcagtatctg gcttgtccat ctggtctaag gtggctgctt cttccccagc | 360 |
| catgagtcag tttgtgccca tgaataatac acgacctgtt atttccatga ctgctttact | 420 |
| gtattttaa ggtcaatata ctgtacattt gataataaaa taatattctc ccaaaaaaaa | 480 |
| aaaaaaa | 487 |

<210> SEQ ID NO 177
<211> LENGTH: 3999
<212> TYPE: DNA
<213> ORGANISM: Homo sapiens

<400> SEQUENCE: 177

| | |
|---|---|
| caagattcca catttgatgg ggtgactgac aaacccatct tagactgctg tgcctgcgga | 60 |
| actgccaagt acagactcac attttatggg aattggtccg agaagacaca cccaaaggat | 120 |
| taccctcgtc gggccaacca ctggtctgcg atcatcggag gatcccactc caagaattat | 180 |
| gtactgtggg aatatggagg atatgccagc gaaggcgtca aacaagttgc agaattgggc | 240 |
| tcacccgtga aaatggagga agaaattcga caacagagtg atgaggtcct caccgtcatc | 300 |
| aaagccaaag cccaatggcc agcctggcag cctctcaacg tgagagcagc accttcagct | 360 |
| gaattttccg tggacagaac gcgccattta atgtccttcc tgaccatgat gggccctagt | 420 |
| cccgactgga acgtaggctt atctgcagaa gatctgtgca ccaaggaatg tggctgggtc | 480 |
| cagaaggtgg tgcaagacct gattccctgg gacgctggca ccgacagcgg ggtgacctat | 540 |
| gagtcaccca acaaacccac cattcccag gagaaaatcc ggcccctgac cagcctggac | 600 |
| catcctcaga gtcctttcta tgacccagag ggtgggtcca tcactcaagt agccagagtt | 660 |
| gtcatcgaga gaatcgcacg gaagggtgaa caatgcaata ttgtacctga caatgtcgat | 720 |
| gatattgtag ctgacctggc tccagaagag aaagatgaag atgacacccc tgaaacctgc | 780 |
| atctactcca ctggtccccc atggtccgcc tgcagctcct ccacctgtga caaaggcaag | 840 |
| aggatgcgac agcgcatgct gaaagcacag ctggacctca gcgtccctg ccctgacacc | 900 |

```
caggacttcc agccctgcat gggccctggc tgcagtgacg aagacggctc cacctgcacc      960
atgtccgagt ggatcacctg gtcgccctgc agcatctcct gcggcatggg catgaggtcc     1020
cgggagaggt atgtgaagca gttcccggag gacggctccg tgtgcacgct gcccactgag     1080
gaaacggaga agtgcacggt caacgaggag tgctctccca gcagctgcct gatgaccgag     1140
tggggcgagt gggacgagtg cagcgccacc tgcggcatgg gcatgaagaa gcggcaccgc     1200
atgatcaaga tgaaccccgc agatggctcc atgtgcaaag ccgagacatc acaggcagag     1260
aagtgcatga tgccagagtg ccacaccatc ccatgcttgc tgtccccatg gtccgagtgg     1320
agtgactgca gcgtgacctg cgggaagggc atgcgaaccc gacagcggat gctcaagtct     1380
ctggcagaac ttggagactg caatgaggat ctggagcagg tggagaagtg catgctccct     1440
gaatgcccca ttgactgtga gctcaccgag tggtcccagt ggtcggaatg taacaagtca     1500
tgtgggaaag gccacgtgat tcgaacccgg atgatccaaa tggagcctca gtttggaggt     1560
gcaccctgcc cagagactgt gcagcgaaaa aagtgccgca tccgaaaatg ccttcgaaat     1620
ccatccatcc aaaagctacg ctggagggag gcccgagaga gccggcggag tgagcagctg     1680
aaggaagagt ctgaagggga gcagttccca ggttgtagga tgcgcccatg gacggcctgg     1740
tcagaatgca ccaaactgtg cggaggtgga attcaggaac gttacatgac tgtaaagaag     1800
agattcaaaa gctcccagtt taccagctgc aaagacaaga aggagatcag agcatgcaat     1860
gttcatcctt gttagcaagg gtacgagttc cccagggctg cactctagat tccagagtca     1920
ccaatggctg gattatttgc ttgtttaaga caatttaaat tgtgtacgct agttttcatt     1980
tttgcagtgt ggttcgccca gtagtcttgt ggatgccaga gacatccttt ctgaatactt     2040
cttgatgggt acaggctgag tggggcgccc tcacctccag ccagcctctt cctgcagagg     2100
agtagtgtca gccaccttgt actaagctga acatgtccc tctggagctt ccacctggcc      2160
agggaggacg gagactttga cctactccac atggagaggc aaccatgtct ggaagtgact     2220
atgcctgagt cccagggtgc ggcaggtagg aaacattcac agatgaagac agcagattcc     2280
ccacattctc atctttggcc tgttcaatga aaccattgtt tgcccatctc ttcttagtgg     2340
aactttaggt ctcttttcaa gtctcctcag tcatcaatag ttcctgggga aaaacagagc     2400
tggtagactt gaagaggagc attgatgttg ggtggctttt gttctttcac tgagaaattc     2460
ggaatacatt tgtctcaccc ctgatattgg ttcctgatgc cccccaaca aaaataaata      2520
aataaattat ggctgcttta tttaaatata aggtagctag ttttacaccc tgagataaat     2580
aataagctta gagtgtattt ttcccttgct tttgggggtt cagaggagta tgtacaattc     2640
ttctgggaag ccagccttct gaactttttg gtactaaatc cttattggaa ccaagacaaa     2700
ggaagcaaaa ttggtctctt tagagaccaa tttgcctaaa ttttaaaatc ttcctacaca     2760
catctagacg ttcaagtttg caaatcagtt tttagcaaga aaacattttt gctatacaaa     2820
cattttgcta agtctgccca aagccccccc aatgcattcc ttcaacaaaa tacaatctct     2880
gtactttaaa gttattttag tcatgaaatt ttatatgcag agagaaaaag ttaccgagac     2940
agaaaacaaa tctaagggaa aggaatatta tgggattaag ctgagcaagc aattctggtg     3000
gaaagtcaaa cctgtcagtg ctccacacca gggctgtggt cctcccagac atgcatagga     3060
atggccacag gttacactg ccttcccagc aattataagc acaccagatt cagggagact      3120
gaccaccaag ggatagtgta aaaggacatt ttctcagttg ggtccatcag cagttttct      3180
tcctgcattt attgttgaaa actattgttt catttcttct tttataggcc ttattactgc     3240
ttaatccaaa tgtgtaccat tggtgagaca catacaatgc tctgaataca ctacgaattt     3300
```

| | |
|---|---|
| gtattaaaca catcagaata tttccaaata caacatagta tagtcctgaa tatgtacttt | 3360 |
| taacacaaga gagactattc aataaaaact cactgggtct ttcatgtctt taagctaagt | 3420 |
| aagtgttcag aaggttcttt tttatattgt cctccacctc catcattttc aataaaagat | 3480 |
| agggcttttg ctcccttgtt cttggaggga ccattattac atctctgaac tacctttgta | 3540 |
| tccaacatgt tttaaatcct taaatgaatt gctttctccc aaaaaaagca caatataaag | 3600 |
| aaacacaaga tttaattatt tttctacttg gggggaaaaa agtcctcatg tagaagcacc | 3660 |
| cacttttgca atgttgttct aagctatcta tctaactctc agcccatgat aaagttcctt | 3720 |
| aagctggtga ttcctaatca aggacaagcc accctagtgt ctcatgtttg tatttggtcc | 3780 |
| cagttgggta cattttaaaa tcctgatttt ggagacttaa aaccaggtta atggctaaga | 3840 |
| atgggtaaca tgactcttgt tggattgtta tttttgttt gcaatgggga atttataaga | 3900 |
| agcatcaagt ctctttctta ccaaagtctt gttaggtggt ttatagttct tttggctaac | 3960 |
| aaatcatttt ggaaataaag atttttact acaaaaatg | 3999 |

<210> SEQ ID NO 178
<211> LENGTH: 1069
<212> TYPE: DNA
<213> ORGANISM: Homo sapiens

<400> SEQUENCE: 178

| | |
|---|---|
| aaaaaagatg aataaatgaa taagagagat gaataaacaa atttacatta catgtgatag | 60 |
| ttatcatggt atggccttca tgacaagatg gatgagaata tcactgatag gatattagcc | 120 |
| ttctttcata tctttatatt gaaatatggg ctttacttca atttgaaggt ctttcatgaa | 180 |
| caataaaaga gagtagaagg actgtctgag aaggcaggag acatataaaa cagatgactg | 240 |
| aaagactgac tagctcctgg aaagggaaac atttggaaca tccagagtaa gggcaaatgg | 300 |
| gcttctacca gcacaacaaa gagcctccag gtggcaacat ggaagcaggt tatcagagaa | 360 |
| aataaatgtg caaattcctt atttacaatg actcacttaa ccccacaaac atgtttcact | 420 |
| gctgccttcc ccagttgtcg cttatgtact gttgttacct ttcagttaca tgcctttgat | 480 |
| cctaaaattc tctactttg gtgccttatc agttctttgc aatctgcctg tggttatcag | 540 |
| cacttaaagc acaattttga aggggaaaaa aatgataatc accttagtcc caagaaaata | 600 |
| atttgtcaaa ctgccttatt agtattaaaa acagacacac tgaatgaagt agcatgatac | 660 |
| gcatatatcc tactcagtat cattggcctt ttatcaaatg gggaaactat acttttgtat | 720 |
| tacatagttt tagaaatcga aagttagaga ctctttataa gtaatgtcaa ggaacagtaa | 780 |
| tttaaaaaca aagttctaac aaatatattg tttgcttaat cacaatgccc tcaacttgta | 840 |
| tttgaataac taaataggac atgtcttcct tggagctgtg ggcattagtt cagaagcact | 900 |
| acctgcatct taattttcaa aacttaagtt ttattagcaa atcctcttct ctgtaagact | 960 |
| tagctatgaa gtggtatatt ttttccaaat attttctga aaacatttgt tgttgtaact | 1020 |
| gcacaataaa agtccagttg caattaaaaa aaaaaaaaa aaaaaaaa | 1069 |

<210> SEQ ID NO 179
<211> LENGTH: 1817
<212> TYPE: DNA
<213> ORGANISM: Homo sapiens

<400> SEQUENCE: 179

| | |
|---|---|
| tgctattctg ccaaaagaca atttctagag tagttttgaa tgggttgatt tccccactc | 60 |
| ccacaaactc tgaagccagt gtctagctta ctaaaaaaag agttgtatat aatatttaag | 120 |

```
atgctgagta tttcatagga aagctgaatg ctgctgtaaa gtgctcttta agtcttttt      180 ttttttaatc cccttctaat gaatgaaact aggggaattt caggggacag agatgggatt     240
tgttgtatga taaactgtat gtagttttta gtctttctgt tttgagaagc agtggttggg     300 gcattttta a datggctggc tactcttgtt ttccctcatg ataataaatt tgtcataact    360
cagtaacatg aacttgcccc tagaggtagt tgttaataat tttgaaatat aaggtcttg     420 ccaagcttct gatgattcac acctgtacta ctgattatta agcaggacag actgagcttt    480
ctgttgcaaa taccttggag gagaaagtaa tttctaaata tacagagagg taacttgact    540
atatatgttg catcctgtgc ctcccttcat attaatattt gataaagatt ttaatttatg    600
taaaacttct aaagcagaat caaagctcct cttggggaaa tggcaagtct ttaggatagg    660
caagaccctg tatgaatagt accaaagcat taccgcatgg tagagaacac actcgattaa    720
aaatgttaag ctatctgaaa aataaaatgt gcaagtcttc aggatggcac aaaacaaagg    780
ttaatgcttc ttggggcaca tttcttagag ggcttgctga gtgtgtaaat ataatcgact    840
tttgtttgtg ttacatgact tctgtgactt cattgaaaat ctgcacaatt cagtttcagc    900
tctggattac ttcagttgac cttttgtgaag gttttatct gtgtagaatg ggtgtttgac    960
ttgttttagc ctattaaatt tttatttct ttcactctgt attaaaagta aaacttacta    1020
aaagaaaaga ggtttgtgtt cacattaaat ggttttggtt tggcttcttt tagtcaggct    1080
ttctgaacat tgagatatcc tgaacttaga gctcttcaat cctaagattt tcatgaaaag    1140
cctctcactt gaacccaaac cagagtactc ttactgcctc ttttctaaat gttcaggaaa    1200
agcattgcca gttcagtctt ttcaaaatga gggagaaaca tttgcctgcc ttgtaataac    1260
aagactcagt gcttattttt taaactgcat tttaaaaatt ggatagtata ataacaataa    1320
ggagtaagcc acctttata ggcaccctgt agttttatag ttcttaatct aaacatttta    1380
tatttccttc ttttggaaaa aacctacatg ctacaagcca ccatatgcac agactataca    1440
gtgagttgag ttggctctcc cacagtcttt gaggtgaatt acaaaagtcc agccattatc    1500
atcctcctga gttatttgaa atgattttt ttgtacattt tggctgcagt attggtggta    1560
gaatatacta atatatggat catctctact tctgtattta tttatttatt actagacctc    1620
aaccacagtc ttcttttcc ccttccacct ctctttgcct gtaggatgta ctgtatgtag    1680
tcatgcactt tgtattaata tattagaaat ctacagatct gttttgtact ttttatactg    1740
ttggatactt ataatcaaaa cttttactag ggtattgaat aaatctagtc ttactagaaa    1800
aaaaaaaaaa aaaaaaa                                                   1817

<210> SEQ ID NO 180
<211> LENGTH: 2382
<212> TYPE: DNA
<213> ORGANISM: Homo sapiens

<400> SEQUENCE: 180
acttttattg gaagcagcag ccacatccct gcatgatttg cattgcaata caaccataac     60
cgggcagcca ctcctgagtg ataaccagta taacataaac gtagcagcct caattttgc    120 ctttatgacg acagcttgtt atggttgcag tttgggtctg gctttacgaa gatggcgacc    180
gtaacactcc ttagaaactg gcagtcgtat gttagtttca cttgtctact ttatatgtct    240
gatcaatttg gataccattt tgtccagatg caaaaacatt ccaaaagtaa tgtgtttagt    300
agagagagac tctaagctca agttctggtt tatttcatgg atggaatgtt aattttatta    360
tgatattaaa gaaatggcct tttatttac atctctcccc ttttccctt tccccttta     420
```

```
ttttcctcct tttctttctg aaagtttcct tttatgtcca taaaatacaa atatattgtt        480
cataaaaaat tagtatccct tttgtttggt tgctgagtca cctgaacctt aattttaatt        540
ggtaattaca gccctaaaa aaacacatt tcaaataggc ttcccactaa actctatatt          600
ttagtgtaaa ccaggaattg gcacactttt tttagaatgg gccagatggt aaatatttat        660
gcttcacggt ccatacagtc tctgtcacaa ctattcagtt ctgctagtat agcgtgaaag        720
cagctataca caatacagaa atgaatgagt gtggttatgt tctaataaaa cttatttata        780
aaaacaaggg gaggctgggt ttagcctgtg ggccatagtt tgtcaaccac tggtgtaaaa        840
ccttagttat atatgatctg cattttcttg aactgatcat tgaaaactta taaacctaac        900
agaaaagcca cataatattt agtgtcatta tgcaataatc acattgcctt tgtgttaata        960
gtcaaatact tacctttgga gaatacttac ctttggagga atgtataaaa tttctcaggc       1020
agagtcctgg atataggaaa aagtaattta tgaagtaaac ttcagttgct taatcaaact       1080
aatgatagtc taacaactga gcaagatcct catctgagag tgcttaaaat gggatcccca       1140
gagaccatta accaatactg gaactggtat ctagctactg atgtcttact ttgagtttat       1200
ttatgcttca gaatacagtt gtttgccctg tgcatgaata tacccatatt tgtgtgtgga       1260
tatgtgaagc ttttccaaat agagctctca gaagaattaa gttttttactt ctaattattt      1320 tgcattactt tgagttaaat ttgaatagag tattaaatat aaagttgtag attcttatgt       1380
gtttttgtat tagcccagac atctgtaatg ttttttgcact ggtgacagac aaaatctgtt      1440
ttaaaatcat atccagcaca aaaactattt ctggctgaat agcacagaaa agtattttaa       1500
cctacctgta gagatcctcg tcatggaaag gtgccaaact gttttgaatg gaaggacaag        1560
taagagtgag gccacagttc ccaccacacg agggcttttg tattgttcta ctttttcagc       1620
cctttacttt ctggctgaag catccccttg gagtgccatg tataagttgg gctattagag       1680
ttcatggaac atagaacaac catgaatgag tggcatgatc cgtgcttaat gatcaagtgt       1740
tacttatcta ataatcctct agaaagaacc ctgttagatc ttggtttgtg ataaaaatat       1800
aaagacagaa gacatgagga aaaacaaaag gtttgaggaa atcaggcata tgactttata       1860
cttaacatca gatcttttct ataatatcct actactttgg ttttcctagc tccataccac       1920
acacctaaac ctgtattatg aattacatat tacaaagtca taaatgtgcc atatggatat       1980
acagtacatt ctagttggaa tcgtttactc tgctagaatt taggtgtgag attttttgtt       2040
tcccaggtat agcaggctta tgtttggtgg cattaaattg gtttctttaa aatgctttgg       2100
tggcactttt gtaaacagat tgcttctaga ttgttacaaa ccaagcctaa gacacatctg       2160
tgaatactta gatttgtagc ttaatcacat tctagacttg tgagttgaat gacaaagcag       2220
ttgaacaaaa attatggcat ttaagaattt aacatgtctt agctgtaaaa atgagaaagt       2280
gttggttggt tttaaaatct ggtaactcca tgatgaaaag aaatttattt tatacgtgtt       2340
atgtctctaa taaagtattc atttgataaa aaaaaaaaa aa                          2382

<210> SEQ ID NO 181
<211> LENGTH: 2377
<212> TYPE: DNA
<213> ORGANISM: Homo sapiens

<400> SEQUENCE: 181
atctttatgc aagacaagag tcagccatca gacactgaaa tatattatga tagattatga         60
agaattttct ctgtagaatt atattcttcc tggaacctgg tagagtagat tagactcaaa        120 ggcttttttct tccttttctt actcctgttt tttccactca ctcttcccaa gagatttcct      180
```

```
aaagcttcaa gcttaataag cctaatagtg aaaaataact gaatttaatg gtataatgaa      240
gttcttcatt tccagacatc tttaattgat cttaaagctc atttgagtct ttgcccctga      300
acaaagacag acccattaaa atctaagaat tctaaatttt cacaactgtt tgagcttctt      360
ttcattttga aggatttgga atatatatgt tttcataaaa gtatcaagtg aaatatagtt      420
acatgggagc tcaatcatgt gcagattgca ttctgttatg ttgactcaat atttaattta      480
caactatcct tatttatatt gacctcaaga actccatttt atgcaatgca gaccactgag      540
atatagctaa cattctttca ataattttc cttttctttt ataattcctc tatagcaaat       600
ttttatgtat aactgattat acatatccat atttatattt cattgattcc aagacatcac      660
tttttcaatt taacatctct gaaattgtga catttcttgc aactgttggc acttcagatg      720
cagtgtttaa aattatgctt gaataaatat tacactaatc caactttacc taaatgttta      780
tgcatctagg caaattttgt ttcttataa agatttgaga gcccatttat gacaaaatat        840
gaaggcgaaa tttaaggaca actgagtcac gcacaactca acatggagcc taactgatta      900
tcagctcaga tcccgcatat cttgagttta caaaagctct ttcaggtccc catttatact      960
ttacgtgagt gcgaatgatt tcagcaaacc ctaacttaac taacaagaat gggtaggtat     1020
gtctacgttt cattaacaaa ttttttattat ttttattcta ttatatgaga tccttttata    1080
ttatcatctc acttttaaac aaaattaact ggaaaaatat tacatggaac tgtcatagtt     1140
aggttttgca gcatcttaca tgtcttgtat caatggcagg agaaaaatat gataaaaaca     1200
atcagtgctg tgaaaaacaa ctttcttcta gagtcctctt acttttatt cttctttatc      1260
atttgtgggt ttttcccct tggctctcac tttaacttca agcttatgta acgactgtta      1320
taaaactgca tatttaaatt atttgaatta tatgaaataa ttgttcagct atctgggcag     1380
ctgttaatgt aaacctgaga gtaataacac tactctttta tctacctgga atactttct      1440
gcataaaatt tatctttgta agctaactct attaatcagg tttcttctag cctctgcaac     1500
ctacttcagt tagaattgtc taatactgct ctattaatca ggtttctacc ctctacaacc     1560
tacttcagtt aaaattgtct aatacagcaa tattaaaaa aaaaacactg caattgtcaa       1620
ggatggaaaa tgtgtgattt gtgtaaacaa ttttaccaa ctttacattt tcctacagat       1680
aaatgtgaaa ttttgataag aagtctacgc aatgacaagt acggtacata aattttatta     1740
agaatattga gtaaagta ctttaattct aaattataag aaaatataca tttgcacata        1800
ttaatataga aattcatttt gtgtatattt aacatagctt ttaaactatt ttacattagc     1860
tacttcatta tggtttcttg aacttctgaa aaaaattaga aatgtattaa acttatcagt     1920
aacataaaaa cttatttgt ttcacctaac gaatactgcg tttgtaaaaa taaatttaat       1980
atagaatata ttttaaatt aaatatttga atataaaata gctctaagaa agaagcaaat      2040
tatcactgaa catatttctt attatttctg gctttgaatt atacgtaact taaattgtct     2100
taaatgatac agaatattgg agaatatgat actttcacat aatatactat gaacctgttc     2160
ataaactct gattgactac taacttctgt tttatgtatt tattaaagag ctgacactgt       2220
agtttgtggt gagatgttta ttttttctaac agagcttata acagttagga caaggcattt    2280
aattaatgca tcattctgtt tagtagtagg tgttaatcaa tatgaaattc tctgttttaa     2340
aataaaaatg taaaaatcta aaaaaaaaaa aaaaaaa                              2377

<210> SEQ ID NO 182
<211> LENGTH: 1370
<212> TYPE: DNA
<213> ORGANISM: Homo sapiens
```

<400> SEQUENCE: 182

```
tgtgagcatg gtattttgtc tcggaagaaa aaaatatggg tcaggcgcaa agtaagccca      60
ccccactggg aactatgtta aaaaaaaatt tcaagattta agggagatta cggtgttact     120
atgacaccag aaaaacttag aactttgtgt gaaatagact ggctaacatt agaggtgggt     180
tggctatcag aagaaagcct ggagaggtcc cttgtttcaa aggtatggca caaggtaacc     240
tgtaagccaa agcacccgga ccagtttcta tacatagaca gttacagctg gtttagaccc     300
cttcccccctc tccccacagt agttaagaga acagcagcat aagcagctgg cagaggcaag     360
gaaagaccag cagagagaaa aaaaggccat ctataccaat tttaagttaa tttagactga     420
acaagggctt attaatagca aaggataatt gaaatcacaa acttataagg gtttcaacaa     480
aagtgaagtt tgctaaaagt taacagtgta acatgtatta tggtaacttc taatcttgtg     540
gccttagaca gtctagtcaa aacacataaa gaaagtttgc tttaaaaaaa caatggttat     600
cttcaaaaat aaaggggaga ggcagaattt atataaaaag agttatatga taaattcttg     660
tcctgaaata aattaactgg ttgtttaaag aaaagaatgt ttgtaataag tcaaaaagtt     720
aaaacatgtt taaaaaattg tctgcaaaag tcataaaaga aaaaatttta ttaaaaaaat     780
tttaagcaaa aaatgttgta taatttaaaa gtaataaggc ctcctgtgta ctattaagac     840
agatgcaaat tcctggttga aatggatcaa atattccatc tgcacattaa acaaaagcaa     900
ttgttatgct tgtgcacatg gcaggccaga ggccctgatt gtccccttc cactaaggtg      960
gtcctctagt cgaccaggcg tggactgcat ggtagctctt ttccaggatt ctacagcctg    1020
gagtaataag tcatgccaag ctctctctgc tatatcccaa agtctctgcg ggtcagcccc    1080
caagggccat gcagcttctg tctcccaaca ctaagttcac ttcgtgtctc tcacggcaga    1140
gaggaaactt agtattcctt ggagacctga agggatgcag tgagcttaag aattttcaag    1200
agcttatcaa tcagtcagcc cttgttcatc cccgagtgga tgtgtggtgg tattgtggtg    1260
gacctttact gggcactctg ccaaataact agtgtgcac ttgtgcttta gtccatttgg    1320
ctatcccttt caccctggca tttcatcaac caaaaaaaaa aaaaaaaaaa              1370
```

<210> SEQ ID NO 183
<211> LENGTH: 2060
<212> TYPE: DNA
<213> ORGANISM: Homo sapiens
<220> FEATURE:
<221> NAME/KEY: misc_feature
<222> LOCATION: 2003
<223> OTHER INFORMATION: n = A,T,C or G

<400> SEQUENCE: 183

```
gtttcagggg aggagacaag gtttcttgtt tgccgtatat gctcctgcag agaagaggaa      60
gtgaccgtgg aggccatctg gccctgtgtt ttgatatggc aaaattaatg aatgcaatca     120
gaagaccttt gagcaagaaa gtaccctgga acaacccaat ttggactgca agtattagtt     180
gggtcttcca ggtgcctctc acagcagcag tcatggcagc agtgactcta gccatgtcca     240
tgaccaactg ctgcataaca aatagccccg agactcagca gcttacaaca gggtccccag     300
cccacagact ggcactggtc catggcttgt taggaacctg actgcgcagc agaaggtgag     360
tgagcattac tgcctgagct ctgcctcctg tcagatcatc aggggcatta gattctcata     420
ggagcgtgaa cccattgca aaccgcgcat gcgaaggatg tacgttgcgt gctccttatg     480
agaatctaac taatgcctga tgatttgagg tggggcagtt tcatccccaa accatctctc     540
tcccttcatg tccatggaaa aattgtcttc tacaaaacca gtccgtggtg ccaaaaaggt     600
```

| | |
|---|---|
| tggagactgc tggtttacaa ccgcaatgaa cattcatcat cccacacagt gtcagagggt | 660 |
| cgggaacacg ggtgccctgc ctgtgtgctt ccggttccag atttctcagt gggttgtgat | 720 |
| caaggtatca gcggaggccg tattcatctg caagcttgac caggaataga agagccactt | 780 |
| catgggtggc tcactcagat gccagcaggt cagtgctggt ggctggcagg cagcctcagc | 840 |
| tcctcacctc atggatctct cctgagcaca gttttcctgt ccttacaacc tggtagctgg | 900 |
| cttctccaga gcaggtgact caggagagga caaggtgaga gcccagcacc ttatggtcta | 960 |
| gtctcagaag tcacacgcca tcatttctgc aatgtcattt tggggttcca ggtcagctgt | 1020 |
| atcactgtgg gaggtgagta tatagatgtc ctagaccatt caggctgcta tgacagaaca | 1080 |
| ccatgaactg agtggctcat gaacaacaga aatttcccac agttctgtag ctgggaaat | 1140 |
| ccaagatcaa ggtggcagca ggttcagcgt ctgctaagct cctgcttttc atggattgca | 1200 |
| tcttctcact gtgtcctcac gtgatggaca gagcaaatga gctctcaggc actagtccca | 1260 |
| gccatgagga ctctgctttc atgactcatc actccgcaaa ggcccacctc catcagaaga | 1320 |
| cagctgctaa ctgcagctgc catcctccaa gacgggagac acagaattgg gggacatata | 1380 |
| cattgagatc tgaaaggcct ggacagcaac aggtggggat cgtgggggca tcttggaggg | 1440 |
| tggctgccgc agtaacattt ctgacccatg ctttctgctt gcactcatct cctgcctttg | 1500 |
| atcttcatta tctcargcag tccccacaac gactgtatct aggagttcat tttaccctca | 1560 |
| ttttacagat gaaacgtctc agagggtaat gtgcttgccc agtgtctcac aaatgcaaag | 1620 |
| tcactgaggt aggatttcaa cctaggtcca atcatctctg cagcattagg ggttcaccat | 1680 |
| tgccatagac ttaactgtgt cccccaaaat ttgtatgttg aagccctacc agcctccccc | 1740 |
| ccccaatgtg ctgatgtttg gagaaagggc ctttgggagg taattaggtt tagatgagat | 1800 |
| catgagggtg ggactctcat aatggcatta atgccatcag gtgaagagat accagagacc | 1860 |
| ttgtgtcctc tctctctgca atgtgaggac acagtgagaa ggcagctgtc tgcaagctgg | 1920 |
| gaagagagta ctgaccagga acttaatcag agggcatctt gatcttggac ttcccagcct | 1980 |
| ccagaactct gaaaagttaa tgnctattat ttaagccacg cagtctatgg aattttgtta | 2040 |
| gagccaaccc caagcttact | 2060 |

<210> SEQ ID NO 184
<211> LENGTH: 3079
<212> TYPE: DNA
<213> ORGANISM: Homo sapiens

<400> SEQUENCE: 184

| | |
|---|---|
| ggcacaaagt tggggccgc gaagatgagg ctgtccccgg cgccctgaa gctgagccgg | 60 |
| actccggcac tgctggccct ggcgctgccc ctggccgcgg cgctggcctt ctccgacgag | 120 |
| accctggaca aagtgcccaa gtcagagggc tactgtagcc gtatcctgcg cgcccagggc | 180 |
| acgcggcgcg agggctacac cgagttcagc ctccgcgtgg agggcgaccc cgacttctac | 240 |
| aagccgggaa ccagctaccg cgtaacactt tcagctgctc ctccctccta cttcagagga | 300 |
| ttcacattaa ttgccctcag agaacagaga gaggtgata aggaagaaga ccatgctggg | 360 |
| accttccaga tcatagacga agaagaaact cagtttatga gcaattgccc tgttgcagtc | 420 |
| actgaaagca ctccacggag gaggacccgg atccaggtgt tttggatagc accaccagcg | 480 |
| ggaacaggct gcgtgattct gaaggccagc atcgtacaaa aacgcattat ttattttcaa | 540 |
| gatgagggct ctctgaccaa gaaactttgt gaacaagatt ccacatttga tggggtgact | 600 |
| gacaaaccca tcttagactg ctgtgcctgc ggaactgcca agtacagact cacatttat | 660 |

```
gggaattggt ccgagaagac acacccaaag gattaccctc gtcgggccaa ccactggtct    720
gcgatcatcg gaggatccca ctccaagaat tatgtactgt gggaatatgg aggatatgcc    780
agcgaaggcg tcaaacaagt tgcagaattg ggctcacccg tgaaaatgga ggaagaaatt    840
cgacaacaga gtgatgaggt cctcaccgtc atcaaagcca agcccaatg gccagcctgg     900 cagcctctca acgtgagagc agcaccttca gctgaatttt ccgtggacag aacgcgccat    960
ttaatgtcct tcctgaccat gatgggccct agtcccgact ggaacgtagg cttatctgca   1020
gaagatctgt gcaccaagga atgtggctgg gtccagaagg tggtgcaaga cctgattccc   1080
tgggacgctg gcaccgacag cggggtgacc tatgagtcac ccaacaaacc caccattccc   1140
caggagaaaa tccggcccct gaccagcctg gaccatcctc agagtccttt ctatgaccca   1200
gagggtgggt ccatcactca gtagccaga gttgtcatcg agagaatcgc acggaagggt    1260
gaacaatgca atattgtacc tgacaatgtc gatgatattg tagctgacct ggctccagaa   1320
gagaaagatg aagatgacac ccctgaaacc tgcatctact ccaactggtc cccatggtcc   1380
gcctgcagct cctccacctg tgacaaaggc aagaggatgc gacagcgcat gctgaaagca   1440
cagctggacc tcagcgtccc ctgccctgac acccaggact ccagccctg catgggccct    1500 ggctgcagtg acgaagacgg ctccacctgc accatgtccg agtggatcac ctggtcgccc   1560
tgcagcatct cctgcggcat gggcatgagg tcccgggaga ggtatgtgaa gcagttcccg   1620
gaggacggct ccgtgtgcac gctgcccact gaggaaatgg agaagtgcac ggtcaacgag   1680
gagtgctctc ccagcagctg cctgatgacc gagtggggcg agtgggacga gtgcagcgcc   1740
acctgcggca tgggcatgaa gaagcggcac cgcatgatca agatgaaccc cgcagatggc   1800
tccatgtgca aagccgagac atcacaggca gagaagtgca tgatgccaga gtgccacacc   1860
atcccatgct tgctgtcccc catggtccgag tggagtgact gcagcgtgac ctgcgggaag   1920
ggcatgcgaa cccgacagcg gatgctcaag tctctggcag aacttggaga ctgcaatgag   1980
gatctggagc aggtggagaa gtgcatgctc cctgaatgcc ccattgactg tgagctcacc   2040
gagtggtccc agtggtcgga atgtaacaag tcatgtggga aaggccacgt gattcgaacc   2100
cggatgatcc aaatgagagcc tcagtttgga ggtgcaccct gcccagagac tgtgcagcga   2160
aaaaagtgcc gcatccgaaa atgccttcga aatccatcca tccaaaagcc acgctggagg   2220
gaggcccgag agagccggcg gagtgagcag ctgaaggaag agtctgaagg ggagcagttc   2280
ccaggttgta ggatgcgccc atggacggcc tggtcagaat gcaccaaact gtgcggaggt   2340
ggaattcagg aacgttacat gactgtaaag aagagattca aaagctccca gtttaccagc   2400
tgcaaagaca agaaggagat cagagcatgc aatgttcatc cttgttagca agggtacgag   2460
ttccccaggg ctgcactcta gattccgag tcaccaatgg ctggattatt tgcttgttta    2520
agacaattta aattgtgtac gctagttttc attttttgcag tgtggttcgc ccagtagtct   2580
tgtggatgcc agagacatcc tttctgaata cttcttgatg ggtacaggct gagtggggcg   2640
ccctcacctc cagccagcct cttcctgcag aggagtagtg tcagccacct tgtactaagc   2700
tgaaacatgt ccctctggag cttccacctg gccaggagg acggagactt tgacctactc    2760
cacatggaga ggcaaccatg tctggaagtg actatgcctg agtcccaggg tgcggcaggt   2820
aggaaacatt cacagatgaa gacagcagat tccccacatt ctcatctttg gcctgttcaa   2880
tgaaaccatt gtttgcccat ctcttcttag tggaacttta ggtctctttt caagtctcct   2940
cagtcatcaa tagttcctgg ggaaaaacag agctggtaga cttgaagagg agcattgatg   3000
ttgggtggct tttgttcttt cactgagaaa ttcggaatac atttgtctca cccctgatat   3060
```
tggttcctga tgccccagc 3079

<210> SEQ ID NO 185
<211> LENGTH: 3000
<212> TYPE: DNA
<213> ORGANISM: Homo sapiens

<400> SEQUENCE: 185

| | | | | | |
|---|---|---|---|---|---|
| gtttcagggg | aggagacaag | gtttcttgtt | tgccgtatat | gctcctgcag | agaagaggaa | 60 |
| gtgaccgtgg | aggccatctg | gccctgtgtt | ttgatatggc | aaaattaatg | aatgcaatca | 120 |
| gaagaccttt | gagcaagaaa | gtaccctgga | acaacccaat | ttggactgca | agtattagtt | 180 |
| gggtcttcca | ggtgcctctc | acagcagcag | tcatggcagc | agtgactcta | gccatgtcca | 240 |
| tgaccaactg | ctgcataaca | aatagccccg | agactcagca | gcttacaaca | gggtccccag | 300 |
| cccacagact | ggcactggtc | catggcttgt | taggaacctg | actgcgcagc | agaaggtgag | 360 |
| tgagcattac | tgcctgagct | ctgcctcctg | tcagatcatc | aggggcatta | gattctcata | 420 |
| ggagcgtgaa | ccctattgca | aaccgcgcat | gcgaaggatg | tacgttgcgt | gctccttatg | 480 |
| agaatctaac | taatgcctga | tgatttgagg | tggggcagtt | tcatccccaa | accatctctc | 540 |
| tcccttcatg | tccatggaaa | aattgtcttc | tacaaaacca | gtccgtggtg | ccaaaaaggt | 600 |
| tggagactgc | tggtttacaa | ccgcaatgaa | cattcatcat | cccacacagt | gtcagagggt | 660 |
| cgggaacacg | ggtgccctgc | ctgtgtgctt | ccggttccag | atttctcagt | gggttgtgat | 720 |
| caaggtatca | gcggaggccg | tattcatctg | caagcttgac | caggaataga | agagccactt | 780 |
| catgggtggc | tcactcagat | gccagcaggt | cagtgctggt | ggctggcagg | cagcctcagc | 840 |
| tcctcacctc | atgatctctc | cctgagcaca | gttttcctgt | ccttacaacc | tggtagctgg | 900 |
| cttctccaga | gcaggtgact | caggagagga | caaggtgaga | gccacagcac | cttatggtct | 960 |
| agtctcagaa | gtcacacgcc | atcatttctg | caatgtcatt | ttgggggttcc | aggtcagctg | 1020 |
| tatcactgtg | ggaggtgagt | atatagatgt | cctagaccat | tcaggctgct | atgacagaac | 1080 |
| accatgaact | gagtggctca | tgaacaacag | aaatttccca | cagttctgta | ggctgggaaa | 1140 |
| tccaagatca | aggtggcagc | aggttcagcg | tctgctaagc | tcctgctttt | catggattgc | 1200 |
| atcttctcac | tgtgtcctca | cgtgatggac | agagcaaatg | agctctcagg | cactagtccc | 1260 |
| agccatgagg | actctgcttt | catgactcat | cactccgcaa | aggcccacct | ccatcagaag | 1320 |
| acagctgcta | actgcagctg | ccatcctcca | agacgggaga | cacagaattg | ggggacatat | 1380 |
| acattgagat | ctgaaaggcc | tggacagcaa | caggtgggga | tcgtggggc | atcttggagg | 1440 |
| gtggctgccg | cagtaacatt | tctgacccat | gctttctgct | tgcactcatc | tcctgccttt | 1500 |
| gatcttcatt | atctcaggca | gtccccacaa | cgactgtatc | taggagttca | ttttacccctc | 1560 |
| attttacaga | tgaaacgtct | cagagggtaa | tgtgcttgcc | cagtgtctca | caaatgcaaa | 1620 |
| gtcactgagg | taggatttca | acctaggtcc | aatcatctct | gcagcattag | gggttcacca | 1680 |
| ttgccataga | cttaactgtg | tcccccaaaa | tttgtatgtt | gaagccctac | cagcctcccc | 1740 |
| cccccaatgt | gctgatgttt | ggagaaaggg | cctttgggag | gtaattaggt | ttagatgaga | 1800 |
| tcatgagggt | gggactctca | taatggcatt | aatgccatca | ggtgaagaga | taccagagac | 1860 |
| cttgtgtcct | ctctctctgc | aatgtgagga | cacagtgaga | aggcagctgt | ctgcaagctg | 1920 |
| ggaagagagt | actgaccagg | aacttaatca | gagggcatct | tgatcttgga | cttcccagcc | 1980 |
| tccagaactc | tgaaaagtta | atgtctatta | tttaagccac | gcagtctatg | gaattttgtt | 2040 |
| agagccaacc | caagcttact | aagataatca | gtatgctgca | ctttctataa | atgtaatttt | 2100 |

```
tacatttata aaaacaaaac aagagatttg ctgctctata caactgtac ctacattgta    2160 gatggaataa caaatctaca tacagattta gtaatctcta tgtagatata gaacatagtg    2220
tatctaatag agacatagtg tctgtggtct gatgttaatt ttaggaatta gccgtcactg    2280
attgggcctt gtccaggtat tcttctccct tgtcctggct ctgtaaccta gttatccttg    2340
tctttgctaa cccataacca actattgtat caggactatt atgccactac agatgatgca    2400
gtttgggttt actgtttctc accatttaga caatacttca tcaaatatat ttctgtatga    2460
ctttagtgat atcagttttt gattcattcc tgcatagatc tgggcaaatt gtagacctta    2520
ggaggtgtat tcaccatcca gttctctgga actgcttatg acatttttct ctgagctttc    2580
ttgtcccaaa aggagccttc ctaaaatagt ctttaagtgc ctttaaaaag agaaagagaa    2640
attaagagaa aaaaaacccc aaactcattc ctttactctg atgtgacagt cctcccagga    2700
cactgcagtg gcctgagttt tgctgttaat ttcattcact tatgtttggg ctatgtaaat    2760
tctgcctaga gctggaatgt cattatgtaa agaaatattt tttgtttata ttctttaata    2820
gtaccagtaa tgtatatctt attcagcttc gagaatataa ttgggttgtt tataaaaacc    2880
acacatcatc aaactcacat tgtaacgatt atttcacttt tcaaaaaaaa tggcattaga    2940
aaaacttgaa tgatgttagt tatcttaaag aagtgtgtac tatgtttaaa aaaaaaaaaa    3000
```

<210> SEQ ID NO 186  
<211> LENGTH: 807  
<212> TYPE: PRT  
<213> ORGANISM: Homo sapiens

<400> SEQUENCE: 186

```
Met Arg Leu Ser Pro Ala Pro Leu Lys Leu Ser Arg Thr Pro Ala Leu
 1               5                  10                  15

Leu Ala Leu Ala Leu Pro Leu Ala Ala Ala Leu Ala Phe Ser Asp Glu
            20                  25                  30

Thr Leu Asp Lys Val Pro Lys Ser Glu Gly Tyr Cys Ser Arg Ile Leu
        35                  40                  45

Arg Ala Gln Gly Thr Arg Arg Glu Gly Tyr Thr Glu Phe Ser Leu Arg
    50                  55                  60

Val Glu Gly Asp Pro Asp Phe Tyr Lys Pro Gly Thr Ser Tyr Arg Val
65                  70                  75                  80

Thr Leu Ser Ala Ala Pro Pro Ser Tyr Phe Arg Gly Phe Thr Leu Ile
                85                  90                  95

Ala Leu Arg Glu Asn Arg Glu Gly Asp Lys Glu Glu Asp His Ala Gly
            100                 105                 110

Thr Phe Gln Ile Ile Asp Glu Glu Thr Gln Phe Met Ser Asn Cys
        115                 120                 125

Pro Val Ala Val Thr Glu Ser Thr Pro Arg Arg Thr Arg Ile Gln
    130                 135                 140

Val Phe Trp Ile Ala Pro Pro Ala Gly Thr Gly Cys Val Ile Leu Lys
145                 150                 155                 160

Ala Ser Ile Val Gln Lys Arg Ile Ile Tyr Phe Gln Asp Glu Gly Ser
                165                 170                 175

Leu Thr Lys Lys Leu Cys Glu Gln Asp Ser Thr Phe Asp Gly Val Thr
            180                 185                 190

Asp Lys Pro Ile Leu Asp Cys Cys Ala Cys Gly Thr Ala Lys Tyr Arg
        195                 200                 205

Leu Thr Phe Tyr Gly Asn Trp Ser Glu Lys Thr His Pro Lys Asp Tyr
    210                 215                 220
```

```
Pro Arg Arg Ala Asn His Trp Ser Ala Ile Ile Gly Gly Ser His Ser
225                 230                 235                 240

Lys Asn Tyr Val Leu Trp Glu Tyr Gly Gly Tyr Ala Ser Glu Gly Val
                245                 250                 255

Lys Gln Val Ala Glu Leu Gly Ser Pro Val Lys Met Glu Glu Glu Ile
            260                 265                 270

Arg Gln Gln Ser Asp Glu Val Leu Thr Val Ile Lys Ala Lys Ala Gln
        275                 280                 285

Trp Pro Ala Trp Gln Pro Leu Asn Val Arg Ala Ala Pro Ser Ala Glu
    290                 295                 300

Phe Ser Val Asp Arg Thr Arg His Leu Met Ser Phe Leu Thr Met Met
305                 310                 315                 320

Gly Pro Ser Pro Asp Trp Asn Val Gly Leu Ser Ala Glu Asp Leu Cys
                325                 330                 335

Thr Lys Glu Cys Gly Trp Val Gln Lys Val Val Gln Asp Leu Ile Pro
            340                 345                 350

Trp Asp Ala Gly Thr Asp Ser Gly Val Thr Tyr Glu Ser Pro Asn Lys
        355                 360                 365

Pro Thr Ile Pro Gln Glu Lys Ile Arg Pro Leu Thr Ser Leu Asp His
    370                 375                 380

Pro Gln Ser Pro Phe Tyr Asp Pro Glu Gly Gly Ser Ile Thr Gln Val
385                 390                 395                 400

Ala Arg Val Val Ile Glu Arg Ile Ala Arg Lys Gly Glu Gln Cys Asn
                405                 410                 415

Ile Val Pro Asp Asn Val Asp Asp Ile Val Ala Asp Leu Ala Pro Glu
            420                 425                 430

Glu Lys Asp Glu Asp Thr Pro Glu Thr Cys Ile Tyr Ser Asn Trp
435                 440                 445

Ser Pro Trp Ser Ala Cys Ser Ser Thr Cys Asp Lys Gly Lys Arg
450                 455                 460

Met Arg Gln Arg Met Leu Lys Ala Gln Leu Asp Leu Ser Val Pro Cys
465                 470                 475                 480

Pro Asp Thr Gln Asp Phe Gln Pro Cys Met Gly Pro Gly Cys Ser Asp
            485                 490                 495

Glu Asp Gly Ser Thr Cys Thr Met Ser Glu Trp Ile Thr Trp Ser Pro
        500                 505                 510

Cys Ser Ile Ser Cys Gly Met Gly Met Arg Ser Arg Glu Arg Tyr Val
    515                 520                 525

Lys Gln Phe Pro Glu Asp Gly Ser Val Cys Thr Leu Pro Thr Glu Glu
530                 535                 540

Met Glu Lys Cys Thr Val Asn Glu Glu Cys Ser Pro Ser Ser Cys Leu
545                 550                 555                 560

Met Thr Glu Trp Gly Glu Trp Asp Glu Cys Ser Ala Thr Cys Gly Met
            565                 570                 575

Gly Met Lys Lys Arg His Arg Met Ile Lys Met Asn Pro Ala Asp Gly
        580                 585                 590

Ser Met Cys Lys Ala Glu Thr Ser Gln Ala Glu Lys Cys Met Met Pro
    595                 600                 605

Glu Cys His Thr Ile Pro Cys Leu Leu Ser Pro Trp Ser Glu Trp Ser
610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Asp Leu Glu Gln
                645                 650                 655
```

```
Val Glu Lys Cys Met Leu Pro Glu Cys Pro Ile Asp Cys Glu Leu Thr
          660                 665                 670
Glu Trp Ser Gln Trp Ser Glu Cys Asn Lys Ser Cys Gly Lys Gly His
675                 680                 685
Val Ile Arg Thr Arg Met Ile Gln Met Glu Pro Gln Phe Gly Gly Ala
    690                 695                 700
Pro Cys Pro Glu Thr Val Gln Arg Lys Lys Cys Arg Ile Arg Lys Cys
705                 710                 715                 720
Leu Arg Asn Pro Ser Ile Gln Lys Pro Arg Trp Arg Glu Ala Arg Glu
                725                 730                 735
Ser Arg Arg Ser Glu Gln Leu Lys Glu Ser Glu Gly Glu Gln Phe
            740                 745                 750
Pro Gly Cys Arg Met Arg Pro Trp Thr Ala Trp Ser Glu Cys Thr Lys
            755                 760                 765
Leu Cys Gly Gly Gly Ile Gln Glu Arg Tyr Met Thr Val Lys Lys Arg
    770                 775                 780
Phe Lys Ser Ser Gln Phe Thr Ser Cys Lys Asp Lys Lys Glu Ile Arg
785                 790                 795                 800
Ala Cys Asn Val His Pro Cys
            805
```

<210> SEQ ID NO 187
<211> LENGTH: 892
<212> TYPE: DNA
<213> ORGANISM: Homo sapiens

<400> SEQUENCE: 187

```
tttattgatg tttcaacagg cacttattca aataagttat atatttgaaa acagccatgg    60
taagcatcct tggcttctca cccattcctc atgtggcatg ctttctagac tttaaaatga   120
ggtaccctga atagcactaa gtgctctgta agctcaagga atctgtgcag tgctacaaag   180
cccacaggca gagaaagaac tcctcaagtg cttgtggtca gagactaggt tccatatgag   240
gcacacctat gatgaaggtc ttcacctcca gaaggtgaca ctgttcagag atcctcattt   300
cctggagagt gggagaaaat ccctcctttg ggaaatccct tttcccagca gcagagccca   360
cctcattgct tagtgatcat ttggaaggca ctgagagcct tcaggggctg acagcagaga   420
aatgaaaatg agtacagttc agatggtgga agaagcatgg cagtgacatc ttccatgctc   480
ttttctcag tgtctgcaac tccaaagatc aaggccataa cccaggagac catcaacgga   540
agattagttc tttgtcaagt gaatgaaatc caaaagcacg catgagacca atgaaagttt   600
ccgcctgttg taaaatctat tttcccccaa ggaaagtcct tgcacagaca ccagtgagtg   660
agttctaaaa gataccttg gaattatcag actcagaaac ttttattttt tttttctgta   720
acagtctcac cagacttctc ataatgctct taatatattg cactttctga atcaaagtgc   780
gagtttatga gggtaaagct ctactttcct actgcagcct tcagattctc atcatttgc    840
atctattttg tagccaataa aactccgcac tagcaaaaaa aaaaaaaaaa aa            892
```

<210> SEQ ID NO 188
<211> LENGTH: 1448
<212> TYPE: DNA
<213> ORGANISM: Homo sapiens
<220> FEATURE:
<221> NAME/KEY: misc_feature
<222> LOCATION: 1124
<223> OTHER INFORMATION: n = A,T,C or G

<400> SEQUENCE: 188

```
tgtgactcac atttcttttta ctgtgacaca ataatgtgat cctaaaactg gcttatcctt      60
gagtgtttac aactcaaaca acttttttgaa tgcagtagtt tttttttttt aaaaacaaac    120
ttttatgtca aatttttttt cttagaagta gtcttcatta ttataaattt gtacaccaaa    180
aggccatggg gaactttgtg caagtacctc atcgctgagc aaatggagct tgctatgttt    240
taatttcaga aaatttcctc atatacgtag tgtgtagaat caagtctttt aataattcat    300
tttttcttca taatatttac tcaaagttaa gcttaaaaat aagttttatc ttaaaatcat    360
atttgaagac agtaagacag taaactatt taggaagtca acccccattg cactctgtgg     420
cagttattct ggtaaaaata ggcaaaagtg acctgaatct acaatggtgt cccaaagtaa    480
ccaagtaaga gagattgtaa atgataaacc gagctttaaa ggataaagtg ttaataaaga    540
aaggaagctg ggcacatgtc aaaaagggag atcgaaatgt taggtaatca tttagaaagg    600
acagaaaata tttaaagtgg ctcataggta atgaatattt ctgacttaga tgtaaatcca    660
tctggaatct ttacatcctt tgccagctga acaagaaag tgaagggaca atgatatttc     720
atggtcagtt tattttgtaa gagacagaag aaattatatc tatacattac cttgtagcag    780
cagtacctgg aagccccagc ccgtcacaga agtgtggagg ggggctcctg actagacaat    840
ttccctagcc cttgtgattt gaagcatgaa agttctggca ggttatgagc agcactaggg    900
ataaagtatg gttttatttt ggtgtaattt aggttttca acaaagccct tgtctaaaat     960
aaaaggcatt attggaaata tttgaaaact agaaaatgat ggataaaagg gctgataaga   1020
aaatttctga ctgtcagtag aagtgagata agatcctcag aggaaacagt aagaagggat   1080
aatcattaag atagtaaaac aggcaaagca gaatcacatg tgcncacaca catacacatg   1140
taaacattgg aatgcataag ttttaatatt ttagcgctat cagtttctaa atgcattaat   1200
tactaactgc cctctcccaa gattcattta gttcaaacag tatccgtaaa ctaggaataa   1260
tgccacatgc attcaatggg atctttttaag tactcttcag tttgttccaa gaatgtgcc    1320 tactgaaatc aaattaattt gtattcaatg tgtacttcaa gactgctaat tgtttcatct   1380
gaaagcctac aatgaatcat tgttcamcct tgaaaaataa aattttgtaa atcaaaaaaa   1440
aaaaaaaa                                                             1448

<210> SEQ ID NO 189
<211> LENGTH: 460
<212> TYPE: DNA
<213> ORGANISM: Homo sapiens

<400> SEQUENCE: 189
ttttgggagc acggactgtc agttctctgg gaagtggtca gcgcatcctg cagggcttct      60
cctcctctgt cttttggaga accagggctc ttctcagggg ctctagggac tgccaggctg    120
tttcagccag gaaggccaaa atcaagagtg agatgtagaa agttgtaaaa tagaaaaagt    180
ggagttggtg aatcggttgt tctttcctca catttggatg attgtcataa ggtttttagc    240
atgttcctcc ttttcttcac cctccccttt tttcttctat taatcaagag aaacttcaaa    300
gttaatggga tggtcggatc tcacaggctg agaactcgtt cacctccaag catttcatga    360 aaagctgct tcttattaat catacaaact ctcaccatga tgtgaagagt ttcacaaatc     420
cttcaaaata aaagtaatg acttaaaaaa aaaaaaaaa                            460

<210> SEQ ID NO 190
<211> LENGTH: 481
<212> TYPE: DNA
<213> ORGANISM: Homo sapiens
```

<400> SEQUENCE: 190

```
aggtggtgga agaaactgtg gcacgaggtg actgaggtat ctgtgggagc taatcctgtc    60
caggtggaag taggagaatt tgatgatggt gcagaggaaa ccgaagagga ggtggtggcg   120
gaaaatccct gccagaacca ccactgcaaa cacggcaagg tgtgcgagct ggatgagaac   180
aacaccccca tgtgcgtgtg ccaggacccc accagctgcc cagccccat tggcgagttt    240
gagaaggtgt gcagcaatga caacaagacc ttcgactctt cctgccactt ctttgccaca   300
aagtgcaccc tggagggcac caagaagggc cacaagctcc acctggacta catcgggcct   360
tgcaaataca tcccccttg cctggactct gagctgaccg aattccccct gcgcatgcgg    420
gactggctca agaacgtcct ggtcaccctg tatgagaggg atgaggacaa caaccttctg   480
a                                                                  481
```

<210> SEQ ID NO 191
<211> LENGTH: 489
<212> TYPE: DNA
<213> ORGANISM: Homo sapiens
<220> FEATURE:
<221> NAME/KEY: misc_feature
<222> LOCATION: 312, 455
<223> OTHER INFORMATION: n = A,T,C or G

<400> SEQUENCE: 191

```
atataaatta gactaagtgt tttcaaataa atctaaatct tcagcatgat gtgttgtgta    60
taattggagt agatattaat taagtcccct gtataatgtt ttgtaatttt gcaaaacata   120
tcttgagttg tttaaacagt caaaatgttt gatatttat accagcttat gagctcaaag    180
tactacagca aagcctagcc tgcatatcat tcacccaaaa caaagtaata gcgcctcttt   240
tattattttg actgaatgtt ttatggaatt gaaagaaaca tacgttcttt tcaagacttc   300
ctcatgaatc tntcaattat aggaaaagtt attgtgataa aataggaaca gctgaaagat   360
tgattaatga actattgtta attcttccta ttttaatgaa tgacattgaa ctgaatttt    420
tgtctgttaa atgaacttga tagctaataa aaagncaact agccatcaaa aaaaaaaaa   480
aaaaaaaaa                                                          489
```

<210> SEQ ID NO 192
<211> LENGTH: 516
<212> TYPE: DNA
<213> ORGANISM: Homo sapiens

<400> SEQUENCE: 192

```
acttcaaagc cagctgaagg aaagaggaag tgctagagag agccccttc agtgtgcttc     60
tgacttttac ggacttggct tgttagaagg ctgaaagatg atggcaggaa tgaaaatcca   120
gcttgtatgc atgctactcc tggctttcag ctcctggagt ctgtgctcag attcagaaga   180
ggaaatgaaa gcattagaag cagatttctt gaccaatatg catacatcaa agattagtaa   240
agcacatgtt ccctcttgga agatgactct gctaaatgtt tgcagtcttg taaataattt   300
gaacagccca gctgaggaaa caggagaagt tcatgaagag gagcttgttg caagaaggaa   360
cttcttactg ctttagatgg ctttagcttg gaagcaatgt tgacaatata ccagctccac   420
aaaatctgtc acagcagggc ttttcaacac tgggagttaa tccaggaaga tattcttgat   480
actggaaatg acaaaaatgg aaaggaagaa gtcata                            516
```

<210> SEQ ID NO 193
<211> LENGTH: 1409

```
<212> TYPE: DNA
<213> ORGANISM: Homo sapiens

<400> SEQUENCE: 193
tgattctttt ccaaaacttt tagccatagg gtcttttata gacagggata gtaaaatgaa    60
aattgagaaa tataagatga aaaggaatgg taaaaatatc ttttagggg cttttaattg   120
gtgatctgaa atcttgggag aagctgttct tttcaggcct gaggtgctct tgactgtcgc   180
ctgcgcactg tgtaccccga gcaacattct aagggtgtgc tttcgccttg gctaactcct   240
ttgacctcat tcttcatata gtagtctagg aaaaagttgc aggtaattta aactgtctag   300
tggtacatag taactgaatt tctattccta tgagaaatga gaattattta tttgccatca   360
acacatttta tactttgcat ctccaaattt attgcggcga gacttgtcca ttgtgaaagt   420
tagagaacat tatgtttgta tcatttcttt cataaaacct caagagcatt tttaagcct    480
tttcatcaga cccagtgaaa actaaggata gatgtttttt aactggaggt ctcctgataa   540
ggagaacaca atccaccatt gtcatttaag taataagaca ggaaattgac cttgacgctt   600
tcttgttaaa tagatttaac aggaacatct gcacatcttt tttccttgtg cactatttgt   660
ttaattgcag tggattaata cagcaagagt gccacattat aactaggcaa ttatccattc   720
ttcaagactt agttattgtc acactaattg atcgtttaag gcataagatg gtctagcatt   780
aggaacatgt gaagctaatc tgctcaaaaa gatcaacaaa ttaatattgt tgctgatatt   840
tgcataattg gctgcaatta tttaatgttt aattgggttg atcaaatgag attcagcaat   900
tcacaagtgc attaatataa acagaactgg ggcacttaaa atgataatga ttaacttata   960
ttgcatgttc tcttcctttc actttttttca gtgtctacat ttcagaccga gtttgtcagc  1020
tttttttgaaa acacatcagt agaaaccaag attttaaaat gaagtgtcaa gacgaaggca  1080
aaacctgagc agttcctaaa aagatttgct gttagaaatt ttctttgtgg cagtcattta  1140
ttaaggattc aactcgtgat acaccaaaag aagagttgac ttcagagatg tgttccatgc  1200
tctctagcac aggaatgaat aaatttataa cacctgcttt agcctttgtt ttcaaaagca  1260
caaaggaaaa gtgaaaggga aagagaaaca agtgactgag aagtcttgtt aaggaatcag  1320
gttttttcta cctggtaaac attctctatt cttttctcaa aagattgttg taagaaaaaa  1380
tgtaagmcaa aaaaaaaaaa aaaaaaaaa                                    1409

<210> SEQ ID NO 194
<211> LENGTH: 441
<212> TYPE: DNA
<213> ORGANISM: Homo sapiens

<400> SEQUENCE: 194
cagatttcgg tagccatctc cctccaaata tgtctctttc tgctttctta gtgcccatta    60
tttccccttc tcctttcttc tgtcactgcc atctccttct tggtcttccc attgttcttt   120
aactggccgt aatgtggaat tgatatttac attttgatac ggttttttc ttggcctgtg   180
tacgggattg cctcatttcc tgctctgaat tttaaaatta gatattaaag ctgtcatatg   240
gtttcctcac aaaagtcaac aaagtccaaa caaaatagt ttgccgtttt actttcatcc   300
attgaaaaag gaaattgtgc ctcttgcagc ctaggcaaag gacatttagt actatcgatt   360
cttttccaccc tcacgatgac ttgcggttct ctctgtagaa aagggatggc ctaagaaata   420
caactaaaaa aaaaaaaaaa a                                             441

<210> SEQ ID NO 195
<211> LENGTH: 707
```

```
<212> TYPE: DNA
<213> ORGANISM: Homo sapiens

<400> SEQUENCE: 195
cagaaaaata tttggaaaaa atataccact tcatagctaa gtcttacaga gaagaggatt      60
tgctaataaa acttaagttt tgaaaattaa gatgcaggta gagcttctga actaatgccc     120
acagctccaa ggaagacatg tcctatttag ttattcaaat acaagttgag ggcattgtga     180
ttaagcaaac aatatatttg ttagaacttt gttttaaat tactgttcct tgacattact      240
tataaagagt ctctaacttt cgatttctaa aactatgtaa tacaaaagta tagtttcccc     300
atttgataaa aggccaatga tactgagtag gatatatgcg tatcatgcta cttcattcag     360
tgtgtctgtt tttaatacta ataaggcagt ttgacagaaa ttatttcttt gggactaagg     420
tgattatcat ttttttcccc ttcaaaattg tgctttaagt gctgataacc acaggcagat     480
tgcaaagaac tgataaggca acaaaagtag agaattttag gatcaaaggc atgtaactga     540
aaggtaacaa cagtacataa gcgacaactg gggaaggcag cagtgaaaca tgtttgtggg     600
gttaagtgag tcattgtaaa taaggaattt gcacatttat tttctgtcga cgcggccgcc     660
actgtgctgg atatctgcag aattccacca cactggacta gtggatc               707

<210> SEQ ID NO 196
<211> LENGTH: 552
<212> TYPE: DNA
<213> ORGANISM: Homo sapiens
<220> FEATURE:
<221> NAME/KEY: misc_feature
<222> LOCATION: 61, 129, 189, 222, 241, 278, 324, 338, 363, 408, 415,
      463, 483
<223> OTHER INFORMATION: n = A,T,C or G

<400> SEQUENCE: 196
tggccagcca gcctgatgtg gatggcttcc ttggggtggt gcttccctca agcccgaatt      60
ngtggacatc atcaatgcca acaatgagc cccatccatt ttccctaccc ttcctgccaa      120
gccagggant aagcagccca gaagcccagt aactgccctt tccctgcata tgcttttgat     180
ggtgtcatnt gctccttcct gtggcctcat ccaaactgta tnttcctta ctgtttatat      240 nttcaccctg taatggttgg gaccaggcca atcccttntc cacttactat aatggttgga     300
actaaacgtc accaaggtgg cttntccttg gctgaganat ggaaggcgtg gtgggatttg     360
ctnctgggtt ccctaggccc tagtgagggc agaagagaaa ccatcctntc ccttnttaca     420
ccgtgaggcc aagatcccct cagaaggcag gagtgctgcc ctntcccatg gtgcccgtgc     480
ctntgtgctg tgtatgtgaa ccacccatgt gagggaataa acctggcact aggaaaaaaa     540
aaaaaaaaaa aa                                                         552

<210> SEQ ID NO 197
<211> LENGTH: 449
<212> TYPE: DNA
<213> ORGANISM: Homo sapiens
<220> FEATURE:
<221> NAME/KEY: misc_feature
<222> LOCATION: 56, 58, 76
<223> OTHER INFORMATION: n = A,T,C or G

<400> SEQUENCE: 197
ctccagagac aacttcgcgg tgtggtgaac tctctgagga aaaacacgtg cgtggnanca      60
agtgactgag acctanaaat ccaagcgttg gaggtcctga ggccagccta agtcgcttca     120
aaatggaacg aaggcgtttg cggggttcca ttcagagccg atacatcagc atgagtgtgt     180
```

```
ggacaagccc acggagactt gtggagctgg cagggcagag cctgctgaag gatgaggccc      240
tggccattgc ccgccctgga gttgctgccc agggagctct tcccgccact cttcatggca      300
gcctttgacg ggagacacag ccagaccctg aaggcaatgg tgcaggcctg gcccttcacc      360
tgcctccctc tgggagtgct gatgaaggga caacatcttc acctggagac cttcaaagct      420
gtgcttgatg gacttgatgt gctccttgc                                         449

<210> SEQ ID NO 198
<211> LENGTH: 606
<212> TYPE: DNA
<213> ORGANISM: Homo sapiens

<400> SEQUENCE: 198
tgagtttgcc cccttacccc catcccagtg aatatttgca attcctaaag acgtgttttg       60
attgtcacac ctgggtgggg aacatgctac tggcatctaa tgcatagagg gcagtaatgc      120
tgctaaacat ctttcaacgc acaggacaga gccccacaaa agagaattat ctagccccaa      180
atgtccataa cactgctgtt gagaaaacct accgcaggat cttactgggc ttcataggta      240
agcttgcctt tgttctggct tctgtagata tataaaataa agacactgcc cagtccctcc      300
ctcaacgtcc cgagccaggg ctcaaggcaa ttccaataac agtagaatga acactaaata      360
ttgatttcaa aatctcagca actagaagaa tgaccaacca tcctggttgg cctgggactg      420
tcctagtttt agcattgaaa gtttcaggtt ccaggaaagc cctcaggcct gggctgctgg      480
tcaccctagc agctgaggga ctcttcaata cagaattagt ctttgtgcac tggagatgaa      540
tatactttaa tttgtaacat gtgaaaacat ctataaacat ctactgaagc ctgttcttgt      600
ctgcac                                                                 606

<210> SEQ ID NO 199
<211> LENGTH: 369
<212> TYPE: DNA
<213> ORGANISM: Homo sapiens
<220> FEATURE:
<221> NAME/KEY: misc_feature
<222> LOCATION: 29, 345
<223> OTHER INFORMATION: n = A,T,C or G

<400> SEQUENCE: 199
ggcaactttt tgcggattgt tcttgcttnc aggctttgcg ctgcaaatcc agtgctacca       60
gtgtgaagaa ttccagctga caacgactg ctcctccccc gagttcattg tgaattgcac      120
ggtgaacgtt caagacatgt gtcagaaaga agtgatggag caaagtgccg ggatcatgta      180
ccgcaagtcc tgtgcatcat cagcggcctg tctcatcgcc tctgccgggt accagtcctt      240
ctgctcccca gggaaactga actcagtttg catcagctgc tgcaacaccc ctctttgtaa      300
cgggccaagg cccaagaaaa ggggaagttc tgcctcggcc ctcangccat ggctccgcac      360
caccatcct                                                              369

<210> SEQ ID NO 200
<211> LENGTH: 55
<212> TYPE: PRT
<213> ORGANISM: Homo sapiens

<400> SEQUENCE: 200

Met Tyr Arg Asn Trp Ser Gly Cys Phe Gly Leu Gln Val Thr Leu Cys
1               5                   10                  15

His Thr Phe Glu Thr Arg Asp Leu Ser Arg Leu Ser Ser Asp Ser Gln
            20                  25                  30
```

```
Pro Thr Ser Asn Val Ser Gln Ser Ile Ser His Lys Val Leu Ser Phe
        35                  40                  45

Ser Gly Val Ile Val Thr Pro
        50                  55
```

<210> SEQ ID NO 201
<211> LENGTH: 67
<212> TYPE: PRT
<213> ORGANISM: Homo sapiens

<400> SEQUENCE: 201

```
Met Gln Leu Leu Ser Pro Asn Thr Lys Phe Thr Ser Cys Leu Ser Arg
 1               5                  10                  15

Gln Arg Gly Asn Leu Val Phe Leu Gly Asp Leu Lys Gly Cys Ser Glu
            20                  25                  30

Leu Lys Asn Phe Gln Glu Leu Ile Asn Gln Ser Ala Leu Val His Pro
        35                  40                  45

Arg Val Asp Val Trp Trp Tyr Cys Gly Gly Pro Leu Leu Gly Thr Leu
    50                  55                  60

Pro Asn Asn
65
```

<210> SEQ ID NO 202
<211> LENGTH: 73
<212> TYPE: PRT
<213> ORGANISM: Homo sapiens

<400> SEQUENCE: 202

```
Met Thr Pro Glu Lys Leu Arg Thr Leu Cys Glu Ile Asp Trp Leu Thr
 1               5                  10                  15

Leu Glu Val Gly Trp Leu Ser Glu Ser Leu Glu Arg Ser Leu Val
            20                  25                  30

Ser Lys Val Trp His Lys Val Thr Cys Lys Pro Lys His Pro Asp Gln
        35                  40                  45

Phe Leu Tyr Ile Asp Ser Tyr Ser Trp Phe Arg Pro Leu Pro Pro Leu
    50                  55                  60

Pro Thr Val Val Lys Arg Thr Ala Ala
65                  70
```

<210> SEQ ID NO 203
<211> LENGTH: 2008
<212> TYPE: DNA
<213> ORGANISM: Homo sapiens

<400> SEQUENCE: 203

```
ctccagagac aacttcgcgg tgtggtgaac tctctgagga aaaacacgtg cgtggtaaca      60
agtgactgag acctagaaat ccaagcgttg gaggtcctga ggccagccta agtcgcttca     120
aaatggaacg aaggcgtttg cggggttcca ttcagagccg atacatcagc atgagtgtgt     180
ggacaagccc acggagactt gtggagctgg cagggcagag cctgctgaag gatgaggccc     240
tggccattgc ccgccctgga gttgctgccc agggagctct tcccgccact cttcatggca     300
gcctttgacg ggagacacag ccagaccctg aaggcaatgg tgcaggcctg gcccttcacc     360
tgcctccctc tgggagtgct gatgaaggga caacatcttc acctgagac cttcaaagct     420
gtgcttgatg gacttgatgt gctccttgcc caggaggttc gccccaggag gtggaaactt     480
caagtgctgg atttacggaa gaactctcat caggacttct ggactgtatg gtctggaaac     540
agggccagtc tgtactcatt tccagagcca gaagcagctc agcccatgac aaagaagcga     600
```

```
aaagtagatg gtttgagcac agaggcagag cagcccttca ttccagtaga ggtgctcgta      660
gacctgttcc tcaaggaagg tgcctgtgat gaattgttct cctacctcat tgagaaagtg      720
aagcgaaaga aaatgtact acgcctgtgc tgtaagaagc tgaagatttt tgcaatgccc       780
atgcaggata tcaagatgat cctgaaaatg gtgcagctgg actctattga agatttggaa      840
gtgacttgta cctggaagct acccaccttg gcgaaatttt ctccttacct gggccagatg      900
attaatctgc gtagactcct cctctcccac atccatgcat cttcctacat tccccggag      960
aaggaagagc agtatatcgc ccagttcacc tctcagttcc tcagtctgca gtgcctgcag     1020
gctctctatg tggactcttt attttttcctt agaggccgcc tggatcagtt gctcaggcac    1080
gtgatgaacc ccttggaaac cctctcaata actaactgcc ggctttcgga aggggatgtg    1140
atgcatctgt cccagagtcc cagcgtcagt cagctaagtg tcctgagtct aagtggggtc    1200
atgctgaccg atgtaagtcc cgagcccctc caagctctgc tggagagagc ctctgccacc    1260
ctccaggacc tggtctttga tgagtgtggg atcacggatg atcagctcct tgccctcctg     1320
ccttccctga gccactgctc ccagcttaca accttaagct tctacgggaa ttccatctcc     1380
atatctgcct tgcagagtct cctgcagcac ctcatcgggc tgagcaatct gacccacgtg     1440
ctgtatcctg tcccctggga gagttatgag acatccatg gtaccctcca cctggagagg     1500
cttgcctatc tgcatgccag gctcaggag ttgctgtgtg agttggggcg gcccagcatg     1560
gtctggctta gtgccaaccc ctgtcctcac tgtggggaca gaaccttcta tgacccggag    1620
cccatcctgt gcccctgttt catgcctaac tagctgggtg cacatatcaa atgcttcatt    1680
ctgcatactt ggacactaaa gccaggatgt gcatgcatct tgaagcaaca aagcagccac    1740
agtttcagac aaatgttcag tgtgagtgag gaaaacatgt tcagtgagga aaaacattc    1800
agacaaatgt tcagtgagga aaaaagggg aagttgggga taggcagatg ttgacttgag     1860
gagttaatgt gatctttggg gagatacatc ttatagagtt agaaatagaa tctgaatttc     1920
taaagggaga ttctggcttg ggaagtacat gtaggagtta atccctgtgt agactgttgt    1980
aaagaaactg ttgaaaaaaa aaaaaaaa                                        2008
```

<210> SEQ ID NO 204
<211> LENGTH: 923
<212> TYPE: DNA
<213> ORGANISM: Homo sapiens

<400> SEQUENCE: 204

```
tgagtttgcc cccttacccc catcccagtg aatatttgca attcctaaag acgtgttttg       60
attgtcacac ctgggtgggg aacatgctac tggcatctaa tgcatagagg gcagtaatgc      120
tgctaaacat ctttcaacgc acaggacaga gccccacaaa agagaattat ctagccccaa      180
atgtccataa cactgctgtt gagaaaacct accgcaggat cttactgggc ttcataggta      240
agcttgcctt tgttctggct tctgtagata tataaaataa agacactgcc cagtccctcc      300
ctcaacgtcc cgagccaggg ctcaaggcaa ttccaataac agtagaatga acactaaata      360
ttgatttcaa aatctcagca actagaagaa tgaccaacca tcctggttgg cctgggactg      420
tcctagtttt agcattgaaa gtttcaggtt ccaggaaagc cctcaggcct gggctgctgg      480
tcaccctagc agctgaggga ctcttcaata cagaattagt ctttgtgcac tggagatgaa      540
tatactttaa tttgtaacat gtgaaaacat ctataaacat ctactgaagc ctgttctgtc      600
tgcaccgaca ttttcattga gtacggattc ttcctaccag atacagctgc tctacaactt      660
tcgagggctg gtataaaact agcttttacc tattttttaaa aattacatga atagtaaaaa     720
```

```
cttggattaa cccagtattc gggtattttc aatttccttg ggagcttaga ggacggacaa      780
ataaaaagat tatttcaaca tcaaatatat gctattgttt acatatgaag ataaccacat      840
atatgtataa attcaccgtt acttttttagc aatactataa aatccaacag aaaaaaatag     900
catttactaa aaaaaaaaaa aaa                                              923

<210> SEQ ID NO 205
<211> LENGTH: 1619
<212> TYPE: DNA
<213> ORGANISM: Homo sapiens

<400> SEQUENCE: 205 ggcaacttttt tgcggattgt tcttgcttcc aggctttgcg ctgcaaatcc agtgctacca     60
gtgtgaagaa ttccagctga caacgactg ctcctccccc gagttcattg tgaattgcac      120
ggtgaacgtt caagacatgt gtcagaaaga agtgatggag caaagtgccg ggatcatgta     180
ccgcaagtcc tgtgcatcat cagcggcctg tctcatcgcc tctgccgggt accagtcctt     240
ctgctcccca gggaaactga actcagtttg catcagctgc tgcaacaccc ctctttgtaa     300
cgggccaagg cccaagaaaa ggggaagttc tgcctcggcc ctcaggccag gctccgcac     360 caccatcctg ttcctcaaat tagccctctt ctcggcacac tgctgaagct gaaggagatg     420 ccacccctc ctgcattgtt cttccagccc tcgcccccaa ccccccacct ccctgagtga     480
gtttcttctg ggtgtccttt tattctgggt agggagcggg agtccgtgtt ctcttttgtt     540
cctgtgcaaa taatgaaaga gctcggtaaa gcattctgaa taaattcagc ctgactgaat    600
tttcagtatg tacttgaagg aaggaggtgg agtgaaagtt cacccccatg tctgtgtaac    660
cggagtcaag gccaggctgg cagagtcagt ccttagaagt cactgaggtg ggcatctgcc    720
ttttgtaaag cctccagtgt ccattccatc cctgatgggg gcatagtttg agactgcaga    780
gtgagagtga cgttttctta gggctggagg gccagttccc actcaaggct ccctcgcttg    840
acattcaaac ttcatgctcc tgaaaaccat tctctgcagc agaattggct ggtttcgcgc    900
ctgagttggg ctctagtgac tcgagactca atgactggga cttagactgg gctcggcct    960 cgctctgaaa agtgcttaag aaaatcttct cagttctcct tgcagaggac tggcgccggg   1020
acgcgaagag caacgggcgc tgcacaaagc gggcgctgtc ggtggtggag tgcgcatgta   1080
cgcgcaggcg cttctcgtgg ttggcgtgct gcagcgacag gcggcagcac agcaccttgc   1140
acgaacaccc gccgaaactg ctgcgaggac accgtgtaca ggagcgggtt gatgaccgag   1200
ctgaggtaga aaaacgtctc cgagaagggg aggaggatca tgtacgcccg gaagtaggac   1260
ctcgtccagt cgtgcttggg tttggccgca gccatgatcc tccgaatctg gttgggcatc   1320
cagcatacgg ccaatgtcac aacaatcagc cctgggcaga cacgagcagg agggagagac   1380
agagaaaaga aaacacagc atgagaacac agtaaatgaa taaaaccata aaatatttag    1440
cccctctgtt ctgtgcttac tggccaggaa atggtaccaa tttttcagtg ttggacttga   1500 cagcttctttt tgccacaagc aagagagaat ttaacactgt ttcaaacccg ggggagttgg   1560
ctgtgttaaa gaaagaccat taaatgcttt agacagtgta aaaaaaaaaa aaaaaaaa    1619

<210> SEQ ID NO 206
<211> LENGTH: 2364
<212> TYPE: DNA
<213> ORGANISM: Homo sapiens

<400> SEQUENCE: 206
atgcagcatc accaccatca ccacttctcc gacgagaccc tggacaaagt gcccaagtca     60
```

```
gagggctact gtagccgtat cctgcgcgcc cagggcacgc ggcgcgaggg ctacaccgag    120
ttcagcctcc gcgtggaggg cgaccccgac ttctacaagc cgggaaccag ctaccgcgta    180
acactttcag ctgctcctcc ctcctacttc agaggattca cattaattgc cctcagagag    240
aacagagagg gtgataagga agaagaccat gctgggacct tccagatcat agacgaagaa    300
gaaactcagt ttatgagcaa ttgccctgtt gcagtcactg aaagcactcc acggaggagg    360
acccggatcc aggtgttttg gatagcacca ccagcgggaa caggctgcgt gattctgaag    420
gccagcatcg tacaaaaacg cattatttat tttcaagatg agggctctct gaccaagaaa    480
ctttgtgaac aagattccac atttgatggg gtgactgaca aacccatctt agactgctgt    540
gcctgcggaa ctgccaagta cagactcaca ttttatggga attggtccga agacacac     600 ccaaaggatt accctcgtcg ggccaaccac tggtctgcga tcatcggagg atcccactcc    660
aagaattatg tactgtggga atatggagga tatgccagcg aaggcgtcaa acaagttgca    720
gaattgggct cacccgtgaa aatggaggaa gaaattcgac aacagagtga tgaggtcctc    780
accgtcatca aagccaaagc ccagtggcca gcctggcagc ctctcaacgt gagagcagca    840
ccttcagctg aattttccgt ggacagaacg cgccatttaa tgtccttcct gaccatgatg    900
ggccctagtc ccgactggaa cgtaggctta tctgcagaag atctgtgcac caaggaatgt    960
ggctgggtcc agaaggtggt gcaagacctg attccctggg acgctggcac cgacagcggg   1020
gtgacctatg agtcacccaa caaacccacc attccccagg agaaaatccg cccctgacc    1080 agcctggacc atcctcagag tcctttctat gacccagagg gtgggtccat cactcaagta   1140
gccagagttg tcatcgagag aatcgcacgg aagggtgaac aatgcaatat tgtacctgac   1200
aatgtcgatg atattgtagc tgacctggct ccagaagaga aagatgaaga tgacacccct   1260
gaaacctgca tctactccaa ctggtcccca tggtccgcct gcagctcctc cacctgtgac   1320
aaaggcaaga ggatgcgaca gcgcatgctg aaagcacagc tggacctcag cgtcccctgc   1380
cctgacaccc aggacttcca gccctgcatg ggccctggct gcagtgacga agacggctcc   1440
acctgcacca tgtccgagtg gatcacctgg tcgccctgca gcatctcctg cggcatgggc   1500
atgaggtccc gggagaggta tgtgaagcag ttccgaggg acggctccgt gtgcacgctg   1560
cccactgagg aaacggagaa gtgcacggtc aacgaggagt gctctcccag cagctgcctg   1620
atgaccgagt ggggcgagtg ggacgagtgc agcgccacct gcggcatggg catgaagaag   1680
cggcaccgca tgatcaagat gaaccccgca gatggctcca tgtgcaaagc cgagacatca   1740
caggcagaga agtgcatgat gccagagtgc cacaccatcc catgcttgct gtccccatgg   1800
tccgagtgga gtgactgcag cgtgacctgc gggaagggca tgcgaaccg acagcggatg   1860 ctcaagtctc tggcagaact tggagactgc aatgaggatc tggagcaggt ggagaagtgc   1920
atgctccctg aatgccccat tgactgtgag ctcaccgagt ggtcccagtg gtcggaatgt   1980
aacaagtcat gtgggaaagg ccacgtgatt cgaacccgga tgatccaaat ggagcctcag   2040
tttggaggtg caccctgccc agagactgtg cagcgaaaaa agtgccgcat ccgaaaatgc   2100
cttcgaaatc catccatcca aaagctacgc tggagggagg cccgagagag ccggcggagt   2160
gagcagctga aggaagagtc tgaaggggag cagttcccag gttgtaggat gcgcccatgg   2220
acggcctggt cagaatgcac caaactgtgc ggaggtggaa ttcaggaacg ttacatgact   2280
gtaaagaaga gattcaaaag ctcccagttt accagctgca aagacaagaa ggagatcaga   2340
gcatgcaatg ttcatccttg ttag                                          2364
```

<210> SEQ ID NO 207

<211> LENGTH: 787
<212> TYPE: PRT
<213> ORGANISM: Homo sapiens

<400> SEQUENCE: 207

```
Met Gln His His His His His His Phe Ser Asp Glu Thr Leu Asp Lys
1               5                   10                  15

Val Pro Lys Ser Glu Gly Tyr Cys Ser Arg Ile Leu Arg Ala Gln Gly
            20                  25                  30

Thr Arg Arg Glu Gly Tyr Thr Glu Phe Ser Leu Arg Val Glu Gly Asp
        35                  40                  45

Pro Asp Phe Tyr Lys Pro Gly Thr Ser Tyr Arg Val Thr Leu Ser Ala
50                  55                  60

Ala Pro Pro Ser Tyr Phe Arg Gly Phe Thr Leu Ile Ala Leu Arg Glu
65                  70                  75                  80

Asn Arg Glu Gly Asp Lys Glu Asp His Ala Gly Thr Phe Gln Ile
            85                  90                  95

Ile Asp Glu Glu Glu Thr Gln Phe Met Ser Asn Cys Pro Val Ala Val
                100                 105                 110

Thr Glu Ser Thr Pro Arg Arg Arg Thr Arg Ile Gln Val Phe Trp Ile
            115                 120                 125

Ala Pro Pro Ala Gly Thr Gly Cys Val Ile Leu Lys Ala Ser Ile Val
130                 135                 140

Gln Lys Arg Ile Ile Tyr Phe Gln Asp Glu Gly Ser Leu Thr Lys Lys
145                 150                 155                 160

Leu Cys Glu Gln Asp Ser Thr Phe Asp Gly Val Thr Asp Lys Pro Ile
                165                 170                 175

Leu Asp Cys Cys Ala Cys Gly Thr Ala Lys Tyr Arg Leu Thr Phe Tyr
            180                 185                 190

Gly Asn Trp Ser Glu Lys Thr His Pro Lys Asp Tyr Pro Arg Arg Ala
        195                 200                 205

Asn His Trp Ser Ala Ile Ile Gly Gly Ser His Ser Lys Asn Tyr Val
    210                 215                 220

Leu Trp Glu Tyr Gly Gly Tyr Ala Ser Glu Gly Val Lys Gln Val Ala
225                 230                 235                 240

Glu Leu Gly Ser Pro Val Lys Met Glu Glu Ile Arg Gln Gln Ser
                245                 250                 255

Asp Glu Val Leu Thr Val Ile Lys Ala Lys Ala Gln Trp Pro Ala Trp
            260                 265                 270

Gln Pro Leu Asn Val Arg Ala Ala Pro Ser Ala Glu Phe Ser Val Asp
        275                 280                 285

Arg Thr Arg His Leu Met Ser Phe Leu Thr Met Met Gly Pro Ser Pro
    290                 295                 300

Asp Trp Asn Val Gly Leu Ser Ala Glu Asp Leu Cys Thr Lys Glu Cys
305                 310                 315                 320

Gly Trp Val Gln Lys Val Val Gln Asp Leu Ile Pro Trp Asp Ala Gly
                325                 330                 335

Thr Asp Ser Gly Val Thr Tyr Glu Ser Pro Asn Lys Pro Thr Ile Pro
            340                 345                 350

Gln Glu Lys Ile Arg Pro Leu Thr Ser Leu Asp His Pro Gln Ser Pro
        355                 360                 365

Phe Tyr Asp Pro Glu Gly Gly Ser Ile Thr Gln Val Ala Arg Val Val
    370                 375                 380

Ile Glu Arg Ile Ala Arg Lys Gly Glu Gln Cys Asn Ile Val Pro Asp
385                 390                 395                 400
```

```
              Asn Val Asp Asp Ile Val Ala Asp Leu Ala Pro Glu Glu Lys Asp Glu
                              405                 410                 415

Asp Asp Thr Pro Glu Thr Cys Ile Tyr Ser Asn Trp Ser Pro Trp Ser
                          420                 425                 430

Ala Cys Ser Ser Ser Thr Cys Asp Lys Gly Lys Arg Met Arg Gln Arg
                          435                 440                 445

Met Leu Lys Ala Gln Leu Asp Leu Ser Val Pro Cys Pro Asp Thr Gln
                  450                 455                 460

Asp Phe Gln Pro Cys Met Gly Pro Gly Cys Ser Asp Glu Asp Gly Ser
              465                 470                 475                 480

Thr Cys Thr Met Ser Glu Trp Ile Thr Trp Ser Pro Cys Ser Ile Ser
                              485                 490                 495

Cys Gly Met Gly Met Arg Ser Arg Glu Arg Tyr Val Lys Gln Phe Pro
                          500                 505                 510

Glu Asp Gly Ser Val Cys Thr Leu Pro Thr Glu Glu Thr Glu Lys Cys
                          515                 520                 525

Thr Val Asn Glu Glu Cys Ser Pro Ser Ser Cys Leu Met Thr Glu Trp
                  530                 535                 540

Gly Glu Trp Asp Glu Cys Ser Ala Thr Cys Gly Met Gly Met Lys Lys
              545                 550                 555                 560

Arg His Arg Met Ile Lys Met Asn Pro Ala Asp Gly Ser Met Cys Lys
                              565                 570                 575

Ala Glu Thr Ser Gln Ala Glu Lys Cys Met Met Pro Glu Cys His Thr
                          580                 585                 590

Ile Pro Cys Leu Leu Ser Pro Trp Ser Glu Trp Ser Asp Cys Ser Val
                          595                 600                 605

Thr Cys Gly Lys Gly Met Arg Thr Arg Gln Arg Met Leu Lys Ser Leu
                  610                 615                 620

Ala Glu Leu Gly Asp Cys Asn Glu Asp Leu Glu Gln Val Glu Lys Cys
              625                 630                 635                 640

Met Leu Pro Glu Cys Pro Ile Asp Cys Glu Leu Thr Glu Trp Ser Gln
                              645                 650                 655

Trp Ser Glu Cys Asn Lys Ser Cys Gly Lys Gly His Val Ile Arg Thr
                          660                 665                 670

Arg Met Ile Gln Met Glu Pro Gln Phe Gly Gly Ala Pro Cys Pro Glu
                          675                 680                 685

Thr Val Gln Arg Lys Lys Cys Arg Ile Arg Lys Cys Leu Arg Asn Pro
                  690                 695                 700

Ser Ile Gln Lys Leu Arg Trp Arg Glu Ala Arg Glu Ser Arg Arg Ser
              705                 710                 715                 720

Glu Gln Leu Lys Glu Glu Ser Glu Gly Glu Gln Phe Pro Gly Cys Arg
                              725                 730                 735

Met Arg Pro Trp Thr Ala Trp Ser Glu Cys Thr Lys Leu Cys Gly Gly
                          740                 745                 750

Gly Ile Gln Glu Arg Tyr Met Thr Val Lys Lys Arg Phe Lys Ser Ser
                          755                 760                 765

Gln Phe Thr Ser Cys Lys Asp Lys Lys Glu Ile Arg Ala Cys Asn Val
                  770                 775                 780

His Pro Cys
              785

<210> SEQ ID NO 208
              <211> LENGTH: 1362
              <212> TYPE: DNA
```

<213> ORGANISM: Homo sapiens

<400> SEQUENCE: 208

```
atggcttcac ccagcctccc gggcagtgac tgctcccaaa tcattgatca cagtcatgtc    60
cccgagtttg aggtggccac ctggatcaaa atcacccctta ttctggtgta cctgatcatc   120
ttcgtgatgg gccttctggg aacagcgcc accattcggg tcacccaggt gctgcagaag    180
aaaggatact gcagaagga ggtgacagac cacatggtga gtttggcttg ctcggacatc    240
ttggtgttcc tcatcggcat gcccatggag ttctacagca tcatctggaa tcccctgacc    300
acgtccagct acaccctgtc ctgcaagctg cacactttcc tcttcgaggc ctgcagctac    360
gctacgctgc tgcacgtgct gacactcagc tttgagcgct acatcgccat ctgtcacccc    420
ttcaggtaca aggctgtgtc gggacccttgc caggtgaagc tgctgattgg cttcgtctgg    480
gtcacctccg ccctggtggc actgcccttg ctgtttgcca tgggtactga gtaccccctg    540
gtgaacgtgc ccagccaccg gggtctcact tgcaaccgct ccagcacccg ccaccacgag    600
cagcccgaga cctccaatat gtccatctgt accaacctct ccagccgctg gaccgtgttc    660
cagtccagca tcttcggcgc cttcgtggtc tacctcgtgg tcctgctctc cgtagccttc    720
atgtgctgga acatgatgca ggtgctcatg aaaagccaga agggctcgct ggccgggggc    780
acgcggcctc cgcagctgag gaagtccgag agcgaagaga gcaggaccgc caggaggcag    840
accatcatct tcctgaggct gattgttgtg acattggccg tatgctggat gcccaaccag    900
attcggagga tcatggctgc ggccaaaccc aagcacgact ggacgaggtc ctacttccgg    960
gcgtacatga tcctcctccc cttctcggag acgtttttct acctcagctc ggtcatcaac   1020
ccgctcctgt acacggtgtc ctcgcagcag tttcggcggg tgttcgtgca ggtgctgtgc   1080
tgccgcctgt cgctgcagca cgccaaccac gagaagcgcc tgcgcgtaca tgcgcactcc   1140
accaccgaca cgcgcccgct ttgtgcagcg ccgttgctct cgcgtcccg gcgccagtcc   1200
tctgcaagga gaactgagaa gattttctta agcactttc agagcgaggc cgagcccag    1260
tctaagtccc agtcattgag tctcgagtca ctagagccca actcaggcgc gaaaccagcc   1320
aattctgctg cagagaatgg ttttcaggag catgaagttt ga                      1362
```

<210> SEQ ID NO 209
<211> LENGTH: 453
<212> TYPE: PRT
<213> ORGANISM: Homo sapiens

<400> SEQUENCE: 209

```
Met Ala Ser Pro Ser Leu Pro Gly Ser Asp Cys Ser Gln Ile Ile Asp
 1               5                  10                  15

His Ser His Val Pro Glu Phe Glu Val Ala Thr Trp Ile Lys Ile Thr
                20                  25                  30

Leu Ile Leu Val Tyr Leu Ile Ile Phe Val Met Gly Leu Leu Gly Asn
            35                  40                  45

Ser Ala Thr Ile Arg Val Thr Gln Val Leu Gln Lys Lys Gly Tyr Leu
        50                  55                  60

Gln Lys Glu Val Thr Asp His Met Val Ser Leu Ala Cys Ser Asp Ile
 65                  70                  75                  80

Leu Val Phe Leu Ile Gly Met Pro Met Glu Phe Tyr Ser Ile Ile Trp
                85                  90                  95

Asn Pro Leu Thr Thr Ser Ser Tyr Thr Leu Ser Cys Lys Leu His Thr
               100                 105                 110

Phe Leu Phe Glu Ala Cys Ser Tyr Ala Thr Leu Leu His Val Leu Thr
```

```
                    115                 120                 125
Leu Ser Phe Glu Arg Tyr Ile Ala Ile Cys His Pro Phe Arg Tyr Lys
130                 135                 140

Ala Val Ser Gly Pro Cys Gln Val Lys Leu Leu Ile Gly Phe Val Trp
145                 150                 155                 160

Val Thr Ser Ala Leu Val Ala Leu Pro Leu Leu Phe Ala Met Gly Thr
                    165                 170                 175

Glu Tyr Pro Leu Val Asn Val Pro Ser His Arg Gly Leu Thr Cys Asn
                    180                 185                 190

Arg Ser Ser Thr Arg His His Glu Gln Pro Glu Thr Ser Asn Met Ser
            195                 200                 205

Ile Cys Thr Asn Leu Ser Ser Arg Trp Thr Val Phe Gln Ser Ser Ile
        210                 215                 220

Phe Gly Ala Phe Val Val Tyr Leu Val Val Leu Leu Ser Val Ala Phe
225                 230                 235                 240

Met Cys Trp Asn Met Met Gln Val Leu Met Lys Ser Gln Lys Gly Ser
                    245                 250                 255

Leu Ala Gly Gly Thr Arg Pro Pro Gln Leu Arg Lys Ser Glu Ser Glu
                    260                 265                 270

Glu Ser Arg Thr Ala Arg Arg Gln Thr Ile Ile Phe Leu Arg Leu Ile
            275                 280                 285

Val Val Thr Leu Ala Val Cys Trp Met Pro Asn Gln Ile Arg Arg Ile
        290                 295                 300

Met Ala Ala Ala Lys Pro Lys His Asp Trp Thr Arg Ser Tyr Phe Arg
305                 310                 315                 320

Ala Tyr Met Ile Leu Leu Pro Phe Ser Glu Thr Phe Phe Tyr Leu Ser
                    325                 330                 335

Ser Val Ile Asn Pro Leu Leu Tyr Thr Val Ser Ser Gln Gln Phe Arg
                    340                 345                 350

Arg Val Phe Val Gln Val Leu Cys Cys Arg Leu Ser Leu Gln His Ala
            355                 360                 365

Asn His Glu Lys Arg Leu Arg Val His Ala His Ser Thr Thr Asp Ser
        370                 375                 380

Ala Arg Phe Val Gln Arg Pro Leu Leu Phe Ala Ser Arg Arg Gln Ser
385                 390                 395                 400

Ser Ala Arg Arg Thr Glu Lys Ile Phe Leu Ser Thr Phe Gln Ser Glu
                    405                 410                 415

Ala Glu Pro Gln Ser Lys Ser Ser Leu Ser Leu Gly Ser Leu Glu
                    420                 425                 430

Pro Asn Ser Gly Ala Lys Pro Ala Asn Ser Ala Ala Glu Asn Gly Phe
            435                 440                 445

Gln Glu His Glu Val
    450
```

<210> SEQ ID NO 210
<211> LENGTH: 625
<212> TYPE: DNA
<213> ORGANISM: Homo sapiens
<220> FEATURE:
<221> NAME/KEY: misc_feature
<222> LOCATION: 607
<223> OTHER INFORMATION: n = A,T,C or G

<400> SEQUENCE: 210
agttctcctt gcagaggact ggcgccggga cgcgaagagc aacgggcgct gcacaaagcg        60
ggcgctgtcg gtggtggagt gcgcatgtac gcgcaggcgc ttctcgtggt tggcgtgctg       120

```
cagcgacagg cggcagcaca gcacctgcac gaacacccgc cgaaactgct gcgaggacac      180
cgtgtacagg agcgggttga tgaccgagct gaggtagaaa aacgtctccg agaaggggag      240
gaggatcatg tacgcccgga agtaggacct cgtccagtcg tgcttgggtt tggccgcagc      300
catgatcctc cgaatctggt tgggcatcca gcatacggcc aatgtcacaa caatcagccc      360
tgggcagaca cgagcaggag gggagagacag agaaaagaaa aacacagcat gagaacacag      420
taaatgaata aaaccataaa atatttagcc cctctgttct gtgcttactg gccaggaaat      480
ggtaccaatt tttcagtgtt ggacttgaca gcttcttttg ccacaagcaa gagagaattt      540
aacactgttt caaacccggg ggagttggct gtgttaaaga aagaccatta aatgctttag      600
acagtgnaaa aaaaaaaaaa aaaaa                                            625

<210> SEQ ID NO 211
<211> LENGTH: 1619
<212> TYPE: DNA
<213> ORGANISM: Homo sapiens

<400> SEQUENCE: 211
ggcaactttt tgcggattgt tcttgcttcc aggctttgcg ctgcaaatcc agtgctacca       60
gtgtgaagaa ttccagctga acaacgactg ctcctccccc gagttcattg tgaattgcac      120
ggtgaacgtt caagacatgt gtcagaaaga agtgatggag caaagtgccg ggatcatgta      180
ccgcaagtcc tgtgcatcat cagcggcctg tctcatcgcc tctgccgggt accagtcctt      240
ctgctcccca gggaaactga actcagtttg catcagctgc tgcaacaccc ctctttgtaa      300
cgggccaagg cccaagaaaa ggggaagttc tgcctcggcc ctcaggccag ggctccgcac      360
caccatcctg ttcctcaaat tagccctctt tcggcacac tgctgaagct gaaggagatg      420 ccacccctc ctgcattgtt cttccagccc tcgcccccaa cccccacct ccctgagtga      480 gtttcttctg ggtgtccttt tattctgggt agggagcggg agtccgtgtt ctcttttgtt      540
cctgtgcaaa taatgaaaga gctcggtaaa gcattctgaa taaattcagc ctgactgaat      600
tttcagtatg tacttgaagg aaggaggtgg agtgaaagtt cacccccatg tctgtgtaac      660
cggagtcaag gccaggctgg cagagtcagt ccttagaagt cactgaggtg ggcatctgcc      720
ttttgtaaag cctccagtgt ccattccatc cctgatgggg gcatagtttg agactgcaga      780
gtgagagtga cgttttctta gggctggagg gccagttccc actcaaggct ccctcgcttg      840
acattcaaac ttcatgctcc tgaaaaccat tctctgcagc agaattggct ggtttcgcgc      900
ctgagttggg ctctagtgac tcgagactca atgactggga cttagactgg ggctcggcct      960
cgctctgaaa agtgcttaag aaaatcttct cagttctcct tgcagaggac tggcgccggg     1020
acgcgaagag caacgggcgc tgcacaaagc gggcgctgtc ggtggtggag tgcgcatgta     1080
cgcgcaggcg cttctcgtgg ttggcgtgct gcagcgacag gcggcagcac agcaccttgc     1140
acgaacaccc gccgaaactg ctgcgaggac accgtgtaca ggagcgggtt gatgaccgag     1200
ctgaggtaga aaacgtctc cgagaagggg aggaggatca tgtacgcccg gaagtaggac     1260
ctcgtccagt cgtgcttggg tttggccgca gccatgatcc tccgaatctg ttgggcatc     1320 cagcatacgg ccaatgtcac aacaatcagc cctgggcaga cacgagcagg agggagagac     1380
agagaaaaga aaacacagc atgagaacac agtaaatgaa taaaaccata aatatttag     1440 ccctctgtt ctgtgcttac tggccaggaa atggtaccaa ttttttcagtg ttggacttga     1500 cagcttcttt tgccacaagc aagagagaat ttaacactgt ttcaaacccg ggggagttgg     1560
ctgtgttaaa gaaagaccat taaatgcttt agacagtgta aaaaaaaaaa aaaaaaaa      1619
```

<210> SEQ ID NO 212
<211> LENGTH: 1010
<212> TYPE: DNA
<213> ORGANISM: Homo sapiens

<400> SEQUENCE: 212

```
ccgcagccgg gagcccgagc gcgggcgatg caggctccgc gagcggcacc tgcggctcct      60
ctaagctacg accgtcgtct ccgctggcag cagctgcggg ccccagcagc ctcggcagcc     120
acagccgctg cagcctgggg cagcctccgc tgctgtcgcc tcctctgatg cgcttgccct     180
ctccctggcc ccgggactcc gggagaatgt gggtcctagg catcgcggca acttttttgcg    240
gattgttctt gcttccaagg ctttgcgctg caaatccagt gctaccagtg tgaagaattc     300
cagctgaaca acgactgctc ctcccccgag ttcattgtga attgcacggt gaacgttcaa     360
gacatgtgtc agaaagaagt gatggagcaa agtgccggga tcatgtaccg caagtcctgt     420
gcatcatcag cggcctgtct catcgcctct gccgggtacc agtccttctg ctccccaggg     480
aaactgaact cagtttgcat cagctgctgc aacacccctc tttgtaaccg gccaaggcc     540
caagaaaagg ggaagttctg cctcggccct caggccaggg ctccgaacca ccatcctgtc     600
cctcaaatta agccctactt ctcggcacac tgctggaagc ttgaagggag aaggcaccca    660
ctcctgcata gtccatccag gcctcgcccc acacacccca ctccctgaga gagcacgccc    720
agggagacca aaaccgggga taggcaacgg acccccagac accacaaggg acccgaggac    780
aaagacgcag acaactcgcg aaagccaccc acgaatacaa cggcccgaac acagatataa    840
cgcacgagcc ccgaccgaca agagaagaag cagaagaaac cccacagac agaaacagac    900
accagcaaca agcgaaaaca gcaaaacgac actagcgaga caccacctgc acacaacacc    960
acagcccaac acagaggaca cgacaacaaa gagacagcac caacgacgaa              1010
```

<210> SEQ ID NO 213
<211> LENGTH: 480
<212> TYPE: DNA
<213> ORGANISM: Homo sapiens

<400> SEQUENCE: 213

```
gccaactccg gaggctctgg tgctcggccc gggagcgcga gcgggaggag cagagacccg      60
cagccgggag cccgagcgcg ggcgatgcag gctccgcgag cggcacctgc ggctcctcta     120
agctacgacc gtcgtctccg cggcagcagc gcgggcccca gcagcctcgg cagccacagc     180
cgctgcagcc ggggcagcct ccgctgctgt cgcctcctct gatgcgcttg ccctctcccg     240
gccccgggac tccggagaa tgtgggtcct aggcatcgcg gcaactttttt gcggattgtt    300
cttgcttcca ggctttgcgc tgcaaatcca gtgctaccag tgtgaagaat tccagctgaa    360
caacgactgc tcctcccccg agttcattgt gaattgcacg gtgaacgttc aagacatgtg    420
tgagaaagaa gtgatggagc aaagtgccgg gatcatgtac cgcaagtcct gtgcatgatc     480
```

<210> SEQ ID NO 214
<211> LENGTH: 1897
<212> TYPE: DNA
<213> ORGANISM: Homo sapiens

<400> SEQUENCE: 214

```
gccaactccg gaggctctgg tgctcggccc gggagcgcga gcgggaggag cagagacccg      60
cagccgggag cccgagcgcg ggcgatgcag gctccgcgag cggcacctgc ggctcctcta     120
agctacgacc gtcgtctccg cggcagcagc gcgggcccca gcagcctcgg cagccacagc     180
```

```
cgctgcagcc ggggcagcct ccgctgctgt cgcctcctct gatgcgcttg ccctctcccg      240
gccccgggac tccgggagaa tgtgggtcct aggcatcgcg gcaactttt gcggattgtt      300 cttgcttcca ggctttgcgc tgcaaatcca gtgctaccag tgtgaagaat tccagctgaa      360
caacgactgc tcctcccccg agttcattgt gaattgcacg gtgaacgttc aagacatgtg      420
tcagaaagaa gtgatggagc aaagtgccgg gatcatgtac cgcaagtcct gtgcatcatc      480
agcggcctgt ctcatcgcct ctgccgggta ccagtccttc tgctcccag ggaaactgaa      540 ctcagtttgc atcagctgct gcaacacccc tctttgtaac gggccaaggc ccaagaaaag      600
gggaagttct gcctcggccc tcaggccagg gctccgcacc accatcctgt tcctcaaatt      660
agccctcttc tcggcacact gctgaagctg aaggagatgc cacccctcc tgcattgttc      720 ttccagccct cgcccccaac cccccacctc cctgagtgag tttcttctgg gtgtccttt      780 attctgggta gggagcggga gtccgtgttc tcttttgttc ctgtgcaaat aatgaaagag      840
ctcggtaaag cattctgaat aaattcagcy tgactgaatt ttcagtatgt acttgaagga      900
aggaggtgga gtgaaagttc accccatgt ctgtgtaacc ggagtcaagg ccaggctggc      960
agagtcwgtc cttagaagtc actgaggtgg gcatctgcct tttgtaaagc ctccagtgtc     1020
cattccatcc ctgatggggg catagtttga gactgcagag tgagagtgac gttttcttag     1080
ggctggaggg ccagttccca ctcaaggctc cctcgcttga cattcaaact tcatgctcct     1140
gaaaaccatt ctctgcagca gaattggctg gtttcgcgcc tgagttgggc tctagtgact     1200
cgagactcaa tgactgggac ttagactggg gctcggcctc gctctgaaaa gtgcttaaga     1260
aaatcttctc agttctcctt gcagaggact ggcgccggga cgcgaagagc aacgggcgct     1320
gcacaaagcg ggcgctgtcg gtggtggagt gcgcatgtac gcgcaggcgc ttctcgtggt     1380
tggcgtgctg cagcgacagg cggcagcaca gcacctgcac gaacacccgc cgaaactgct     1440
gcgaggacac cgtgtacagg agcgggttga tgaccgagct gaggtagaaa acgtctccg      1500 agaaggggag gaggatcatg tacgcccgga gtaggacct cgtccagtcg tgcttgggtt     1560
tggccgcagc catgatcctc cgaatctggt tgggcatcca gcatacggcc aatgtcacaa     1620
caatcagccc tgggcagaca cgagcaggag ggagagacag agaaaagaaa acacagcat      1680 gagaacacag taaatgaata aaaccataaa atatttagcc cctctgttct gtgcttactg     1740
gccaggaaat ggtaccaatt tttcagtgtt ggacttgaca gcttctttg ccacaagcaa      1800 gagagaattt aacactgttt caaacccggg ggagttggct gtgttaaaga aagaccatta     1860
aatgctttag acagtgtaaa aaaaaaaaaa aaaaaaa                              1897
```

<210> SEQ ID NO 215
<211> LENGTH: 141
<212> TYPE: PRT
<213> ORGANISM: Homo sapiens

<400> SEQUENCE: 215

```
Met Trp Val Leu Gly Ile Ala Ala Thr Phe Cys Gly Leu Phe Leu Leu
  1               5                  10                  15

Pro Gly Phe Ala Leu Gln Ile Gln Cys Tyr Gln Cys Glu Glu Phe Gln
             20                  25                  30

Leu Asn Asn Asp Cys Ser Ser Pro Glu Phe Ile Val Asn Cys Thr Val
         35                  40                  45

Asn Val Gln Asp Met Cys Gln Lys Glu Val Met Glu Gln Ser Ala Gly
     50                  55                  60

Ile Met Tyr Arg Lys Ser Cys Ala Ser Ser Ala Ala Cys Leu Ile Ala
```

```
                65                  70                  75                  80
Ser Ala Gly Tyr Gln Ser Phe Cys Ser Pro Gly Lys Leu Asn Ser Val
                    85                  90                  95

Cys Ile Ser Cys Cys Asn Thr Pro Leu Cys Asn Gly Pro Arg Pro Lys
                100                 105                 110

Lys Arg Gly Ser Ser Ala Ser Ala Leu Arg Pro Gly Leu Arg Thr Thr
            115                 120                 125

Ile Leu Phe Leu Lys Leu Ala Leu Phe Ser Ala His Cys
        130                 135                 140

<210> SEQ ID NO 216
<211> LENGTH: 443
<212> TYPE: DNA
<213> ORGANISM: Homo sapiens
<220> FEATURE:
<221> NAME/KEY: misc_feature
<222> LOCATION: 185,208,304,339,348,386,421,428
<223> OTHER INFORMATION: n = A,T,C or G

<400> SEQUENCE: 216 ccttttttt tttttttctc agttattgac tggctgggtg tgacttagta cataagtact       60
caatattata aaaacctcaa ataattgact tgattttaca caacatcctt cccttttcta      120
caagttaatt tttttacaaa tcatttgggt tatctcctaa ataggttata ttttattgct      180
tctanaaaca atgtttcaaa atatatgngc attatcagta ataatttgta taaatatttc      240
ccacaacaat tttcataatt ttcaaagact aattttcttga ctgaagatat tttgctaggg     300
aagngaaact ttaaaatttt gagattttaa aaaaattgng tgaatggngg catgcaaagg     360
atttatatag tggctcccct aactgngtgc cgatcaggac acatattttt agacatctaa     420
ntctgganct taaatggagg gac                                              443

<210> SEQ ID NO 217
<211> LENGTH: 527
<212> TYPE: DNA
<213> ORGANISM: Homo sapiens
<220> FEATURE:
<221> NAME/KEY: misc_feature
<222> LOCATION: 521,523
<223> OTHER INFORMATION: n = A,T,C or G

<400> SEQUENCE: 217
agacacaaca gtctgactat gagtgaggaa aatatctggg tcttttcgtc agtttggtgc       60
atttgctgct gctgttgcta ctgtttgcct caaacgctgt gtttaaacaa cgttaaactc     120
ttagcctaca aggtggctct tatgtacata gttgttaata catccaatta atgatgtctg     180
acatgctatt tttgtaggga gaaaatatgt gctaatgata ttttgagtta aaatatcttt     240
tggggaggat ttgctgaaaa gttgcacttt tgttacaatg cttatgcttg gtacaagctt     300
atgctgtctt aaattatttt aaaaaaataa atactgtctg tgagaaacca gctggtttag     360
aaaagtttag tatgtgacga taaactagaa attacctta tattctagta ttttcagcac      420
tccataaatt ctattaccta aatattgcca cactattttg tgatttaaaa attcttacta      480
aggaataaaa actttaatat acaaaaaaaa aaaaagggg ngnccgc                     527

<210> SEQ ID NO 218
<211> LENGTH: 896
<212> TYPE: DNA
<213> ORGANISM: Homo sapiens
<220> FEATURE:
<221> NAME/KEY: misc_feature
<222> LOCATION: 531,587,589,592,619,636,649,662,663,694,
```

```
        723,729,735,737,741,752,783,816,817,819,
        820,822,826,828,830,833,834,839,841,842,
        869,892
<223> OTHER INFORMATION: n = A,T,C or G

<400> SEQUENCE: 218
gcagaacatt attttacaga cagcaaggat gcttctgagt gacacctagg aaattatttg      60
aagaaattct ttttatatct acacctgttg tgtaagaaac tttaaaacat tggttatttt     120 ctcaccttttt tttctaattc actttgattg ctaggggtca tgtatgcttc gaagttacag    180
gactaaaaga gcaaactgac cggcctaaaa ctaaaatgac atttattccc tagctacaaa     240
catcagcgtt attatgttaa ttataccttg ccctctatca ttataaatgg ttgccatggt     300
gtttctaaaa ataagtgttt taccattaat gtgtagaggg caaacaaagc ataaagtact     360
aagggatcat gcttatccta gggtctcaca gaagagagga catatttaat taatcttgtg     420
aattacagaa caggttgtgg tccagacacc aagaatcata ggggttttt tttaaaaaac      480 ctaatagaag taggggggacc tctctctttg gctaagagtc taaaggaagg naggcatctg    540
tttaattagt tggttcaccc tggctttacc tctggttaat gctttgngnt antaggaagg     600
aaaaatcctt tatcttttnt tccaagccct ccctgnctga cttacccana ctgggattac     660
cnngaaaccc caggggggatt tatgggggga gaaggatttt tttcacccctt taaacctctt    720 aanccccang gggananaaa ncctcttggg anagcctatg gccctatttt ttaatatcca     780
ggnccccttg gaaaacttttt tttttttaa aagccnntnn antttnantn aannaaaana     840 nncaacctttt tggccccaaa aaaaaggnc cccccctaag gccccacccc tntttt         896

<210> SEQ ID NO 219
<211> LENGTH: 770
<212> TYPE: DNA
<213> ORGANISM: Homo sapiens
<220> FEATURE:
<221> NAME/KEY: misc_feature
<222> LOCATION: 525,527,574,619,628,730,752
<223> OTHER INFORMATION: n = A,T,C or G

<400> SEQUENCE: 219
aaagaaggtt cacttccatt acagtatgag tggcaaaaat tgtctgactc acagaaaatg      60
cccacttcat ggttagcaga aatgacttca tctgttatat ctgtaaaaaa tgcctcttct     120
gagtactctg ggacatacag ctgtacagtc agaaacagag tgggctctga tcagtgcctg     180
ttgcgtctaa acgttgtccc tccttcaaat aaagctggac taattgcagg agccattata     240
ggaactttgc ttgctctagc gctcattggt cttatcatct tttgctgtcg taaaaagcgc     300
agagaagaaa aatatgaaaa ggaagttcat cacgatatca gggaagatgt gccacctcca     360
aagagccgta cgtccactgc cagaagctac atcggcagta atcattcatc cctggggtcc     420
atgtctcctt ccaacatgga aggatattcc aagactcagt ataaccaagt accaagtgaa     480
gactttgaac gcactcctca gagtccgact ctcccacctg ctaangnagc tgcccctaat     540
ctaagtcgaa tgggtgcgat tcctgtgatg attncagcac agagcaagga tgggtctata     600
gtatagagcc tccatatgnc tcatctgngc tctccggggt cctttccttt ttttgatata     660
tgaaaaccta ttctgggcta aattgggtac tagcctcaaa tcatcaaaaa ataagttaat     720
caggaactgn accgaaaata ttttttaaaa anttttgttt gggtatattc                770

<210> SEQ ID NO 220
<211> LENGTH: 892
<212> TYPE: DNA
<213> ORGANISM: Homo sapiens
```

```
<220> FEATURE:
<221> NAME/KEY: misc_feature
<222> LOCATION: 2,3,208,321,337,542,551,560,590,606,
      613,614,620,639,640,645,646,652,659,661,
      663,666,676,679,707,708,709,717,718,719,
      726,728,730,732,738,742,751,764,773,777,
      782,792,821,825,827,828,831,832,833,870,
      880
<223> OTHER INFORMATION: n = A,T,C or G

<400> SEQUENCE: 220
tnnacactca ccgccctcgc cgccgcgcca tggacgcccc caggcaggtg gtcaactttg    60
ggcctggtcc cgccaagctg ccgcactcag tgttgttaga gatacaaaag gaattattag   120
actacaaagg agttggcatt agtgttcttg aaatgagtca caggtcatca gattttgcca   180
agattattaa caatacagag aatcttgngc gggaattgct agctgttcca gacaactata   240
aggtgatttt tctgcaagga ggtgggtgcg gccagttcag tgctgtcccc ttaaacctca   300
ttggcttgaa agcaggaagg ngtgcggact atgtggngac aggagcttgg tcagctaagg   360
ccgcagaaga agccaagaag tttgggacta taaatatcgt tcaccctaaa cttgggagtt   420
atacaaaaat tccagatcca agcacctgga acctcaccca gatgcctcct acgtgtatta   480
ttgcgcaaat gagacggtgc atggtggtgg agtttgactt tatacccgat gtccagggag   540
cnagtactgg ntttgtgacn tgtcctcaaa cttttcctgtc caagccaggn gggatgtttt   600
cccaantttg ggnnggtgan tttttttgctg gggggcccnn aaaannaaat gnttggggnt   660
ncntgncttt gggggnccna ccccgggggg gcggaaattg gttccnnnnc gggaatnnna   720 acccncntngn cngggggngg gnttttttggc ncccccttccc cggnaaaagg cgnggcnccc   780
cnttcggggg gnccccttggg ggaaaataaa ccaaaggggt nggcncnngg nnntttgggg   840
gaaacacacc gagcgcttcc cttttttgttn acccaacaan gggcccttttc ca          892

<210> SEQ ID NO 221
<211> LENGTH: 629
<212> TYPE: DNA
<213> ORGANISM: Homo sapiens
<220> FEATURE:
<221> NAME/KEY: misc_feature
<222> LOCATION: 408,502,507,540,542,545,550,562,572,576,
      623,628
<223> OTHER INFORMATION: n = A,T,C or G

<400> SEQUENCE: 221 ccttttttt tttttttggt acaaattatg taaaacattt gtgctaagaa ctttttctccc    60 tccccaaacc aaaagaaaa taaaaaataa aaaattaaa aaaattaaaa attgagtatt   120
ctaactacag ctcaacaatt gaatcaaatg tcactgtttt gtaaatactt tatccataac   180
gaaagatata aacatgcaaa aaacctgaat ccatagtcca aataatacat acacatgttc   240
tgaagtttct gcacttctcc atagactatg ccaataaaac attatgtaca catactatt   300 ttacagtgaa gtggaaaaat acagaaataa aaaagtgtac atggattaag accaaaatgt   360
gtctaacatt ctagtttatg aaaaaattca attttgctac aaattggnga tatgaaaact   420 cccttttattt gcaaccagct gagtaagttt taagatttta gtgaaaaaaa aaaaaaacaa   480
actaaagtct aaaactagaa gnaatgngca ttttccaatc tcatgggctc atccccaan    540 anaanaaaan cgctccatga gntttttttgg tnggtnaatt ttggattttta aaaaagcaa   600 atgcaatgta acaaaagcgg ggntgaanc                                     629

<210> SEQ ID NO 222
<211> LENGTH: 763
```

```
<212> TYPE: DNA
<213> ORGANISM: Homo sapiens
<220> FEATURE:
<221> NAME/KEY: misc_feature
<222> LOCATION: 626,628,634,661,748,751
<223> OTHER INFORMATION: n = A,T,C or G

<400> SEQUENCE: 222
ggaagtgctg aatggtgttg cagggggtat taaacgtgca tttttactca actacctcag    60
gtattcagta atacaatgaa agcaaaatt gttcctttt tttgaaaatt ttatatactt    120
tataatgata gaagtccaac cgttttttaa aaaataaatt taaaatttaa cagcaatcag   180
ctaacaggca aattaagatt tttacttctg gctggtgaca gtaaagctgg aaaattaatt   240
tcagggtttt ttgaggcttt tgacacagtt attagttaaa tcaaatgttc aaaaatacgg   300
agcagtgcct agtatctgga gagcagcact accatttatt ctttcattta tagttgggaa   360
agtttttgac ggtactaaca aagtggtcgc aggagatttt ggaacggctg gtttaaatgg   420
cttcaggaga cttcagtttt ttgtttagct acatgattga atgcataata aatgctttgt   480
gcttctgact atcaatacct aaagaaagtg catcagtgaa gagatgcaag actttcaact   540
gactggcaaa aagcaagctt tagcttgtct tataggatgc ttagtttgcc actacacttc   600
agaccaatgg gacagtcata gatggngnga cagngttaaa cgcaacaaaa ggctacattt   660
ncatggggcc agcactggca tgagcctccc taagcttttt tgaagaattt taagccctgg   720
taaattaaaa aaaaaaaaaa aaaaggggngg nccccctcca aat                    763

<210> SEQ ID NO 223
<211> LENGTH: 885
<212> TYPE: DNA
<213> ORGANISM: Homo sapiens
<220> FEATURE:
<221> NAME/KEY: misc_feature
<222> LOCATION: 21,571,599,653,714,717,746,755,756,761,
      762,781,782,790,814,849,884
<223> OTHER INFORMATION: n = A,T,C or G

<400> SEQUENCE: 223
tggagccgct gtggttgctg nccgcggagt ggaagcgcgt gcttttgttt gtgtccctgg    60
ccatggcgct gcagctctcc cgggagcagg gaatcaccct gcgcgggagc gccgaaatcg   120
tggccgagtt cttctcattc ggcatcaaca gcatttttata tcagcgtggc atatatccat   180
ctgaaacctt tactcgagtg cagaaatacg gactcacctt gcttgtaact actgatcttg   240
agctcataaa atacctaaat aatgtggtgg aacaactgaa agattggtta tacaagtgtt   300
cagttcagaa actggttgta gttatctcaa atattgaaag tggtgaggtc ctggaaagat   360
ggcagtttga tattgagtgt gacaagactg caaaagatga cagtgcaccc agagaaaagt   420
ctcagaaagc tatccaggat gaaatccgtt cagtgatcag acagatcaca gctacggtga   480
catttctgcc actgttggaa gtttcttgtc atttgatctg ctgatttata cagacaaaga   540
tttggttgta cctgaaaaat gggaagagtc nggaccacag tttattaccc aattctgang   600
aagtcccgcc ttcgttcatt tactactaca atccacaaag taaatagcat ggngggctac   660
aaaaaattcc tgtcaatgac tgaggatgac atgaaggaaa aaatggaaa ttgnaanttt    720
tgaaaagggg gttccctgaa aacagncatc tatanntgaa nnttggttta tttcattggg   780
nnaattttn cctggggggg aaaaaccccca aanggatac ctttactgga accggggggg    840
gaaattggnc cttttatttt ttttttggg cccccaattt tggnc                    885

<210> SEQ ID NO 224
```

```
<211> LENGTH: 541
<212> TYPE: DNA
<213> ORGANISM: Homo sapiens
<220> FEATURE:
<221> NAME/KEY: misc_feature
<222> LOCATION: 300,311,350,422,490,508,526
<223> OTHER INFORMATION: n = A,T,C or G

<400> SEQUENCE: 224 ccttttttt  tttttttaaa  acaaacttaa  ctttatttcc  tcactttcac  ttaaaacttg    60
attttataaa  acacatgaaa  aaacattttt  aagagttctg  tatcacagaa  cattaaacag   120
tacaaatatc  cattgcttca  taggttcaag  ttacataaat  taaagtcaaa  taattggaaa   180
ctgattcaat  agggaaaact  atacatgaaa  tgaaggtcaa  aaggagctat  acagcaatat   240
ttcattggtt  atagattatg  agttactttc  aggaccttaa  caaagattct  gaatatttan   300
acttcctttg  ntggatttta  tacttaaata  tctccctacc  tatactgagn  caaactactt   360
gaccaaaaca  tctgatttag  gaaagcatct  agctttatag  cacaagtttt  tccatctaca   420
gntactatct  tcaaaggaat  atacatcaca  atgttgacaa  aaaaacctcc  tggttccttt   480
tgaacaatgn  gcaataaatt  catgatgnta  acccatggg  gaaggncaaa  aaggggaccc    540
a                                                                        541

<210> SEQ ID NO 225
<211> LENGTH: 543
<212> TYPE: DNA
<213> ORGANISM: Homo sapiens
<220> FEATURE:
<221> NAME/KEY: misc_feature
<222> LOCATION: 23,226,295,316,327,345,428,445,476,479,
       521,522
<223> OTHER INFORMATION: n = A,T,C or G

<400> SEQUENCE: 225
cctttttttt  tttttttgta  agnttaaatt  tatttttaa   aaatgcttgt  cttcctcact    60
agacaatcaa  ctctatgagg  gcagagacta  tgtcaccact  gtcccaccag  ccctggcac   120 acagtaggta  ctcaataaat  atatgttgga  aggatggatg  gaggtaatgg  atggaaagat  180
ggatggaagg  atgaatggag  ggatggatgt  gacccagctg  aagtgngagt  aggaacattc  240
tcttattatg  ggtggaggaa  agagagagga  gattgagaaa  ataagataaa  atacnttgat  300
gagcatcatt  tttggngttc  gaaaagnagg  attgaattag  gactnataaa  tctagagaat  360
tttacctctt  tcaatgccca  agccacactt  ttctatcact  ttgaaaccga  aaaagaaata  420 cttttcccnac atttgctttg  ctggnaggaa  atgctttaat  aaaaatgcaa  tctctnagnt  480
gccatggcat  cattaaaaga  aaggatgtca  tgcccaggcc  nnaacttgaa  gggggaggc   540 ccc                                                                      543

<210> SEQ ID NO 226
<211> LENGTH: 703
<212> TYPE: DNA
<213> ORGANISM: Homo sapiens
<220> FEATURE:
<221> NAME/KEY: misc_feature
<222> LOCATION: 530,535,560,567,584,600,664,671
<223> OTHER INFORMATION: n = A,T,C or G

<400> SEQUENCE: 226
tgttaatgca  attatagaaa  tacatcggag  acacaacatg  atgtggccat  tacaggtttc    60
ataaaattac  actgacttgg  ctgttacttg  atcttaggaa  acagcacagt  ttaagatatt   120
gtgaattctg  acttatactt  tattaaatgc  tataaatcta  aatagatcct  gttggatgtg  180
```

```
atgggtctag tccagtttat ttaagttcat gtttcactgt ttgcactttg cattgaacaa    240
tgggtttatt cgctgatgta aacggttcga gtgaagaatt aatgcagtaa gtatgacaac    300
acatacacac ttgcctctcc ccatctccag aagaggggag cagagtccga gcttatctaa    360
atatgaatgt ggccacaaag ctgtggaagg tgacaaagct taaacacctt tgccctggct    420
ctgcattgtc acctagagag caagaggtct atagaaacat catgtcacat gaaacgattc    480
tctgcttttt ggtctgaact tgaaggccct aaactgcaaa atctaagagn tgggngggta    540
ttaaaatgct tttaaaaagn taactgnggc accaattcta atgnaatccc acttgggacn    600
gggttttttt ggtttggttt ggttttgggg ggggggggg ggggccctg ggaaaggggg     660 aacnaacatg nttttgaaat acatattggg aaaaaaatg ggg                      703
```

<210> SEQ ID NO 227
<211> LENGTH: 501
<212> TYPE: DNA
<213> ORGANISM: Homo sapiens
<220> FEATURE:
<221> NAME/KEY: misc_feature
<222> LOCATION: 1,5,154,239,281,292,336,421,459,470
<223> OTHER INFORMATION: n = A,T,C or G

<400> SEQUENCE: 227

```
ngtgncectg gccatggcgc tgcagctctc ccgggagcag ggaatcaccc tgcgcgggag     60
cgccgaaatc gtggccgagt tcttctcatt cggcatcaac agcatttat atcagcgtgg    120 catatatcca tctgaaacct ttactcgagt gcanaaatac ggactcacct tgcttgtaac    180
tactgatctt gagctcataa ataccctaaa taatgtggtg gaacaactga aagattggnt    240
atacaagtgt tcagttcaga aactggttgt agttatctca natattgaaa gnggtgaggt    300
cctggaaaga tggcagtttg atattgagtg tgacangact gcaaagatg acagtgcacc    360 cagagaaaag tctcagaaag ctatccagga tgaaatccgt tcagtgatca gacagatcac    420
ngctacgggg acatttctgc cctgttggaa ggttcttgnt catttgatcn gctgatttat    480
acagacaaaa gatttggttt g                                              501
```

<210> SEQ ID NO 228
<211> LENGTH: 539
<212> TYPE: DNA
<213> ORGANISM: Homo sapiens
<220> FEATURE:
<221> NAME/KEY: misc_feature
<222> LOCATION: 3,13,101,405,440,456,465,513,526
<223> OTHER INFORMATION: n = A,T,C or G

<400> SEQUENCE: 228

```
ggnttatact gcnaaagtta tgcattacac catattcagt tggtaacata aaccgagata     60
taagaattta tatattggct tctggttatt ttcttagcac nggagtgcct tttccaacca    120
ttgagtgcat gatcagatta cacaaataca agcacatatc atgtgttctc ccatgagaca    180
ttattcactt aggattgtct acaataaaaa aagttaaagt acaagcaata ataaattcat    240
aagaattttt tgaatttaaa ataaatgcat gtgtctttga gaacatttct tttgaaattc    300
atatttttaa aaataacaag tttcttaaat cagtcttta gtcgtgtttt catatggtat    360
ttatcagtag gtggaaacac ttcacatcat ttaaccccaa aaggnataat aattaaactg    420
caattaaagg gaggaacagn tgaatcatta caacantaat acggngtaca aatcagagtt    480
ggccacacaa tacacatgtg taatactgga aanaaataca atatcngaat cctggatgg    539
```

-continued

```
<210> SEQ ID NO 229
<211> LENGTH: 790
<212> TYPE: DNA
<213> ORGANISM: Homo sapiens
<220> FEATURE:
<221> NAME/KEY: misc_feature
<222> LOCATION: 576,622,678,706,738,755,766
<223> OTHER INFORMATION: n = A,T,C or G

<400> SEQUENCE: 229
cagagagcat gatcagtgct gatactgaca agtactttt  taccttaaaa tcaacttcta      60
tggaactaca agatcaatct agctcccgag tgacattttc cattgtctgt aataatgccc     120
tcggatgagt tgtgtctaaa attaagttca tctttattta tatgcgaact taactgccat     180
agtccctaat gtattgcgtt tgtaacctga tcgtattatg tttacagctg aaagatttca     240
tctagacatg tctttcgtcc ttattattca aagtgtaatt gaaagagata tttagtatta     300
agacatgttc cccaattgag aattttccag aatattctac ttaagaagaa gaagagcaat     360
taactgccctt tagtgtaagg gcgagagtgc atagaaatat gcaatgtaaa atgtttgcat    420
gaattatttc acatcatgta agctttccca tattcataag atgaacacta tagaagtctc     480
atttctctgt gatcttctgc cattaggaaa gtaaggagat tggtatctat atctagtctc     540
ctttccatat tgaactgcat ggctctaatc ctcagnggat ttttatccct tctccggtta     600
tttaaaattt gccctattta anctggaagc ctggataaac tgctgagccc cgaatattcc     660
tggggattgg gagtttantt gctgggagaa ccacttggtt gaagancacc atttttttcc     720
cttttttttc tttttccnga atttttttccc tcaanccatt ggtttnctct taaatggaaa    780
aaccccccg                                                             790

<210> SEQ ID NO 230
<211> LENGTH: 744
<212> TYPE: DNA
<213> ORGANISM: Homo sapiens
<220> FEATURE:
<221> NAME/KEY: misc_feature
<222> LOCATION: 603,618,636,723,724
<223> OTHER INFORMATION: n = A,T,C or G

<400> SEQUENCE: 230
aaattttatg ggtgggtgcc aaatactgct gtgaatctat ttgtatagta tccatgaatg      60
aatttatgga aatagatatt tgtgcagctc aatttatgca gagattaaat gacatcataa     120
tactggatga aaacttgcat agaattctga ttaaatagtg ggtctgtttc acatgtgcag     180
tttgaagtat ttaaataacc actcctttca cagtttattt tcttctcaag cgttttcaag     240
atctagcatg tggattttaa aagatttgcc ctcattaaca agaataacat ttaaaggaga     300
ttgtttcaaa atattttttgc aaattgagat aaggacagaa agattgagaa acattgtata    360
ttttgcaaaa acaagatgtt tgtagctgtt tcagagagag tacggtatat ttatggtaat     420
tttatccact agcaaatctt gatttagttt gatagtgtgt ggaattttat tttgaaggat     480
aagaccatgg gaaaattgtg gtaaagactg tttgacccct catgaaataa ttctgaagtt     540
gccatcagtt ttactaatct tctgtgaaag catagatatg cgcatggtca cttttattgg     600
ggncttataa ttaaatgnaa aattgaaatt catttntgtt caaggggat  atcttccaat     660
agccttttta gtagtattca aatatcagtc tatggataat gatttatttt ctttcttagg    720
agnntcaatg tggactaatt cagt                                           744

<210> SEQ ID NO 231
<211> LENGTH: 797
```

```
<212> TYPE: DNA
<213> ORGANISM: Homo sapiens
<220> FEATURE:
<221> NAME/KEY: misc_feature
<222> LOCATION: 429,446,495,523,537,626,628,642,664,707,
      711,713,727,733,786,793
<223> OTHER INFORMATION: n = A,T,C or G

<400> SEQUENCE: 231
gtgccgcctc caaagagccg tacgtccgct gccagaagct gcataggcag taatcattca    60
tccctggaat ccatgtctcc ttccaacatg gagggatatt ccaagactca gtataaacaa   120
gtaccgagtg aagactttga acgcactcct cagagtccaa ctctcccacc tgctaaggta   180 gctgcccta atctaggtcg aatgggcgtg attcctgtga tgattcccgc acagagcaag    240
gatgggtcta tagtatagag cctccatacg tctcatctgt gctttccgtg ttcctttcct   300
tttttgatat atgaaaacct attctggtct aaattttgtt actagcctca aaatgtatcc   360
aaaaataagt taatcaggag ctgtaaggaa tatatttttt aaaatttttc tttggttata   420
tcgaaatang ttacaggcat taaagntagt aaagacaagt ttaccatctg aaaaagctgg   480
atttctttaa gaggntgatt ataaagggtt ctaaatttat cantacctaa gtaagangta   540
gcacttttga atatgaaatc ataagtgaag acattggtga acttacttgc atacccaagt   600
tgatactttg agtaaccatc tgaaangngg gacttggata anttttacca ttatttttaa   660
gganggggat cttaattatt tatgggcccc cagtctcccc cccaaantaa ntnccgaaaa   720
cattccnttg acnaaaatta ccccctgggg gggggttgga cctttggttt tcccaggttt   780
cttggnaaaa ctntggg                                                  797

<210> SEQ ID NO 232
<211> LENGTH: 635
<212> TYPE: DNA
<213> ORGANISM: Homo sapiens
<220> FEATURE:
<221> NAME/KEY: misc_feature
<222> LOCATION: 501,531,556,623,633
<223> OTHER INFORMATION: n = A,T,C or G

<400> SEQUENCE: 232
tattattagg atggtaagag tattataagg attggtacaa ggcatgatga gtccttttgc    60
ttttaggctt ttgacttctg gttttagact ttctttagct tctgttgtta gacaacattg   120
tgcaagcttg gttttttataa gtttgcatgg attaaactga acttaatgaa attgtccctc   180 ccccaaatt ctcagcacaa tttttaggcc cacaaggagt caagcacctc aaggagatct    240
tcagtttgaa cttggtgtag acacagggat actgatgaat caatattcaa attagctgtt   300
acctacttaa gaaagagagg agaccttggg gatttcgagg aagggttcat aagggagatt   360
ttagctgaga ataccatttt gcacagtcaa tcacttctga ccaagttatc agaaaaagga   420
gaaaagaatg tctccccact aaatgttcta gggtggtgag aaatctaggg tgggtatcta   480
aatcacaata tttggatatt ncaatatcta aatattggtg gaaatactct nctgaagtgt   540
cattgactct aaaaanacac ttgtgatcat ggcaggggtt aaggtcattt ttattcctat   600
aatccttata ttaacaattc ctntgattaa ganaa                              635

<210> SEQ ID NO 233
<211> LENGTH: 663
<212> TYPE: DNA
<213> ORGANISM: Homo sapiens
<220> FEATURE:
<221> NAME/KEY: misc_feature
<222> LOCATION: 429,432,437,475,485,491,493,535,550,555,
```

571,612,640,653
<223> OTHER INFORMATION: n = A,T,C or G

<400> SEQUENCE: 233
cctctgtata gaaatctaaa agaattttac cattcagtta attcaatgtg aacactggca      60
cactgctctt aagaaactat gaagatctga gattttttg tgtatgtttt tgactctttt     120
gagtggtaat catatgtgtc tttatagatg tacataccte cttgcacaaa tggaggggaa    180
ttcattttca tcactgggag tgtccttagt gtatgaaaac catgctggta tatggcttca    240
agttgtaaaa atgaaagtga ctttaaaaga aaatagggga tggtccagga tctccactga    300
taagactgtt tttaagtaac ttaaggacct ttgggtctac aagtatatgt gaaaaaaatg    360
agacttactg ggtgaggaaa tccattgttt aaagatggtc cgtgtgtgtg tgtgtgtgtg    420
tgtgtgtgnt gngttgngtt ttgttttta agggaggggaa tttattattt accgntgctt    480
gaaantactg ngnaaatata tgtctgataa tgatttgctc tttgacaact aaaantagga    540
ctgtataagn cctanatgcc tcctgggggg ntgatcttac aagatattgg tgataccct     600 ttaaaaattg gncccccggc attttccccc tttgcttctn caaattaaaa ggncttttc     660 cca                                                                   663

<210> SEQ ID NO 234
<211> LENGTH: 873
<212> TYPE: DNA
<213> ORGANISM: Homo sapiens
<220> FEATURE:
<221> NAME/KEY: misc_feature
<222> LOCATION: 20,29,58,603,630,652,678,711,715,745,
       752,756,766,774,789,820,823,840,873
<223> OTHER INFORMATION: n = A,T,C or G

<400> SEQUENCE: 234
acttggggat tctcatgttn atggatacng tttggcaatc actacattga atgtagtntt      60 ttaaaaaat taacttatgc tattagttga cccatcattg ctaattttgg cccacacagt     120
gtttgcatta caaaaacctg ttctttactt cctagtcttg tttcagtctt aatatcagaa    180
gttcttgagt tcaaaataag cacaacatgt catccaggga tggctagctt gtttgggatt    240
catctaaact gctggcaata tctagacaaa acattccac agtccagcta atatggttgt     300
cacaactctt gaaaagggcc caacatctgg atggcaagtg aaaatgtgat cagggtttaa    360
gaactaccca ctaataaata aacatggagc tatttccatg tcttgggtgt tgtgtttcta    420
agaagagaca gcctttccat cagaaaattt ctgggaggga agaaaagaa cagttttgat     480 gaattcgctt tgcaaatcat catccaatgt tctttgtaac cagaaaggtt ttcttctgct    540
ttcttgcagc tggtatactt tctgctgagt gccctggggc ctgacggtct gtgtgctggc    600
cgnggccttt gcccgcccac cactattcgn cagctcacac cagtttacct gngagacccc    660
ctccgacttt tggccagngc aaactggccc cttccttcgg gagccggctc nagcnaggac    720 cctttggtt ttacccgggg atggngaccg gnctgnaccc agccgnccac tggnccctt     780 tcaaacctng ttcctttccc tcatccccag aaggaatttn ttnaaatttt gggccttggn    840
ggcccttggg ggggcctttg ggttgggccc ctn                                  873

<210> SEQ ID NO 235
<211> LENGTH: 51
<212> TYPE: DNA
<213> ORGANISM: Homo sapiens
<220> FEATURE:
<221> NAME/KEY: misc_feature
<222> LOCATION: 26,48

<223> OTHER INFORMATION: n = A,T,C or G

<400> SEQUENCE: 235

```
tttttttttt tttttttttta attttngttt tttttttttt tttttttngg g         51
```

<210> SEQ ID NO 236
<211> LENGTH: 765
<212> TYPE: DNA
<213> ORGANISM: Homo sapiens
<220> FEATURE:
<221> NAME/KEY: misc_feature
<222> LOCATION: 540,555,590,593,670,685,708,711,714,733,
    760
<223> OTHER INFORMATION: n = A,T,C or G

<400> SEQUENCE: 236

```
ggagacctaa tgtttcatat gcagcgacaa agaaaacttc ctgaagaaca tgccagattt    60
tactctgcag aaatcagtct agcattaaat tatcttcatg agcgagggat aatttataga   120
gatttgaaac tggacaatgt attactggac tctgaaggcc acattaaact cactgactac   180
ggcatgtgta aggaaggatt acggccagga gatacaacca gcactttctg tggtactcct   240
aattacattg ctcctgaaat tttaaggaga gaagattatg gtttcagtgt tgactggtgg   300
gctcttggag tgctcatgtt tgagatgatg gcaggaaggt ctccatttga tattgttggg   360
agctccgata accctgacca gaacacagag gattatctct tccaagttat tttgaaaaaa   420
caaattcgca taccacgttc tctgtctgta aaagctgcaa gtgttctgaa gagttttctt   480
aataaggacc ctaaggaacg attgggttgt catcctcaaa caggatttgc tgatattcan   540
ggaccccgtc tttcnaaatg ttgattggga tatgatggac aaaaacaggn ggaccttcc    600 tttaaccaaa tatttctggg gaatttgggt ttggacacct tgattctca atttactaat    660 ggaacctggn ccagctcact cccanaatga cgaatgacct ttggggangg naanaattgg   720
gatcaagtct ggnaattttg gaaagggttt ttggaggtan tattc                  765
```

<210> SEQ ID NO 237
<211> LENGTH: 739
<212> TYPE: DNA
<213> ORGANISM: Homo sapiens
<220> FEATURE:
<221> NAME/KEY: misc_feature
<222> LOCATION: 460,478,485,509,527,529,554,573,575,578,
    603,607,609,616,621,643,651,674,675,689,
    696,729
<223> OTHER INFORMATION: n = A,T,C or G

<400> SEQUENCE: 237

```
ctctactgga agtttgaccc tgtgaaggtg aaggctctgg aaggcttccc ccgtctcgtg    60
ggtcctgact tctttggctg tgccgagcct gccaacactt tcctctgacc atggcttgga   120
tgccctcagg ggtgctgacc cctgccaggc cacgaatatc aggctagaga cccatggcca   180
tctttgtggc tgtgggcacc aggcatggga ctgagcccat gtctcctcag ggggatgggg   240
tggggtacaa ccaccatgac aactgccggg agggccacgc aggtcgtggt cacctgccag   300
cgactgtctc agactgggca gggaggcttt ggcatgactt aagaggaagg gcagtcttgg   360
gcccgctatg caggtcctgg caaacctggc tgcctgtctc catccctgtc cctcagggta   420
gcaccatggc aggactgggg gaactggagt gccttgctgn atccctgttg ggagggtnct   480
ttcangggct ggcactgaaa caaaggggnt ggggcccat gggcttnanc ctgggtgaac   540
aactgggctt gtanggcaag ggcactttct gangncangg cttgggaagg ggcctgcatc   600
tgnctgncnt tttggntgac naatcctggg aaatctggtt ttnccaaaat nccaggccaa   660
```

| aaaagtttac cagnncaaaa tggggggang ggggantttt ttttatggca aggaaaaaac | 720 |
| ccccagggnc ccttgggaa | 739 |

<210> SEQ ID NO 238
<211> LENGTH: 818
<212> TYPE: DNA
<213> ORGANISM: Homo sapiens
<220> FEATURE:
<221> NAME/KEY: misc_feature
<222> LOCATION: 311,378,441,442,494,505,520,525,540,545,
551,570,600,602,616,619,639,641,650,656,
671,684,686,697,701,724,726,732,738,749,
759,762,792,797
<223> OTHER INFORMATION: n = A,T,C or G

<400> SEQUENCE: 238

| cctggtgatc gcttcagtag agatgtctgg tgatatggtg aactgatcag gccctgacat | 60 |
| ggatgttccc ctagaggata tcacttctgt cctggagacc tcagtggtag caccactggg | 120 |
| cacttcagaa aggacagtgc ttccctctgt ggctgagctg gtcccttcag agccgctgga | 180 |
| ctccctcaat ccagggtca gggaggaagc tagctctgtc tgaatcctcc tagtctcaag | 240 |
| gaaggcagga gttgatgtga aacacttgt atccccatg gtggaggtgg tacacattgg | 300 |
| agatgagtca nctaggacag aggactgtga tttatatcca gagctggtgg ttgccacatt | 360 |
| ggtccctcct gtgtttgngg aaggatgcac ggcttctgta tgtgcagtgt ctttgtaagt | 420 |
| ggtaagtctc tcatgggagg nngggctcaa acttgaagat gaactggttc caggttcttg | 480 |
| tgcttgtacc caanatatct gtggntgtcc ccggccagan gggana aagt gaagtcacan | 540 |
| ggaangggaa naggggggga tatgtgctan gaatgtggtg gaaaacaagg atgaagtgan | 600 |
| gncccggcag gtaaanacna gcgggggaag gaatggaang ncttggtttn ttttcncaaa | 660 |
| agggaagggc ntaggccaat gacncnccct cccgganctt ntgcccattg ggaagggggc | 720 |
| attntnttgg gnggggg naa aatccctgna attaactana anaaagggg tttcccccc | 780 |
| aaaaaggggg gnggttnctt ggggttcaaa ataaaggg | 818 |

<210> SEQ ID NO 239
<211> LENGTH: 829
<212> TYPE: DNA
<213> ORGANISM: Homo sapiens
<220> FEATURE:
<221> NAME/KEY: misc_feature
<222> LOCATION: 207,379,714,717,736,762,770
<223> OTHER INFORMATION: n = A,T,C or G

<400> SEQUENCE: 239

| ctggtcttgg actcctgacc tcaagtgatc caccccctc agcctcccaa agtgctagga | 60 |
| ttacaggcat gagtcactgc gtcaggccaa aattctgtat tttcaattag agtcaaagcc | 120 |
| caaggatgtc tctaccatct tgtagcccct gccaatagcc tactcttgtc ttccagggtt | 180 |
| cctccaaatc tctctccaaa tatttgntat ctactcattc aatacccttc ttcaaccatc | 240 |
| ctcttgcttt ggaattgaca tgaaccaact aggcccgcct tattggtagg aattcatttg | 300 |
| ccctgcctgc cagcccccat agagacagaa ccattgccta gtgaaagaag attttaatga | 360 |
| cgtgatgaaa atattttana aagcaccttg aagattagta ttttatgta acttctgttg | 420 |
| gagagatgtc ttcaggagac tgaagtagaa gagcgactgt caaaatggaa agtcccagag | 480 |
| acatccaatt tatgtaaatc aacatcacct gaattcagaa tctcatccag atttcaacaa | 540 |
| agacttctga atgccaacca aagaagagga ctgaatttac agactctcac tctaacaata | 600 |

-continued

```
tatgctggtc aatttgaaaa acagaataaa attattttgg caagaaactg gattttaat     660 ggacatatat tggtttaaaa tggtaccaac ttttatttt tacccatttt tggnggnaaa      720
aaacccgggg aataanggga aaagcaaaag ggaaaatata tncaaatatn gggaaggttt    780
ttacctttaa ttttggttca ttaaacctaa cccagaaggc caaacaatt                829
```

<210> SEQ ID NO 240
<211> LENGTH: 177
<212> TYPE: DNA
<213> ORGANISM: Homo sapiens

<400> SEQUENCE: 240

```
ccttttttt ttttttaca tacaaaatgt tttaattgag aaaaaaattc aaaacagtca       60
cacatatcca ttatcatcat ggttctctga aatattttct tatacaaatg aaatatttaa    120
aatggaaaaa ttacattttt caaatctaat taactaatta tttttgtcct ggtcgac       177
```

<210> SEQ ID NO 241
<211> LENGTH: 591
<212> TYPE: DNA
<213> ORGANISM: Homo sapiens
<220> FEATURE:
<221> NAME/KEY: misc_feature
<222> LOCATION: 96,152,212,246,280,403,436,491,494,501,
      519,568,579
<223> OTHER INFORMATION: n = A,T,C or G

<400> SEQUENCE: 241

```
ccttttttt tttttcatt aaataatcca tcatcacatt agtacaatac aatttatat       60 tttttaaata tactatatat gttaaggata aggggngaag ttttcttcct tgtaatacc     120 tgttcaagag tttaatggat taggagatta gngttaacct tgaggataaa agtacaaatt   180
tgtctcatta ggacacttct accaagcatt tnttaaggct atagtttaac atttggtttc   240
aaaaanaaaa aaaaaggttt catttaaaaa ataatttagn gaattacatt ctttcataac    300 ttccaccta attagttaca aagataagtc taaagattct tagttttggg tactaattta    360
catttatatt taaagattaa ttttacttgg atcttaaaac aanaatttta tgttggaaaa   420
aagagaacta aatacntttg tataaaggct gtaaatgtcc catggcaaat gctctgtctc   480 aatatttct nccncaatta naaacagggc tctgcaaana gagacttggg ttgttcaggt    540
tcacctttcc cgaggaattg ggggctgnca tctgaaganc atagagaaac a            591
```

<210> SEQ ID NO 242
<211> LENGTH: 924
<212> TYPE: DNA
<213> ORGANISM: Homo sapiens
<220> FEATURE:
<221> NAME/KEY: misc_feature
<222> LOCATION: 102,104,591,592,595,596,640,641,650,683,
      706,708,720,734,735,757,759,779,791,804,
      806,825,837,905,912
<223> OTHER INFORMATION: n = A,T,C or G

<400> SEQUENCE: 242

```
aacctttcag gaaatccaa ggaaatacag aagcaaggca gcaccatagt cttcccagcc     60
aaggtggaag tgcctctggt tcctccagca attcccactg gngntatcat aactcaacag    120
tctgttgcaa tcagttgtag aaaggcacag agtgacagct ggaatgcaaa gaaatgtgca   180
caacccagag ctctgtcagc cttgccaaaa ctcaagtgcc cccatgggag ggtcttgcaa   240
catatgttct gttgagcaaa gaggttgcaa accaagcggt tattgcaata aacaccactt   300
gtgacaaaca aagtttgtaa gtttaaattt attttttaaa aatgcttgtc ttcctcacta   360
```

```
gacaatcaac tctatgaggg cagagactat gtcaccactg tcccaccagc ccctggcaca    420
cagtaggtac tcaataaata tatgttggga aggatggatg gaggtaatgg atggaaagat    480
ggatggaagg atgaatggag ggaatggatg tgacccagct gaagtgtgag taggaacatt    540
ctcttattat gggtggagga agagagagg agattgagaa aaataagata nnatnncatt    600
ggatgaagcc atcattttt gggggttcc gaaaaaagtn ngggatttgn aaatttaagg    660
gaacttaaat aaaaatcctt aanaaaaaaa attttttaa cccctncntt tttccaaaan    720 gggccccca aaanncccca acccaacttt tttttttncnt tatttccacc ttttttggna    780 aaaaccccc naaaaaaaaa aggntnaaaa attacccctt ttttncccc aaacccnttt    840 ttggccttt tgccttgggg aagggaaaa aaggctttt aaataaaaaa aatggccaat    900
tcttnttaaa anttggccaa tggg                                          924

<210> SEQ ID NO 243
<211> LENGTH: 278
<212> TYPE: DNA
<213> ORGANISM: Homo sapiens
<220> FEATURE:
<221> NAME/KEY: misc_feature
<222> LOCATION: 211,276,277
<223> OTHER INFORMATION: n = A,T,C or G

<400> SEQUENCE: 243 ccttttttt ttttttaag atttaactct gaatacaaat gtattttttt cttcttctct    60
ccctacatat attctaaacc ttctaaagtt tttttatttt tttaaggatc actttatcat    120
aaaataaaat atccttttca tataataaat tacctaataa aaagtctttt tttttcatat    180
tagcccaggt tctttgctac atttatatgg naataaacgc ctttattaaa atagaatatt    240
aaattataaa gaactgcttt ttttttttt ttttgnna                            278

<210> SEQ ID NO 244
<211> LENGTH: 3072
<212> TYPE: DNA
<213> ORGANISM: Homo sapiens

<400> SEQUENCE: 244
gcgcagacgc cccagccccc caccgccccc aaagggcga gcgacgccaa gctctgcgct    60
ctctacaaag aggccgagct gcgcctgaag ggcagcagca acaccacgga gtgtgttccc    120
gtgcccacct ccgagcacgt ggccgagatc gtgggcaggc aaggctgcaa gattaaggcc    180
ttgagggcca agaccaacac ctacatcaag acaccggtga ggggcgagga accagtgttc    240
atggtgacag gcgacggga ggacgtggcc acagcccggc gggaaatcat ctcagcagcg    300
gagcacttct ccatgatccg tgcctcccgc aacaagtcag gcgccgcctt tggtgtggct    360
cctgctctgc ccggccaggt gaccatccgt gtgcgggtgc cctaccgcgt ggtgggctg    420 gtggtgggcc ccaaaggggc aaccatcaag cgcatccagc agcaaaccaa cacatacatt    480
atcacaccaa gccgtgaccg cgaccccgtg ttcgagatca cgggtgcccc aggcaacgtg    540
gagcgtgcgc gcgaggagat cgagacgcac atcgcggtgc gcactggcaa gatcctcgag    600
tacaacaatg aaaacgactt cctggcgggg agccccgacg cagcaatcga tagccgctac    660
tccgacgcct ggcgggtgca ccagcccggc tgcaagcccc tctccacctt ccggcagaac    720
agcctgggct gcatcggcga gtgcggagtg gactctggct ttgaggcccc acgcctgggt    780
gagcagggcg gggactttgg ctacggcggg tacctctttc cgggctatgg cgtgggcaag    840
caggatgtgt actacggcgt ggccgagact agccccccgc tgtgggcggg ccaggagaac    900
```

```
gccacgccca cctccgtgct cttctcctct gcctcctcct cctcctctc ttccgccaag      960 gcccgcgctg ggccccgggg cgcacaccgc tccctgcca cttccgcggg acccgagctg     1020
gccggactcc cgaggcgccc cccgggagag ccgctccagg gcttctctaa acttggtggg     1080
ggcggcctgc ggagccccgg cggcgggcgg gattgcatgg tctgctttga gagcgaagtg     1140
actgccgccc ttgtgccctg cggacacaac ctgttctgca tggagtgtgc agtacgcatc     1200
tgcgagagga cggacccaga gtgtcccgtc tgccacatca cagccacgca agccatccga     1260
atattctcct aagcccgtg ccccatgcct ccggggccca ctccactggg cccaccctgg      1320
acctgttttc cactaaagcc ttttggaaag cggtgatttg aggggcaagg tgcttagaga     1380
tactcgctcg ctggggaagg ggggagggag gcagtggtgg ctggagggtg cgccactttc     1440
agagcctctg gtcaccctgt cctggaaaga ttgggagggg gccagactga aaattttact     1500
agagttacaa ctctgatacc tcaacacacc cttaaatctg gaagcagcta agagaaactt     1560
ttgttttgcc agaggtggcc actaaggcat tctgacgccc tctgcccacc tccccgctg     1620 tgtgtcactc caccccttct tccgaggagg gggtgggtaa aagggagagg gagaattacc    1680
acctgtatct agaggtgctc tttgcaatcc ctaagccctc tggtcctgac ctccgacctc     1740
ccagctctgt cttgttcctt gtctttgtct ttcttcccctt ccccctgccc ctgcccctac     1800
cagcccagct ttggggacac catccttctg gggagaagta gggggaggaa tatttggatg     1860
gtccctccat tcctcttcag gcatctggag gccctctccc ccactcctcc aaagaaacat     1920
ctcaaattat tgatggaatg tatccccatt tcagtgaaaa atgtgaggag gggactaata    1980
ctggggtaaa gggtcaaacc cccaccttca tcactatggg cattatattt agggagtagt     2040
tcttgggctg gattttctgg ttgtggaagt ggggcgcca gagtagtgtg tctgctattt      2100
aaaggagcag gaaagggcgt gaggcaggag gagagactgg tggagggaag agctgctcct    2160
cccatgcagt gcccgactcc ctgcacccct ctcaacctga cctgaacctt tattgaatcc    2220
ttattagctt gaatccttat tagcttgaat cctccatgca aatcatggag tctgtgtccc    2280
acctgatgtg gttgaggaga agccaggtct tcaaagaggg gtcagcctgg ggcaaagcag    2340
gactgggggg aggtgggcag cagggcctat tctgagaatc acatattgtt acaggccttg    2400
cacccccttt gctgcttccc tcctgctcat ttggggctgc caccagctct ccaccctcct    2460
ggttccgctg gccgggccaa gagaggatgg agggatggga gtcccaggag atccttgtaa    2520
atagtggggt gggactgttc tgagtgatca cccgagcact taaagctcca gagtcccatt     2580
cttcctggat ggagcaggtg gaggtgcaga ggggatttcc tcctctcctt cctcctgtcg    2640
agaattaaca cctctccaca gccttcccct ccagaacacc agccaggag gggtgggaa       2700 ggaggtcaca gccaagaaaa ctgccctgtg acgacttccc tccttcccgc ctatgtgagc    2760
catcctgaga tgtctgtaca atagaaacca aaccaaatgg gcaccctcgg ttgccggggg    2820
gcaggtgggg aggggggtgg gaagaaggga tgtctgtctg tcgtccccct cccctctcc    2880 actctttacc cacaaaggca gaagactgtt acactagggg gctcagcaaa ttcaatccca     2940
cccttaccaa ttgagccaaa cctagaaaca aacacaaaac acgaatagtg agagacaaaa    3000
tagaggagag aaagagagca tgagagggag cgagacaggc gaccaacaca gaggagagaa    3060
aacaaaaata gc                                                        3072

<210> SEQ ID NO 245
<211> LENGTH: 2323
<212> TYPE: DNA
<213> ORGANISM: Homo sapiens
```

<400> SEQUENCE: 245

```
ggactctggc tttgaggccc cacgcctggg tgagcagggc ggggactttg gctacggcgg      60
gtacctcttt ccgggctatg gcgtgggcaa gcaggatgtg tactacgcgc tggccgagac     120
tagcccccg ctgtgggcgg gccaggagaa cgccacgccc acctccgtgc tcttctcctc     180
ctcctcctcc tcctcctctt ccgccaaggc ccgcgctggg ccccggggcg cacaccgctc     240
ccctgccact tccgcgggac ccgagctggc cggactcccg aggcgccccc cgggagagcc     300
gctccggggc ttctctaaac ttggtggggg cggcctgcgg agccccgcag ccggcgggcg     360
ggattgcatg gtctgctttg agagcgaagt gactgccgcc cttgtgccct gcggacacaa     420
cctgttctgc atggagtgtg cagtacgcat ctgcgagagg acggacccag agtgtcccgt     480
ctgccacatc acagccacgc aagccatccg aatattctcc taagcccgt gccccatgcc     540
tccgggccc actccactgg gcccaccctg gacctgtttt ccactaaagc cttttggaaa     600
gcggtgattt gaggggcaag gtgcttagag atactcgctc gctggggaag gggggaggga     660
ggcagtggtg gctggagggt gcgccacttt cagagcctct ggtcaccctg tcctggaaag     720
attgggaggg ggccagactg aaaattttac tagagttaca actctgatac ctcaacacac     780
ccttaaatct ggaagcagct aagagaaact tttgttttgc cagaggtggc cactaaggca     840
ttctgacgcc ctctgcccac ctcccccgct gtgtgtcact ccaccccttc ttccgaggag     900
gggtgggta aagggagag ggagaattac cacctgtatc tagaggtgct cttttgcaatc     960
cctaagcccc ctggtcctga cctccgacct cccagctctg tcttgttcct tgtctttgtc    1020
tttcttccct tccccctgcc cctgccccta ccagcccagc tttggggaca ccatccttct    1080
ggggagaagt aggggagga atatttggat ggtccctcca ttcctcttca ggcatctgga    1140
ggccctctcc cccactcctc caaagaaaca tctcaaatta ttgatggaat gtatccccat    1200
tctcagtgaa aatgtgagga ggggactaat actggggtaa agggtcaaac ccccaccttc    1260
atcactatgg gcattatatt tagggagtag ttcttgggct ggattttctg gttgtggaag    1320
tgggggcgcc agagtagtgt gtctgctatt taaaggagca ggaaagggcg tgaggcagga    1380
ggagagactg gtggagggaa gagctgctcc tcccatgcag tgcccgactc cctgcacccc    1440
tctcaacctg acctgaacct ttattgaatc cttattagct tgaatcctta ttagcttgaa    1500
tcctccatgc aaatcatgga gtctgtgtcc cacctgatgt ggttgaggag aagccaggtc    1560
ttcaaagagg ggtcagcctg ggcaaagca ggactggggg gaggtgggca gcagggccta    1620
ttctgagaat cacatattgt tacaggcctt gcacccccctt tgctgcttcc ctcctgctca    1680
tttgggctg ccaccagctc tccacccctcc tggttccgct ggcgggcca agagaggatg    1740
gagggatggg agtcccagga gatccttgta aatagtgggg tgggactgtt ctgagtgatc    1800
acccgagcac ttaaagctcc agagtccat tcttcctgga tggagcaggt ggaggtgcag    1860
agggatttc ctcctctcct tcctcctgtc gagaattaac acctctccac agccttcccc    1920
tccagaacac cagccaggga ggggtgggga aggaggtcac agccaagaaa actgccctgt    1980
gacgacttcc ctccttcccg cctatgtgag ccatcctgag atgtctgtac aatagaaacc    2040
aaaccaaatg ggcaccctcg gttgccgggg ggcaggtggg gaggggggtg ggaagaaggg    2100
atgtctgtct gtcgtccccc tccccctctc cactctttac ccacaaaggc agaagactgt    2160
tacactaggg ggctcagcaa attcaatccc accccttacca attgagccaa acctagaaac    2220
aaacacaaaa cacgaatagt gagagacaaa atagaggaga gaaagagagc atgagaggga    2280
gcgagacagg cgaccaacac agaggagaga aaacaaaaat agc                       2323
```

<210> SEQ ID NO 246
<211> LENGTH: 5882
<212> TYPE: DNA
<213> ORGANISM: Homo sapiens
<220> FEATURE:
<221> NAME/KEY: misc_feature
<222> LOCATION: 1100,1975,4288,5859,5862,5863,5868
<223> OTHER INFORMATION: n = A,T,C or G

<400> SEQUENCE: 246

| | | | | | |
|---|---|---|---|---|---|
| gcgcagacgc | cccagccccc | caccgccccc | aaagggggcga | gcgacgccaa | gctctgcgct | 60 |
| ctctacaaag | aggccgagct | gcgcctgaag | ggcagcagca | acaccacgga | gtgtgttccc | 120 |
| gtgcccacct | ccgagcacgt | ggccgagatc | gtgggcaggc | aaggctgcaa | gattaaggcc | 180 |
| ttgagggcca | agaccaacac | ctacatcaag | acaccggtga | ggggcgagga | accagtgttc | 240 |
| atggtgacag | gcgacggga | ggacgtggcc | acagcccggc | gggaaatcat | ctcagcagcg | 300 |
| gagcacttct | ccatgatccg | tgcctcccgc | aacaagtcag | gcgccgcctt | tggtgtggct | 360 |
| cctgctctgc | ccggccaggt | gaccatccgt | gtgcgggtgc | cctaccgcgt | ggtgggctg | 420 |
| gtggtgggcc | ccaaaggggc | aaccatcaag | cgcatccagc | agcaaaccaa | cacatacatt | 480 |
| atcacaccaa | gccgtgaccg | cgaccccgtg | ttcgagatca | cgggtgcccc | aggcaacgtg | 540 |
| gagcgtgcgc | gcgaggagat | cgagacgcac | atcgcggtgc | gcactggcaa | gatcctcgag | 600 |
| tacaacaatg | aaaacgactt | cctggcgggg | agccccgacg | cagcaatcga | tagccgctac | 660 |
| tccgacgcct | ggcgggtgca | ccagcccggc | tgcaagcccc | tctccacctt | ccggcagaac | 720 |
| agcctgggct | gcatcggcga | gtgcggagtg | gactctggct | ttgaggcccc | acgcctgggt | 780 |
| gagcagggcg | gggactttgg | ctacggcggg | tacctctttc | cgggctatgg | cgtgggcaag | 840 |
| caggatgtgt | actacggcgt | ggccgagact | agccccccgc | tgtgggcggg | ccaggagaac | 900 |
| gccacgccca | cctccgtgct | cttctcctct | gcctcctcct | cctcctcctc | ttccgccaag | 960 |
| gcccgcgctg | ggccccgggc | cgcacaccgc | tcccctgcca | cttccgcggg | acccgagctg | 1020 |
| gccggactcc | cgaggcgccc | ccggggagag | ccgctccagg | gcttctctaa | acttggtggg | 1080 |
| ggcggcctgc | ggagccccgs | cggcgggcgg | gattgcatgg | tctgctttga | gagcgaagtg | 1140 |
| actgccgccc | ttgtgccctg | cggacacaac | ctgttctgca | tggagtgtgc | agtacgcatc | 1200 |
| tgcgagagga | cggacccaga | gtgtcccgtc | tgccacatca | cagccacgca | agccatccga | 1260 |
| atattctcct | aagcccgtg | ccccatgcct | ccggggccca | ctccactggg | cccaccctgg | 1320 |
| acctgttttc | cactaaagcc | ttttggaaag | cggtgatttg | aggggcaagg | tgcttagaga | 1380 |
| tactcgctcg | ctggggaagg | ggggagggag | gcagtggtgg | ctggagggtg | cgccactttc | 1440 |
| agagcctctg | gtcaccctgt | cctggaaaga | ttggagggg | gccagactga | aaattttact | 1500 |
| agagttacaa | ctctgatacc | tcaacacacc | cttaaatctg | gaagcagcta | agagaaactt | 1560 |
| ttgttttgcc | agaggtggcc | actaaggcat | tctgacgccc | tctgcccacc | tccccgctg | 1620 |
| tgtgtcactc | caccccttct | tccgaggagg | gggtgggtaa | aagggagagg | gagaattacc | 1680 |
| acctgtatct | agaggtgctc | tttgcaatcc | ctaagccctc | tggtcctgac | ctccgacctc | 1740 |
| ctaacatgac | cctttacctc | ccaccccacc | cccatatcct | gtttgggaaa | ctgtcaccag | 1800 |
| tttccagcag | tgtaagggag | ttggagtcct | atcagaagtt | gcatagatct | tctaggggtt | 1860 |
| ggggagagaa | gcatgtcaat | cgtttctgtg | gctgaaaggc | tcagaagcca | tctgtcccca | 1920 |
| caaagctggg | ctagaggaat | ctggagagga | gtcctcctct | ctgcccctgt | ccccygcagt | 1980 |
| gtttcccttc | actctctccg | cctatcttcc | cttcctttgg | gatcttccct | ttcctcaact | 2040 |

```
ctttcctttc cctccagctc tttgctttgc tttcttttgg tggctgtcac tcccagctct    2100
gtcttgttcc ttgtctttgt cttcttccc ttccccctgc ccctgcccct accagcccag     2160
ctttggggac accatccttc tggggagaag taggggagg aatatttgga tggtccctcc     2220
attcctcttc aggcatctgg aggccctctc ccccactcct ccaaagaaac atctcaaatt    2280
attgatggaa tgtatcccca ttctcagtga aaatgtgagg aggggactaa tactgggta     2340
aagggtcaaa cccccacctt catcactatg ggcattatat ttagggagta gttcttgggc    2400
tggattttct ggttgtggaa gtggggggcgc cagagtagtg tgtctgctat ttaaaggagc   2460
aggaaagggc gtgaggcagg aggagagact ggtggaggga agagctgctc ctcccatgca    2520
gtgcccgact ccctgcaccc ctctcaacct gacctgaacc tttattgaat ccttattagc    2580
ttgaatcctt attagcttga atcctccatg caaatcatgg agtctgtgtc ccacctgatg    2640
tggttgagga gaagccaggt cttcaaagag gggtcagcct ggggcaaagc aggactgggg    2700
ggaggtgggc agcagggcct attctgagaa tcacatattg ttacaggcct tgcacccct    2760
ttgctgcttc cctcctgctc atttggggct gccaccagct ctccaccctc ctggttccgc   2820
tggccgggcc aagagaggat ggagggatgg gagtcccagg agatccttgt aaatagtggg   2880
gtgggactgt tctgagtgat cacccgagca cttaaagctc cagagtccca ttcttcctgg   2940
atggagcagg tggaggtgca gagggattt cctcctctcc ttcctcctgt cgagaattaa    3000
cacctctcca cagccttccc ctccagaaca ccagccaggg aggggtgggg aaggaggtca   3060
cagccaagaa aactgccctg tgacgacttc cctccttccc gcctatgtga gccatcctga   3120
gatgtctgta caatagaaac caaccaaat gggcaccctc ggttgccggg gggcaggtgg    3180
ggagggggt gggaagaagg gatgtctgtc tgtcgtcccc ctcccctct ccactcttta    3240
cccacaaagg cagaagactg ttacactagg gggctcagca aattcaatcc caccttacc    3300
aattgagcca aacctagaaa caaacacaaa acacgaatag tgagagacaa aatagaggag   3360
agaaagagag catgagaggg agcgagacag gcgaccaaca cagaggagag aaaacaaaaa   3420
tagcaaaaaa aaaaaaaaaa aagcagttct ttataattta atattctatt ttaataaagg   3480
cgtttattac catataaatg tagcaaagaa cctgggctaa tatgaaaaaa aaagactttt   3540
tattaggtaa tttattatat gaaaaggata ttttattttta tgataaagtg atccttaaaa   3600
aaataaaaaa actttagaag gtttagaata tatgtaggga gagaagaaga aaaaaataca   3660
tttgtattca gagttaaatc ttaaaaaaaa aaagtgtttt taatatatgt ttgggtttac   3720
gttgctttt tccccactt tttttttggg gaggaatgtc atttgctttt cttggggag     3780
catcccgggg gtgaatggtg gagagaggag ctggggaac ccggtccctc ctgggaccct    3840
tccagtagat tggatttcac tccatggact cctcctcccc tctcccctc ccctcaggg    3900
gagccggcag agccaaacaa agaaagggat taacaagaaa ggaagaagct gtaggactaa   3960
ggactgagga tcctgggtg tcccccacca ctttccctg ccctgtcgca ggggcaagtg    4020
aggagggga atccagaatt aaggcctagc aggcctatag gaaccctcag agatgtgtga   4080
gatttaagag atctagattt tttttttaacc aaaaacaaga gagaagaga agaaaaagag   4140
aaaccgaggg gtttaaaaga aaagaatact acaaaataat aattattaat aataataatt   4200
caaatttatt tcatataatc ctagagagag aaagaaacaa ttactagtta cttagtagac   4260
aatattaaga tagcttaaag tttagtasca ttgagggccc ctgggtccag tagaatgtat   4320
aaaagttgta aggaaaagat aaatagagga gggaagtggc tgagtccacc ctgagttgcc   4380
caatcttcag ataccagggt tggatcaggt tgctagttta agattgggag cttccagtct   4440
```

```
gctgggttg attctgagaa tccttggatt tttaaattgt aggacaaaga aatgaggggt    4500
tcatttccca gggtcttgga aaggatgcac actgatcatc tcaataagac aggggctggg    4560 ttggggggcag cagaggaggc caagcacatt cacctgcacc cctagtacct gggcagccca    4620
tactccaatg tggtatgtcc cctcctgggg ctcccagctc aaaccctccc atgcctgctt    4680
cccccaggcc taactgagga agtccttctt gaagtgtgac ctcggtccac ttctctacag    4740
attgatttaa gagcctggga agtcattcca caaacagaca cacatgcaca cacgcttctc    4800
accttcagag cttcaagagc actgaggcga tcagtcccct accctgttc ccatccagct    4860 ttccacttag ctttgacctc catggcagca gtagcagtaa caatctcagt aattgttctt    4920
taaagctgac tcgttcttca cctacttgca aagtgctttc ttgtctcata aaagttagat    4980
tccaagaagg acttcccacg gagtggagtg gaaacactgt ccttgaaggc ctgggagaaa    5040
ggcatcccca tgggcacaga ggctggggaa aggcacaggg actttgggtg accctaaccc    5100
tgaccctctg ctccagttca cctccatcta tatgtgttca ggtaggggtc atctactgta    5160
ccctggcctg ggaacacatt gccctcccca cacaaaactg gagggcttgg cttctgcgtg    5220
tgagaaatca acattttaa agcacttgcc ttctaccaac cccagcttgc aatcactggg    5280 ccttccctc ctatccaagg ggttggaggg gccccttggc tctccttttg gcaggaggag    5340
cctgcttcat tacaccaatg actctgccat cccctccct ggcctagac cccaaacaca    5400 tctccctcta cccaatttac tcttctcgcc ccacctaggg acagattccc cctgctcttt    5460
ttgtcctaga aaccccgcta gtttgggatg gtagcgtctg gggtggggag ggcttccct    5520 tccccactcg agggtgcggg tggggaaggg ggggtgggtg gagacagccc tggggcaggg    5580
aggatggtct ctcccactgta gaaagtagag taggattgtg gtcagactta atttgaggca    5640
tctagtgaag acacgtacaa atccaccaag gaaaaagatt tcaaaagcaa aataaaagcg    5700
ggaaataaaa cagacccaag aataatcaag tcaaagtgat gttgcacaaa atgcagagaa    5760
accaagaagg gggagggtta atgtattaaa tgtgctatta agaacttaat tttattaaaa    5820
gtactattac ttaaaaaaaa aaaaaaaaaa aaaaaaawa arwagtcrta tcgaatcgat    5880
gt                                                                  5882
```

<210> SEQ ID NO 247
<211> LENGTH: 343
<212> TYPE: PRT
<213> ORGANISM: Homo sapiens

<400> SEQUENCE: 247

```
Met Val Thr Gly Arg Arg Glu Asp Val Ala Thr Ala Arg Arg Glu Ile
                 5                  10                  15

Ile Ser Ala Ala Glu His Phe Ser Met Ile Arg Ala Ser Arg Asn Lys
             20                  25                  30

Ser Gly Ala Ala Phe Gly Val Ala Pro Ala Leu Pro Gly Gln Val Thr
         35                  40                  45

Ile Arg Val Arg Val Pro Tyr Arg Val Gly Leu Val Val Gly Pro
     50                  55                  60

Lys Gly Ala Thr Ile Lys Arg Ile Gln Gln Gln Thr Asn Thr Tyr Ile
 65                  70                  75                  80

Ile Thr Pro Ser Arg Asp Arg Asp Pro Val Phe Glu Ile Thr Gly Ala
                 85                  90                  95

Pro Gly Asn Val Glu Arg Ala Arg Glu Glu Ile Glu Thr His Ile Ala
            100                 105                 110
```

Val Arg Thr Gly Lys Ile Leu Glu Tyr Asn Asn Glu Asn Asp Phe Leu
            115                 120                 125

Ala Gly Ser Pro Asp Ala Ala Ile Asp Ser Arg Tyr Ser Asp Ala Trp
        130                 135                 140

Arg Val His Gln Pro Gly Cys Lys Pro Leu Ser Thr Phe Arg Gln Asn
145                 150                 155                 160

Ser Leu Gly Cys Ile Gly Glu Cys Gly Val Asp Ser Gly Phe Glu Ala
                165                 170                 175

Pro Arg Leu Gly Glu Gln Gly Asp Phe Gly Tyr Gly Gly Tyr Leu
            180                 185                 190

Phe Pro Gly Tyr Gly Val Gly Lys Gln Asp Val Tyr Tyr Gly Val Ala
        195                 200                 205

Glu Thr Ser Pro Pro Leu Trp Ala Gly Gln Glu Asn Ala Thr Pro Thr
210                 215                 220

Ser Val Leu Phe Ser Ser Ala Ser Ser Ser Ser Ser Ser Ala Lys
225                 230                 235                 240

Ala Arg Ala Gly Pro Pro Gly Ala His Arg Ser Pro Ala Thr Ser Ala
                245                 250                 255

Gly Pro Glu Leu Ala Gly Leu Pro Arg Arg Pro Pro Gly Glu Pro Leu
            260                 265                 270

Gln Gly Phe Ser Lys Leu Gly Gly Gly Leu Arg Ser Pro Gly Gly
        275                 280                 285

Gly Arg Asp Cys Met Val Cys Phe Glu Ser Glu Val Thr Ala Ala Leu
290                 295                 300

Val Pro Cys Gly His Asn Leu Phe Cys Met Glu Cys Ala Val Arg Ile
305                 310                 315                 320

Cys Glu Arg Thr Asp Pro Glu Cys Pro Val Cys His Ile Thr Ala Thr
                325                 330                 335

Gln Ala Ile Arg Ile Phe Ser
            340

<210> SEQ ID NO 248
<211> LENGTH: 343
<212> TYPE: PRT
<213> ORGANISM: Homo sapiens

<400> SEQUENCE: 248

Met Val Thr Gly Arg Arg Glu Asp Val Ala Thr Ala Arg Arg Glu Ile
                5                   10                  15

Ile Ser Ala Ala Glu His Phe Ser Met Ile Arg Ala Ser Arg Asn Lys
            20                  25                  30

Ser Gly Ala Ala Phe Gly Val Ala Pro Ala Leu Pro Gly Gln Val Thr
        35                  40                  45

Ile Arg Val Arg Val Pro Tyr Arg Val Val Gly Leu Val Val Gly Pro
    50                  55                  60

Lys Gly Ala Thr Ile Lys Arg Ile Gln Gln Gln Thr Asn Thr Tyr Ile
65                  70                  75                  80

Ile Thr Pro Ser Arg Asp Arg Asp Pro Val Phe Glu Ile Thr Gly Ala
                85                  90                  95

Pro Gly Asn Val Glu Arg Ala Arg Glu Glu Ile Glu Thr His Ile Ala
            100                 105                 110

Val Arg Thr Gly Lys Ile Leu Glu Tyr Asn Asn Glu Asn Asp Phe Leu
        115                 120                 125

Ala Gly Ser Pro Asp Ala Ala Ile Asp Ser Arg Tyr Ser Asp Ala Trp
    130                 135                 140

```
Arg Val His Gln Pro Gly Cys Lys Pro Leu Ser Thr Phe Arg Gln Asn
145                 150                 155                 160

Ser Leu Gly Cys Ile Gly Glu Cys Gly Val Asp Ser Gly Phe Glu Ala
            165                 170                 175

Pro Arg Leu Gly Glu Gln Gly Gly Asp Phe Gly Tyr Gly Gly Tyr Leu
            180                 185                 190

Phe Pro Gly Tyr Gly Val Gly Lys Gln Asp Val Tyr Gly Val Ala
        195                 200                 205

Glu Thr Ser Pro Pro Leu Trp Ala Gly Gln Glu Asn Ala Thr Pro Thr
210                 215                 220

Ser Val Leu Phe Ser Ser Ala Ser Ser Ser Ser Ser Ser Ala Lys
225                 230                 235                 240

Ala Arg Ala Gly Pro Pro Gly Ala His Arg Ser Pro Ala Thr Ser Ala
            245                 250                 255

Gly Pro Glu Leu Ala Gly Leu Pro Arg Arg Pro Pro Gly Glu Pro Leu
            260                 265                 270

Gln Gly Phe Ser Lys Leu Gly Gly Gly Leu Arg Ser Pro Gly Gly
            275                 280                 285

Gly Arg Asp Cys Met Val Cys Phe Glu Ser Glu Val Thr Ala Ala Leu
290                 295                 300

Val Pro Cys Gly His Asn Leu Phe Cys Met Glu Cys Ala Val Arg Ile
305                 310                 315                 320

Cys Glu Arg Thr Asp Pro Glu Cys Pro Val Cys His Ile Thr Ala Thr
                325                 330                 335

Gln Ala Ile Arg Ile Phe Ser
            340

<210> SEQ ID NO 249
<211> LENGTH: 343
<212> TYPE: PRT
<213> ORGANISM: Homo sapiens
<220> FEATURE:
<221> NAME/KEY: variant
<222> LOCATION: 287
<223> OTHER INFORMATION: Xaa = Any amino acid

<400> SEQUENCE: 249

Met Val Thr Gly Arg Arg Glu Asp Val Ala Thr Ala Arg Arg Glu Ile
                5                   10                  15

Ile Ser Ala Ala Glu His Phe Ser Met Ile Arg Ala Ser Arg Asn Lys
            20                  25                  30

Ser Gly Ala Ala Phe Gly Val Ala Pro Ala Leu Pro Gly Gln Val Thr
        35                  40                  45

Ile Arg Val Arg Val Pro Tyr Arg Val Val Gly Leu Val Val Gly Pro
    50                  55                  60

Lys Gly Ala Thr Ile Lys Arg Ile Gln Gln Gln Thr Asn Thr Tyr Ile
65                  70                  75                  80

Ile Thr Pro Ser Arg Asp Arg Asp Pro Val Phe Glu Ile Thr Gly Ala
                85                  90                  95

Pro Gly Asn Val Glu Arg Ala Arg Glu Glu Ile Glu Thr His Ile Ala
            100                 105                 110

Val Arg Thr Gly Lys Ile Leu Glu Tyr Asn Asn Glu Asn Asp Phe Leu
        115                 120                 125

Ala Gly Ser Pro Asp Ala Ala Ile Asp Ser Arg Tyr Ser Asp Ala Trp
    130                 135                 140

Arg Val His Gln Pro Gly Cys Lys Pro Leu Ser Thr Phe Arg Gln Asn
145                 150                 155                 160
```

```
Ser Leu Gly Cys Ile Gly Glu Cys Val Asp Ser Gly Phe Glu Ala
            165                 170                 175
Pro Arg Leu Gly Glu Gln Gly Asp Phe Gly Tyr Gly Gly Tyr Leu
        180                 185                 190
Phe Pro Gly Tyr Gly Val Gly Lys Gln Asp Val Tyr Tyr Gly Val Ala
    195                 200                 205
Glu Thr Ser Pro Pro Leu Trp Ala Gly Gln Gly Asn Ala Thr Pro Thr
210                 215                 220
Ser Val Leu Phe Ser Ser Ala Ser Ser Ser Ser Ser Ser Ala Lys
225                 230                 235                 240
Ala Arg Ala Gly Pro Pro Gly Ala His Arg Ser Pro Ala Thr Ser Ala
            245                 250                 255
Gly Pro Glu Leu Ala Gly Leu Pro Arg Arg Pro Gly Glu Pro Leu
        260                 265                 270
Gln Gly Phe Ser Lys Leu Gly Gly Gly Leu Arg Ser Pro Xaa Gly
        275                 280                 285
Gly Arg Asp Cys Met Val Cys Phe Glu Ser Glu Val Thr Ala Ala Leu
    290                 295                 300
Val Pro Cys Gly His Asn Leu Phe Cys Met Glu Cys Ala Val Arg Ile
305                 310                 315                 320
Cys Glu Arg Thr Asp Pro Glu Cys Pro Val Cys His Ile Thr Ala Thr
            325                 330                 335
Gln Ala Ile Arg Ile Phe Ser
            340

<210> SEQ ID NO 250
<211> LENGTH: 7993
<212> TYPE: DNA
<213> ORGANISM: Homo sapiens

<400> SEQUENCE: 250
aaaaatgttt tcctttatat ttctgaggtg aaattcttcc ataggcattt caggaggttt      60
tttgtcaaac attttaaaag caaaattgat accatgtttc tataaaatac gatatgcgaa     120
atgatgccta ttgctatttg ctactgggct ggaagttagg aaatagtgac ggaaaaaccc     180
caaatgcata cagagatcat gagtacagcc agtgatgcca gtgatgtatt acgaagatta     240
caaaaaaggc cacaaaagtt caatgctaat cccttctggg tcgaacacag agtgacacat     300
tcggcagaca attatatttt acttatgtaa cgaataagtc atatttttct gtactgggca     360
tttttagagg aacatataaa gaaatggata gtgtcttagg ggtctcattt tctaatttag     420
aaatgttttc actcccatgt gaaagatttt gctaatatat aacagacaat ctaacttggg     480
gcatcctatt aaaataatct atttcccata acttcaacct tttaaaaaa taaagtcagt      540
gggaatttct aatttccctg tgggttttat ctatatgcat ttttaggtt tttttttcc      600
ttatcatata ccttccagat tttatgttta aataaataaa tgatatttca agataaagtt     660
agtctataaa gggacactaa atcagcctac agatgtcaat ctctaggttt aactacagag     720
atagttccac ataaatgcca aaaagaagtg gttttgatgt caatctttat gaaaatggtt     780
ttatttaacc attgtatcaa gtctaactat acttgggcag atttgagctt taaaaataaa     840
gctatgtatt tcgttttttaa aaatgtgctt ctctgtttct tcatttactt acaactgtgg     900
aacagaatca cgagtttgtg gacgaacaag tctttgaaga agctgcatg gaagttgcaa      960
ctgttaatcg tccttcaagt cacagtcctt cactgtcttc acaacaagga gtcaccagca    1020
cctgctgttc acgacgacac aaaaaaactt ttcgcatccc aaatgccaat gtatcaggaa    1080
```

```
gccatcaagg tagtatacaa gaactcagca cgattcagat cagatgtgtg gagagaacac    1140
ctctgtctaa caggtacctg agattaatct gtgttgtcta cacacctgtg ctggttccca    1200
gggtgtgtct tctgcactca tgttgtcact tacatggcat ctaaatccct agctcctatg    1260
gttcaggaag agacaaaaat ggtagcgtaa caagtaggaa aatggttctg cttgcatatc    1320
cattaagggt taaaaatagt ggttatatca gtattaaaag agtcgaaaga agaagagatg    1380
attgagtgca cacaaatgtg ttttttctctc ttctgttcca caacctttttc ttatttgggc    1440 aaggactttt atactcagga gtctcttata tattcaatag tctgaaatga tggtggacac    1500
tactaaaaga gtcaaatgaa attgagatca acatggctaa aaattattga acagcatgta    1560
aaaatataca aacacactgt ctgtaacagt aaaaatgaaa actttgccta cataagtcat    1620
ttctatcaat atataatttt gatcagaaag gtattttttgg ccatatcaaa cacaaaatca    1680
acataataca aaaataagt gaagtactaa aattgtttgc ctctggttag tttatgaaca    1740
aattaagtaa aacttccata ttgatatatt tcctttgctt ttccttattc actgttttta    1800
ccacaaatgt gtaaaaataa aaagttgtac atttaaacaa tatatgtcat taaaaatcag    1860
tttctgccaa ataatttta ttctgttttc aaattgaaca gcatatattg ttagagtgag    1920
agtctgtaaa ttcagtcctc ttctttgttg gcattcagaa gtctttgttg aaatctggat    1980
gagattctga attcaggtga tgttgattta cataaattgg atgtctctgg gactagaaaa    2040
ttaaaattag gagccataag acttctatct tcaagatatt ttagctttgc agttttatat    2100
cctttataaa gtgaagtcga caatggaaaa ttatctagca agaaaatctt aggacataaa    2160
catcttaatt atgttttcca tgaaaataaa ataatcagtt tcaagcttct gtgtatatcc    2220
ttctctctca tttcccttttt atcccctttcc ccacatagag tatacaattc atccaataat    2280
accatttggg agcttgaagt gttagatagt aatagataat ttttttatttt ctgtaatatg    2340 tgatcatcat taagttcaga ggtttgaggg cattatatat cccaaaaaga catgaaaata    2400
aaaatattct gtggtcaaag gaattaagaa atcaatgtga tatggctctt tcatagtggt    2460
ttctcaaacc tctcagaggt ctgtcttaaa taaaacttct ttgctcagcc caggctgtcc    2520
aaatcttact tgaagctctt tcttttcttac atttttttat aatacattta gtttgataaa    2580
tacttgatgg aaccaagtca aactgtcttt tagaaattta tttaatgtta attactatgt    2640
tcatctttaa catagattaa gatttggtgt ttcatatttt taattataat aacttttcctt    2700 agacaattaa aatatttta taagcattac aacacatatt cttcagttgt atgaaaaaca    2760
ttttaagtaa acaacttact ttcctaaata tttttttttc tatcagccga tccagtttaa    2820
atgccaaaat ggaagagtgt gttaaactaa actgtgaaca accttatgtg actacagcaa    2880
taataagcat cccaacacct ccagtaacca caccagaagg agacgatagg ccagaatccc    2940
ctgagtactc aggaggaaat attgtcagag tttctgcttt gtaagacaat tggaataagg    3000
tctaagagaa ttcgagccct ggctgtgaaa agaatctcaa catagaagaa agaagaaaca    3060
ataaatattc tgcagattaa tgcagcaaag aaagaaggtt ggtagtgaaa cacaaagctt    3120
ccaatcttaa ggatgtgaat aaaaccacca aatggcatttt ctagacagtt tgacctgtta    3180
tacagagtaa tattctgtgg ccctttgact ttgtgaatga gcacaatgaa atgccgccta    3240
ctgatgcttc ttatgatcag aactctttttt taataaaaata aataacataa atcgttgaac    3300
ataatgttcc agttgaatgc aaaacaaaaa aaatatggaa acatttttga taaaattttt    3360
tcctgttaaa accatgaaca ttggctatga tgaagattat tacatatgaa aaaaaaactc    3420
acacaacata tttgtattga ctgaaggaaa ccatcataat gcatgctaga attctttgaa    3480
```

```
gcagtgatct cagtttcctt atgttgtctt cagaataggc atgataaact ataattgtag    3540
aaaggggtaa tttctgtgca cttacaacaa gctgagtgtt catgttccat ggtgggctgt    3600
gcaaataaac tccttttaga cctgcagtat ttctcatggg gatgctcatt agtaaatcta    3660
aagtgttcag atagttcagt attcattatc gtttaacttt gcacctagat actgttacaa    3720
ctgcaataat ttgttgtaca actgttgtat caggaatcag gattttttg ttgttgtact     3780 ttccagatcc ttatagatac ggtaagagcc acattcgtag aaaaacttct ggtgtggcca    3840
ggttttaggt aacttttaa tccaaaacta ttgtgccata aatgttttc agtaatattt      3900 tttggtccac tgtattcctg tgacacagtg cattatctgt tcttgtattt ctatagcacc    3960
tctctattgg gttatcatc atcaacaaga ctactgttta ctgtagttca agtgactttc     4020 ctactttgt atttccaaaa aaaattatct tgtaagtagc ttgtcatcaa tccccttgtc     4080
gaaaactaga aaaaaggag ttgacccata taaattatct ctaacgtctt tgttgtttat     4140
ggaaaagccc agatactgga tatatcacta tgtattttat gaacagaatt gactgggact    4200
aatatcacag gatcaatcat ctcagaatct tacttgatgc attatttatt ttgctttaga    4260
tcttgaatac attttgagaa taactaatgt ggattgaaat gtagagatac actggagtgc    4320
tttatttagc aatatttgat gaaagcatgc tttctacgcc attcaggaag gcagcacaaa    4380
tttatctcag aaaggttcct gtgtattgca aggtacaatt ttctccaata aatcaggaga    4440
acaggagttt gatgatgcaa agttgatctc tgtacattta agtgaaaagt ctttataact    4500 tttcacccctt aaaatatttc agcagacatg tctgcacatg acagtgtaaa aaagtttaat   4560
gtcaaatgca agttttat tcattccaag ccaccactgt aaggaataaa gcttagcttc      4620
tgtacatgga aagagctaat aattatccct ctgtcagaga tgagattttt aaatgcttat    4680
gatatttaat cataaaaagg gattaatcca accatttct agtaaagcca gaaattcttg     4740
cttcccattt ctagaatagt ttctagaaca gtgctatgca catattagat cttaataaac    4800
atttgctgag tgaaagtaag ataaactcaa ctatctcttg ggaagaactg gcttcattcc    4860
tagtacatct tttaaaaagt tactaatttt ccagcagtac aaatattaac aattatatta    4920
acacctgcct catgtcagtt tatgcttcta gagcaatgtc tagtgaaact tatctgatgg    4980
catttattga aaaccttcta aaaagtagac taaggaaacc ataatcagaa ttactatgtc    5040
ttttgattcc caatgagaag ttctattttc atgttcttaa tattacatac aagaaaatgc    5100
agttaggtta tttcaattga caattctgcc tcctcttttg atttatcact acccaaaat     5160 tattaatttt attaggcttt tggaaaagaa aaaaaacttt ttgatgtttt aggtgattta    5220
aaaatatacc gtgttggtgg tgaatgacta ttgatgactg tgttaagtgc atctgtattg    5280
taagtgaaat gtaattattt ctgtgtacca tatggagtaa ctaaggtcat tgtttttgac    5340
aattttgttt gaaattcata tatcttattt caaaggatag cataatatct gcattatgct    5400 ggaaaaaat agacctttgg agaatactta aataaaacat gtgcatgctt gaacaggaca    5460
aaatgttgac tgttgccta tttttcttaga tttcattcct ttcccaaaat taggatatgc    5520
cacactcata atacacatgt tggaggacct tgtgagacat acaactcaaa ggacacagca    5580
attgaaagta atgcttaaat ctcatctgaa tgggtggaga cagtagcttt tgctagtaat    5640
gggaattaag gcagggactt taacagaaaa gatagtatca attaaggaaa gccagtcoct   5700 gaaccttata tacttcttaa acaccactac ttgcattaag cagagaagct caggggtaat   5760
ggttttggtc agaacttaaa taattcttta atcaaaggct ttattctacc taggaaagcg    5820
gggtgattta tttgcctagc catttgtgtg catgtatgtg tatatgtaga tataaatttg    5880
```

```
ttcatacaca tatacataga ttttcattca tttttaatat gcaaccacta atggtttctc    5940
ttaatatctt gaaagggcta aaaagcaaga aaatgttaag agtttataga agaaggaaaa    6000
agacacaaag gaaattattt agtagaaaga ctgattttaa ctggtgatat atatggtcct    6060
cttggtggat agtctctatc ttttcttgtt aattattttc atttatagcc tttgatttat    6120
taggtatcaa tcttgcatta aaaagttcaa tatgcctccc tattccttca acttagtcac    6180
aatgttggct tagaaatagc ctcttgggag ctataatgtg tctgccagta acattgctca    6240
aaagaataaa aaagggttct tgaaagtaaa ttgataactc cttagagttt cataagaaag    6300
gcatcttctc ttccctacag tgtcattaag gtgtttgttt tattaactca ctggtacaag    6360
aatggttatt actctgcact gtgtaaacat ctgaattttc aacacaattg tgtaggcaca    6420 cagtatttt ttaatgaagg tttaaattgt acctacgaag gtttaagtct tatctacttc    6480
agctggttgt attaggatac taaaatattc tttacagagt ttgatttttt acttctaagg    6540
aattactagc tttgaacagc aagtttgctt aagataatta taaaatataa ttttacaaaa    6600 tattttagt tgaaaataat attaaataca tagcatacct ttaatctttc tcttactgc    6660 ctgccctgcc ttttttctcc tttatcttca agcattaatt attattgtag cagatctttg    6720
cctttcccta attactttt tctctagctt ttctatggaa atcctttagg ttacataact    6780
aatattcatt ctacatataa tccagtttat taaatacaga tgatgggcca gacatggtga    6840
tagagaaata cagattaaga aaccagatca aatcctttt aaggaattat ctagtggaaa    6900
atatctcaac tctcttcttt acactactat tcattatctt acacttcaaa tcttcacctt    6960
tccattttga cagtcgctct tctacttcag tctcctgaag acatctctcc aacagaagtt    7020
acataaaaat actaatcttc aaggtgcttt ctaaaatatt ttcatcacgt cattaaaatc    7080 ttcttcact aggcaatggt tctgtctcta tgggggctgg caggcagggc aaatgaattc    7140
ctacctgccc agagaaagaa caggaaacaa taaggtaaa acaaaaccca aaggaagaag    7200
agcttcatgt ttatgcatta cattaaagtt aaaaggaaat aaactttctc aagtatccac    7260
tctacctttt caactataat ttcagagaat gtgaagaaag ctattaaaat agttttgcag    7320
gaggactgat acacaatgcg tctgtgaatc tgaacaccac acctcaaatt ctattatctg    7380
atgaatccta ttgaaatatc tgagtaattg ggacaacaga aaggtaagtc tgtaatcagg    7440
ggcactcacc aataaggcgg gcctagttgg ttcatgtcaa ttccaaagca agaggatggt    7500
tgaagaaggg tattgaatga gtagataaca aatatttgga gagagatttg gaggaaccct    7560
ggaagacaag agtaggctat tggcaagggc tacaagatgg tagagacatc cttgggcttt    7620
gactctaatt gaaaatacag aattttggcc tgacgcagtg actcatgcct gtaatcctag    7680
cactttggga ggctgagggg ggtggatcac ttgaggtcag gagtccaaga ccagcctcat    7740
caactggtga aacccatct ctactaaaaa aagaaaaaaa aaaatagcc aggtgtcctg    7800 gtgcatgcct gtaatctcag ctactcagga gtctgaggca ggagaattgc ttgaactcgg    7860
gaggtggagg ttgcaatgag ctgagattgt gccactgcat tccagcctgg gtgacagggg    7920
gagactccgt cttaaaaaaa gaaaaagaa aaaccagaat tttaaagttc aatttagatc    7980
aaattaattc ctt                                                     7993
```

<210> SEQ ID NO 251
<211> LENGTH: 3254
<212> TYPE: DNA
<213> ORGANISM: Homo sapiens

<400> SEQUENCE: 251

-continued

```
ggtatggtga catggtgcca aaaccatag cagggaagat ttttggttct atctgttcgc      60 tgagtgggt cttggtcatt gctctacctg ttccggtgat tgtatccaac ttcagtcgca    120
tctaccacca gaatcaacga gcagacaaac gaagggcaca aaagaaagct agactggcca    180
ggatccgggc agccaaaagc ggaagcgcaa atgcttacat gcagagcaaa cggaatggtt    240
tactcagtaa tcagctgcag tcctcagagg atgagcaggc ttttgttagc aaatccggct    300
ccagctttga aacccagcac caccacctgc ttcactgcct ggaaaaaacc acgaatcacg    360
agtttgtgga cgaacaagtc tttgaagaaa gctgcatgga agttgcaact gttaatcgtc    420
cttcaagtca cagtccttca ctgtcttcac aacaaggagt caccagcacc tgctgttcac    480
gacgacacaa aaaactttt cgcatcccaa atgccaatgt atcaggaagc catcaaggta    540
gtatacaaga actcagcacg attcagatca gatgtgtgga gagaacacct ctgtctaaca    600
gccgatccag tttaaatgcc aaaatggaag agtgtgttaa actaaactgt gaacaacctt    660
atgtgactac agcaataata agcatcccaa cacctccagt aaccacacca gaaggagacg    720
ataggccaga atcccctgag tactcaggag gaaatattgt cagagtttct gctttgtaag    780
acaattggaa taaggtctaa gagaattcga gccctggctg tgaaaagaat ctcaacatag    840 aagaagaag aaacaataaa tattctgcag attaatgcag caaagaaaga aggttggtag    900
tgaaacacaa agcttccaat cttaaggatg tgaataaaac caccaaatgg catttctaga    960
cagtttgacc tgttatacag agtaatattc tgtggccctt tgactttgtg aatgagcaca   1020
atgaaatgcc gcctactgat gcttcttatg atcagaactc ttttttaata aaataaataa   1080
cataaatcgt tgaacataat gttccagttg aatgcaaaac aaaaaaaata tggaaaacat   1140
tttgataaaa ttttttcctg ttaaaaccat gaacattggc tatgatgaag attattacat   1200
atgaaaaaaa aactcacaca acatatttgt attgactgaa ggaaaccatc ataatgcatg   1260
ctagaattct ttgaagcagt gatctcagtt tccttatgtt gtcttcagaa taggcatgat   1320
aaactataat tgtagaaagg ggtaatttct gtgcacttac aacaagctga gtgttcatgt   1380
tccatggtgg gctgtgcaaa taaactcctt ttagacctgc agtatttctc atggggatgc   1440
tcattagtaa atctaaagtg ttcagatagt tcagtattca ttatcgttta actttgcacc   1500
tagatactgt tacaactgca ataatttgtt gtacaactgt tgtatcagga atcaggattt   1560
ttttgttgtt gtactttcca gatccttata gatacggtaa gagccacatt cgtagaaaaa   1620
cttctggtgt ggccaggttt taggtaactt tttaatccaa aactattgtg ccataaatgt   1680
ttttcagtaa tattttttgg tccactgtat tcctgtgaca cagtgcatta tctgttcttg   1740
tatttctata gcacctctct attgggttta tcatcatcaa caagactact gtttactgta   1800
gttcaagtga ctttcctact tttgtatttc caaaaaaaat tatcttgtaa gtagcttgtc   1860
atcaatcccc ttgtcgaaaa ctagaaaaaa aggagttgac ccatataaat tatctctaac   1920
gtctttgttg tttatggaaa agcccagata ctggatatat cactatgtat tttatgaaca   1980
gaattgactg ggactaatat cacaggatca atcatctcag aatcttactt gatgcattat   2040
ttattttgct ttagatcttg aatacatttt gagaataact aatgtggatt gaaatgtaga   2100
gatacactgg agtgctttat ttagcaatat ttgatgaaag catgctttct acgccattca   2160
ggaaggcagc acaaattat ctcagaaagg ttcctgtgta ttgcaaggta caattttctc   2220
caataaatca ggagaacagg agtttgatga tgcaaagttg atctctgtac atttaagtga   2280
aaagtcttta taacttttca cccttaaaat atttcagcag acatgtctgc acatgacagt   2340
gtaaaaaagt ttaatgtcaa atgcaaagtt tttattcatt ccaagccacc actgtaagga   2400
```

| | |
|---|---|
| ataaagctta gcttctgtac atggaaagag ctaataatta tccctctgtc agagatgaga | 2460 |
| tttttaaatg cttatgatat ttaatcataa aaagggatta atccaaccat tttctagtaa | 2520 |
| agccagaaat tcttgcttcc catttctaga atagtttcta gaacagtgct atgcacatat | 2580 |
| tagatcttaa taaacatttg ctgagtgaaa gtaagataaa ctcaactatc tcttgggaag | 2640 |
| aactggcttc attcctagta catctttaa aaagttacta atttccagc agtacaaata | 2700 |
| ttaacaatta tattaacacc tgcctcatgt cagtttatgc ttctagagca atgtctagtg | 2760 |
| aaacttatct gatggcattt attgaaaacc ttctaaaaag tagactaagg aaaccataat | 2820 |
| cagaattact atgtcttttg attcccaatg agaagttcta ttttcatgtt cttaatatta | 2880 |
| catacaagaa aatgcagtta ggttatttca attgacaatt ctgcctcctc tttttgattta | 2940 |
| tcacttaccc aaaattatta atttattag gcttttggaa aagaaaaaaa acttttgat | 3000 |
| gttttaggtg atttaaaaat ataccgtgtt ggtggtgaat gactattgat gactgtgtta | 3060 |
| agtgcatctg tattgtaagt gaaatgtaat tatttctgtg taccatatgg agtaactaag | 3120 |
| gtcattgttt ttgacaattt tgtttgaaat tcatatatct tatttcaaag gatagcataa | 3180 |
| tatctgcatt atgctggaaa aaaatagacc tttggagaat acttaaataa aacatgtgca | 3240 |
| tgcttgaaca ggac | 3254 |

<210> SEQ ID NO 252
<211> LENGTH: 5333
<212> TYPE: DNA
<213> ORGANISM: Homo sapiens

<400> SEQUENCE: 252

| | |
|---|---|
| cggctgctcg cgagctgctt tctctcctct tcccttccg ggtgcacggc gaggagaaag | 60 |
| tctctatgca actaagcccc ggcgcgcact tggccaggta tgtaccgcgg gagcggcgcg | 120 |
| ttctgcgcgg aagcagatgc tgctgccgcc acgcgcgcgg cggctgccag ctcctgagct | 180 |
| ctgtaactgt cacactgcac ctgagctgaa cttgaaaaga gagtgaaggg gcgattgggc | 240 |
| gaacgctttt ggcagacaca gagggtgttt gtagacgtgg gggaggagaa tctctattaa | 300 |
| cgccccccac cgtaaccact gcacatcacc tccatctctg caaatacagc ccgaggagta | 360 |
| gaggcagcag cagctggacc cccaaagaga gacgtgggc agcggctgtg accgcatctc | 420 |
| ctgagctaca acaacaggtc gcctttttga gactcctttg gcgggaaggg ctacttggaa | 480 |
| aggaaggttt gaaagagtga aagggtagg tgtaagggtt ccctaattcg tcgaaagaat | 540 |
| tctattgggt gactctcgtt cgtcttctct atcctacact ccacatactg accctatatt | 600 |
| atccagactg tgccggggag aaatcaaaaa cacctgtttg aagaaacggc tgcacctgtg | 660 |
| tgcttatttg tgccagaggg tggcctagcc cacctgcagg aagagatttg gctgggttct | 720 |
| gttgagggtg attgttagga cgttgtattt tgttgccatt attccaaata cctgtcttgg | 780 |
| agggaaagtt gcccttctga gaactgtgac tttaccagga gccctatctt ggaataagag | 840 |
| ttacacctct ggaccacgtt tctcactagt actttgcttg actggaggaa gtgggtgact | 900 |
| tttggctgct tcggtgaccc attgtagacg cctcgttacc cttcttcctt ccgcttcaag | 960 |
| taatcatggc ggcggggtg gcagcgtggc tgccttttgc aagggcagcg gctatcgggt | 1020 |
| ggatgcctgt ggcctcgggg cctatgccgg ctcccccgag gcaggagagg aaaaggaccc | 1080 |
| aagatgctct cattgtgctg aatgtgagtg gcacccgctt ccagacgtgg caggacaccc | 1140 |
| tggaacgtta cccagacact ctactgggca gttctgagag ggactttttc taccacccag | 1200 |
| aaactcagca gtatttcttt gaccgtgacc cagacatctt ccgccacatc ctgaatttct | 1260 |

```
accgcactgg gaagctccac tatcctcgcc acgagtgcat ctctgcttac gatgaagaac    1320
tggccttctt tggcctcatc ccggaaatca tcggcgactg ctgttatgag gagtacaagg    1380
atcgcaggcg agagaacgcc gagcgcctgc aggacgacgc ggataccgac accgctgggg    1440
agagcgcctt gcccaccatg actgcaaggc agagggtctg gagggccttc gagaaccccc    1500
acaccagcac gatggccctg tgttctact atgtcacggg gtttttcatt gccgtctctg      1560
tcatcgcgaa tgtggtggaa acagtgccgt gcggatcaag cccaggtcac attaaagaac    1620
tgccctgtgg agagcggtat gctgtggcct tcttctgctt ggacacggcc tgcgtcatga    1680
tcttcacagt tgagtatttg cttcgcctgg ctgcagcgcc tagtcgttac cgttttgtgc    1740
gtagtgtcat gagtatcatc gacgtggtgg ccatcctgcc ttattacatt gggctggtga    1800
tgacagacaa tgaggacgtc agcggagcct tgtcacact ccgagtcttc cgggtcttca     1860
ggatctttaa gttttcccgc cactctcaag gcctgcgcat cctggggtac acactgaaga    1920
gttgtgcctc agaattgggc ttcttgcttt tctcgctcac catggctatc atcatcttcg    1980
ctacagttat gttctacgca gagaagggt cttcggctag caagttcacc agcatccctg      2040
cagccttctg gtataccatc gtcaccatga caacactagg gtatggtgac atggtgccaa    2100
aaaccatagc agggaagatt tttggttcta tctgttcgct gagtggggtc ttggtcattg    2160
ctctacctgt tccggtgatt gtatccaact tcagtcgcat ctaccaccag aatcaacgag    2220
cagacaaacg aagggcacaa agaaagcta gactggccag gatccgggca gccaaaagcg     2280
gaagcgcaaa tgcttacatg cagagcaaac ggaatggttt actcagtaat cagctgcagt    2340
cctcagagga tgagcaggct tttgttagca atccggctc cagctttgaa acccagcacc     2400
accacctgct tcactgcctg gaaaaaacca cgaatcacga gtttgtggac gaacaagtct    2460
ttgaagaaag ctgcatggaa gttgcaactg ttaatcgtcc ttcaagtcac agtccttcac    2520
tgtcttcaca acaaggagtc accagcacct gctgttcacg acgacacaaa aaacttttc     2580 gcatcccaaa tgccaatgta tcaggaagcc atcaaggtag tatacaagaa ctcagcacga    2640
ttcagatcag atgtgtggag agaacacctc tgtctaacag ccgatccagt ttaaatgcca    2700
aaatggaaga gtgtgttaaa ctaaactgtg aacaaccta tgtgactaca gcaataataa     2760
gcatcccaac acctccagta accacaccag aaggagacga taggccagaa tcccctgagt    2820
actcaggagg aaatattgtc agagtttctg cttttgtaaga caattggaat aaggtctaag   2880
agaattcgag ccctggctgt gaaaagaatc tcaacataga agaagaaga acaataaat      2940 attctgcaga ttaatgcagc aaagaaagaa ggttggtagt gaaacacaaa gcttccaatc    3000
ttaaggatgt gaataaaacc accaaatggc atttctagac agtttgacct gttatacaga    3060
gtaatattct gtggcccttt gactttgtga atgagcacaa tgaaatgccg cctactgatg    3120
cttcttatga tcagaactct tttttaataa aataaataac ataaatcgtt gaacataatg    3180
ttccagttga atgcaaaaca aaaaaatat ggaaaacatt ttgataaaat ttttcctgt      3240 taaaaccatg aacattggct atgatgaaga ttattacata tgaaaaaaa actcacacaa     3300 catatttgta ttgactgaag gaaaccatca taatgcatgc tagaattctt tgaagcagtg    3360
atctcagttt ccttatgttg tcttcagaat aggcatgata aactataatt gtagaagggg    3420
gtaatttctg tgcacttaca acaagctgag tgttcatgtt ccatggtggg ctgtgcaaat    3480
aaactccttt tagacctgca gtatttctca tggggatgct cattagtaaa tctaaagtgt    3540
tcagatagtt cagtattcat tatcgtttaa ctttgcacct agatactgtt acaactgcaa    3600
taatttgttg tacaactgtt gtatcaggaa tcaggatttt tttgttgttg tactttccag    3660
```

| | |
|---|---|
| atccttatag atacggtaag agccacattc gtagaaaaac ttctggtgtg gccaggtttt | 3720 |
| aggtaacttt ttaatccaaa actattgtgc cataaatgtt tttcagtaat attttttggt | 3780 |
| ccactgtatt cctgtgacac agtgcattat ctgttcttgt atttctatag cacctctcta | 3840 |
| ttgggtttat catcatcaac aagactactg tttactgtag ttcaagtgac tttcctactt | 3900 |
| ttgtatttcc aaaaaaaatt atcttgtaag tagcttgtca tcaatcccct tgtcgaaaac | 3960 |
| tagaaaaaaa ggagttgacc catataaatt atctctaacg tctttgttgt ttatggaaaa | 4020 |
| gcccagatac tggatatatc actatgtatt ttatgaacag aattgactgg gactaatatc | 4080 |
| acaggatcaa tcatctcaga atcttacttg atgcattatt tattttgctt tagatcttga | 4140 |
| atacattttg agaataacta atgtggattg aaatgtagag atacactgga gtgctttatt | 4200 |
| tagcaatatt tgatgaaagc atgctttcta cgccattcag gaaggcagca caaatttatc | 4260 |
| tcagaaaggt tcctgtgtat tgcaaggtac aatttttctcc aataaatcag gagaacagga | 4320 |
| gtttgatgat gcaaagttga tctctgtaca tttaagtgaa aagtctttat aacttttcac | 4380 |
| ccttaaaata tttcagcaga catgtctgca catgacagtg taaaaaagtt taatgtcaaa | 4440 |
| tgcaaagttt ttattcattc caagccacca ctgtaaggaa taaagcttag cttctgtaca | 4500 |
| tggaaagagc taataattat ccctctgtca gagatgagat ttttaaatgc ttatgatatt | 4560 |
| taatcataaa aagggattaa tccaaccatt ttcaagtaaa gccagaaatt cttgcttccc | 4620 |
| atttctagaa tagtttctag aacagtgcta tgcacatatt agatcttaat aaacatttgc | 4680 |
| tgagtgaaag taagataaac tcaactatct cttgggaaga actggcttca ttcctagtac | 4740 |
| atcttttaaa aagttactaa ttttccagca gtacaaatat taacaattat attaacacct | 4800 |
| gcctcatgtc agtttatgct tctagagcaa tgtctagtga aacttatctg atggcattta | 4860 |
| ttgaaaacct tctaaaaagt agactaagga aaccataatc agaattacta tgtcttttga | 4920 |
| ttcccaatga gaagttctat tttcatgttc ttaatattac atacaagaaa atgcagttag | 4980 |
| gttatttcaa ttgacaattc tgcctcctct tttgatttat cacttaccca aaattattaa | 5040 |
| ttttattagg cttttggaaa agaaaaaaaa cttttttgatg ttttaggtga tttaaaaata | 5100 |
| taccgtgttg gtggtgaatg actattgatg actgtgttaa gtgcatctgt attgtaagtg | 5160 |
| aaatgtaatt atttctgtgt accatatgga gtaactaagg tcattgtttt tgacaatttt | 5220 |
| gtttgaaatt catatatctt atttcaaagg atagcataat atctgcatta tgctggaaaa | 5280 |
| aaatagacct tggagaata cttaaataaa acatgtgcat gcttgaacag gac | 5333 |

<210> SEQ ID NO 253
<211> LENGTH: 2351
<212> TYPE: DNA
<213> ORGANISM: Homo sapiens

<400> SEQUENCE: 253

| | |
|---|---|
| gaattctatt gggtgactct cgttcgtctt ctctatccta cactccacat actgaccta | 60 |
| tattatccag actgtgccgg ggagaaatca aaaacacctg tttgaagaaa cggctgcacc | 120 |
| tgtgtgctta tttgtgccag agggtggcct agcccacctg caggaagaga tttggctggg | 180 |
| ttctgttgag ggtgattgtt aggacgttgt attttgttgc cattattcca aatacctgtc | 240 |
| ttggagggaa agttgccctt ctgagaactg tgactttacc aggagcccta tcttggaata | 300 |
| agagttacac ctctggacca cgtttctcac tagtactttg cttgactgga ggaagtgggt | 360 |
| gacttttggc tgcttcggtg acccattgta gacgcctcgt tacccttctt ccttccgctt | 420 |
| caagtaatca tggcggcggg ggtggcagcg tggctgcctt ttgcaagggc agcggctatc | 480 |

```
gggtggatgc ctgtggcctc ggggcctatg ccggctcccc cgaggcagga gaggaaaagg    540
acccaagatg ctctcattgt gctgaatgtg agtggcaccc gcttccagac gtggcaggac    600
accctggaac gttacccaga cactctactg ggcagttctg agagggactt tttctaccac    660
ccagaaactc agcagtattt ctttgaccgt gacccagaca tcttccgcca catcctgaat    720
ttctaccgca ctgggaagct ccactatcct cgccacgagt gcatctctgc ttacgatgaa    780
gaactggcct tctttggcct catcccggaa atcatcggcg actgctgtta tgaggagtac    840
aaggatcgca ggcgagagaa cgccgagcgc ctgcaggacg acgcggatac cgacaccgct    900
ggggagagcg ccttgcccac catgactgca aggcagaggg tctggagggc cttcgagaac    960
ccccacacca gcacgatggc cctggtgttc tactatgtca cggggttttt cattgccgtc    1020
tctgtcatcg cgaatgtggt ggaaacagtg ccgtgcggat caagcccagg tcacattaaa    1080
gaactgccct gtggagagcg gtatgctgtg gccttcttct gcttggacac ggcctgcgtc    1140
atgatcttca cagttgagta tttgcttcgc ctggctgcag cgcctagtcg ttaccgtttt    1200
gtgcgtagtg tcatgagtat catcgacgtg gtggccatcc tgccttatta cattgggctg    1260
gtgatgacag acaatgagga cgtcagcgga gcctttgtca cactccgagt cttccgggtc    1320
ttcaggatct ttaagttttc ccgccactct caaggcctgc gcatcctggg gtacacactg    1380
aagagttgtg cctcagaatt gggcttcttg cttttctcgc tcaccatggc tatcatcatc    1440
ttcgctacag ttatgttcta cgcagagaag gggtcttcgg ctagcaagtt caccagcatc    1500
cctgcagcct ctggtatac  catcgtcacc atgacaacac tagggtatgg tgacatggtg    1560
ccaaaaacca tagcagggaa gattttggt  tctatctgtt cgctgagtgg ggtcttggtc    1620
attgctctac ctgttccggt gattgtatcc aacttcagtc gcatctacca ccagaatcaa    1680
cgagcagaca aacgaagggc acaaaagaaa gctagactgg ccaggatccg ggcagccaaa    1740
agcggaagcg caaatgctta catgcagagc aaacggaatg gtttactcag taatcagctg    1800
cagtcctcag aggatgagca ggcttttgtt agcaaatccg gctccagctt tgaaacccag    1860
caccaccacc tgcttcactg cctggaaaaa accacgaatc acgagtttgt ggacgaacaa    1920
gtctttgaag aaagctgcat ggaagttgca actgttaatc gtccttcaag tcacagtcct    1980
tcactgtctt cacaacaagg agtcaccagc acctgctgtt cacgacgaca caaaaaaact    2040
tttcgcatcc caaatgccaa tgtatcagga agccatcaag gtagtataca agaactcagc    2100
acgattcaga tcagatgtgt ggagagaaca cctctgtcta acagccgatc cagtttaaat    2160
gccaaaatgg aagagtgtgt taaactaaac tgtgaacaac cttatgtgac tacagcaata    2220
ataagcatcc caacacctcc agtaaccaca ccagaaggag acgataggcc agaatcccct    2280
gagtactcag gaggaaatat tgtcagagtt tctgctttgt aagacaattg gaataaggtc    2340
taagagaatt c                                                         2351

<210> SEQ ID NO 254
<211> LENGTH: 5333
<212> TYPE: DNA
<213> ORGANISM: Homo sapiens

<400> SEQUENCE: 254
cggctgctcg cgagctgctt tctctcctct tcccttttccg ggtgcacggc gaggagaaag    60
tctctatgca actaagcccc ggcgcgcact tggccaggta tgtaccgcgg gagcggcgcg    120 ttctgcgcg  aagcagatgc tgctgccgcc acggcggcgg cggctgccag ctcctgagct    180
ctgtaactgt cacactgcac ctgagctgaa cttgaaaaga gagtgaaggg gcgattgggc    240
```

```
gaacgctttt ggcagacaca gagggtgttt gtagacgtgg gggaggagaa tctctattaa    300 cgcccccac cgtaaccact gcacatcacc tccatctctg caaatacagc ccgaggagta     360
gaggcagcag cagctggacc cccaaagaga gacgtgggc agcggctgtg accgcatctc     420
ctgagctaca acaacaggtc gccttttga dactcctttg gcgggaaggg ctacttggaa     480
aggaaggttt gaaagagtga aagggtagg tgtaagggtt ccctaattcg tcgaaagaat    540
tctattgggt gactctcgtt cgtcttctct atcctacact ccacatactg accctatatt    600
atccagactg tgccggggag aaatcaaaaa cacctgtttg aagaaacggc tgcacctgtg    660
tgcttatttg tgccagaggg tggcctagcc cacctgcagg aagagatttg gctgggttct    720
gttgagggtg attgttagga cgttgtattt tgttgccatt attccaaata cctgtcttgg    780
agggaaagtt gcccttctga gaactgtgac tttaccagga gccctatctt ggaataagag    840
ttacacctct ggaccacgtt tctcactagt actttgcttg actggaggaa gtgggtgact    900
tttggctgct tcggtgaccc attgtagacg cctcgttacc cttcttcctt ccgcttcaag    960
taatcatggc ggcggggtg gcagcgtggc tgccttttgc aagggcagcg gctatcgggt    1020
ggatgcctgt ggcctcgggg cctatgccgg ctcccccgag gcaggagagg aaaaggaccc    1080
aagatgctct cattgtgctg aatgtgagtg gcacccgctt ccagacgtgg caggacaccc    1140
tggaacgtta cccagacact ctactgggca gttctgagag ggactttttc taccacccag    1200
aaactcagca gtatttcttt gaccgtgacc cagacatctt ccgccacatc ctgaatttct    1260
accgcactgg gaagctccac tatcctcgcc acgagtgcat ctctgcttac gatgaagaac    1320
tggccttctt tggcctcatc ccggaaatca tcggcgactg ctgttatgag gagtacaagg    1380
atcgcaggcg agagaacgcc gagcgcctgc aggacgacgc ggataccgac accgctgggg    1440
agagcgcctt gcccaccatg actgcaaggc agagggtctg gagggccttc gagaaccccc    1500
acaccagcac gatggccctg tgttctact atgtcacggg gttttcatt gccgtctctg    1560 tcatcgcgaa tgtggtggaa acagtgccgt gcggatcaag cccaggtcac attaaagaac    1620
tgccctgtgg agagcggtat gctgtggcct tcttctgctt ggacacggcc tgcgtcatga    1680
tcttcacagt tgagtatttg cttcgcctgg ctgcagcgcc tagtcgttac cgttttgtgc    1740
gtagtgtcat gagtatcatc gacgtggtgg ccatcctgcc ttattacatt gggctggtga    1800
tgacagacaa tgaggacgtc agcggagcct tgtcacact ccgagtcttc cgggtcttca    1860
ggatctttaa gttttcccgc cactctcaag gcctgcgcat cctggggtac acactgaaga    1920
gttgtgcctc agaattgggc ttcttgcttt tctcgctcac catggctatc atcatcttcg    1980
ctacagttat gttctacgca gagaagggt cttcggctag caagttcacc agcatccctg    2040
cagccttctg gtataccatc gtcaccatga caacactagg gtatggtgac atggtgccaa    2100
aaaccatagc agggaagatt tttggttcta tctgttcgct gagtgggtc ttggtcattg    2160 ctctacctgt tccggtgatt gtatccaact tcagtcgcat ctaccaccag aatcaacgag    2220
cagacaaacg aagggcacaa aagaaagcta gactggccag gatccgggca gccaaaagcg    2280
gaagcgcaaa tgcttacatg cagagcaaac ggaatggttt actcagtaat cagctgcagt    2340
cctcagagga tgagcaggct tttgttagca aatccggctc cagctttgaa acccagcacc    2400
accacctgct tcactgcctg gaaaaaacca cgaatcacga gtttgtggac gaacaagtct    2460
ttgaagaaag ctgcatggaa gttgcaactg ttaatcgtcc ttcaagtcac agtccttcac    2520
tgtcttcaca acaaggagtc accagcacct gctgttcacg acgacacaaa aaacttttc    2580 gcatcccaaa tgccaatgta tcaggaagcc atcaaggtag tatacaagaa ctcagcacga    2640
```

```
ttcagatcag atgtgtggag agaacacctc tgtctaacag ccgatccagt ttaaatgcca    2700
aaatggaaga gtgtgttaaa ctaaactgtg aacaacctta tgtgactaca gcaataataa    2760
gcatcccaac acctccagta accacaccag aaggagacga taggccagaa tcccctgagt    2820
actcaggagg aaatattgtc agagtttctg ctttgtaaga caattggaat aaggtctaag    2880
agaattcgag ccctggctgt gaaaagaatc tcaacataga agaaagaaga acaataaat     2940 attctgcaga ttaatgcagc aaagaaagaa ggttggtagt gaaacacaaa gcttccaatc    3000
ttaaggatgt gaataaaacc accaaatggc atttctagac agtttgacct gttatacaga    3060
gtaatattct gtggcccttt gactttgtga atgagcacaa tgaaatgccg cctactgatg    3120
cttcttatga tcagaactct tttttaataa aataaataac ataaatcgtt gaacataatg    3180
ttccagttga atgcaaaaca aaaaaaatat ggaaaacatt ttgataaaat ttttcctgt     3240 taaaaccatg aacattggct atgatgaaga ttattacata tgaaaaaaaa actcacacaa    3300
catatttgta ttgactgaag gaaaccatca taatgcatgc tagaattctt tgaagcagtg    3360
atctcagttt ccttatgttg tcttcagaat aggcatgata aactataatt gtagaaaggg    3420
gtaatttctg tgcacttaca acaagctgag tgttcatgtt ccatggtggg ctgtgcaaat    3480
aaactccttt tagacctgca gtatttctca tggggatgct cattagtaaa tctaaagtgt    3540
tcagatagtt cagtattcat tatcgtttaa ctttgcacct agatactgtt acaactgcaa    3600
taatttgttg tacaactgtt gtatcaggaa tcaggatttt tttgttgttg tactttccag    3660
atccttatag atacggtaag agccacattc gtagaaaaac ttctggtgtg gccaggtttt    3720
aggtaacttt ttaatccaaa actattgtgc cataaatgtt tttcagtaat attttttggt    3780
ccactgtatt cctgtgacac agtgcattat ctgttcttgt atttctatag cacctctcta    3840
ttgggtttat catcatcaac aagactactg tttactgtag ttcaagtgac tttcctactt    3900
ttgtatttcc aaaaaaaatt atcttgtaag tagcttgtca tcaatcccct tgtcgaaaac    3960
tagaaaaaaa ggagttgacc catataaatt atctctaacg tctttgttgt ttatggaaaa    4020
gcccagatac tggatatatc actatgtatt ttatgaacag aattgactgg gactaatatc    4080
acaggatcaa tcatctcaga atcttacttg atgcattatt tattttgctt tagatcttga    4140
atacattttg agaataacta atgtggattg aaatgtagag atacactgga gtgctttatt    4200
tagcaatatt tgatgaaagc atgctttcta cgccattcag gaaggcagca caaatttatc    4260
tcagaaaggt tcctgtgtat tgcaaggtac aattttctcc aataaatcag gagaacagga    4320
gtttgatgat gcaaagttga tctctgtaca tttaagtgaa aagtctttat aacttttcac    4380
ccttaaaata tttcagcaga catgtctgca catgacagtg taaaaaagtt taatgtcaaa    4440
tgcaaagttt ttattcattc caagccacca ctgtaaggaa taaagcttag cttctgtaca    4500
tggaaagagc taataattat ccctctgtca gagatgagat ttttaaatgc ttatgatatt    4560
taatcataaa aagggattaa tccaaccatt ttcaagtaaa gccagaaatt cttgcttccc    4620
atttctagaa tagtttctag aacagtgcta tgcacatatt agatcttaat aaacatttgc    4680
tgagtgaaag taagataaac tcaactatct cttgggaaga actggcttca ttcctagtac    4740 atctttttaaa aagttactaa ttttccagca gtacaaatat taacaattat attaacacct    4800
gcctcatgtc agtttatgct tctagagcaa tgtctagtga aacttatctg atggcattta    4860
ttgaaaacct tctaaaaagt agactaagga aaccataatc agaattacta tgtctttga    4920 ttcccaatga gaagttctat tttcatgttc ttaatattac atacaagaaa atgcagttag    4980
gttatttcaa ttgacaattc tgcctcctct tttgatttat cacttaccca aaattattaa    5040
```

```
tttattagg cttttggaaa agaaaaaaaa cttttgatg ttttaggtga tttaaaaata    5100
taccgtgttg gtggtgaatg actattgatg actgtgttaa gtgcatctgt attgtaagtg    5160
aaatgtaatt atttctgtgt accatatgga gtaactaagg tcattgtttt tgacaatttt    5220
gtttgaaatt catatatctt atttcaaagg atagcataat atctgcatta tgctggaaaa    5280
aaatagacct ttggagaata cttaaataaa acatgtgcat gcttgaacag gac          5333

<210> SEQ ID NO 255
<211> LENGTH: 5404
<212> TYPE: DNA
<213> ORGANISM: Homo sapiens

<400> SEQUENCE: 255
ggagatgcag gaccacccac tggcggggaa gcagctagca gccctcccgc gccccgcgc      60 tgccgagcgc cttctgcctc cgcgctcgga cgagagcccg tgccggcccc ggccccggcc    120
ccaccgcgcc aacgccgccc gcccggccgc cccgcagccc cgccgcccg cagccccgca     180 ccgcgctggc caggctcccg cgacagtggc cccgcagtaa gttggcagga gcgagtcccc    240
tccgttctcg cctcccccgc acctttgaa cttgttgctg ctgctctgct cgcctgcgcc     300
tggcttttgg aaggtgaaaa ggaggaggga ggcacggagg gatggggaa gggaaagaag     360 agctcgcttg agctttattt atgctctctc ggcgcatcgg attcggctgc tcgcgagctg    420 cttctctcc tcttcccttt ccgggtgcac ggcgaggaga aagtctctat gcaactaagc     480
cccggcgcgc acttggccag gtatgtaccg cgggagcggc gcgttctgcg cggaagcaga    540
tgctgctgcc gccacggcgg cggcggctgc cagctcctga gctctgtaac tgtcacactg    600
cacctgagct gaacttgaaa agagagtgaa ggggcgattg ggcgaacgct tttggcagac    660
acagagggtg tttgtagacg tgggggagga gaatctctat taacgcccc caccgtaacc     720 actgcacatc acctccatct ctgcaaatac agcccgagga gtagaggcag cagcagctgg    780
acccccaaag agagacgtgg ggcagcggct gtgaccgcat ctcctgagct acaacaacag    840
gtcgcctttt tgagactcct ttggcgggaa gggctacttg gaaaggaagg tttgaaagag    900
tgagaagggt aggtgtaagg gttccctaat tcgtcgaaag aattctattg ggtgactctc    960
gttcgtcttc tctatcctac actccacata ctgaccctat attatccaga ctgtgccggg    1020
gagaaatcaa aaacacctgt ttgaagaaac ggctgcacct gtgtgcttat ttgtgccaga    1080
gggtggccta gcccacctgc aggaagagat ttggctgggt tctgttgagg gtgattgtta    1140
ggacgttgta ttttgttgcc attattccaa atacctgtct tggagggaaa gttgcccttc    1200
tgagaactgt gactttacca ggagccctat cttggaataa gagttacacc tctgaccac    1260 gtttctcact agtactttgc ttgactggag gaagtgggtg acttttggct gcttcggtga    1320
cccattgtag acgcctcgtt acccttcttc cttccgcttc aagtaatcat ggcggcgggg    1380
gtggcagcgt ggctgccttt tgcaagggca gcggctatcg ggtggatgcc tgtggcctcg    1440
gggcctatgc cggctccccc gaggcaggag aggaaaagga cccaagatgc tctcattgtg    1500
ctgaatgtga gtggcacccg cttccagacg tggcaggaca ccctggaacg ttacccagac    1560
actctactgg gcagttctga gagggacttt ttctaccacc cagaaactca gcagtatttc    1620
tttgaccgtg acccagacat cttccgccac atcctgaatt tctaccgcac tgggaagctc    1680
cactatcctc gccacgagtg catctctgct tacgatgaag aactggcctt ctttggcctc    1740 atcccgaaa tcatcggcga ctgctgttat gaggagtaca aggatcgcag gcgagagaac    1800
gccgagcgcc tgcaggacga cgcggatacc gacaccgctg gggagagcgc cttgcccacc    1860
```

```
atgactgcaa ggcagagggt ctggagggcc ttcgagaacc cccacaccag cacgatggcc    1920
ctggtgttct actatgtcac ggggttttc attgccgtct ctgtcatcgc gaatgtggtg    1980
gaaacagtgc cgtgcggatc aagcccaggt cacattaaag aactgccctg tggagagcgg    2040
tatgctgtgg ccttcttctg cttggacacg gcctgcgtca tgatcttcac agttgagtat    2100
ttgcttcgcc tggctgcagc gcctagtcgt taccgttttg tgcgtagtgt catgagtatc    2160
atcgacgtgg tggccatcct gccttattac attgggctgg tgatgacaga caatgaggac    2220
gtcagcggag cctttgtcac actccgagtc ttccgggtct tcaggatctt aagttttcc    2280 cgccactctc aaggcctgcg catcctgggg tacacactga gagttgtgc ctcagaattg    2340 ggcttcttgc ttttctcgct caccatggct atcatcatct tcgctacagt tatgttctac    2400
gcagagaagg ggtcttcggc tagcaagttc accagcatcc ctgcagcctt ctggtatacc    2460
atcgtcacca tgacaacact agggtaggtg ccataatggg aaatgggatg gaggttgggt    2520
atgggtgagg cgattgtgga cccatcgagg ttacatggta actccgggga aatcatttgt    2580
tttctttcct gagtttagga aagcattatc taaatggttt ggcaaaactc ttttcatctg    2640
tgaaatgggt ataatacaca cgttgaagta ttaaggcatt gctggcaaat gttgatgcct    2700
gaaagtgata aagatacaaa gaaattttag aattcctgaa tatatgaaag tagtagcaat    2760
atttatatta atatataaaa atatgacaat gaaaacaaa atctatgccc taataaagac    2820
acaaatatat acaatgtata ttgaaatgtc tataaagtgg ttcaatgcat ttaaatgaaa    2880
agtttccagg tatacttgaa ctattatttt catatgaata gatacttatg gtgtacattt    2940
ttcctctaag aaccataatt cctatttac atcgtaatac atagattgta gatgtaatta    3000
tcaaagtatt ttataatata tatgcacata ttcatatgta tgcactttaa ttatggttga    3060
taggttattc agtcttttag aatatcagag ctgaaactga tcaactctac aatatgcagt    3120
ggaattaaat ttgcaacata tttcaagctc taggttcata gtttcaaaaa agaagcaaa    3180 agactgtcat ccacacattt ttttttagaa tctacagatc ccatcaggca atgggtccac    3240
acccattaaa tacacataga agatagagca gtatctggta agattgatgg tcaccaaggc    3300
tggctgtatt ataaatttg gggtcctaat ttccttttag aatttttttg tgaattcttt    3360 tttggggta taatgaagtt ctgcaaccaa agggacaaat ttctgaattc atgctgttgt    3420 tttaatata cttttagggc tagaattaag ttttttttagg tagtagagaa aaggaaagga    3480
ggcaaatgat taataatgtt aaactgcaga aaagtagcag cattttacat attagagaat    3540
ctaataaaat aaaatggtta gatcttttta cttttatgag ttcttagata agctggggag    3600
tgatgtgagt gccttttctt cagctttgtg ctactattct tgcataggta atcagtttag    3660
tgaggatttg gtaatggcta taagaaaaaa gttattccca aggctactct ttaagctttg    3720 tgttttgga taatttaatt ggcttcttta aatgacattg tggttaaagt caacttaatt    3780
ttattagaca tattgtgttg tacagaattt ctcatgtcat gtggccagct aatggaatag    3840
tttatatatg aagaattta ggctaggtta acaagaaat tggggtaaag aaaaatacaa    3900
tgatttatga ttttattta gtctcatttt tttaaagacc tactggtaca tttaaaaaat    3960
gaattagtga aaatccatgt tctacttctt atatttcctt tttatcttgt tggcaaattt    4020
gtgacagttt ataaggataa ggatgatgca gaatgccttc gcagtgtagg tgctgattct    4080
ttatcaaaga ggtttgtttt tgttgtcttg tcattttgta gcaggagatc cttattaagg    4140
acaaatgggt agtgcaaatc accatcatga cgtcaaatta gaagtacact tgaataaaaa    4200
agattctgtt ttaataggaa gggagaacta ttaaaatgaa atacacttta aaaatttggt    4260
```

-continued

| | |
|---|---|
| atatatggct gtgtttcttg aggtatcagt gaatcatttt aatgctatat agtgtctata | 4320 |
| tgattgaata taggtataaa aagaatgttg atgagaattc taatttcata tagctaatag | 4380 |
| ttctatacta gacttgagaa gttagcatta ttttaaaact tgtttctgga aatgactttc | 4440 |
| caattttttat tttattttga agcttatttt tgtttcaagg aaaatatgag acaacattaa | 4500 |
| acattagtga caattttttta ttatgtaaat aaaatactta aaagcaccca ttttttgaaaa | 4560 |
| tatttaagaa attgaattat attgcctgag taaaatctat gcagtggatt tagttcacat | 4620 |
| gtttcatagg taagtaagtg gattagaagc attgaataca cacgctttct cagaacttgg | 4680 |
| aagctaagtg gaagttactt taaagactta gcttcactga atttgaacat tttaattttc | 4740 |
| aggaaattaa gctaattaat gatcctgatg gaatagagca gtcatacttt taagatgtgg | 4800 |
| aaatgtcgat gtaatcaaaa tgagaacata tatggacact tgacaaatca tatgctttat | 4860 |
| aatataacag aatttcatag aaaaatgtct ttaatttctc atcaaaatgt attatgtatt | 4920 |
| gtaccctgaa gaaacagatt cttataagcc ctgcctttt ggtgccatct ttgtgactca | 4980 |
| gttatttaat aatacaaaat attcaataaa agccattgcc taactttatt gtttaggctg | 5040 |
| tagttctata cttagaggat gaagtgtaag gtgcaaactt tctgggaaat aatagttgaa | 5100 |
| gccaatatcc aactatgtct gaatgattat caagagttat ctgagctctt tttatggggc | 5160 |
| tattaatttt aatggagcta aatgttcttc aattagtgat aatagaagtg aaaatgtgat | 5220 |
| tgtaaacagt ggttattgaa agttccatct cgtatgaacg ttatctacat gagaataaat | 5280 |
| aaccaagagc tttgtcattc aggactggca gaatcatttg cagcttctag agtatttag | 5340 |
| acaatattca gttggtttta tgatctaaag aactgagtgt gtctatctta gaaccaaggt | 5400 |
| gtat | 5404 |

<210> SEQ ID NO 256
<211> LENGTH: 1597
<212> TYPE: DNA
<213> ORGANISM: Homo sapiens

<400> SEQUENCE: 256

| | |
|---|---|
| cggctgctcg cgagctgctt tctctcctct tcccttccg ggtgcacggc gaggagaaag | 60 |
| tctctatgca actaagcccc ggcgcgcact tggccaggta tgtaccgcgg gagcggcgcg | 120 |
| ttctgcgcgg aagcagatgc tgctgccgcc acggcggcgg cggctgccag ctcctgagct | 180 |
| ctgtaactgt cacactgcac ctgagctgaa cttgaaaaga gagtgaaggg gcgattgggc | 240 |
| gaacgctttt ggcagacaca gagggtgttt gtagacgtgg gggaggagaa tctctattaa | 300 |
| cgccccccac cgtaaccact gcacatcacc tccatctctg caaatacagc ccgaggagta | 360 |
| gaggcagcag cagctggacc cccaaagaga gacgtggggc agcggctgtg accgcatctc | 420 |
| ctgagctaca caacaggtc gcctttttga gactcctttg gcgggaaggg ctacttggaa | 480 |
| aggaaggttt gaaagagtga gaagggtagg tgtaagggtt ccctaattcg tcgaaagaat | 540 |
| tctattgggt gactctcgtt cgtcttctct atcctacact ccacatactg acctatatt | 600 |
| atccagactg tgccggggag aaatcaaaaa cacctgtttg aagaacggc tgcacctgtg | 660 |
| tgcttatttg tgccagaggg tggcctagcc cacctgcagg aagagatttg gctgggttct | 720 |
| gttgagggtg attgttagga cgttgtattt tgttgccatt attccaaata cctgtcttgg | 780 |
| agggaaagtt gccctctga gaactgtgac tttaccagga gccctatctt ggaataagag | 840 |
| ttacacctct ggaccacgtt tctcactagt actttgcttg actggaggaa gtgggtgact | 900 |
| tttggctgct tcggtgaccc attgtagacg cctcgttacc cttcttcctt ccgcttcaag | 960 |

-continued

```
taatcatggc ggcggggtg gcagcgtggc tgccttttgc aagggcagcg gctatcgggt      1020
ggatgcctgt ggcctcgggg cctatgccgg ctcccccgag gcaggagagg aaaaggaccc      1080
aagatgctct cattgtgctg aatgtgagtg gcacccgctt ccagacgtgg caggacaccc      1140
tggaacgtta cccagacact ctactgggca gttctgagag ggacttttc taccacccag       1200 aaactcagca gtatttcttt gaccgtgacc cagacatctt ccgccacatc ctgaatttct      1260
accgcactgg gaagctccac tatcctcgcc acgagtgcat ctctgcttac gatgaagaac      1320
tggccttctt tggcctcatc ccggaaatca tcggcgactg ctgttatgag gagtacaagg      1380
atcgcaggcg agagaacgcc gagcgcctgc aggacgacgc ggataccgac accgctgggg      1440
agagcgcctt gcccaccatg actgcaaggc agagggtctg gagggccttc gagaaccccc      1500
acaccagcac gatggccctg gtgttctact atgtcacggg gttttcatt gccgtctctg       1560 tcatcgcgaa tgtggtggaa acagtgccgt gcggatc                               1597
```

<210> SEQ ID NO 257
<211> LENGTH: 255
<212> TYPE: PRT
<213> ORGANISM: Homo sapiens

<400> SEQUENCE: 257

```
Met Val Pro Lys Thr Ile Ala Gly Lys Ile Phe Gly Ser Ile Cys Ser
                 5                  10                  15

Leu Ser Gly Val Leu Val Ile Ala Leu Pro Val Pro Val Ile Val Ser
             20                  25                  30

Asn Phe Ser Arg Ile Tyr His Gln Asn Gln Arg Ala Asp Lys Arg Arg
         35                  40                  45

Ala Gln Lys Lys Ala Arg Leu Ala Arg Ile Arg Ala Ala Lys Ser Gly
     50                  55                  60

Ser Ala Asn Ala Tyr Met Gln Ser Lys Arg Asn Gly Leu Leu Ser Asn
 65                  70                  75                  80

Gln Leu Gln Ser Ser Glu Asp Glu Gln Ala Phe Val Ser Lys Ser Gly
                 85                  90                  95

Ser Ser Phe Glu Thr Gln His His His Leu Leu His Cys Leu Glu Lys
            100                 105                 110

Thr Thr Asn His Glu Phe Val Asp Glu Gln Val Phe Glu Glu Ser Cys
        115                 120                 125

Met Glu Val Ala Thr Val Asn Arg Pro Ser Ser His Ser Pro Ser Leu
    130                 135                 140

Ser Ser Gln Gln Gly Val Thr Ser Thr Cys Cys Ser Arg Arg His Lys
145                 150                 155                 160

Lys Thr Phe Arg Ile Pro Asn Ala Asn Val Ser Gly Ser His Gln Gly
                165                 170                 175

Ser Ile Gln Glu Leu Ser Thr Ile Gln Ile Arg Cys Val Glu Arg Thr
            180                 185                 190

Pro Leu Ser Asn Ser Arg Ser Ser Leu Asn Ala Lys Met Glu Glu Cys
        195                 200                 205

Val Lys Leu Asn Cys Glu Gln Pro Tyr Val Thr Thr Ala Ile Ile Ser
    210                 215                 220

Ile Pro Thr Pro Pro Val Thr Pro Thr Pro Glu Gly Asp Asp Arg Pro Glu
225                 230                 235                 240

Ser Pro Glu Tyr Ser Gly Gly Asn Ile Val Arg Val Ser Ala Leu
                245                 250                 255
```

-continued

```
<210> SEQ ID NO 258
<211> LENGTH: 630
<212> TYPE: PRT
<213> ORGANISM: Homo sapiens

<400> SEQUENCE: 258
```

| Met | Ala | Ala | Gly | Val | Ala | Ala | Trp | Leu | Pro | Phe | Ala | Arg | Ala | Ala |
|---|---|---|---|---|---|---|---|---|---|---|---|---|---|---|
|  |  |  |  | 5 |  |  |  |  | 10 |  |  |  |  | 15 |

| Ile | Gly | Trp | Met | Pro | Val | Ala | Ser | Gly | Pro | Met | Pro | Ala | Pro | Pro | Arg |
|---|---|---|---|---|---|---|---|---|---|---|---|---|---|---|---|
|  |  |  | 20 |  |  |  |  | 25 |  |  |  |  | 30 |  |  |

| Gln | Glu | Arg | Lys | Arg | Thr | Gln | Asp | Ala | Leu | Ile | Val | Leu | Asn | Val | Ser |
|---|---|---|---|---|---|---|---|---|---|---|---|---|---|---|---|
|  |  | 35 |  |  |  |  | 40 |  |  |  |  | 45 |  |  |  |

| Gly | Thr | Arg | Phe | Gln | Thr | Trp | Gln | Asp | Thr | Leu | Glu | Arg | Tyr | Pro | Asp |
|---|---|---|---|---|---|---|---|---|---|---|---|---|---|---|---|
| 50 |  |  |  |  | 55 |  |  |  |  | 60 |  |  |  |  |  |

| Thr | Leu | Leu | Gly | Ser | Ser | Glu | Arg | Asp | Phe | Phe | Tyr | His | Pro | Glu | Thr |
|---|---|---|---|---|---|---|---|---|---|---|---|---|---|---|---|
| 65 |  |  |  |  | 70 |  |  |  |  | 75 |  |  |  |  | 80 |

| Gln | Gln | Tyr | Phe | Phe | Asp | Arg | Asp | Pro | Asp | Ile | Phe | Arg | His | Ile | Leu |
|---|---|---|---|---|---|---|---|---|---|---|---|---|---|---|---|
|  |  |  |  | 85 |  |  |  |  | 90 |  |  |  |  | 95 |  |

| Asn | Phe | Tyr | Arg | Thr | Gly | Lys | Leu | His | Tyr | Pro | Arg | His | Glu | Cys | Ile |
|---|---|---|---|---|---|---|---|---|---|---|---|---|---|---|---|
|  |  |  | 100 |  |  |  |  | 105 |  |  |  |  | 110 |  |  |

| Ser | Ala | Tyr | Asp | Glu | Glu | Leu | Ala | Phe | Phe | Gly | Leu | Ile | Pro | Glu | Ile |
|---|---|---|---|---|---|---|---|---|---|---|---|---|---|---|---|
|  |  | 115 |  |  |  |  | 120 |  |  |  |  | 125 |  |  |  |

| Ile | Gly | Asp | Cys | Cys | Tyr | Glu | Glu | Tyr | Lys | Asp | Arg | Arg | Arg | Glu | Asn |
|---|---|---|---|---|---|---|---|---|---|---|---|---|---|---|---|
| 130 |  |  |  |  | 135 |  |  |  |  | 140 |  |  |  |  |  |

| Ala | Glu | Arg | Leu | Gln | Asp | Asp | Ala | Asp | Thr | Asp | Thr | Ala | Gly | Glu | Ser |
|---|---|---|---|---|---|---|---|---|---|---|---|---|---|---|---|
| 145 |  |  |  |  | 150 |  |  |  |  | 155 |  |  |  |  | 160 |

| Ala | Leu | Pro | Thr | Met | Thr | Ala | Arg | Gln | Arg | Val | Trp | Arg | Ala | Phe | Glu |
|---|---|---|---|---|---|---|---|---|---|---|---|---|---|---|---|
|  |  |  |  | 165 |  |  |  |  | 170 |  |  |  |  | 175 |  |

| Asn | Pro | His | Thr | Ser | Thr | Met | Ala | Leu | Val | Phe | Tyr | Tyr | Val | Thr | Gly |
|---|---|---|---|---|---|---|---|---|---|---|---|---|---|---|---|
|  |  |  | 180 |  |  |  |  | 185 |  |  |  |  | 190 |  |  |

| Phe | Phe | Ile | Ala | Val | Ser | Val | Ile | Ala | Asn | Val | Val | Glu | Thr | Val | Pro |
|---|---|---|---|---|---|---|---|---|---|---|---|---|---|---|---|
|  |  | 195 |  |  |  |  | 200 |  |  |  |  | 205 |  |  |  |

| Cys | Gly | Ser | Ser | Pro | Gly | His | Ile | Lys | Glu | Leu | Pro | Cys | Gly | Glu | Arg |
|---|---|---|---|---|---|---|---|---|---|---|---|---|---|---|---|
| 210 |  |  |  |  | 215 |  |  |  |  | 220 |  |  |  |  |  |

| Tyr | Ala | Val | Ala | Phe | Phe | Cys | Leu | Asp | Thr | Ala | Cys | Val | Met | Ile | Phe |
|---|---|---|---|---|---|---|---|---|---|---|---|---|---|---|---|
| 225 |  |  |  |  | 230 |  |  |  |  | 235 |  |  |  |  | 240 |

| Thr | Val | Glu | Tyr | Leu | Leu | Arg | Leu | Ala | Ala | Pro | Ser | Arg | Tyr | Arg |
|---|---|---|---|---|---|---|---|---|---|---|---|---|---|---|
|  |  |  |  | 245 |  |  |  |  | 250 |  |  |  |  | 255 |

| Phe | Val | Arg | Ser | Val | Met | Ser | Ile | Ile | Asp | Val | Val | Ala | Ile | Leu | Pro |
|---|---|---|---|---|---|---|---|---|---|---|---|---|---|---|---|
|  |  |  | 260 |  |  |  |  | 265 |  |  |  |  | 270 |  |  |

| Tyr | Tyr | Ile | Gly | Leu | Val | Met | Thr | Asp | Asn | Glu | Asp | Val | Ser | Gly | Ala |
|---|---|---|---|---|---|---|---|---|---|---|---|---|---|---|---|
|  |  | 275 |  |  |  |  | 280 |  |  |  |  | 285 |  |  |  |

| Phe | Val | Thr | Leu | Arg | Val | Phe | Arg | Val | Phe | Arg | Ile | Phe | Lys | Phe | Ser |
|---|---|---|---|---|---|---|---|---|---|---|---|---|---|---|---|
| 290 |  |  |  |  | 295 |  |  |  |  | 300 |  |  |  |  |  |

| Arg | His | Ser | Gln | Gly | Leu | Arg | Ile | Leu | Gly | Tyr | Thr | Leu | Lys | Ser | Cys |
|---|---|---|---|---|---|---|---|---|---|---|---|---|---|---|---|
| 305 |  |  |  |  | 310 |  |  |  |  | 315 |  |  |  |  | 320 |

| Ala | Ser | Glu | Leu | Gly | Phe | Leu | Leu | Phe | Ser | Leu | Thr | Met | Ala | Ile | Ile |
|---|---|---|---|---|---|---|---|---|---|---|---|---|---|---|---|
|  |  |  |  | 325 |  |  |  |  | 330 |  |  |  |  | 335 |  |

| Ile | Phe | Ala | Thr | Val | Met | Phe | Tyr | Ala | Glu | Lys | Gly | Ser | Ser | Ala | Ser |
|---|---|---|---|---|---|---|---|---|---|---|---|---|---|---|---|
|  |  |  | 340 |  |  |  |  | 345 |  |  |  |  | 350 |  |  |

| Lys | Phe | Thr | Ser | Ile | Pro | Ala | Ala | Phe | Trp | Tyr | Thr | Ile | Val | Thr | Met |
|---|---|---|---|---|---|---|---|---|---|---|---|---|---|---|---|
|  |  |  | 355 |  |  |  |  | 360 |  |  |  |  | 365 |  |  |

| Thr | Thr | Leu | Gly | Tyr | Gly | Asp | Met | Val | Pro | Lys | Thr | Ile | Ala | Gly | Lys |
|---|---|---|---|---|---|---|---|---|---|---|---|---|---|---|---|
| 370 |  |  |  |  | 375 |  |  |  |  | 380 |  |  |  |  |  |

| Ile | Phe | Gly | Ser | Ile | Cys | Ser | Leu | Ser | Gly | Val | Leu | Val | Ile | Ala | Leu |

```
            385                 390                 395                 400
Pro Val Pro Val Ile Val Ser Asn Phe Ser Arg Ile Tyr His Gln Asn
                405                 410                 415

Gln Arg Ala Asp Lys Arg Arg Ala Gln Lys Lys Ala Arg Leu Ala Arg
                420                 425                 430

Ile Arg Ala Ala Lys Ser Gly Ser Ala Asn Ala Tyr Met Gln Ser Lys
                435                 440                 445

Arg Asn Gly Leu Leu Ser Asn Gln Leu Gln Ser Glu Asp Glu Gln
                450                 455                 460

Ala Phe Val Ser Lys Ser Gly Ser Ser Phe Glu Thr Gln His His His
465                 470                 475                 480

Leu Leu His Cys Leu Glu Lys Thr Thr Asn His Glu Phe Val Asp Glu
                485                 490                 495

Gln Val Phe Glu Glu Ser Cys Met Glu Val Ala Thr Val Asn Arg Pro
                500                 505                 510

Ser Ser His Ser Pro Ser Leu Ser Ser Gln Gln Gly Val Thr Ser Thr
                515                 520                 525

Cys Cys Ser Arg Arg His Lys Lys Thr Phe Arg Ile Pro Asn Ala Asn
                530                 535                 540

Val Ser Gly Ser His Gln Gly Ser Ile Gln Glu Leu Ser Thr Ile Gln
545                 550                 555                 560

Ile Arg Cys Val Glu Arg Thr Pro Leu Ser Asn Ser Arg Ser Ser Leu
                565                 570                 575

Asn Ala Lys Met Glu Glu Cys Val Lys Leu Asn Cys Glu Gln Pro Tyr
                580                 585                 590

Val Thr Thr Ala Ile Ile Ser Ile Pro Thr Pro Val Thr Thr Pro
                595                 600                 605

Glu Gly Asp Asp Arg Pro Glu Ser Pro Glu Tyr Ser Gly Gly Asn Ile
                610                 615                 620

Val Arg Val Ser Ala Leu
625                 630

<210> SEQ ID NO 259
<211> LENGTH: 630
<212> TYPE: PRT
<213> ORGANISM: Homo sapiens

<400> SEQUENCE: 259

Met Ala Ala Gly Val Ala Ala Trp Leu Pro Phe Ala Arg Ala Ala Ala
                5                   10                  15

Ile Gly Trp Met Pro Val Ala Ser Gly Pro Met Pro Ala Pro Pro Arg
                20                  25                  30

Gln Glu Arg Lys Arg Thr Gln Asp Ala Leu Ile Val Leu Asn Val Ser
                35                  40                  45

Gly Thr Arg Phe Gln Thr Trp Gln Asp Thr Leu Glu Arg Tyr Pro Asp
                50                  55                  60

Thr Leu Leu Gly Ser Ser Glu Arg Asp Phe Phe Tyr His Pro Glu Thr
65                  70                  75                  80

Gln Gln Tyr Phe Phe Asp Arg Asp Pro Asp Ile Phe Arg His Ile Leu
                85                  90                  95

Asn Phe Tyr Arg Thr Gly Lys Leu His Tyr Pro Arg His Glu Cys Ile
                100                 105                 110

Ser Ala Tyr Asp Glu Glu Leu Ala Phe Phe Gly Leu Ile Pro Glu Ile
                115                 120                 125

Ile Gly Asp Cys Cys Tyr Glu Glu Tyr Lys Asp Arg Arg Arg Glu Asn
```

```
              130                 135                 140
Ala Glu Arg Leu Gln Asp Asp Ala Asp Thr Thr Ala Gly Glu Ser
145                 150                 155                 160

Ala Leu Pro Thr Met Thr Ala Arg Gln Arg Val Trp Arg Ala Phe Glu
                165                 170                 175

Asn Pro His Thr Ser Thr Met Ala Leu Val Phe Tyr Val Thr Gly
                180                 185                 190

Phe Phe Ile Ala Val Ser Val Ile Ala Asn Val Val Glu Thr Val Pro
            195                 200                 205

Cys Gly Ser Ser Pro Gly His Ile Lys Glu Leu Pro Cys Gly Glu Arg
210                 215                 220

Tyr Ala Val Ala Phe Phe Cys Leu Asp Thr Ala Cys Val Met Ile Phe
225                 230                 235                 240

Thr Val Glu Tyr Leu Leu Arg Leu Ala Ala Pro Ser Arg Tyr Arg
                245                 250                 255

Phe Val Arg Ser Val Met Ser Ile Ile Asp Val Val Ala Ile Leu Pro
                260                 265                 270

Tyr Tyr Ile Gly Leu Val Met Thr Asp Asn Glu Asp Val Ser Gly Ala
            275                 280                 285

Phe Val Thr Leu Arg Val Phe Arg Val Phe Arg Ile Phe Lys Phe Ser
290                 295                 300

Arg His Ser Gln Gly Leu Arg Ile Leu Gly Tyr Thr Leu Lys Ser Cys
305                 310                 315                 320

Ala Ser Glu Leu Gly Phe Leu Leu Phe Ser Leu Thr Met Ala Ile Ile
                325                 330                 335

Ile Phe Ala Thr Val Met Phe Tyr Ala Glu Lys Gly Ser Ser Ala Ser
            340                 345                 350

Lys Phe Thr Ser Ile Pro Ala Ala Phe Trp Tyr Thr Ile Val Thr Met
                355                 360                 365

Thr Thr Leu Gly Tyr Gly Asp Met Val Pro Lys Thr Ile Ala Gly Lys
            370                 375                 380

Ile Phe Gly Ser Ile Cys Ser Leu Ser Gly Val Leu Val Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Arg Ala Gln Lys Lys Ala Arg Leu Ala Arg
                420                 425                 430

Ile Arg Ala Ala Lys Ser Gly Ser Ala Asn Ala Tyr Met Gln Ser Lys
            435                 440                 445

Arg Asn Gly Leu Leu Ser Asn Gln Leu Gln Ser Ser Glu Asp Glu Gln
450                 455                 460

Ala Phe Val Ser Lys Ser Gly Ser Ser Phe Glu Thr Gln His His His
465                 470                 475                 480

Leu Leu His Cys Leu Glu Lys Thr Thr Asn His Glu Phe Val Asp Glu
                485                 490                 495

Gln Val Phe Glu Glu Ser Cys Met Glu Val Ala Thr Val Asn Arg Pro
                500                 505                 510

Ser Ser His Ser Pro Ser Leu Ser Ser Gln Gln Gly Val Thr Ser Thr
            515                 520                 525

Cys Cys Ser Arg Arg His Lys Lys Thr Phe Arg Ile Pro Asn Ala Asn
530                 535                 540

Val Ser Gly Ser His Gln Gly Ser Ile Gln Glu Leu Ser Thr Ile Gln
545                 550                 555                 560
```

```
Ile Arg Cys Val Glu Arg Thr Pro Leu Ser Asn Ser Arg Ser Ser Leu
            565                 570                 575

Asn Ala Lys Met Glu Glu Cys Val Lys Leu Asn Cys Glu Gln Pro Tyr
            580                 585                 590

Val Thr Thr Ala Ile Ile Ser Ile Pro Thr Pro Pro Val Thr Thr Pro
            595                 600                 605

Glu Gly Asp Asp Arg Pro Glu Ser Pro Glu Tyr Ser Gly Gly Asn Ile
            610                 615                 620

Val Arg Val Ser Ala Leu
625             630

<210> SEQ ID NO 260
<211> LENGTH: 630
<212> TYPE: PRT
<213> ORGANISM: Homo sapiens

<400> SEQUENCE: 260

Met Ala Ala Gly Val Ala Ala Trp Leu Pro Phe Ala Arg Ala Ala Ala
                 5                  10                  15

Ile Gly Trp Met Pro Val Ala Ser Gly Pro Met Pro Ala Pro Pro Arg
            20                  25                  30

Gln Glu Arg Lys Arg Thr Gln Asp Ala Leu Ile Val Leu Asn Val Ser
        35                  40                  45

Gly Thr Arg Phe Gln Thr Trp Gln Asp Thr Leu Glu Arg Tyr Pro Asp
    50                  55                  60

Thr Leu Leu Gly Ser Ser Glu Arg Asp Phe Phe Tyr His Pro Glu Thr
65                  70                  75                  80

Gln Gln Tyr Phe Phe Asp Arg Asp Pro Asp Ile Phe Arg His Ile Leu
                85                  90                  95

Asn Phe Tyr Arg Thr Gly Lys Leu His Tyr Pro Arg His Glu Cys Ile
            100                 105                 110

Ser Ala Tyr Asp Glu Glu Leu Ala Phe Phe Gly Leu Ile Pro Glu Ile
        115                 120                 125

Ile Gly Asp Cys Cys Tyr Glu Glu Tyr Lys Asp Arg Arg Arg Glu Asn
    130                 135                 140

Ala Glu Arg Leu Gln Asp Asp Ala Asp Thr Asp Thr Ala Gly Glu Ser
145                 150                 155                 160

Ala Leu Pro Thr Met Thr Ala Arg Gln Arg Val Trp Arg Ala Phe Glu
                165                 170                 175

Asn Pro His Thr Ser Thr Met Ala Leu Val Phe Tyr Tyr Val Thr Gly
            180                 185                 190

Phe Phe Ile Ala Val Ser Val Ile Ala Asn Val Val Glu Thr Val Pro
        195                 200                 205

Cys Gly Ser Ser Pro Gly His Ile Lys Glu Leu Pro Cys Gly Glu Arg
    210                 215                 220

Tyr Ala Val Ala Phe Phe Cys Leu Asp Thr Ala Cys Val Met Ile Phe
225                 230                 235                 240

Thr Val Glu Tyr Leu Leu Arg Leu Ala Ala Ala Pro Ser Arg Tyr Arg
                245                 250                 255

Phe Val Arg Ser Val Met Ser Ile Ile Asp Val Val Ala Ile Leu Pro
            260                 265                 270

Tyr Tyr Ile Gly Leu Val Met Thr Asp Asn Glu Asp Val Ser Gly Ala
        275                 280                 285

Phe Val Thr Leu Arg Val Phe Arg Val Phe Arg Ile Phe Lys Phe Ser
    290                 295                 300
```

```
Arg His Ser Gln Gly Leu Arg Ile Leu Gly Tyr Thr Leu Lys Ser Cys
305                 310                 315                 320

Ala Ser Glu Leu Gly Phe Leu Leu Phe Ser Leu Thr Met Ala Ile Ile
                325                 330                 335

Ile Phe Ala Thr Val Met Phe Tyr Ala Glu Lys Gly Ser Ser Ala Ser
            340                 345                 350

Lys Phe Thr Ser Ile Pro Ala Ala Phe Trp Tyr Thr Ile Val Thr Met
        355                 360                 365

Thr Thr Leu Gly Tyr Gly Asp Met Val Pro Lys Thr Ile Ala Gly Lys
    370                 375                 380

Ile Phe Gly Ser Ile Cys Ser Leu Ser Gly Val Leu Val Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Arg Ala Gln Lys Lys Ala Arg Leu Ala Arg
                420                 425                 430

Ile Arg Ala Ala Lys Ser Gly Ser Ala Asn Ala Tyr Met Gln Ser Lys
            435                 440                 445

Arg Asn Gly Leu Leu Ser Asn Gln Leu Gln Ser Ser Glu Asp Glu Gln
        450                 455                 460

Ala Phe Val Ser Lys Ser Gly Ser Ser Phe Glu Thr Gln His His His
465                 470                 475                 480

Leu Leu His Cys Leu Glu Lys Thr Thr Asn His Glu Phe Val Asp Glu
                485                 490                 495

Gln Val Phe Glu Glu Ser Cys Met Glu Val Ala Thr Val Asn Arg Pro
                500                 505                 510

Ser Ser His Ser Pro Ser Leu Ser Ser Gln Gln Gly Val Thr Ser Thr
            515                 520                 525

Cys Cys Ser Arg Arg His Lys Lys Thr Phe Arg Ile Pro Asn Ala Asn
        530                 535                 540

Val Ser Gly Ser His Gln Gly Ser Ile Gln Glu Leu Ser Thr Ile Gln
545                 550                 555                 560

Ile Arg Cys Val Glu Arg Thr Pro Leu Ser Asn Ser Arg Ser Ser Leu
                565                 570                 575

Asn Ala Lys Met Glu Glu Cys Val Lys Leu Asn Cys Glu Gln Pro Tyr
                580                 585                 590

Val Thr Thr Ala Ile Ile Ser Ile Pro Thr Pro Pro Val Thr Thr Pro
            595                 600                 605

Glu Gly Asp Asp Arg Pro Glu Ser Pro Glu Tyr Ser Gly Gly Asn Ile
        610                 615                 620

Val Arg Val Ser Ala Leu
625                 630

<210> SEQ ID NO 261
<211> LENGTH: 630
<212> TYPE: PRT
<213> ORGANISM: Homo sapiens

<400> SEQUENCE: 261

Met Ala Ala Gly Val Ala Ala Trp Leu Pro Phe Ala Arg Ala Ala Ala
                5                   10                  15

Ile Gly Trp Met Pro Val Ala Ser Gly Pro Met Pro Ala Pro Pro Arg
            20                  25                  30

Gln Glu Arg Lys Arg Thr Gln Asp Ala Leu Ile Val Leu Asn Val Ser
        35                  40                  45
```

-continued

```
Gly Thr Arg Phe Gln Thr Trp Gln Asp Thr Leu Glu Arg Tyr Pro Asp
 50                  55                  60

Thr Leu Leu Gly Ser Ser Glu Arg Asp Phe Phe Tyr His Pro Glu Thr
 65                  70                  75                  80

Gln Gln Tyr Phe Phe Asp Arg Asp Pro Asp Ile Phe Arg His Ile Leu
                 85                  90                  95

Asn Phe Tyr Arg Thr Gly Lys Leu His Tyr Pro Arg His Glu Cys Ile
                100                 105                 110

Ser Ala Tyr Asp Glu Glu Leu Ala Phe Phe Gly Leu Ile Pro Glu Ile
                115                 120                 125

Ile Gly Asp Cys Cys Tyr Glu Glu Tyr Lys Asp Arg Arg Arg Glu Asn
130                 135                 140

Ala Glu Arg Leu Gln Asp Asp Ala Asp Thr Asp Thr Ala Gly Glu Ser
145                 150                 155                 160

Ala Leu Pro Thr Met Thr Ala Arg Gln Arg Val Trp Arg Ala Phe Glu
                165                 170                 175

Asn Pro His Thr Ser Thr Met Ala Leu Val Phe Tyr Tyr Val Thr Gly
                180                 185                 190

Phe Phe Ile Ala Val Ser Val Ile Ala Asn Val Val Glu Thr Val Pro
                195                 200                 205

Cys Gly Ser Ser Pro Gly His Ile Lys Glu Leu Pro Cys Gly Glu Arg
210                 215                 220

Tyr Ala Val Ala Phe Phe Cys Leu Asp Thr Ala Cys Val Met Ile Phe
225                 230                 235                 240

Thr Val Glu Tyr Leu Leu Arg Leu Ala Ala Ala Pro Ser Arg Tyr Arg
                245                 250                 255

Phe Val Arg Ser Val Met Ser Ile Ile Asp Val Val Ala Ile Leu Pro
                260                 265                 270

Tyr Tyr Ile Gly Leu Val Met Thr Asp Asn Glu Asp Val Ser Gly Ala
                275                 280                 285

Phe Val Thr Leu Arg Val Phe Arg Val Phe Arg Ile Phe Lys Phe Ser
                290                 295                 300

Arg His Ser Gln Gly Leu Arg Ile Leu Gly Tyr Thr Leu Lys Ser Cys
305                 310                 315                 320

Ala Ser Glu Leu Gly Phe Leu Leu Phe Ser Leu Thr Met Ala Ile Ile
                325                 330                 335

Ile Phe Ala Thr Val Met Phe Tyr Ala Glu Lys Gly Ser Ser Ala Ser
                340                 345                 350

Lys Phe Thr Ser Ile Pro Ala Ala Phe Trp Tyr Thr Ile Val Thr Met
                355                 360                 365

Thr Thr Leu Gly Tyr Gly Asp Met Val Pro Lys Thr Ile Ala Gly Lys
                370                 375                 380

Ile Phe Gly Ser Ile Cys Ser Leu Ser Gly Val Leu Val Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Arg Ala Gln Lys Lys Ala Arg Leu Ala Arg
                420                 425                 430

Ile Arg Ala Ala Lys Ser Gly Ser Ala Asn Ala Tyr Met Gln Ser Lys
                435                 440                 445

Arg Asn Gly Leu Leu Ser Asn Gln Leu Gln Ser Ser Glu Asp Glu Gln
450                 455                 460

Ala Phe Val Ser Lys Ser Gly Ser Ser Phe Glu Thr Gln His His His
465                 470                 475                 480
```

```
Leu Leu His Cys Leu Glu Lys Thr Thr Asn His Glu Phe Val Asp Glu
            485                 490                 495
Gln Val Phe Glu Glu Ser Cys Met Glu Val Ala Thr Val Asn Arg Pro
        500                 505                 510
Ser Ser His Ser Pro Ser Leu Ser Gln Gln Gly Val Thr Ser Thr
    515                 520                 525
Cys Cys Ser Arg Arg His Lys Lys Thr Phe Arg Ile Pro Asn Ala Asn
530                 535                 540
Val Ser Gly Ser His Gln Gly Ser Ile Gln Glu Leu Ser Thr Ile Gln
545                 550                 555                 560
Ile Arg Cys Val Glu Arg Thr Pro Leu Ser Asn Ser Arg Ser Leu
                565                 570                 575
Asn Ala Lys Met Glu Glu Cys Val Lys Leu Asn Cys Glu Gln Pro Tyr
                580                 585                 590
Val Thr Thr Ala Ile Ile Ser Ile Pro Thr Pro Pro Val Thr Thr Pro
                595                 600                 605
Glu Gly Asp Asp Arg Pro Glu Ser Pro Glu Tyr Ser Gly Gly Asn Ile
    610                 615                 620
Val Arg Val Ser Ala Leu
625                 630

<210> SEQ ID NO 262
<211> LENGTH: 2707
<212> TYPE: DNA
<213> ORGANISM: Homo sapiens

<400> SEQUENCE: 262
```

| | | | | |
|---|---|---|---|---|
| ggcaggccga gccagccgtg cgccgcgctc cagggcccag ggcgccgcac acgcacccac | 60 |
| ccacccaccc agcctcgcag cgccatgggc aagaacaagc agccacgcgg ccagcagagg | 120 |
| caggggggcc cgccggccgc ggacgccgct gggcccgacg acatggagcc gaagaagggc | 180 |
| acggggggccc ccaaggagtg cggggaggag gagccccgga cctgctgcgg ctgccggttc | 240 |
| ccgctgctgc tcgccctgct gcagctggcc ctgggcatcg ccgtgaccgt ggtgggcttc | 300 |
| ctcatggcga gcatcagctc ctccctgcta gtcagggaca ctccattttg ggctgggatc | 360 |
| attgtctgct tagtggccta tcttggcttg tttatgcttt gtgtctcata tcaggttgac | 420 |
| gaacggacat gtattcaatt ttctatgaaa ctgttatact ttctgctgag tgccctgggc | 480 |
| ctgacggtct gtgtgctggc cgtggccttt gccgccacc actattcgca gctcacacag | 540 |
| tttacctgtg agaccacact cgactcttgc cagtgcaaac tgccctcctc ggagccgctc | 600 |
| agcaggacct tgttttaccg ggatgtgacg gactgtacca gcgtcactgg cactttcaaa | 660 |
| ctgttcttac tcatccagat gattcttaat ttggtctgcg gccttgtgtg cttgttggcc | 720 |
| tgctttgtga tgtggaaaca taggtaccag gtcttctatg tgggtgtcag gatatgctcc | 780 |
| ctcacggctt ccgaaggccc ccagcaaaag atctaacatt cttgctcaaa gttgcgagag | 840 |
| aaagtagcac atggagtagc tgaggttaaa caaacaaaaa aaaattttaa acaaagaaag | 900 |
| gaaaaaaatt gacaataaaa gtcactcttc taattgaata ttttatatt tttatgaaac | 960 |
| aaaagagcat ttcttcaggt ttctattgta ttttttttaa cattcttgca gagaaagcaa | 1020 |
| gatccaaatt gattttggga tattaaaagt taacagaaca ctgaacaagg aaagaatggc | 1080 |
| atagatctat ctttacagtc tggagttaat tcctgttaac tcattttatc cattccttac | 1140 |
| ataatcttct ttcctgttag tccagtttga tggtgtgaat ggtgaatttc aggcccagtt | 1200 |
| gctaaatttt gtggcatctt cctctagtcc ttcccacctc cagtcatcag ccccactctg | 1260 |

```
tcttggagac aggcaggagg tgggggaaga gctgaatctc tttatttcc ctggtagaga      1320 catcttcaag gcatgaaata gcttaaagag cagagtagaa atggaagagg ctttgcaaaa      1380
ggctagataa ctaacaacac ctgggttggg gcggcggcct cttctcttca gctcccttag      1440
cttggctccg taagtggatc acttgccaaa tgctttagat gattgcctct caataattga      1500
aaggtggtgg tagttgtatt ctaaatgatg tagaaggttt aaaaataatt acattatgct      1560
tctattctat catctaaaac aaatcattaa aactaatttc tagctaattg ttaattataa      1620
ttatgctcag aagtctattt aatgagctct gactgtactt acgctgcact gtcggtgtta      1680
agagaaatta ctctcacaag agcagaggcc tgaagattct ttcttctgaa agccaagcac      1740
cacaaggaaa aaaaaattat taatagctca ggttaaaaac acccatttaa acaaaaacaa      1800
gagcatttgt aataggaagt gtttatacaa acagcacatt tgtgatatgt tgaaaagcat      1860
ctctcttggc aaccaatcta tgtttgagga agattgggta atgctgatgt gttccattca      1920
tgaaactgta tttgatacat aatcctatta ttaattcgta tgcttagtca acctaggaaa      1980 tcaaataat gttttgaagt tcttatttga gcaatatggc cttgacttgg agggtagttt      2040
tagttgtttt gttttaagt gactgtggtt taaagcacaa atgccccaag gtggggagac      2100
ttctctctgt gattattgtt gctattaaat tctgaactgt atccatattt taaggaagga      2160
gctaaaaatg gaaattcatg aaacataaat ggtatcaaga actttatcag tatgctttgt      2220
tgaaagcaga aattaagata ataattgagt tcaattcgcc tctccgcatt gcctattgat      2280
acactttact aatcatgaaa ttctaaccta aaaggaaaac attttcctgc ttgtcttaga      2340
agaaagtgga ataattccac tgattgtgat aatggtttca atttctacac aatataaata      2400
tccagtataa aggaaagcgt taagtcggta agctagagga ttgtaaatat cttttatgtc      2460
ctctagataa acacccgat taacagatgt taaaccttt aatgttttga tttgctttaa      2520
aaatggcctt cctacacatt agctccagct aaaaagacac attggagagc ttagaggata      2580
agtctctgga gcagaattta tcacacacaa aagttacacc aacagaatac caagcagaat      2640
gatgaggacc tgtaaaatac cttgtgccct attaaaaaaa aaaaaaaaaa aaaaaaaaa      2700 aaaaaaa                                                                2707
```

<210> SEQ ID NO 263
<211> LENGTH: 2707
<212> TYPE: DNA
<213> ORGANISM: Homo sapiens

<400> SEQUENCE: 263

```
ggcaggccga gccagccgtg cgccgcgctc cagggcccag ggcgccgcac acgcacccac        60
ccacccaccc agcctcgcag cgccatgggc aagaacaagc agccacgcgg ccagcagagg       120
caggggggcc cgccggccgc ggacgccgct gggccccgacg acatggagcc gaagaagggc       180 acggggggccc ccaaggagtg cggggaggag gagccccgga cctgctgcgg ctgccggttc       240
ccgctgctgc tcgccctgct gcagctggcc ctgggcatcg ccgtgaccgt ggtgggcttc       300
ctcatggcga gcatcagctc ctccctgcta gtcagggaca ctccatttg ggctgggatc       360 attgtctgct tagtggccta tcttggcttg tttatgcttt gtgtctcata tcaggttgac       420
gaacggacat gtattcaatt ttctatgaaa ctgttatact ttctgctgag tgccctgggc       480
ctgacggtct gtgtgctggc cgtggccttt gccgcccacc actattcgca gctcacacag       540
tttacctgtg agaccacact cgactcttgc cagtgcaaac tgcccctcctc ggagccgctc       600 agcaggacct tgtttaccg ggatgtgacg gactgtacca gcgtcactgg cactttcaaa       660
```

```
ctgttcttac tcatccagat gattcttaat ttggtctgcg gccttgtgtg cttgttggcc      720
tgctttgtga tgtggaaaca taggtaccag gtcttctatg tgggtgtcag gatatgctcc      780
ctcacggctt ccgaaggccc ccagcaaaag atctaacatt cttgctcaaa gttgcgagag      840
aaagtagcac atggagtagc tgaggttaaa caaacaaaaa aaattttaa acaaagaaag       900 gaaaaaatt gacaataaaa gtcactcttc taattgaata tttttatatt tttatgaaac       960
aaaagagcat ttcttcaggt ttctattgta tttttttaa cattcttgca gagaaagcaa      1020
gatccaaatt gattttggga tattaaaagt taacagaaca ctgaacaagg aaagaatggc     1080
atagatctat ctttacagtc tggagttaat tcctgttaac tcattttatc cattccttac     1140
ataatcttct ttcctgttag tccagtttga tggtgtgaat ggtgaatttc aggcccagtt     1200
gctaaatttt gtggcatctt cctctagtcc ttcccacctc cagtcatcag ccccactctg     1260
tcttggagac aggcaggagg tgggggaaga gctgaatctc tttattttcc ctggtagaga     1320
catcttcaag gcatgaaata gcttaaagag cagagtagaa atggaagagg ctttgcaaaa     1380
ggctagataa ctaacaacac ctgggttggg gcggcggcct cttctcttca gctcccttag     1440
cttggctccg taagtggatc acttgccaaa tgctttagat gattgcctct caataattga     1500
aaggtggtgg tagttgtatt ctaaatgatg tagaaggttt aaaaataatt acattatgct     1560
tctattctat catctaaaac aaatcattaa aactaaattc tagctaattg ttaattataa     1620
ttatgctcag aagtctattt aatgagctct gactgtactt acgctgcact gtcggtgtta     1680
agagaaatta ctctcacaag agcagaggcc tgaagattct ttcttctgaa agccaagcac     1740
cacaaggaaa aaaaaattat taatagctca ggttaaaaac acccatttaa acaaaaacaa     1800
gagcatttgt aataggaagt gtttatacaa acagcacatt tgtgatatgt tgaaaagcat     1860
ctctcttggc aaccaatcta tgtttgagga agattgggta atgctgatgt gttccattca     1920
tgaaactgta tttgatacat aatcctatta ttaattcgta tgcttagtca acctaggaaa     1980
tcaaaataat gttttgaagt tcttatttga gcaatatggc cttgacttgg agggtagttt     2040
tagttgtttt gtttttaagt gactgtggtt taaagcacaa atgccccaag gtggggagac     2100
ttctctctgt gattattgtt gctattaaat tctgaactgt atccatattt taaggaagga     2160
gctaaaaatg gaaattcatg aaacataaat ggtatcaaga actttatcag tatgctttgt     2220
tgaaagcaga aattaagata ataattgagt tcaattcgcc tctccgcatt gcctattgat     2280
acactttact aatcatgaaa ttctaaccta aaaggaaaac attttcctgc ttgtcttaga     2340
agaaagtgga ataattccac tgattgtgat aatggtttca atttctacac aatataaata     2400
tccagtataa aggaaagcgt taagtcggta agctagagga ttgtaaatat ctttatgtc      2460 ctctagataa aacacccgat taacagatgt taaaccttt aatgttttga tttgctttaa      2520
aaatggcctt cctacacatt agctccagct aaaaagacac attggagagc ttagaggata     2580
agtctctgga gcagaattta tcacacacaa aagttacacc aacagaatac caagcagaat     2640
gatgaggacc tgtaaaatac cttgtgccct attaaaaaaa aaaaaaaaa aaaaaaaaa      2700 aaaaaaa                                                              2707

<210> SEQ ID NO 264
<211> LENGTH: 732
<212> TYPE: DNA
<213> ORGANISM: Homo sapiens

<400> SEQUENCE: 264
atgggcaaga acaagcagcc acgcggccag cagaggcagg ggggcccgcc ggccgcggac       60
```

```
gccgctgggc cgacgacat ggagccgaag aagggcacgg gggcccccaa ggagtgcggg      120
gaggaggagc cccggacctg ctgcggctgc cggttcccgc tgctgctcgc cctgctgcag      180
ctggccctgg gcatcgccgt gaccgtggtg ggcttcctca tggcgagcat cagctcctcc      240
ctgctagtca gggacactcc attttgggct gggatcattg tctgcttagt ggcctatctt      300
ggcttgttta tgctttgtgt ctcatatcag gttgacgaac ggacatgtat tcaattttct      360
atgaaactgt tatactttct gctgagtgcc ctgggctga cggtctgtgt gctggccgtg      420
gcctttgccg cccaccacta ttcgcagctc acacagttta cctgtgagac cacactcgac      480
tcttgccagt gcaaactgcc ctcctcggag ccgctcagca ggacctttgt ttaccgggat      540
gtgacggact gtaccagcgt cactggcact ttcaaactgt tcttactcat ccagatgatt      600
cttaatttgg tctgcggcct tgtgtgcttg ttggcctgct tgtgatgtg gaaacatagg      660 taccaggtct tctatgtggg tgtcaggata tgctccctca cggcttccga aggccccag       720 caaaagatct aa                                                          732

<210> SEQ ID NO 265
<211> LENGTH: 681
<212> TYPE: DNA
<213> ORGANISM: Homo sapiens

<400> SEQUENCE: 265
atggagccga agaagggcac ggggggcccc aaggagtgcg ggaggaggga gccccggacc      60
tgctgcggct gccggttccc gctgctgctc gccctgctgc agctggccct gggcatcgcc      120
gtgaccgtgg tgggcttcct catggcgagc atcagctcct ccctgctagt cagggacact      180
ccattttggg ctgggatcat tgtctgctta gtggcctatc ttggcttgtt tatgctttgt      240
gtctcatatc aggttgacga acggacatgt attcaatttt ctatgaaact gttatacttt      300
ctgctgagtg ccctgggcct gacggtctgt gtgctggccg tggcctttgc cgcccaccac      360
tattcgcagc tcacacagtt tacctgtgag accacactcg actcttgcca gtgcaaactg      420
ccctcctcgg agccgctcag caggaccttt gtttaccggg atgtgacgga ctgtaccagc      480
gtcactggca ctttcaaact gttcttactc atccagatga ttcttaattt ggtctgcggc      540
cttgtgtgct gttggcctg cttttgtgatg tggaaacata ggtaccaggt cttctatgtg      600
ggtgtcagga tatgctccct cacggcttcc gaaggccccc agcaaaagat ctaacattct      660
tgctcaaagt tgcgagagaa a                                                681

<210> SEQ ID NO 266
<211> LENGTH: 1502
<212> TYPE: DNA
<213> ORGANISM: Homo sapiens

<400> SEQUENCE: 266
gtgaatttca ggcccagttg ctaaattttg tggcatcttc ctctagtcct tcccacctcc      60
agtcatcagc cccactctgt cttggagaca ggcaggaggt gggggaagag ctgaatctct      120
ttattttccc tggtagagac atcttcaagg catgaaatag cttaaagagc agagtagaaa      180
cggaagaggc tttgcaaaag gctagataac taacaacacc tgggttgggg cggcggcctc      240
ttctcttcag ctcccttagc ttggctccgt aagtggatca cttgccaaat gctttagatg      300
attgcctctc aataattgaa aggtggtggt agttgtattc taaatgatgt agaaggttta      360 aaataatta cattatgctt ctattctatc atctaaaaca aatcattaaa actaatttct      420
agctaattgt taattataat tatgctcaga agtctattta atgagctctg actgtactta      480
```

```
cgctgcactg tcggtgttaa gagaaattac tctcacaaga gcagaggcct gaagattctt      540
tcttctgaaa gccaagcacc acaaggaaaa acaaattatt aatagctcag gttaaaaaca      600
cccatttaaa caaaaacaag agcatttgta ataggaagtg tttatacaaa tagcacattt      660
gtgatatgtt gaaaagcatc tctcttggca accaatctat gtttgaggaa gattgggtaa      720
tgctgatgtg ttccattcat gaaactgtat ttgatacata atcctattat taattcgtat      780
gcttagtcaa cctaggaaat caaaataatg ttttgaagtt cttatttgag caatatggcc      840
ttgacttgga gggtagtttt agttgttttg tttttaagtg actgtggttt aaagcacaaa      900
tgccccaagg tggggagact tctctctgtg attattgttg ctattaaatt ctgaactgta      960
tccatatttt aaggaaggag ctaaaaatgg aaattcatga acataaatg gtatcaagaa      1020 ctttatcagt atgctttgtt gaaagcagaa attaagataa taattgagtt caattcgcct     1080
ctccgcattg cctattgata cactttacta atcatgaaat tctaacctaa aaggaaaaca     1140
ttttcctgct tgtcttagaa gaaagtggaa taattccact gattgtgata atggtttcaa     1200
tttctacaca atataaatat ccagtataaa ggaaagcgtt aagtcggtaa gctagaggat     1260
tgtaaatatc tttatgtcc tctagataaa acacccgatt aacagatgtt aaacctttta      1320
atgttttgat ttgctttaaa aatggccttc ctacacatta gctccagcta aaaagacaca     1380
ttggagagct tagaggataa gtctctggag cagaatttat cacacacaaa agttacacca     1440
acagaatacc aagcagaatg atgaggacct gtaaaatacc ttgtgcccta ttaaaaaaaa     1500
aa                                                                    1502

<210> SEQ ID NO 267
<211> LENGTH: 4013
<212> TYPE: DNA
<213> ORGANISM: Homo sapiens

<400> SEQUENCE: 267
tgtgtggaac acactcattt ggaggacttt tgtacacata ttttgtagtg tcacatatat       60
gttttaattt tgaattatat ataagggaag gtggggaag gcatcatct tctcagagct        120 actttcctct gaacctggaa atgactggaa ctaatattac tttgtgaagt gtccatttac      180
cagaattgtt ctctgtagag agcaacttt gactgtggta atgtaattct tgcactaaga      240
actatgtgta ctagtctcaa aagctgggga ctctgagcct tacctagagt ctcagcaggt     300
ggaccattaa gattaacatt tctagtaggt gagttcaatc acaaaaatat ttcttgttcc      360 atagattta ttgtggccat gtcagtgaac acccacaagt tttgctcaga atattttagg      420
tgtaagctaa atccctaaat tgttcagagt tcccacagcc ctgtagcagc agagcgagaa     480
ctttaaccag acttttttcaa tcccaaagct aatctggagg ccaacagtgt tcaaaacctt    540
ggtgactgag gaaccattta gagtttttc aggctcagga atcacatggt cgttgttggg     600 cttgggtaa gtttcacagg cgatgaagct gacgttgagt cacttgactt ctggagccat     660
aatttatttt ctcccagcaa cctcctactg gggattctca tgtttatgga tacagtttgg    720
caatcactac attgaatgta gtcttttaaa aaaattaact tatgctatta gttgacccat     780
cattgctaat tttggcccac acagtgtttg cattacaaaa acctgttctt tacttcctag     840
tcttgtttca gtcttaatat cagaagttct tgagttcaaa ataagcacaa catgtcatcc    900
agggatggct agcttgtttg ggattcatct aaactgctgg caatatctag acaaaaacat    960
tccacagtcc agctaatatg gttgtcacaa ctcttgaaaa gggcccaaca tctgatggc     1020 aagtgaaaat gtgatcaggg tttaagaact acccactaat aaataaacat ggagctattt   1080
```

```
ccatgtcttg ggtgttgtgt ttctaagaag agacagcctt tccatcagaa aatttctggg   1140
agggaagaaa aagaacagtt ttgatgaatt cgctttgcaa atcatcatcc aatgttcttt   1200
gtaaccagaa aggttttctt ctgctttctt gcagctgtta tactttctgc tgagtgccct   1260
gggcctgacg gtctgtgtgc tggccgtggc ctttgccgcc caccactatt cgcagctcac   1320
acagtttacc tgtgagacca cactcgactc ttgccagtgc aaactgccct cctcggagcc   1380
gctcagcagg acctttgttt accgggatgt gacggactgt accagcgtca ctggcacttt   1440
caaactgttc ttactcatcc agatgattct taatttggtc tgcggccttg tgtgcttgtt   1500
ggcctgcttt gtgatgtgga acataggta ccaggtcttc tatgtgggtg tcaggatatg    1560
ctccctcacg gcttccgaag gcccccagca aagatctaa cattcttgct caaagttgcg    1620
agagaaagta gcacatggag tagctgaggt taaacaaaca aaaaaaaatt ttaaacaaag    1680
aaaggaaaaa aattgacaat aaaagtcact cttctaattg aatattttta tattttatg    1740 aaacaaaaga gcatttcttc aggtttctat tgtattttt ttaacattct tgcagagaaa    1800
gcaagatcca aattgatttt gggatattaa aagttaacag aacactgaac aaggaaagaa   1860
tggcatagat ctatctttac agtctggagt taattcctgt taactcattt tatccattcc   1920
ttacataatc ttctttcctg ttagtccagt ttgatggtgt gaatggtgaa tttcaggccc   1980
agttgctaaa ttttgtggca tcttcctcta gtccttccca cctccagtca tcagccccac   2040
tctgtcttgg agacaggcag gaggtggggg aagagctgaa tctctttatt ttccctggta   2100
gagacatctt caaggcatga aatagcttaa agagcagagt agaaacggaa gaggctttgc   2160
aaaaggctag ataactaaca acacctgggt tggggcggcg gcctcttctc ttcagctccc   2220
ttagcttggc tccgtaagtg gatcacttgc caaatgcttt agatgattgc ctctcaataa   2280
ttgaaaggtg gtggtagttg tattctaaat gatgtagaag gtttaaaaat aattacatta   2340
tgcttctatt ctatcatcta aaacaaatca ttaaaactaa tttctagcta attgttaatt   2400
ataattatgc tcagaagtct atttaatgag ctctgactgt acttacgctg cactgtcggt   2460
gttaagagaa attactctca caagagcaga ggcctgaaga ttctttcttc tgaaagccaa   2520
gcaccacaag gaaaaaaaaa attattaata gctcaggtta aaaacaccca tttaaacaaa   2580
aacaagagca tttgtaatag gaagtgttta tacaaacagc acatttgtga tatgttgaaa   2640
agcatctctc ttggcaacca atctatgttt gaggaagatt gggtaatgct gatgtgttcc   2700
attcatgaaa ctgtatttga tacataatcc tattattaat tcgtatgctt agtcaaccta   2760
ggaaatcaaa ataatgtttt gaagttctta tttgagcaat atggccttga cttggagggt   2820
agttttagtt gttttgtttt taagtgactg tggtttaaag cacaaatgcc ccaaggtggg   2880
gagacttctc tctgtgatta ttgttgctat taaattctga actgtatcca tattttaagg   2940
aaggagctaa aaatgaaat tcatgaaaca taaatggtat caagaacttt atcagtatgc    3000
tttgttgaaa gcagaaatta agataataat tgagttcaat tcgcctctcc gcattgccta   3060
ttgatacact ttactaatca tgaaattcta acctaaaagg aaaacatttt cctgcttgtc   3120
ttagaagaaa gtggaataat tccactgatt gtgataatgg tttcaatttc tacacaatat   3180
aaatatccag tataaaggaa agcgttaagt cggtaagcta gaggattgta aatatctttt   3240
atgtcctcta gataaaacac ccgattaaca gatgttaaac cttttaatgt tttgatttgc   3300
tttaaaaatg gccttcctac acattagctc cagctaaaaa gacacattgg agagcttaga   3360
ggataagtct ctggagcaga atttatcaca cacaaaagtt acaccaacag aataccaagc   3420
agaatgatga ggacctgtaa aataccttgt gccctattaa aaaaaaaaaa aaaaaaaaag   3480
```

| | | |
|---|---|---|
| ccagtaactg aatccatttt gatttttggt tgagtttcct acacaaagaa gaaaataact | 3540 |
| gagaatctgg aatgttgtag tccatccttt aaagagtaag aaagtagcag ttaatgctag | 3600 |
| taaccgtgaa ttaggcacca ctgaaagcac atcccgaatt tctttaacaa caacatttta | 3660 |
| tagtgaacac tacaagtttt tatatttaaa aattaagact ctgtatatcc ttaaggtgct | 3720 |
| ctatgcttta ccagtaattc acagggtatt tcaaatggta gaatcatttt agcttctgtg | 3780 |
| cttccttttt ctaaataatg caacttgtaa gagttgacat tgtaataagc tttataatag | 3840 |
| tataaccgtc aggagatata tatatatata tatacacata cacacacaca cacacatata | 3900 |
| tactatacat atataaaatg gggatattac tattgtatga ttaaatcatt cttaagtccc | 3960 |
| caaggaaaaa aaatcataaa caaatagaaa gaactaaaca gaaaagaaag aaa | 4013 |

```
<210> SEQ ID NO 268
<211> LENGTH: 4003
<212> TYPE: DNA
<213> ORGANISM: Homo sapiens
<220> FEATURE:
<221> NAME/KEY: misc_feature
<222> LOCATION: 1,2,3,4,6,7,8,9,10,11,
      12,13,14,16,17,266,764,769,773,774,
      777,781,783,784,788,789,790,791,792,796,
      797,802,808,809,813,814,815,819,820,821,
      825,826,830,831,832,833,835,836,839,842,
      845,855,856,857,860,861,862,863,867,868,
      870,871,877,879,880,881,882,887,892,893,
      899,903,904,907,908,910,911,912,913,917,
      918,920,921,924,925,926,929,931,933,935,
      1011,1012,1015,1023,1026,1081,1098,1133,1136,1137,
      3472,3996,4000
<223> OTHER INFORMATION: n = A,T,C or G

<400> SEQUENCE: 268
```

| | | |
|---|---|---|
| yswktkkwwy wywytywttt ggaggacttt tgtacacata ttttgtagtg tcacatatat | 60 |
| gttttaattt tgaattatac ataagggaag gtggggaag ggcatcatct tctcagagct | 120 |
| actttcctct gaacctggaa atgactggaa ctaatattac tttgtgaagt gtccatttac | 180 |
| cagaattgtt ctctgtagag agcaacttttt gactgtggta atgtaattct tgcactaaga | 240 |
| actatgtgta ctagtctcaa aagctkgggg actctgagcc ttacctagag tctcagcagg | 300 |
| tggaccatta agattaacat ttctagtagg tgagttcaat cacaaaaata tttcttgttc | 360 |
| catagatttt attgtggcca tgtcagtgaa cacccacaag ttttgctcag aatattttag | 420 |
| gtgtaagcta aatccctaaa ttgttcagag ttcccacagc cctgtagcag cagagcgaga | 480 |
| actttaacca gactttttca atcccaaagc taatctggag gccaacagtg ttcaaaacct | 540 |
| tggtgactga ggaaccattt agagtttttt caggctcagg aatcacatgg tcgttgttgg | 600 |
| gcttggggta agtttcacag gcgatgaagc tgacgttgag tcacttgact tctggagcca | 660 |
| taatttattt tctcccagca acctcctact ggggattctc atgtttatgg atacagtttg | 720 |
| gcaatcacta cattgaatgt agtctttaa aaaaattaac ttakgctakt agyygascca | 780 |
| kcmktgckmm kyttgsycca cmcagtgkyt gcmkyacamr maccyrttcy ywmcywccya | 840 |
| gyctygtttc agtckymatr ksmaagwwcw wgcagcmamr yrgccarcag akscaggggrg | 900 |
| gcymgcykgy yksggaykcm kctrrrccyg rcrayatgga gccgaagaag ggcacggggg | 960 |
| ccccaagga gtgcggggag gaggagcccc ggacctgctg cggctgccgg kkccmgctgc | 1020 |
| tgmtcmgccc tgctgcagct ggcctgggc atcgccgtga ccgtggtggg cttcctcatg | 1080 |
| kcgagcatca gctcctcyct gctagtcagg gacactccat tttgggctgg gartcwytgt | 1140 |
| ctgcttagtg gccatcttg gcttgtttat gctttgtgtc tcatatcagg ttgacgaacg | 1200 |

```
gacatgtatt caattttcta tgaaactgtt atactttctg ctgagtgccc tgggcctgac    1260
ggtctgtgtg ctggccgtgg cctttgccgc ccaccactat tcgcagctca cacagtttac    1320
ctgtgagacc acactcgact cttgccagtg caaactgccc tcctcggagc cgctcagcag    1380
gacctttgtt taccgggatg tgacggactg taccagcgtc actggcactt tcaaactgtt    1440
cttactcatc cagatgattc ttaatttggt ctgcggcctt gtgtgcttgt tggcctgctt    1500
tgtgatgtgg aaacataggt accaggtctt ctatgtgggt gtcaggatat gctccctcac    1560
ggcttccgaa ggcccccagc aaagatcta acattcttgc tcaaagttgc gagagaaagt     1620
agcacatgga gtagctgagg ttaaacaaac aaaaaaaaat tttaaacaaa gaaggaaaa     1680 aaattgacaa taaagtcac tcttctaatt gaatatttt atattttat gaaacaaaag       1740 agcatttctt caggtttcta ttgtatttt tttaacattc ttgcagagaa agcaagatcc     1800
aaattgattt tgggatatta aaagttaaca gaacactgaa caaggaaaga atggcataga   1860
tctatcttta cagtctggag ttaattcctg ttaactcatt ttatccattc cttacataat    1920
cttctttcct gttagtccag tttgatggtg tgaatggtga atttcaggcc cagttgctaa   1980
attttgtggc atcttcctct agtccttccc acctccagtc atcagcccca ctctgtcttg    2040
gagacaggca ggaggtgggg gaagagctga atctctttat tttccctggt agagacatct    2100
tcaaggcatg aaatagctta aagagcagag tagaaatgga agaggctttg caaaaggcta    2160
gataactaac aacacctggg ttggggcggc ggcctcttct cttcagctcc cttagcttgg    2220
ctccgtaagt ggatcacttg ccaaatgctt tagatgattg cctctcaata attgaaaggt    2280
ggtggtagtt gtattctaaa tgatgtagaa ggtttaaaaa taattacatt atgcttctat    2340
tctatcatct aaaacaaatc attaaaacta atttctagct aattgttaat tataattatg    2400
ctcagaagtc tatttaatga gctctgactg tacttacgct gcactgtcgg tgttaagaga    2460
aattactctc acaagagcag aggcctgaag attctttctt ctgaaagcca agcaccacaa    2520
ggaaaaaaaa attattaata gctcaggtta aaaacaccca tttaaacaaa acaagagca    2580 tttgtaatag gaagtgttta tacaaacagc acatttgtga tatgttgaaa agcatctctc    2640
ttggcaacca atctatgttt gaggaagatt gggtaatgct gatgtgttcc attcatgaaa    2700
ctgtatttga tacataatcc tattattaat tcgtatgctt agtcaaccta ggaaatcaaa   2760
ataatgtttt gaagttctta tttgagcaat atggccttga cttggagggt agttttagtt    2820
gttttgtttt taagtgactg tggtttaaag cacaaatgcc ccaaggtggg gagacttctc    2880
tctgtgatta ttgttgctat taaattctga actgtatccc atattttaag gaaggagcta    2940
aaaatggaaa ttcatgaaac ataaatggta tcaagaactt tatcagtatg ctttgttgaa    3000
agcagaaatt aagataataa ttgagttcaa ttcgcctctc cgcattgcct attgatacac    3060
tttactaatc atgaaattct aacctaaaag gaaaacattt tcctgcttgt cttagaagaa    3120
agtggaataa ttccactgat tgtgataatg gtttcaattt ctacacaata taaatatcca    3180
gtataaagga aagcgttaag tcggtaagct agaggattgt aaatatcttt tatgtcctct    3240
agataaaaca cccgattaac agatgttaaa ccttttaatg ttttgatttg ctttaaaaat    3300
ggccttccta cacattagct ccagctaaaa agacacattg gagagcttag aggataagtc    3360
tctggagcag aatttatcac acacaaaagt tacaccaaca gaataccaag cagaatgatg   3420
aggacctgta aaataccttg tgccctatta aaaaaaaaa aaaaaaaaa arccagtaac    3480 tgaatccatt ttgattttg gttgagtttc ctacacaaag aagaaaataa ctgagaatct    3540
ggaatgttgt agtccatcct ttaaagagta agaaagtagc agttaatgct agtaaccgtg    3600
```

-continued

```
aattaggcac cactgaaagc acatcccgaa tttctttaac aacaacattt tatagtgaac    3660
actacaagtt tttatattta aaaattaaga ctctgtatat ccttaaggtg ctctatgctt    3720
taccagtaat tcacagggta tttcaaatgg tagaatcatt ttagcttctg tgcttccttt    3780
ttctaaataa tgcaacttgt aagagttgac attgtaataa gctttataat agtataaccg    3840
tcaggagata tatatatata tatacacata cacacacaca cacacatata tactatacat    3900
atataaaatg gggatattac tattgtatga ttaaatcatt cttaagtccc caaggaaaaa    3960
aaatcataaa caaatagaaa gaactaaaca aaaaraaaar aaa                      4003
```

<210> SEQ ID NO 269
<211> LENGTH: 243
<212> TYPE: PRT
<213> ORGANISM: Homo sapiens

<400> SEQUENCE: 269

```
Met Gly Lys Asn Lys Gln Pro Arg Gly Gln Gln Arg Gln Gly Gly Pro
 1               5                  10                  15

Pro Ala Asp Ala Ala Gly Pro Asp Asp Met Glu Pro Lys Lys Gly
            20                  25                  30

Thr Gly Ala Pro Lys Glu Cys Gly Glu Glu Pro Arg Thr Cys Cys
        35                  40                  45

Gly Cys Arg Phe Pro Leu Leu Ala Leu Leu Gln Leu Ala Leu Gly
    50                  55                  60

Ile Ala Val Thr Val Gly Phe Leu Met Ala Ser Ile Ser Ser Ser
65                  70                  75                  80

Leu Leu Val Arg Asp Thr Pro Phe Trp Ala Gly Ile Ile Val Cys Leu
                85                  90                  95

Val Ala Tyr Leu Gly Leu Phe Met Leu Cys Val Ser Tyr Gln Val Asp
            100                 105                 110

Glu Arg Thr Cys Ile Gln Phe Ser Met Lys Leu Leu Tyr Phe Leu Leu
        115                 120                 125

Ser Ala Leu Gly Leu Thr Val Cys Val Leu Ala Val Ala Phe Ala Ala
    130                 135                 140

His His Tyr Ser Gln Leu Thr Gln Phe Thr Cys Glu Thr Thr Leu Asp
145                 150                 155                 160

Ser Cys Gln Cys Lys Leu Pro Ser Ser Glu Pro Leu Ser Arg Thr Phe
                165                 170                 175

Val Tyr Arg Asp Val Thr Asp Cys Thr Ser Val Thr Gly Thr Phe Lys
            180                 185                 190

Leu Phe Leu Leu Ile Gln Met Ile Leu Asn Leu Val Cys Gly Leu Val
        195                 200                 205

Cys Leu Leu Ala Cys Phe Val Met Trp Lys His Arg Tyr Gln Val Phe
    210                 215                 220

Tyr Val Gly Val Arg Ile Cys Ser Leu Thr Ala Ser Glu Gly Pro Gln
225                 230                 235                 240

Gln Lys Ile
```

<210> SEQ ID NO 270
<211> LENGTH: 243
<212> TYPE: PRT
<213> ORGANISM: Homo sapiens

<400> SEQUENCE: 270

```
Met Gly Lys Asn Lys Gln Pro Arg Gly Gln Gln Arg Gln Gly Gly Pro
 1               5                  10                  15
```

Pro Ala Ala Asp Ala Ala Gly Pro Asp Asp Met Glu Pro Lys Lys Gly
            20                  25                  30

Thr Gly Ala Pro Lys Glu Cys Gly Glu Glu Pro Arg Thr Cys Cys
        35                  40                  45

Gly Cys Arg Phe Pro Leu Leu Leu Ala Leu Leu Gln Leu Ala Leu Gly
    50                  55                  60

Ile Ala Val Thr Val Val Gly Phe Leu Met Ala Ser Ile Ser Ser Ser
65                  70                  75                  80

Leu Leu Val Arg Asp Thr Pro Phe Trp Ala Gly Ile Ile Val Cys Leu
                85                  90                  95

Val Ala Tyr Leu Gly Leu Phe Met Leu Cys Val Ser Tyr Gln Val Asp
            100                 105                 110

Glu Arg Thr Cys Ile Gln Phe Ser Met Lys Leu Leu Tyr Phe Leu Leu
        115                 120                 125

Ser Ala Leu Gly Leu Thr Val Cys Val Leu Ala Val Ala Phe Ala Ala
    130                 135                 140

His His Tyr Ser Gln Leu Thr Gln Phe Thr Cys Glu Thr Thr Leu Asp
145                 150                 155                 160

Ser Cys Gln Cys Lys Leu Pro Ser Ser Glu Pro Leu Ser Arg Thr Phe
                165                 170                 175

Val Tyr Arg Asp Val Thr Asp Cys Thr Ser Val Thr Gly Thr Phe Lys
            180                 185                 190

Leu Phe Leu Leu Ile Gln Met Ile Leu Asn Leu Val Cys Gly Leu Val
        195                 200                 205

Cys Leu Leu Ala Cys Phe Val Met Trp Lys His Arg Tyr Gln Val Phe
210                 215                 220

Tyr Val Gly Val Arg Ile Cys Ser Leu Thr Ala Ser Glu Gly Pro Gln
225                 230                 235                 240

Gln Lys Ile

<210> SEQ ID NO 271
<211> LENGTH: 243
<212> TYPE: PRT
<213> ORGANISM: Homo sapiens

<400> SEQUENCE: 271

Met Gly Lys Asn Lys Gln Pro Arg Gly Gln Gln Arg Gln Gly Gly Pro
                5                   10                  15

Pro Ala Ala Asp Ala Ala Gly Pro Asp Asp Met Glu Pro Lys Lys Gly
            20                  25                  30

Thr Gly Ala Pro Lys Glu Cys Gly Glu Glu Pro Arg Thr Cys Cys
        35                  40                  45

Gly Cys Arg Phe Pro Leu Leu Leu Ala Leu Leu Gln Leu Ala Leu Gly
    50                  55                  60

Ile Ala Val Thr Val Val Gly Phe Leu Met Ala Ser Ile Ser Ser Ser
65                  70                  75                  80

Leu Leu Val Arg Asp Thr Pro Phe Trp Ala Gly Ile Ile Val Cys Leu
                85                  90                  95

Val Ala Tyr Leu Gly Leu Phe Met Leu Cys Val Ser Tyr Gln Val Asp
            100                 105                 110

Glu Arg Thr Cys Ile Gln Phe Ser Met Lys Leu Leu Tyr Phe Leu Leu
        115                 120                 125

Ser Ala Leu Gly Leu Thr Val Cys Val Leu Ala Val Ala Phe Ala Ala
    130                 135                 140

```
His His Tyr Ser Gln Leu Thr Gln Phe Thr Cys Glu Thr Thr Leu Asp
145                 150                 155                 160

Ser Cys Gln Cys Lys Leu Pro Ser Ser Glu Pro Leu Ser Arg Thr Phe
                165                 170                 175

Val Tyr Arg Asp Val Thr Asp Cys Thr Ser Val Thr Gly Thr Phe Lys
            180                 185                 190

Leu Phe Leu Leu Ile Gln Met Ile Leu Asn Leu Val Cys Gly Leu Val
        195                 200                 205

Cys Leu Leu Ala Cys Phe Val Met Trp Lys His Arg Tyr Gln Val Phe
210                 215                 220

Tyr Val Gly Val Arg Ile Cys Ser Leu Thr Ala Ser Glu Gly Pro Gln
225                 230                 235                 240

Gln Lys Ile

<210> SEQ ID NO 272
<211> LENGTH: 217
<212> TYPE: PRT
<213> ORGANISM: Homo sapiens

<400> SEQUENCE: 272

Met Glu Pro Lys Lys Gly Thr Gly Ala Pro Lys Glu Cys Gly Glu Glu
                5                   10                  15

Glu Pro Arg Thr Cys Cys Gly Cys Arg Phe Pro Leu Leu Leu Ala Leu
            20                  25                  30

Leu Gln Leu Ala Leu Gly Ile Ala Val Thr Val Val Gly Phe Leu Met
        35                  40                  45

Ala Ser Ile Ser Ser Leu Leu Val Arg Asp Thr Pro Phe Trp Ala
50                  55                  60

Gly Ile Ile Val Cys Leu Val Ala Tyr Leu Gly Leu Phe Met Leu Cys
65                  70                  75                  80

Val Ser Tyr Gln Val Asp Glu Arg Thr Cys Ile Gln Phe Ser Met Lys
                85                  90                  95

Leu Leu Tyr Phe Leu Leu Ser Ala Leu Gly Leu Thr Val Cys Val Leu
            100                 105                 110

Ala Val Ala Phe Ala Ala His His Tyr Ser Gln Leu Thr Gln Phe Thr
        115                 120                 125

Cys Glu Thr Thr Leu Asp Ser Cys Gln Cys Lys Leu Pro Ser Ser Glu
130                 135                 140

Pro Leu Ser Arg Thr Phe Val Tyr Arg Asp Val Thr Asp Cys Thr Ser
145                 150                 155                 160

Val Thr Gly Thr Phe Lys Leu Phe Leu Leu Ile Gln Met Ile Leu Asn
                165                 170                 175

Leu Val Cys Gly Leu Val Cys Leu Leu Ala Cys Phe Val Met Trp Lys
            180                 185                 190

His Arg Tyr Gln Val Phe Tyr Val Gly Val Arg Ile Cys Ser Leu Thr
        195                 200                 205

Ala Ser Glu Gly Pro Gln Gln Lys Ile
    210                 215

<210> SEQ ID NO 273
<211> LENGTH: 5738
<212> TYPE: DNA
<213> ORGANISM: Homo sapiens
<220> FEATURE:
<221> NAME/KEY: misc_feature
<222> LOCATION: 356,357,358,396,627,691,1719,1722,1731,1739,
      3019,3228,3702,3946,3960,4004,4014,4015,4019,4024,
      4026,4038,4039,4044,4046,4047,4048,4050,4053,4083,
```

4085,4087,4089,4090,4092,4094,4097,4098,4100,4105,
4108,4322,4935,4937,5401,5514,5519,5531,5532,5534
<223> OTHER INFORMATION: n = A,T,C or G

<400> SEQUENCE: 273

| | | | | | |
|---|---|---|---|---|---|
| atgttgccag | aaatatccac | acaagaaaa | atcattaagt | tccctacttc | ccccatcctg | 60 |
| gcagaatcat | cagaaatgac | catcaagacc | caaacaagtc | ctcctgggtc | tacatcagag | 120 |
| agtaccttta | cattagacac | atcaaccact | ccctccttgg | taataaccca | ttcgactatg | 180 |
| actcagagat | tgccacactc | agagataacc | actcttgtga | gtagaggtgc | tggggatgtg | 240 |
| ccacggccca | gctctctccc | tgtggaagaa | acaagccctc | catcttccca | gctgtcttta | 300 |
| tctgccatga | tctcaccttc | tcctgtttct | tccacattac | cagcaagtag | ccactmskct | 360 |
| tctgcttctg | tgacttcact | tctcacacca | ggccamgtga | agactactga | ggtgttggac | 420 |
| gcaagtgcag | aacctgaaac | cagttcacct | ccaagtttga | gcagcacctc | agttgaaata | 480 |
| ctggccacct | ctgaagtcac | cacagatacg | gagaaaattc | atcctttctc | aaacacggca | 540 |
| gtaaccaaag | ttggaacttc | cagttctgga | catgaatccc | cttcctctgt | cctacctgac | 600 |
| tcagagacaa | ccaaagccac | atcggcwatg | ggtaccatct | ccattatggg | ggatacaagt | 660 |
| gtttctacat | taactcctgc | cttatctaac | rctaggaaaa | ttcagtcaga | gccagcttcc | 720 |
| tcactgacca | ccagattgag | ggagaccagc | acctctgaag | agaccagctt | agccacagaa | 780 |
| gcaaacactg | ttcttttctaa | agtgtccact | ggtgctacta | ctgaggtctc | caggacagaa | 840 |
| gccatctcct | ttagcagaac | atccatgtca | ggccctgagc | agtccacaat | gtcacaagac | 900 |
| atctccatag | gaaccatccc | caggatttct | gcctcctctg | tcctgacaga | atctgcaaaa | 960 |
| atgaccatca | caacccaaac | aggtccttcg | gagtctacac | tagaaagtac | ccttaatttg | 1020 |
| aacacagcaa | ccacaccctc | ttgggtggaa | acccactcta | tagtaattca | gggatttcca | 1080 |
| cacccagaga | tgaccacttc | catgggcaga | ggtcctggag | gtgtgtcatg | gcctagccct | 1140 |
| cccttttgtga | aagaaaccag | ccctccatcc | tccccgctgt | ctttacctgc | cgtgacctca | 1200 |
| cctcatcctg | tttccaccac | attcctagca | catatccccc | cctctcccct | tcctgtgact | 1260 |
| tcactttctc | acctctggcc | cggcgacaac | cacagatatc | ttgggtacaa | gcacagaacc | 1320 |
| tggaaccagt | tcatcttcaa | gtttgagcac | cacctcccat | gagagactga | ccacttacaa | 1380 |
| agacactgca | catacagaag | ccgtgcatcc | ttccacaaac | acaggaggga | ccaatgtggc | 1440 |
| aaccaccagc | tctggatata | aatcacagtc | ctctgtccta | gctgactcat | ctccaatgtg | 1500 |
| taccacctcc | accatgggggg | atacaagtgt | tctcacatca | actcctgcct | tccttgagac | 1560 |
| taggaggatt | cagacagagc | tagcttcctc | cctgacccct | ggattgaggg | agtccagcgg | 1620 |
| ctctgaaggg | accagctcag | gcaccaagat | gagcactgtc | ctctctaaag | tgcccactgg | 1680 |
| tgctactact | gagatctcca | aggaagacgt | cacctcggrg | arcatccatc | hcaggtccyg | 1740 |
| ctcaatccac | aatatcacca | gacatctcca | caagaaccgt | cagctggttc | tctacatccc | 1800 |
| ctgtcatgac | agaatcagca | gaaataacca | tgaacaccca | tacaagtcct | ttaggggcca | 1860 |
| caacacaagg | caccagtact | ttggccacgt | caagcacaac | ctctttgaca | atgcacact | 1920 |
| caactatatc | tcaaggattt | tcacactcac | agatgagcac | tcttatgagg | aggggtcctg | 1980 |
| aggatgtatc | atggatgagc | cctccccttc | tggaaaaaac | tagaccttcc | ttttctctga | 2040 |
| tgtcttcacc | agccacaact | tcaccttctc | ctgtttcctc | cacattacca | gagagcatct | 2100 |
| cttcctctcc | tcttcctgtg | acttcactcc | tcacgtctgg | cttggcaaaa | actacagata | 2160 |
| tgttgcacaa | aagctcagaa | cctgtaacca | actcacctgc | aaatttgagc | agcacctcag | 2220 |

```
ttgaaatact ggccacctct gaagtcacca cagatacaga gaaaactcat ccttcttcaa    2280
acagaacagt gaccgatgtg gggacctcca gttctggaca tgaatccact tcctttgtcc    2340
tagctgactc acagacatcc aaagtcacat ctccaatggt tattacctcc accatggagg    2400
atacgagtgt ctccacatca actcctggct tttttgagac tagcagaatt cagacagaac    2460
caacatcctc cctgacccct tggactgaga agaccagcag ctctgagggg accagcttag    2520
ccacagagat gagcactgtc ctttctggag tgcccactgg tgccactgct gaagtctcca    2580
ggacagaagt cacctcctct agcagaacat ccatctcagg cttttgctcag ctcacagtgt    2640
caccagagac ttccacagaa accatcacca gactccctac ctccagcata atgcagaat     2700
cagcagaaat gatgatcaag acacaaacag atcctcctgg gtctacacca gagagtactc    2760
atactgtgga catatcaaca acacccaact gggtagaaac ccactcgact gtgactcaga    2820
gattttcaca ctcagagatg accactcttg tgagcagaag ccctggtgat atgttatggc    2880
ctagtcaatc ctctgtggaa gaaaccagct ctgcctcttc cctgctgtct ctgcctgcca    2940
cgacctcacc ttctcctgtt tcctctacat tagtagagga tttcccttcc gcttctcttc    3000
ctgtgacttc tcttctcamc cctggcctgg tgataaccac agacaggatg ggcataagca    3060
gagaacctgg aaccagttcc acttcaaatt tgagcagcac ctcccatgag agactgacca    3120
ctttggaaga cactgtagat acagaagaca tgcagcctc cacacacaca gcagtgacca    3180
acgtgaggac ctccatttct ggacatgaat cacaatcttc tgtcctakct gactcagaga    3240
cacccaaagc cacatctcca atgggtacca cctacaccat gggggaaacg agtgtttcca    3300
tatccacttc tgacttcttt gagaccagca gaattcagat agaaccaaca tcctccctga    3360
cttctggatt gagggagacc agcagctctg agaggatcag ctcagccaca gagggaagca    3420
ctgtcctttc tgaagtgccc agtggtgcta ccactgaggt ctccaggaca gaagtgatat    3480
cctctagggg aacatccatg tcagggcctg atcagttcac catatcacca gacatctcta    3540
ctgaagcgat caccaggctt tctacttccc ccattatgac agaatcagca gaaagtgcca    3600
tcactattga cacaggttct cctgggggcta catcagaggg taccctcacc ttggacacct    3660
caacaacaac cttttggtca gggacccact caactgcatc tycaggattt tcacactcag    3720
agatgaccac tcttatgagt agaactcctg gagatgtgcc atggccgagc cttccctctg    3780
tggaagaagc cagctctgtc tcttcctcac tgtcttcacc tgccatgacc tcaacttctt    3840
ttttctccac attaccagag agcatctcct cctctcctca tcctgtgact gcacttctca    3900
cccttggccc agtgaagacc acagacatgt tgcgcacaag ctcagracct gaaaccagty    3960
cacctccaaa tttgagcagc acctcagctg aaatattagc cacstctgaa gtcrscaarg    4020
atasakagaa aattcatmmc tccycmmmcr camctgtagt caatgtaggg actgtgattt    4080
atrawcwtmw aycmcckycm tctgwttygg ctgacttagt gacaacaaaa cccacatctc    4140
caatggctac cacctccact ctggggaata caagtgtttc cacatcaact cctgccttcc    4200
cagaaactat gatgacacag ccaacttcct ccctgacttc tggattaagg gagatcagta    4260
cctctcaaga gaccagctca gcaacagaga gaagtgcttc tctttctgga atgcccactg    4320
gygctactac taaggtctcc agaacagaag ccctctcctt aggcagaaca tccaccccag    4380
gtcctgctca atccacaata tcaccagaaa tctccacgga aaccatcact agaatttcta    4440
ctccccctcac cacgacagga tcagcagaaa tgaccatcac ccccaaaaca ggtcattctg    4500
ggcatcctc acaaggtacc tttaccttgg acacatcaag cagagcctcc tggccaggaa    4560
ctcactcagc tgcaactcac agatctccac actcagggat gaccactcct tatgagcaga    4620
```

```
ggtcctgagg atgtgtcatg gccaagccgc ccatcagtgg aaaaaactag ccctccatct    4680
tccctggtgt ctttatctgc agtaacctca ccttcgccac tttattccac accatctgag    4740
agtagccact catctcctct ccgggtgact tctcttttca ccctgtcat  gatgaagacc    4800 acagacatgt tggacacaag cttggaacct gtgaccactt cacctcccag tatgaatatc    4860
acctcagatg agagtctggc cacttctaaa gccaccatgg agacagaggc aattcagctt    4920
tcagaaaaca cagcwgygac tcagatgggc accatcagtg ctagacaaga attctattcc    4980
tcttatccag gcctcccaga gccatccaaa gtgacatctc cagtggtcac ctcttccacc    5040
ataaaagaca ttgtttctac aaccatacct gcttcctctg agataacaag aattgagatg    5100
gagtcaacat ccaccctgac ccccacacca agggagacca gcacctccca ggagatccac    5160
tcagccacaa agccaagcac tgttccttac aaggcactca ctagtgccac gattgaggac    5220
tccatgacac aagtcatgtc ctctagcaga ggacctagcc ctgatcagtc cacaatgtca    5280
caagacatat ccactgaagt gatcaccagg ctctctacct cccccatcaa gacagaatct    5340
acagaaatga cattaccacc caaacaggtt ctcctggggc tacatcaagg ggtaccctta    5400
kccttggaca cttcaacaac ttttatgtca gggacccact tcaactgcat ctcaaggatt    5460
ttcacactca cagatgaccg ctcttatgag tagactcctg gagatgtgcc atgrctaasc    5520
catccctctg skgmagagcc cgcctctgcc tctttctcac tggcttcacc tgtcttgacc    5580
tcattttttt cgttttttgc ccattcccaa aaacctccac cttttttggt tcctgggcaa    5640 acttttttccc tagggctggg gaaacccaaa atgtggggcc aacccagaac tgaaacattc    5700
cccccaatgg acaaccttt  tgaaaagggc ccctttgc                            5738

<210> SEQ ID NO 274
<211> LENGTH: 1024
<212> TYPE: DNA
<213> ORGANISM: Homo sapiens

<400> SEQUENCE: 274 cccccacccga aacacactca gcccttgcac tgacctgcct tctgattgga ggctggttgc      60
ttcggataat gacctccagg accccactgt tggttacagc ctgtttgtat tattcttact     120
gcaactcaag acacctgcag cagggcgtga gaaaaagtaa agaccagta  ttttcacatt     180 gccaggtacc agaaacacag aagactgaca cccgccactt aagtgggggcc agggctggtg     240 tctgcccatg ttgccatcct gatgggctgc ttgccacaat gagggatctt cttcaataca     300
tcgcttgctt ctttgccttt ttctctgctg ggttttttgat tgtggccacc tggactgact     360
gttggatggt gaatgctgat gactctctgg aggtgagcac aaaatgccga ggcctctggt     420
gggaatgcgt cacaaatgct tttgatggga ttcgcacctg tgatgagtac gattccatac     480
ttgcggagca tcccttgaag ctggtggtaa ctcgagcgtt gatgattact gcagatattc     540
tagctgggtt tggatttctc accctgctcc ttggtcttga ctgcgtgaaa ttcctccctg     600
atgagccgta cattaaagtc cgcatctgct tgttgctgg  agccacgtta ctaatagcag     660
gtaccccagg aatcattggc tctgtgtggt atgctgttga tgtgtatgtg aacgttcta      720 ctttggtttt gcacaatata tttcttggta tccaatataa atttggttgg tcctgttggc     780
tcggaatggc tgggtctctg ggttgctttt ggctggagc  tgttctcacc tgctgcttat     840 atcttttttaa agatgttgga cctgagagaa actatcctta ttccttgagg aaagcctatt     900
cagccgcggg tgtttccatg gccaagtcat actcagcccc tcgcacagag acggccaaaa     960
tgtatgctgt agacacaagg gtgtaaaatg cacgtttcag ggtgtgtttg catatgattt    1020
```

```
aatc                                                              1024

<210> SEQ ID NO 275
<211> LENGTH: 1024
<212> TYPE: DNA
<213> ORGANISM: Homo sapiens

<400> SEQUENCE: 275
ccccacccga aacacactca gcccttgcac tgacctgcct tctgattgga ggctggttgc    60
ttcggataat gacctccagg accccactgt tggttacagc ctgtttgtat tattcttact   120
gcaactcaag acacctgcag cagggcgtga gaaaaagtaa aagaccagta ttttcacatt   180
gccaggtacc agaaacacag aagactgaca cccgccactt aagtggggcc agggctggtg   240
tctgcccatg ttgccatcct gatgggctgc ttgccacaat gagggatctt cttcaataca   300
tcgcttgctt ctttgccttt ttctctgctg gttttttgat tgtggccacc tggactgact   360
gttggatggt gaatgctgat gactctctgg aggtgagcac aaaatgccga ggcctctggt   420
gggaatgcgt cacaaatgct tttgatggga ttcgcacctg tgatgagtac gattccatac   480
ttgcggagca tcccttgaag ctggtggtaa ctcgagcgtt gatgattact gcagatattc   540
tagctgggtt tggatttctc accctgctcc ttggtcttga ctgcgtgaaa ttcctccctg   600
atgagccgta cattaaagtc cgcatctgct ttgttgctgg agccacgtta ctaatagcag   660
gtaccccagg aatcattggc tctgtgtggt atgctgttga tgtgtatgtg aacgttcta    720 ctttggtttt gcacaatata tttcttggta tccaatataa atttggttgg tcctgttggc   780
tcggaatggc tgggtctctg ggttgctttt tggctggagc tgttctcacc tgctgcttat   840
atctttttaa agatgttgga cctgagagaa actatcctta ttccttgagg aaagcctatt   900
cagccgcggg tgtttccatg gccaagtcat actcagcccc tcgcacagag acggccaaaa   960
tgtatgctgt agacacaagg gtgtaaaatg cacgtttcag ggtgtgtttg catatgattt  1020
aatc                                                              1024

<210> SEQ ID NO 276
<211> LENGTH: 24110
<212> TYPE: DNA
<213> ORGANISM: Homo sapiens

<400> SEQUENCE: 276
ccccacccga aacacactca gcccttgcac tgacctgcct tctgattgga ggctggttgc    60
ttcggataat gacctccagg accccactgt tggttacagc ctgtttgtat tattcttact   120
gcaactcaag acacctgcag cagggcgtga gaaaaagtaa aagaccagta ttttcacatt   180
gccaggtacc agaaacacag aagactgaca cccgccactt aagtggggcc agggctggtg   240
tctgcccatg ttgccatcct gatgggctgc ttgccacaat gagggatctt cttcaataca   300
tcgcttgctt ctttgccttt ttctctgctg gttttttgat tgtggccacc tggactgact   360
gttggatggt gaatgctgat gactctctgg aggtaagaag atagcagctt cttttcatga   420
tccaggccag cccaaatttt cgctaagtcc caactgccat gtacaacatt cagtatcttt   480
actaaggcta atgataccaa aaataggcaa catggactat ttattgagtc tttacattat   540
tagctcattt aatcctcata gttaatttat gaggtaggtc ttgttatccc attaaacaga   600
tgaagttact aaatagttcc tccttttttc acaaggataa atttccacaa gggtaattaa   660
gtgatctctg ctactgagac ctccagaaat tcacgtcttc cattgctgca tatatcatat   720
tgagtaacat ttcagtacca ccctttttc taagataaat ttttactct tgatgacagc   780
```

```
attaagaata gtgtgataga cttttttaa ggagtgttaa taatctaaaa cgttgagaaa     840
gaaaatgcaa ggcatgcaaa acctacccaa ttaacatgca agaggaaaaa acattatctt    900
aatgatttcc aagtaaaaga aaaaatgttg agggagaaaa tgtctttcca gtgcatccca    960
atgtacgggg gacaggcatg gatttaaatc ctcccttaaa atgagttgct ctagggaact   1020
gactactatt caaagatga gtgagtgggt tcacatttga ggatttatt tttctcgctg     1080
gagaagctca gaaagaagta attttgaagt tcaaaccat tacctgtggc cataggaatc    1140
tgagagaggc agaactgagt aaaaaatcaa atcttcagaa ttagctgctg ttcattaatg   1200
aggcttagga aaacacaggt aagaaaaga aacaatattt caagagctca aaaaaggag     1260
tatatagcaa aacaatttgc ttttaatgt gcatcctgaa gggaacaatt taccctagca    1320
aatgctataa tgtcacctct ataaagttta agaaagatac tcgactgagt ttatatattt   1380
ttcttctaat tttcttatt aaactctcaa attggagttc caaatggaaa gtaataatga    1440
ttctattttg ctgtgcatta tttttgctgc tcgcttttc ttgcttttaa tttgcctctg    1500
acttgaacat ggcatttcaa aaccaatgga gttaggaata cctctttaat gctagaaaat   1560
tacatttcca aaaattgtga tagaattgaa ctactgtaaa ggatgtctgc tataagtgag   1620
cccagtgatg cattttatct ggccatgaat atatgcaaag aatgaaataa atgccctttg   1680
aacagtgctc agggaaaagt gcagataaaa cgttctgctg tcattagttt gccattatct   1740
agatggccag tggtaggtga tgaatacaga aatatgttta acttgagcat aattataatt   1800
atgtttttta aaatacaaaa aaatgtaaaa tcccatctag gggcattgtt aaaatatttt   1860
ctaaaacaat ttaaaagtct ttctgcttaa gctgacataa ttgctaactt catttgataa   1920
gaaatagttt tagaaagggt caaaccttgc tgagagagag attgagagtc ctggaattta   1980
aagtgtcttc tttcatttta gtataaccaa ccaatttgcc atctgtccca tgaaagaata   2040
cttctagtta aaacgaatgg aatgagcagt ccaggttaca cacctcaagt aaaccccttgc 2100
taaccttgaa aaatagttaa tatttcttag cttccttctt atttcccata cttaaaatgt   2160
attgctataa tattcccaag aagccttcac atttaaagga agaggctggg catggtggct   2220
tatgcctgta atcccaatac tttggaaggc cgaggcgggc agatcacagg tcaagagatt   2280
gagaccatcc tggccgacat agtgaaaccc catctctaac aaaaatacaa aaattagctg   2340
ggtgtggtgg caggggcctg tagtcccagc tactaaggag gctgaggcag gagaatcgct   2400
tgaactaggg aggaggaggt tgcactgagc cgagattgtg ccactgcact ccagcctggc   2460
gacagagcga gactccatct taaaaaagaa gaagaagaag aagaaccctg taacaaatcc   2520
ggctcccttc tctttcaaca atctctttag ttgtcaatat ttttaaagag acaataatct   2580
cttataataa ttgctacttc aacaggccag gatagaaact tatattttcc acaaatttga   2640
aggttctgat gctagctcaa ttgctcttct cttttcttgc cgccatcctc atttatatat   2700
caccctttggt ccatataaca actcacttta tgttttatt tttatttttt tatagatttg   2760
gtctcacgct gtcacccagg atagagtgta ctggtgtgat catatctcac tgcagattca   2820
aacttctagg ctcaagtcat cctcccacct cagcctccct agtagctagg cctacaggtg   2880
catgtcccca caactggcta attttaaaaa tttttgtaa gaacaaggac tttctctgtt    2940
ctctaggctg gtctccaact ccaggcctca agtgatcctc ttgcctcggc ctcctaaagt   3000
actgggatta taggagtgaa ccaccacagc agctcacttt aatccattgt tggacaaaag   3060
tcaacgaaac aagtgttttg ttttgttttg attttttaag aaaaaaaagg aataccaata   3120
gacaatttaa ataagaagga gtattatact tttccagttt ttttttttt ttttagtata   3180
```

```
tttggatgat gttggcacgg gatttagaag aagagttttg tggttcaatt cagtataaaa    3240
atatatacaa ttatatcata taaaaggaat gatgctactc ctactagaag agacaaagat    3300
aaagcaaaaa ttgctcctgc ctctcaggag tgcacattta atgaggggaa aacaaagata    3360
cacatgaaac tataataaaa agcataaata aattcatatt ttgagcaaga aataaacgaa    3420
gtatcattgg ggaagaaaat atgcgatgat tacttcctat cagggccatc gaagcaggtc    3480
tcatgaaaga aaaggcattt gagcaaagcc ttgaaacgat gtaaagcatt tcaaattgta    3540
gaaatggcag caggggcctt tcagataagg ggacagagtg gcaaaagtgc aaagagagga    3600
gaagctcagg gcttgttaga ggactaaagt gggcaacaca aagaaggagg cagaaaaagc    3660
tcagatattc ttttttgccta ccacactcta cctatctcaa atgaagttct tcgtattagg    3720
taaaaatgct aggaaagaaa atagcacaca gaattacgat gtgcacaacc ctacatcagt    3780
gactagaggc cctcagctac catcctgctc ttgtcattat tgattcattt gtgtctctga    3840
gaagactgat agggagaaga gaatttgggt tttgagattt tcaagcgta  tgtttgcatc    3900 ttaacccctta ttaactgcct tctattaagc aagtcacatt tcttgtcttt ggctcagttt    3960
tttcaattgt atagttgaac tcagttgttt ctaaggtcct tttcagtctt ttttttttt    4020 tttttaacat catgtctcca tgactgtctg aaacttcaga gagttggaca ctcactaatg    4080
gactggtggt gtctggcact tctccagaca tttccattgg gaatctagtg gaaggatcct    4140 ccattttttct gtagcttcat acactctccc ttccttcatt ccaacttctc tttttccttc    4200
atttccttgt tccttccttc ctcttcttta ttcccctct ctcttttcct ccctttttctt    4260 aactctctct ctttccctcc tatatcctc tttttctttc tttctctttc ttcttcatct    4320 ctttaccccct tcatttctct ctcttttcttt tctacctttt gtcatttcac aaataatctc    4380
tgacaacttc tgtatacttg gcaccatggt gggtacatgg ttatgaagta ggatgagacc    4440
tggagcctcc ctaggctact gccagtgtag tgagtgggac aaataggtga accgacagtt    4500
atagcaccat gtagcacaca ctatgataat gaaaaccta  agcgagtggc tcacttggtc    4560
ttggataacc agtgaaagct acccaaaaga agagatatct aaactaggac ttgaagaaca    4620
ggtgagtgaa gcaggagaag tagagagtat tccaagctca ggaaatggca ggaactgagg    4680
tcaaggtaca agagcgttgt atgtttgcgg tattttgtat atttcatcat agtaagaatt    4740
tccagtttag agaaaagaat acaggggttg ggtcattaag agtttgcat  aacatgtaaa    4800 atatagatct tataccatag gcaagggttt gtcgctgtaa gcaatatgta catgtatttt    4860
agaaagatta atcattctgg ctatctgtgg ggagagattg gaagggtaaa atgaggtatg    4920
gggagaacaa ctaggagact tttgttatag accagaaggg agacaatagt ggtctgtact    4980 tcagtgcacag caagcatgaa gaaatatgaa ataaggagg ctctaaaaat gtcaaattga    5040
tgagagttat aattgactgc atgtggggaa gtaggtgatg aagagacaca gtcaaagatg    5100
aaatctgcct ttctgatctg gggcaattgg aggggtggtg atgttactca ccaagagttt    5160
aaatgaatga aaattagtat ctatacagaa accttcatgg agcaatgtcc ctgaaccatc    5220
ctactatttt tttctgctta gcttattata caatacttag aggtaggaac acaattcttt    5280
acaatggaga tgtttataga tttaacttta tatcagaggg acctgaggtt aaatcccacc    5340
ttaccaggca gtggctgtat gaatttagac agactcttaa atagctataa accacatttc    5400
ctattcagta atgagagaat aacaatacac acatcataag tttcttgtga gaattaaatg    5460
agcttgtgta tctaaagcat ttgccacagc agcaggcaga tatgaatcag ccaataaata    5520
ttagatacat tattgtctat ttgcagttta ttggtttgtt tttgttctgg agaaggagat    5580
```

```
gacattttgc ataatgttcg ctgaacagag aaatataagg tttaaattct attcctattt    5640
ttggtattgc ttctcttgga gaaattttgt ttcctcctct aaagctgtca tttgcctttt    5700
tttttttttt ttttttttaaa tcagaatctc tctctgtcgc ccaagctgga gtgcagtggc   5760
atgatcttgg ctcactgcag cctccacctc ctgagttcaa gcgattctcc tgcctcagcc    5820
tcctgagtag ccgggactac aggcaagcac caccacccc ggctaatttt tttgtatttt     5880
ttgtagagac ggggtttcac catattggcc aggctcgtct tgaactcctg acctcaggtg    5940
atccgcccac ctcatcctcc caaagtgctg ggattacagg tgtgaaccag catggctggc    6000
cacccatttt tatatttaca tctatttcct ttttgtctga ccagggaaat aagacagata    6060
ataagtcaaa tagtgaaggt tatttatcaa atgctcacat ttacaaagaa aataaattga    6120
gataatagca ttgttaatat gttaactaca agatatgcaa ttcttaatta tttacactga    6180
aatagtttct tcacacagta gttactgatc tctcaattat aaaaaggaaa aagtgttttc    6240
acaagaagat ttcattttca gttcatcttt gttaattatt tattgagaac ctgctatgta    6300
ctgagcacta gtatgattaa aatttttatta cctcaaaaca aagttgctca cattagtatt   6360
tattttatct gtataatcag gttctcttct gggatttcta tttgcattaa tattacaatt    6420
cttttaaata taaagtaaat attaaaatta ttatatccag catgcccgtt gattatatcc    6480 attttaaac tttccaattg atttcaaact cttcagcag atgtttgagg ctacaaatgt      6540
tctcttattt atctcatgat ttcctaagta cctagcactg atgtacatta atgtgaactc    6600
atgatgcatt tgctcacatg agttgataga gcgcctagta acacacttag catacctgtt   6660
gaaagaatga atatattaat gatatgaggt gattattgaa aatctcacat tgaaccttaa    6720
ataagaagta tgtctgtaat gaaatgatca ttttttttaaa gcaagatttc gtatcttgct   6780
acaatttaaa tattttcagg atatgtattt ggttcatttt taaaaataaa attggaatac    6840
aaatctgatt cttgggatat ctaataaggt tgatgaagag tatattctgg actagagaat    6900
gtggcttttt gcttagtgct ttaaagagag aaataaagaa aacagagaga aaaagaaat     6960 tgataatttg taataattta ctcaacataa attgtgatct ttatcactgg gcaataatca    7020
ttacaaagtt gtaatgccat acttttaaaa ggaagacatt ttaacgtatg taaccattta    7080
aaaatgttaa aatgaaaata tttagaaagt tcagatatat aacgtaggtc atatacctgt    7140
gaagagcaca aaattttatt tttctactaa gttggcatta cccatttctt atgatttata    7200
cctttagcca gtgctccaca aataaccaga actaaaacaa ataaatttta gcaaataaag    7260
tcatgttttt ctttcgtatc ttataaatgt aagatataaa gtaaaagaa aaggcaacat     7320 tgattatgat tattttagtc ttgctcctc atctttatta aggcctgtat tgactccatt     7380
taggccctgg gatagtaaaa aatataatat aaaatgtaaa ggtaaaatgt tcagagtctt    7440
ggttggaaaa tttaaatgca ttttatgtta aaattgaaaa tgtttccaat tttagtagtc    7500
aaacgttatt tactacaata ttattaaaac ttttgcgtct taataaatat aagtaagtac    7560
taagtaggta tctaagtagg aaagtcacat cttcaaggtt aaaatatatt agcacatgga    7620
tagtaaagtg gtgtgaaaat tataaattct tacaatttgt atatgcaagg tggttttta    7680 aaataatata tcttaatagc ttattttctt ttagttgtct gtacatttat aatcttaatg   7740
catattgaca aaaataatc ttgatagcgg ttaaccaaca ataaacattt acaaaatctg     7800
ctgtgtatat ttactctctc tctctctctg tagatagata catagataga tagatagata    7860
gacacacaca cagacataat ttcctatgtt actagaaag agataaatgc cgaacattgt     7920
tgaatgtctc taattctcaa gtattttta gtgtttctaa ttctcaaaag atacataaaa     7980
```

```
agacaaggca ggcaaaattg ttgctgctta tatttcaaga ttgataacaa aagagaaact    8040
gggaaaaact aggttagaga agtcttaatg ggagactgct atagagtcca gaataagaaa    8100
tcccaggatt aaggaactaa tttatgtcac tgtaactcaa gttggaagag tcatcatctc    8160 tatggttttcc taacactttt aagtgacatc ctactcattt ttagtactgt ggtaaacact   8220
ttccagagcc agttgagtaa acaaggtcca gaatgacacc aaatcaatgt aagctcttca    8280
gtctaaatca taatttttg gcttctggat ttagctgttt ttgtttattt agtcaagtag     8340
aaattgcact tattaagtag caactgtgca tataataacc attttctgct ccaaacttcc    8400
aatgagagta tatgaattga ttgacaaatt gagattttct tatcctcact aaacatttat    8460
taagcaccta ttatgtatca agagtaagag actgtatgct ccttgaagcc agctgccatg    8520 tttgtctta ttatcgctgt atctccagca ttaatatagt cggcatgttg actagtaaat     8580
gacaggcatt aataaatat agtttgaaga ataacagatg acctataatt gcacatacaa     8640
aagataatgc aatattttaa atgctataat aatatgaca aattcctgtg ggatttcagg     8700
atagaaagtg ataaatgcca gctagagaga cttgggtggt gggaggctaa tgaaaaaaca    8760
gaagtcttta aaatgggct tgaataataa gtagaagttt gacaggttga gagcaaggag     8820
ttattctcat tagtataatt agtatatacc aggaagagaa aactcaaatg ccttaaggaa    8880
ccaagtagcc agcgttcacg agagaggcag gttgggtagg atctgtgggg aacctggtga   8940
gcctgagctc cacctaaatg ggagcagcca ctcctttctt gccagttgtt gctttgtgag   9000
actggtgagt tcaggtaccc agaatgacca agtttctaag ggaaccctga aatctgaact   9060
gttctgtaaa atctctacac atttttggca actaattaag agatttttg ctttcctcat    9120 gcttgtgact tctactttat tattgtacct taaataaacc tacctctctc catttagcag    9180
gtaatccact cttcacttt gggaacaata gatattcatt gaaacaatac aaattagcat    9240
tgttttaacg ttatttatca atatataagt tgcatgttag aaggagaaat tttaaattta   9300
taatcctcta tttcagacaa ctctgtcaga ttaaaagtta ttacttaaca tttgcatttt   9360 ttaccctta agaaaggtta actatgatat ttgaaacatc agtctgcttt tttaagaacc    9420
ctgtcttaaa attttcaaga atttagattt gcttgctttt tagtttctaa taagccattt   9480
tacaacagag gaataagtaa atgaagatga taaatcatac cagagagcat tcctaaatat   9540
aataaaaaac atgaaaaatt gtaaccttgt cttttgtgca caaaggcacc tttaagggtg   9600
tctccagtga gtgctacatt aacacagaag tttagttaat tacagccact attctcacgt   9660
accttaactg agtgtgaata ccaagccatc taatagtgtg cccctgagca ttaataccta   9720
atgaaattgg attccttgtt ttctctaatg agctcattgc ttttctaaat atggtcattg   9780
caggtaaatg atcaatagcc ttgaaactga taccactact gaattatttt ggcaagatgg   9840
aaatactctt atttgtgtaa aataagaatt tttgaatatg catttcagat cactttctaa   9900
ataatgtcat gtatgacagg aatgaccata gtaggctagt ttgtttcagt ggctggctta   9960
tacagtaaga aattgtggag agtcgctgtc tgatttacag cacagtgcct tcaaacttgt   10020
atcacctagc ttgagctaaa gtgaactgga tgcagcgtgt tcctgttcat taagacacta   10080
cagggcagtc agctttgaga agatctgttt tctgttatga tatagcagtt ctgtacaaac   10140
tgtctctaat atactaattt cctatagttg ccgtaacaaa tgaccataaa ctcggtggct   10200
taacaaaaga taactttatt ctctcacagt tctggaggct ggaagcttat aatcaagaag   10260
ttggcaaggc tgcgctgccc ctgaaagttc tggaagaatc cgttcttagc ctcttccagc   10320
ttctggtggc tgtaggcatt ccttgacttg tagctttatc cctccaatgt ctctgcctca   10380
```

```
gaggtcacat tgcatctttc ttttgtctgt ttctctcctg catgtgtctc ttataatgaa   10440
atttgtcagc ccacctgtat aacccaatat gatctcaagg tcctcagtta cattttcaaa   10500
gatccttttt ccaaataagg tcatatactg gtggtaagaa tgtggacata tctttctgag   10560
ggcctccatc tttctccacc ttcactgtgg ttagttagta aagcctaaca cagccactac   10620
tcaagtcatt atgatgttta agcactttac taccactatt tttatttatt gagcatatca   10680
tttatattgc gtgtgtattt gtaatttta attcttataa ccatcctatg attatctccc    10740
gtatacagat aaggagattg aggatcaaaa aaggtaagat cttccccaag gttacaacat   10800
agatagtaag agtttcaatc tatatttaat atttaatgca tatataaatt taatttacgt   10860
gtaatgcaca tataaattta gacgtccaca ttatttagaa atttatatgt tgaatttcac   10920
aagatagctg tttatcatta gattttttga tctctgtgtt acacaggatg agataatcct   10980
ccagaaagtc caagaattgt ttccaactta aacctaagga ggagcatgcc aaggtgaagt   11040
tcgcagaata atagccttgg gatgagatcc aagttagggc ttacttcacc caaagctatc   11100
atccaatacc caattctgga ttactttatt ttaaaatgga tttggaattc tttttaaaaa   11160
aatgttttta ggctgggcac ggtgcctcac gcctgtaatc ccagcacttt gggaggccga   11220
ggtgggcgga tcacctgagg tcaggagttc gagatcagcc tgaccaacat ggggaaaccc   11280
cgtctctact aaaaatactt aaaaaaaaaa agtagcctgg cgtggtggcg catgcctgta   11340
atcccatcta ctcgggaggc tgaggcagga gaatcgcttg aacccagaag gtggaggttg   11400
ccgtgagccg atcgcgccat tgcactccag cctggggaaa acagcgagac tctgcctcaa   11460
aaaaaattgt ttttaaacat ttgtaactgt ttaaacaatt tttagcaca tatgcatctt     11520
cttaaatggg gtacctagtg atgttttgat acatataatg tatagtgatc ccattagggt   11580
aattagcata cccatcatct caaacattta tttttgttg gaaacattaa atatccttt     11640
ttctagctat ttgaaattat atcattatta acaatagcca tcctagagtg ctatagaaca   11700
ggggtccaca accccaggc cacagaccag tactagtccg tggcctgtta gtaactgggc    11760
tgtgcagtgg gaggtgagca gtgagcaagt gagcattacc gcctaatggt ggacagaagc   11820
tccaccttct gtcggatcag cggcagtatt cgattctcat aggagtgcaa accctgttgt   11880
gaactgcaca tgcgagggtt ctgagttgca tgctccttac aagcacctaa tgcctgatga   11940
tctgagctgg aacagtttca tccaaaagca tccccaaccc cctacccact ggttccatgg   12000
aaaaattgtc ttgcacgaaa ccggtccctg gtgccaaaaa ggttgaagac cactggtata   12060
gaacactgga acttattcct cttatctagc tgcaattttg tatctcttaa caaatctctc   12120
cttgttcctt ggcccctacc cttcccagcc ttcagtatcc tctgtcttat tttttacctc   12180
gaggtttttt tttctgtttg tttgtttaga cggaatctcg ctctgtcgcc aggctgcagt   12240
gcagtggcgc gatctcggct cactgcaaca tccgactcag tggttcaagc gatgctcctg   12300
cctcccgagt ggctgggatt acaggcacgc accaccacgc ctagctaatt tttgtatttt   12360
tagtagagac ggggtttcac catgttagcc aggatgatcc cgatctcctg acctcttgat   12420
ccgtccgcct cagcctccca aagtgctggg attacaggcg tgagccaccg tgcccgaccg   12480
agatcaactt cttatagctt ccacatatga gtaaaaatat gcaatgttta actttctatt   12540
cctggcttat ttcatttaac attattcagt tccatccatg ctgacttaaa taaaagaatt   12600
tcatttttta aattgttaaa tagtattcca ttgtgtagat ataccatatt gtatttaccc   12660
attgctctgt ggttggatat ctaggttgat tccatgtctt ggctattgtg aatagtgtca   12720
caaagagcat ggaggtgcgc acatactgat ttcctttcct ttgaataaat gcccagtagt   12780
```

```
gagatttgtt ggatcataaa gaatgggttt taaacacact gcaatgctca ggagcacacc   12840
cacacactgc tgtgtttgag tcctatctcc tccattaact atgctttctt ggggttactt   12900
aactttcctg tgccccaatt tcctcatttg taaaatggat gataaataat atctcttaac   12960
gtcccttaag aaataagaaa aataataata tgctaaatag taactgcttt atggtataga   13020
ctctgtattg aataattatt accaactata agtattttac atataaagta gtaatagagg   13080
taaaacattc agaatcgcga tgaagttgca agcagtagaa ttttatttgg cacataacac   13140
ggcctcaaaa aatagcatgg ggcagagagt ttcatagtgc atgtattcct gaatattatt   13200
ttattttcca aagcaaagtg ttcttatgtt ttttttctc cccacagcaa tttaacccccc   13260 tcctttgcat tcctcatccc accctgctct gttattatt ctttcttggg gaaaaaatta   13320 agttttatt ttccaagata attcatagtt aaactttact aaactattcc cagatacaga   13380
aggtaatttg aatccataac tgggtcagag gaaacaattg tattagctct gttccatatg   13440
cgtgagctct atcaagaaca cctgaaacta ttttctgttg gcatgtttac gattctaaga   13500
aatctattgt gacttacggt ttgtagataa agtatgagaa ggttcaggga actggtacct   13560
tctagctcta agtggattct tagagtcatc tgcacatcat ttccaagtaa aaatggatta   13620
cagtcgtcaa gttgtatgaa attaatgctc aatctgctta catcctttac atagcttaag   13680
catttataat atatcattgg agcaataaat aagactgggg gcctttatat attttattta   13740
ttggcatctt ttcatttatt ggttttcttt gctaattatt ttatatttat aaacttcata   13800
tataaagata atattttctct tcatggaact cagtattcgt gataaagaaa caatatatat   13860
ttttaataga ctcaaggtgt caacagttat catctattgt tatatatata tatatttttt   13920
ggtgagtaaa tgtcagcaca gtgacatgaa atgatgtttt tccataacca taactcaatg   13980
gtggaagcag ccacagatat ttaaatatat ttagctctgg ttttatctct tccagacgtg   14040
acttatttct ctaccccccac ccttcatgag gaagtggatt catttcctgg cccagaaagg   14100
cttcaattgt cagtgcttaa gggaaaatat tctaatacgc attgtttgtt gtaaatgaag   14160
ttctgatcac atgtgtaacc acttactttg ctatcaaaca caaccaccaa cttctctttt   14220
tgatcaaggg gaactgaact gtgcctgcat gaattgtttc acacggtgtc ttctctaaca   14280
tctaggtgag cacaaaatgc cgaggcctct ggtgggaatg cgtcacaaat gcttttgatg   14340
ggattcgcac ctgtgatgag tacgattcca tacttgcgga gcatccctgt acgtatgcct   14400
tagagctcac tgcttgccag gaagggaaag ggacagaaaa ctgagttcag gtttccattt   14460
tgtgctttgt tttctattgt actatattaa ggttcggtcc agtttgtaat ggttagaaat   14520
tgagctcatc tcggaaatgt gaattgaaat atatacttca gcacattttc tcttttctca   14580
tatatttgta aattcattga gggaaaaata ttatcttatt aatctctgct gtccctcaga   14640
gggccaggca tagtgcttca tactcagcag gcttacagta aatggttttt taatcgaaat   14700
aaactcttta gggtgctgta atttcattat taaactggac gggttagggg gaaagcatttt   14760 cagagatgtt ttaagctatg acttagttca aatagaaagt ttacagttat ttcagttgaa   14820
ggttagctaa gaaagagaga gtggcagagg cagaaagagg cagacagcca gagagagaga   14880
catagactat ggggatcagt ggaagaaaaa accaacacat gtgacgcact gttacaggca   14940
atattgaagc tggctcccctt atcttcctta cttttagctt taaattatag ttaaagccag   15000
gtgcagtggc tcacacttgt aatcctagca ctttgggagg ccaaggcggg tggatcactg   15060
gaggtcagga gttcgaaacc agcctggcca acatggtgaa accccatccc taataaaatt   15120
accaaaaaaa gttagctcat catggtggtg ggagcctgta gttccagcta gtcaggagac   15180
```

```
tgaggcagga gaatcacttg aacccagaag gcagaggtta cagtgagccg agatcacacc   15240
actgcactcc agcctgggag acagagcaag acttcatctc aaaaataaaa taataaataa   15300
ataaattata gttacatgtc agcagagccc atgttgctat gaataaagaa atgtcttaaa   15360
tttaaaaatc ttactgttga ttctctcaat ccttctccat agtgtttatt tgtttattta   15420
taagaacatc gaaccctgct aagaaacatc tgttctgtta tgaaagcaaa gtggttttag   15480
tctctttcaa agcaaatgat gggtgatggc accataaggc aacttctttt ctcaagataa   15540
ataaaaaatt aagcccttgg aatgtgactt ttcccctgaa cctctatttc agtccagagg   15600
aaagcactta aaaacagcag cactctaaaa ttcttcatct gctatttaaa agttgggtgc   15660
gtggaacatt tttaaaaaca tagttcataa ggtctttgtt ttattttttgt taaaaaggat   15720 tttcttaatt ctttttcttt tcccctctct gtgctaacct agttctacct acaaagaaac   15780
actatttgct gaataggaat ggacattttg tctattctaa aaattcatta aaatggattt   15840
taattcataa gctgataaga aaatgaaaaa ttaaaaaaaa tttaaaactt ttaaatactg   15900
ttatatacat ttatgcaaga agaaaatata atcactcata agctcactac gtagagaaaa   15960
ccactgttta tatttaatat gttccttttt catctttgac ctatgtaacc tattaacata   16020
tgggggtaga gaaataagtc acgtctggaa gagataaaac ccatatggcc taatatgtaa   16080
tattggccaa gaagagtcat gatttaaata gctgaaagag aaaatgatct aatttccaga   16140
aattaccttc tacttaatag cacaaactaa ctctccttct tctaaagatc tccttatggc   16200
ttcttctatc ctgaactggc aaaaagaagt cttgaaatat tttattctgc ttccctgtgt   16260
caaattttag ccaattatta tttttaaata aaaaaaaatt aaagtgatta tttattcaat   16320
atttattaag aaattttgt aggacagata tgctaccttc gattcagcaa tcggctacaa   16380
tatttgtgaa tgagacattt tccagagtag gaggcaaaaa ggaaacatt tatttagttt   16440 ccactatcta ccaggatgct ctctgctagc ataccaacaa caaaactaag tagtgaactg   16500
tggttaaaca agcaataatg tcaataatct catattttt agttttatga aaacattagg   16560
ggtacttatg ttcaagttca tacaaagtct gacttttacc ggaggggtgt gttaatgtta   16620
cctacttgtc tgttttttt gctatgtctc tgtgagttaa tatggttcct tcttctgact   16680
ctgctttaac catatgccct ggtcttccag tgaagctggt ggtaactcga gcgttgatga   16740
ttactgcaga tattctagct ggggttggat ttctcaccct gctccttggt cttgactgcg   16800
tgaaattcct ccctgatgag ccgtacatta agtccgcat ctgctttgtt gctggagcca   16860
cgttactaat agcaggtacc ggtctggctg gactagcaac aggggtaggg agactctgct   16920
aagggcttga ggtgaaggag agagttgtgc tgaagctgct cattttcgga ttatatgtgg   16980 cttcccttttc tagattgaaa aactaaaggt cacttctacc agcccctgcat actttagctt   17040 tgaagtcagc taattagtct tttgttaata tctcagaaca aaatatgaag ctctcaggcc   17100
gggtgtggtg gctatgcct atattcccag cactttggga ggccaaggca ggcagatcac   17160
ttgaggccag gagtttgaaa ccagctggcc atcatggtga aaccctatcc ccactaaaaa   17220
tacaaatcca ggcatggtgg tgcacacctg tagtcccagc tactcggcgg ggctgaggca   17280
ggagaatcgc tcgaacccag gaggcggagg ttgcagtgag cagagatcgc gccactgcac   17340
tccagcctgg gcaacagagc aagactccgt ctcacggaaa aaaaaaaaa aaaaaggaa   17400 ataagaaaa aaaaagctc taaaactatg ttttggccat ttaaaaagtt acataacttc   17460 aattttaaa ataatttatc ttgtgattat tactgaagtt aaaatcctaa agtaagcccc   17520
aaacttctac ctccttacct atacccacca ccaccaactc caccaattct ttttaacaat   17580
```

```
aaactaacaa ttgtgccaag tcctatgtta aacttgtccc acgtactaac ccatttgttc   17640
ataaatgtaa caataaacag atcatattgt tatcctcact taagatgcag ataaataatt   17700
gaagttctga ggactggtca agcatattta ttagtcaagc atgactaata aacaacatat   17760
caaaaagcac tttaagtagt atttattagt gaaacagcaa aaatgatact ttattcaggt   17820
ctgtcttcaa cttcaaagct tagtcctctt cttttgcaac ataatgtctt cttcttgtct   17880
gttagcagga aaaatcttgt ctgctaacaa agcgaatata agtggcagcc tgaccaggca   17940
gtgtggggta gtacatcgat atggagtttg gaactagaaa cacttgtaga tatgtatgtg   18000
tgatatattc acccgtgtct ctgtttcctg atctgcaaag aggcatgagg ctaaggtagt   18060
aacatgtagc ctgaattgct atggtgaaga tgcaatgtgg gcacagcaaa ctgttagctg   18120
actgcctaac cctttgtatg ctcagaactt gggcctccct gacttttgac acagaaatgt   18180
taagtcaacg tcctaataat cctcagattg tattataaag ttacaaaaat ttagaattct   18240
tcccttctgt aagtcattta tttaattatc ccacctactg acagcataga acttttttaat  18300 atacaatgta attcatttaa cagatttaaa cattatttaa tctaattatt tacggctata   18360
taattttgtt cgagaatatt tttgagctat catcagtaaa taaccatcct tatgtaaaac   18420
aacaaaacaa atagcattta aaaaataagt cactgaagaa aatcctgata ggaatgactg   18480
aagaaataac taaattgaaa gacaaagcat gtcctaagct ttggaaactt tagaattagt   18540
gtgctataaa atttattttt aaagtctata atctgttttg aaggtttaga aagggaattt   18600
ctaactgaaa actgcagata atggcattat agcaatgcta ttgcaatata tactgcgttt   18660
tctaaaggtt atgtgtttat tatctggctt tttttttttt ttttttttga gatggagtct   18720
cgctctgtcg cccaggctgg agtgcagtgg cgtgatctcg gctcactgca agctccacct   18780
cctgggttca cgccattctc ctgcctcagc ctcccaagta gctgggacta caggcgccca   18840
ccaccacgcc tggctacttt ttgtatttttt agtagagaag gggtttcacc atgttggcca   18900
ggatggtctc aatctcttga cctcgtgatc cgcccgcctc ggccccccaa agcgctggga   18960
ttacaggtgt gagccaatgt gcccggccta tctgctcctt cttaaagttc ttacattaaa   19020
caattaggag aagaatacag ttaaatagtg atttaaatag atatcacaga ctatctaggg   19080
aaaaaaatgt aaaattttt ggagactaca tattttattt tattttttta gatttgggaa   19140
agacaaatat ttctctcatt agacagtaaa acaactctgg aaagtaatct gaagagattg   19200
tttgtgaaca catgcatcta acttagcaca gagtagcaga actttgaaat gaaggaaaag   19260
taggatccag ttatttgggt gttggtgggc aagatcttaa cactaacgtt gatacagctt   19320
caggatatca gtaagcatac atttacaagt aaataactga aaatccaact caagcagact   19380
tagacaacat atagattact gatttcttgt aattgccttc tgctaggcat tgagcatgtg   19440
gagagtacat attttaaaaa cactcttttta attcagtgtt ttgtcctcca actcaccaca   19500
tttcttattg catctaggct tcaacatgca atttatacct ttaaaataac aggacactag   19560
tggcgtcatt tcaaaccagt taattgtcag agaggctaag ctgtggagat gtatttaaag   19620
ggaataacat ttcttggtcc attcttatat ggtgtgaggg tagtagataa agatttattt   19680
gaaaataaaa acatttttta cttcaattat ttgtgtttga cctcaagaca ctgaaatcag   19740
tgactttaaa aacagttttc acatgggtgc tgattacgta gctggcatag cttcaaaagg   19800
gggtacaggg agcattaaat acaatgatat ttactcacaa tttaaaaatc attacagaat   19860
gaacatatgc tctatgttgt ttgtgttaga ctacattctt tttctgtttt gtttggtttt   19920
gttttagtat tttcctttat acaatactaa catggcattg gaaagacagg agaatcaaag   19980
```

```
aaaaccataa cgatgaattt cgatttacac agataagcac tgtgttattt cattttttgca   20040
ttttctttat gtataaactg agataaaatt taaaaaagat acaagatgga aggcaaaagg   20100
aagagacaga agaagtgtcc gaagttcggg ttgcccatga atccatgtta ctgttttttac  20160
ctctctgaat cacgccagcc attttgtgta gtaagcaggt attttttggat ttaaattcag  20220
aaaatgtccc ctattatttg tagcatcctc cctttctttc aggtacccca ggaatcattg   20280
gctctgtgtg gtatgctgtt gatgtgtatg tggaacgttc tactttggtt ttgcacaata   20340
tatttcttgg tatccaatat aaatttggtt ggtcctgttg gctcggaatg gctgggtctc   20400
tgggttgctt tttggctgga gctgttctca cctgctgctt atatctttttt aaaggtaaga  20460
ataaaataaa atagcaaatt tccttgcctc cactatcgtt tttcccaatc cagtggaaac   20520
aaatttcaaa aggaaaaaaa tgttatttat ttgaattcct acctattgcc attaaaaatt   20580
ccaattgttc aagggcaatt gaattgtaat actcaaacat tattacccag ttagttctat   20640
attaattgaa aaataaaatc cacaactaca agcatgtcca atattcaaat gtataatagt   20700
tatcttgatg tattacaatt atacatatat acatatatac acacatatac ataccgtata   20760
tatactatat atgtatatat actatataca tatatataca catatagtat atatactata   20820
tatacatact gtatatatac ccttgtatat atacgtatac atagtacata tgtatacaca   20880
tatacacata tgtatatgca tatatgtata tgtatacata tatgtataat tgtaatacat   20940
caaaataact attgtacatt tgaatattgg acatagttgt agttgtggat tttttcaatt   21000
aatgtaacac taacttggta ataatgtttg agtattgtaa ttcagttgcc cttgaacaat   21060
tggaattttt aatggtaatt ggaatttttta atggtaacag gtaggaatac acccatgtat  21120
atgcatgtat atatacacac acgtatatgc atgtatatat gcacacacgt atatgcatgt   21180
atatatgcac acacgtatat gcatgtatat atgcacacat gtatatgtat gtatatatgc   21240
acacatgtat atgtatgtat atgcacac atgtatatgt atattagaat tatacatata   21300
tgtgtgtcta tatatacaat tatacccttta taattgtatg catatatgta gatatacata   21360
taattgtaat acattaaaat aactattata catttgaata ttggacatgg ttgtagttgt   21420
gaattttcta tatatatata ttttgatgta ttacaattat acatgcatat atatcttcac   21480
ccactcaact aaatgtatat ttagtgttaa actgagaagt ggactaagat ccagccaaat   21540
acttctttttt aaagaattta acatgttatg ttgggtttct aaaatatca cctaaaaaac  21600
taagggaata cctctcctga tgaagaaaaa aaaataaca ggaaatctac ttggctgaat   21660
tttaaaccta aaagaaactt tcagaatgaa aatcttaaat tgtcttctag gattcttctt   21720
agagttccaa aatgatacct tctttgagta tctatattct tgttccttttt gaggaagaac  21780
atataaaatg gtattttata attttcccaa gttcactgag ttctacttat ttttatattt   21840
ctttcaaaca gatgttggac ctgagagaaa ctatccttat tccttgagga aagcctattc   21900
agccgcgggt gtttccatgg ccaagtcata ctcagcccct cgcacagaga cggccaaaat   21960
gtatgctgta gacacaaggg tgtaaaatgc acgtttcagg gtgtgtttgc atatgattta   22020
atcaatcagt atggttacat tgataaaata gtaagtcaat ccaggaacag ttatttagaa   22080
ttcatattga attaaattaa ttgctagctt aatcaaaatg tttgattctc ctatactttt   22140
tcttctatt actcttatat ttttcccgtca ttctctctgc taaccttcca ccttatgcac    22200
acactttccc tatatttttaa gataagtctg ctaggatgta gaaatatttg tttgtgattt   22260
ctatatagct attagagatt atgacatagt aatattaaaa tgaaatgata cttaaacaga   22320
aagcaattttc caagagggcc agggaccccta atctttgaag agatgaagaa acttactttt  22380
```

```
ctccctggct tttggttcac tttttgtact tttaacaagt gggtgaatta tttgataatt    22440
ttgaggaaga ttattctttt aaattcaaac tagtatgtca atgcctacca ttactctgat    22500
tatattaaaa cagaaaaagg aaataacaac ttcgtatacc agccactggt gagagttaaa    22560
gacaagagct gcccccccac ccccaaatgt caaaggcaaa tgctaaattg atactggagc    22620
tcgtggtgac tttctacctc actaacaaca taagggatct ccatattatt tcaccactat    22680
tctagctttg ctgatatatt gccaaatgat tagactacag aatagttcaa ccagagaatt    22740
tactcattta ttgattaaac atccaaatac tattgtaata tactatgtta aaattcatca    22800
attcaagtgc ccacacacca ctgaatcatc agcaccaagc aatatattag acatatggca    22860
aaattcaaca aatatatttt gatataaata aataaacgtt cacgacttta cttaaaaaat    22920
caatgttgcg gctgggcacg gtagctcgcg tctgtaatcc ccgcactttg ggaggccaag    22980
gcgggtggat cacgaggtca agagacggag accatcctgg ctaacatggt gaaaccctgt    23040
ctctactaaa aatacaaaaa ttagccgggc gtggtggcgg tgcctgtagt cccagctact    23100
cgggaggctg aggcaggaga atcgtttgaa cccaggaggt ggaggttgca gtgagcggag    23160
atcgcaccat tgcactccag tctggcaaca gagcgagact ccatctcaaa aacaaaaat     23220 aaataaataa ataaatattc ttcataaaat gtgggttttg gggaaaatat agaattacat    23280
atacatttaa cgaagtcgct aatgacattt cattcatatt cataatgtaa ccatcttgaa    23340
tttttttaat tgtagcgatt ttaaaaatgt ttgtaaaatt taatttccag ttttctaatt    23400
acttgtcagt cacattaata acattagtac ctttatggta cccttgcagt acctgaaaag    23460
aatatcaacc tgaaaagaat atcaactcac ccagaaatta gttctttgaa aaaaagaaa     23520 ttaagttgtg aatttctaaa gaccttgaaa taagtgtttc aaatttaaag aacaaagaat    23580
gatgtgaaaa tgagattatg attcctacta catgaattaa cgtttcgaga ttgctgttta    23640
ttacttccca gagtatcttt aacagtattc tctgaagcag ttccaatcta gttggagaat    23700
taacagcaat tgatttaact atctcatttt tattaactgt aatttacttt aaaaatattt    23760
gcaaatcata ctcattagtt atttgatcat tgttctatgc attttaaaat taattttgtg    23820
ttgttcctct caatatttgt ttttaacatt tattcccatt tttatttat actattgtct     23880 gtcatgcttt atgtattcca ataagtgtct tgaaatcctt gtggggaaag gcaggacaaa    23940
aataattagt taattagatt tgaaaaatgt aattttttcca ttttaaatat ttcatttgta    24000
taagaaaata tttcagagaa ccatgatgat aatggatatg tgtgactgtt tgaatttt      24060 ttctcaatta aaacattttg tatgtaatgg gaggaatgtc aagatttgtt                24110
```

<210> SEQ ID NO 277
<211> LENGTH: 3111
<212> TYPE: DNA
<213> ORGANISM: Homo sapiens
<220> FEATURE:
<221> NAME/KEY: misc_feature
<222> LOCATION: 2411,3089,3090,3091,3092,3094,3095,3098,3099,3100, 3101
<223> OTHER INFORMATION: n = A,T,C or G

<400> SEQUENCE: 277

```
ccccacccga acacactca gcccttgcac tgacctgcct tctgattgga ggctggttgc     60
ttcggataat gacctccagg accccactgt tggttacagc tgtttgtat tattcttact    120 gcaactcaag acacctgcag cagggcgtga gaaaaagtaa agaccagta ttttcacatt    180 gccaggtacc agaaacacag aagactgaca cccgccactt aagtgggcc agggctggtg     240 tctgcccatg ttgccatcct gatgggctgc ttgccacaat gagggatctt cttcaataca    300
```

```
tcgcttgctt ctttgccttt ttctctgctg ggttttgat tgtggccacc tggactgact    360
gttggatggt gaatgctgat gactctctgg aggtgagcac aaaatgccga ggcctctggt    420
gggaatgcgt cacaaatgct tttgatggga ttcgcacctg tgatgagtac gattccatac    480
ttgcggagca tcccttgaag ctggtggtaa ctcgagcgtt gatgattact gcagatattc    540
tagctgggtt tggatttctc accctgctcc ttggtcttga ctgcgtgaaa ttcctccctg    600
atgagccgta cattaaagtc cgcatctgct tgttgctgg agccacgtta ctaatagcag    660 gtacccagg aatcattggc tctgtgtggt atgctgttga tgtgtatgtg aacgttcta    720 ctttggtttt gcacaatata tttcttggta tccaatataa atttggttgg tcctgttggc    780
tcggaatggc tgggtctctg ggttgctttt ggctggagc tgttctcacc tgctgcttat    840 atcttttaa agatgttgga cctgagagaa actatcctta ttccttgagg aaagcctatt    900
cagccgcggg tgtttccatg gccaagtcat actcagcccc tcgcacagag acggccaaaa    960
tgtatgctgt agacacaagg gtgtaaaatg cacgtttcag ggtgtgtttg catatgattt   1020
aatcaatcag tatggttaca ttgataaaat agtaagtcaa tccaggaaca gttatttaga   1080
attcatattg aattaaatta attgctagct taatcaaaat gtttgattct cctatacttt   1140
ttctttctat tactcttata ttttcccgtc attctctctg ctaaccttcc accttatgca   1200
cacactttcc ctatatttta agataagtct gctaggatgt agaaatattt gtttgtgatt   1260
tctatatagc tattagagat tatgacatag taatattaaa atgaaatgat acttaaacag   1320
aaagcaattt ccaaagaggc cagggaccct aatctttgaa gagatgaaga aacttacttt   1380
tctccctggc ttttggttca cttttttgtac ttttaacaag tgggtgaatt atttgataat   1440
tttgaggaag attattcttt taaattcaaa ctagtatgtc aatgcctacc attactctga   1500
ttatattaaa acagaaaaag gaaataacaa cttcgtatac cagccactgg tgagagttaa   1560
agacaagagc tgcccccca ccccaaatg tcaaaggcaa atgctaaatt gatactggag   1620
ctcgtggtga ctttctacct cactaacaac ataagggatc tccatattat ttcaccacta   1680
ttctagcttt gctgatatat tgccaaatga ttagactaca gaatagttca accagagaat   1740
ttactcattt attgattaaa catccaaata ctattgtaat atactatgtt aaaattcatc   1800
aattcaagtg cccacacacc actgaatcat cagcaccaag caatatatta gacatatggc   1860
aaaattcaac aaatatattt tgatataaat aaataaacgt tcacgacttt acttaaaaaa   1920
tcaatgttgc ggctgggcac ggtagctcgc gtctgtaatc cccgcacttt gggaggccaa   1980
ggcgggtgga tcacgaggtc aagagacgga gaccatcctg gctaacatgg tgaaaccctg   2040
tctctactaa aaatacaaaa attagccggg cgtggtggcg gtgcctgtag tcccagctac   2100
tcgggaggct gaggcaggag aatcgtttga acccaggagg tggaggttgc agtgagcgga   2160
gatcgcacca ttgcactcca gtctggcaac agagcgagac tccatctcaa aaaacaaaaa   2220
taaataaata aataaatatt cttcataaaa tgtgggtttt ggggaaaata tagaattaca   2280
tatacattta acgaagtcgc taatgacatt tcattcatat tcataatgta accatcttga   2340 attttttaa ttgtagcgat tttaaaaatg tttgtaaaat ttaatttcca gttttctaat   2400
tacttgtcag ycacattaat aacattagta cctttatggt acccttgcag tacctgaaaa   2460
gaatatcaac ctgaaaagaa tatcaactca cccagaaatt agttctttga aaaaaaagaa   2520
attaagttgt gaatttctaa agaccttgaa ataagtgttt caaatttaaa gaacaaagaa   2580
tgatgtgaaa atgagattat gattcctact acatgaatta acgtttcgag attgctgttt   2640
attacttccc agagtatctt taacagtatt ctctgaagca gttccaatct agttggagaa   2700
```

-continued

```
ttaacagcaa ttgatttaac tatctcattt ttattaactg taatttactt taaaaatatt    2760
tgcaaatcat actcattagt tatttgatca ttgttctatg cattttaaaa ttaattttgt    2820
gttgttcctc tcaatatttg tttttaacat ttattcccat ttttatttta tactattgtc    2880
tgtcatgctt tatgtattcc ataagtgtc ttgaaatcct tgtggggaaa ggcaggacaa     2940
aaataattag ttaattagat ttgaaaaatg taatttttcc attttaaata tttcatttgt    3000
ataagaaaat atttcagaga accatgatga taatggatat gtgtgactgt tttgaatttt    3060
tttctcaatt aaaacatttt gtatgtaawr rrarraawrw maagatttgt t             3111
```

<210> SEQ ID NO 278
<211> LENGTH: 305
<212> TYPE: PRT
<213> ORGANISM: Homo sapiens

<400> SEQUENCE: 278

| | | | | | | | | | | | | | | |
|---|---|---|---|---|---|---|---|---|---|---|---|---|---|---|
| Met | Thr | Ser | Arg | Thr | Pro | Leu | Leu | Val | Thr | Ala | Cys | Leu | Tyr | Tyr |
| | | | | 5 | | | | | 10 | | | | | 15 |
| Ser | Tyr | Cys | Asn | Ser | Arg | His | Leu | Gln | Gln | Gly | Val | Arg | Lys | Ser |
| | | | | 20 | | | | | 25 | | | | | 30 |
| Lys | Arg | Pro | Val | Phe | Ser | His | Cys | Gln | Val | Pro | Glu | Thr | Gln | Lys |
| | | | | 35 | | | | | 40 | | | | | 45 |
| Thr | Asp | Thr | Arg | His | Leu | Ser | Gly | Ala | Arg | Ala | Gly | Val | Cys | Pro |
| | | | | 50 | | | | | 55 | | | | | 60 |
| Cys | His | Pro | Asp | Gly | Leu | Leu | Ala | Thr | Met | Arg | Asp | Leu | Leu | Gln |
| 65 | | | | | 70 | | | | | 75 | | | | | 80 |
| Tyr | Ile | Ala | Cys | Phe | Phe | Ala | Phe | Phe | Ser | Ala | Gly | Phe | Leu | Ile |
| | | | | 85 | | | | | 90 | | | | | 95 |
| Val | Ala | Thr | Trp | Thr | Asp | Cys | Trp | Met | Val | Asn | Ala | Asp | Asp | Ser |
| | | | | 100 | | | | | 105 | | | | | 110 |

Met Thr Ser Arg Thr Pro Leu Leu Val Thr Ala Cys Leu Tyr Tyr
                 5                  10                  15

Tyr Cys Asn Ser Arg His Leu Gln Gln Gly Val Arg Lys Ser Lys Arg
             20                  25                  30

Pro Val Phe Ser His Cys Gln Val Pro Glu Thr Gln Lys Thr Asp Thr
         35                  40                  45

Arg His Leu Ser Gly Ala Arg Ala Gly Val Cys Pro Cys Cys His Pro
     50                  55                  60

Asp Gly Leu Leu Ala Thr Met Arg Asp Leu Leu Gln Tyr Ile Ala Cys
65                  70                  75                  80

Phe Phe Ala Phe Phe Ser Ala Gly Phe Leu Ile Val Ala Thr Trp Thr
                 85                  90                  95

Asp Cys Trp Met Val Asn Ala Asp Asp Ser Leu Glu Val Ser Thr Lys
            100                 105                 110

Cys Arg Gly Leu Trp Trp Glu Cys Val Thr Asn Ala Phe Asp Gly Ile
            115                 120                 125

Arg Thr Cys Asp Glu Tyr Asp Ser Ile Leu Ala Glu His Pro Leu Lys
        130                 135                 140

Leu Val Val Thr Arg Ala Leu Met Ile Thr Ala Asp Ile Leu Ala Gly
145                 150                 155                 160

Phe Gly Phe Leu Thr Leu Leu Gly Leu Asp Cys Val Lys Phe Leu
                165                 170                 175

Pro Asp Glu Pro Tyr Ile Lys Val Arg Ile Cys Phe Val Ala Gly Ala
            180                 185                 190

Thr Leu Leu Ile Ala Gly Thr Pro Gly Ile Ile Gly Ser Val Trp Tyr
        195                 200                 205

Ala Val Asp Val Tyr Val Glu Arg Ser Thr Leu Val Leu His Asn Ile
    210                 215                 220

Phe Leu Gly Ile Gln Tyr Lys Phe Gly Trp Ser Cys Trp Leu Gly Met
225                 230                 235                 240

Ala Gly Ser Leu Gly Cys Phe Leu Ala Gly Ala Val Leu Thr Cys Cys
                245                 250                 255

Leu Tyr Leu Phe Lys Asp Val Gly Pro Glu Arg Asn Tyr Pro Tyr Ser
            260                 265                 270

Leu Arg Lys Ala Tyr Ser Ala Ala Gly Val Ser Met Ala Lys Ser Tyr
        275                 280                 285

Ser Ala Pro Arg Thr Glu Thr Ala Lys Met Tyr Ala Val Asp Thr Arg
    290                 295                 300

Val
305

<210> SEQ ID NO 279
<211> LENGTH: 305
<212> TYPE: PRT
<213> ORGANISM: Homo sapiens

<400> SEQUENCE: 279

Met Thr Ser Arg Thr Pro Leu Leu Val Thr Ala Cys Leu Tyr Tyr Ser
                5                   10                  15

Tyr Cys Asn Ser Arg His Leu Gln Gln Gly Val Arg Lys Ser Lys Arg
            20                  25                  30

Pro Val Phe Ser His Cys Gln Val Pro Glu Thr Gln Lys Thr Asp Thr
        35                  40                  45

Arg His Leu Ser Gly Ala Arg Ala Gly Val Cys Pro Cys His Pro
    50                  55                  60

Asp Gly Leu Leu Ala Thr Met Arg Asp Leu Leu Gln Tyr Ile Ala Cys
65                  70                  75                  80

Phe Phe Ala Phe Phe Ser Ala Gly Phe Leu Ile Val Ala Thr Trp Thr
                85                  90                  95

Asp Cys Trp Met Val Asn Ala Asp Asp Ser Leu Glu Val Ser Thr Lys
            100                 105                 110

Cys Arg Gly Leu Trp Trp Glu Cys Val Thr Asn Ala Phe Asp Gly Ile
        115                 120                 125

Arg Thr Cys Asp Glu Tyr Asp Ser Ile Leu Ala Glu His Pro Leu Lys
    130                 135                 140

Leu Val Val Thr Arg Ala Leu Met Ile Thr Ala Asp Ile Leu Ala Gly
145                 150                 155                 160

Phe Gly Phe Leu Thr Leu Leu Gly Leu Asp Cys Val Lys Phe Leu
                165                 170                 175

Pro Asp Glu Pro Tyr Ile Lys Val Arg Ile Cys Phe Val Ala Gly Ala
            180                 185                 190

Thr Leu Leu Ile Ala Gly Thr Pro Gly Ile Ile Gly Ser Val Trp Tyr
        195                 200                 205

Ala Val Asp Val Tyr Val Glu Arg Ser Thr Leu Val Leu His Asn Ile
    210                 215                 220

Phe Leu Gly Ile Gln Tyr Lys Phe Gly Trp Ser Cys Trp Leu Gly Met
225                 230                 235                 240

Ala Gly Ser Leu Gly Cys Phe Leu Ala Gly Ala Val Leu Thr Cys Cys
                245                 250                 255

Leu Tyr Leu Phe Lys Asp Val Gly Pro Glu Arg Asn Tyr Pro Tyr Ser
            260                 265                 270

Leu Arg Lys Ala Tyr Ser Ala Ala Gly Val Ser Met Ala Lys Ser Tyr
        275                 280                 285

Ser Ala Pro Arg Thr Glu Thr Ala Lys Met Tyr Ala Val Asp Thr Arg
    290                 295                 300

Val
305

<210> SEQ ID NO 280
<211> LENGTH: 305
<212> TYPE: PRT
<213> ORGANISM: Homo sapiens

<400> SEQUENCE: 280

Met Thr Ser Arg Thr Pro Leu Leu Val Thr Ala Cys Leu Tyr Tyr Ser

```
            5                  10                 15
Tyr Cys Asn Ser Arg His Leu Gln Gln Gly Val Arg Lys Ser Lys Arg
                20                 25                 30

Pro Val Phe Ser His Cys Gln Val Pro Glu Thr Gln Lys Thr Asp Thr
                35                 40                 45

Arg His Leu Ser Gly Ala Arg Ala Gly Val Cys Pro Cys His Pro
50                  55                 60

Asp Gly Leu Leu Ala Thr Met Arg Asp Leu Leu Gln Tyr Ile Ala Cys
65                  70                 75                 80

Phe Phe Ala Phe Phe Ser Ala Gly Phe Leu Ile Val Ala Thr Trp Thr
                85                 90                 95

Asp Cys Trp Met Val Asn Ala Asp Ser Leu Glu Val Ser Thr Lys
                100                105                110

Cys Arg Gly Leu Trp Trp Glu Cys Val Thr Asn Ala Phe Asp Gly Ile
                115                120                125

Arg Thr Cys Asp Glu Tyr Asp Ser Ile Leu Ala Glu His Pro Leu Lys
                130                135                140

Leu Val Val Thr Arg Ala Leu Met Ile Thr Ala Asp Ile Leu Ala Gly
145                 150                155                160

Phe Gly Phe Leu Thr Leu Leu Gly Leu Asp Cys Val Lys Phe Leu
                165                170                175

Pro Asp Glu Pro Tyr Ile Lys Val Arg Ile Cys Phe Val Ala Gly Ala
                180                185                190

Thr Leu Leu Ile Ala Gly Thr Pro Gly Ile Ile Gly Ser Val Trp Tyr
                195                200                205

Ala Val Asp Val Tyr Val Glu Arg Ser Thr Leu Val Leu His Asn Ile
                210                215                220

Phe Leu Gly Ile Gln Tyr Lys Phe Gly Trp Ser Cys Trp Leu Gly Met
225                 230                235                240

Ala Gly Ser Leu Gly Cys Phe Leu Ala Gly Ala Val Leu Thr Cys Cys
                245                250                255

Leu Tyr Leu Phe Lys Asp Val Gly Pro Glu Arg Asn Tyr Pro Tyr Ser
                260                265                270

Leu Arg Lys Ala Tyr Ser Ala Ala Gly Val Ser Met Ala Lys Ser Tyr
                275                280                285

Ser Ala Pro Arg Thr Glu Thr Ala Lys Met Tyr Ala Val Asp Thr Arg
                290                295                300

Val
305

<210> SEQ ID NO 281
<211> LENGTH: 58
<212> TYPE: PRT
<213> ORGANISM: Homo sapiens

<400> SEQUENCE: 281

Met Ile Arg Leu Gln Asn Ser Ser Thr Arg Glu Phe Thr His Leu Leu
                5                  10                 15

Ile Lys His Pro Asn Thr Ile Val Ile Tyr Tyr Val Lys Ile His Gln
                20                 25                 30

Phe Lys Cys Pro His Thr Glu Ser Ser Ala Pro Ser Asn Ile Leu
                35                 40                 45

Asp Ile Trp Gln Asn Ser Thr Asn Ile Phe
50                  55
```

<210> SEQ ID NO 282
<211> LENGTH: 75
<212> TYPE: PRT
<213> ORGANISM: Homo sapiens

<400> SEQUENCE: 282

Met Asn Met Asn Glu Met Ser Leu Ala Thr Ser Leu Asn Val Tyr Val
1               5                   10                  15
Ile Leu Tyr Phe Pro Gln Asn Pro His Phe Met Lys Asn Ile Tyr Leu
            20                  25                  30
Phe Ile Tyr Phe Cys Phe Leu Arg Trp Ser Leu Ala Leu Leu Pro Asp
        35                  40                  45
Trp Ser Ala Met Val Arg Ser Pro Leu Thr Ala Thr Ser Thr Ser Trp
    50                  55                  60
Val Gln Thr Ile Leu Leu Pro Gln Pro Glu
65                  70                  75

<210> SEQ ID NO 283
<211> LENGTH: 414
<212> TYPE: DNA
<213> ORGANISM: Homo sapiens

<400> SEQUENCE: 283
atgcagcatc accaccatca ccaccacttc ttgcttccag gctttgcgct gcaaatccag      60
tgctaccagt gtgaagaatt ccagctgaac aacgactgct cctcccccga gttcattgtg     120
aattgcacgg tgaacgttca agacatgtgt cagaaagaag tgatggagca aagtgccggg     180
atcatgtacc gcaagtcctg tgcatcatca gcggcctgtc tcatcgcctc tgccgggtac     240
cagtccttct gctccccagg gaaactgaac tcagtttgca tcagctgctg caacaccccc     300
ctttgtaacg ggccaaggcc aagaaaaggg gaagttctgc cctcggccct caggccaggg     360
ctccgcacca ccatcctgtt cctcaaatta gccctcttct cggcacactg ctga           414

<210> SEQ ID NO 284
<211> LENGTH: 137
<212> TYPE: PRT
<213> ORGANISM: Homo sapiens

<400> SEQUENCE: 284

Met Gln His His His His His His Phe Leu Leu Pro Gly Phe Ala
1               5                   10                  15
Leu Gln Ile Gln Cys Tyr Gln Cys Glu Glu Phe Gln Leu Asn Asn Asp
            20                  25                  30
Cys Ser Ser Pro Glu Phe Ile Val Asn Cys Thr Val Asn Val Gln Asp
        35                  40                  45
Met Cys Gln Lys Glu Val Met Glu Gln Ser Ala Gly Ile Met Tyr Arg
    50                  55                  60
Lys Ser Cys Ala Ser Ser Ala Ala Cys Leu Ile Ala Ser Ala Gly Tyr
65                  70                  75                  80
Gln Ser Phe Cys Ser Pro Gly Lys Leu Asn Ser Val Cys Ile Ser Cys
                85                  90                  95
Cys Asn Thr Pro Leu Cys Asn Gly Pro Arg Pro Lys Lys Arg Gly Ser
            100                 105                 110
Ser Ala Ser Ala Leu Arg Pro Gly Leu Arg Thr Thr Ile Leu Phe Leu
        115                 120                 125
Lys Leu Ala Leu Phe Ser Ala His Cys
    130                 135

<210> SEQ ID NO 285
<211> LENGTH: 1740
<212> TYPE: DNA
<213> ORGANISM: Homo sapiens
<220> FEATURE:
<221> NAME/KEY: misc_feature
<222> LOCATION: 755,756,757,758,759,760,761,762,763,764,
    765,766,767,768,769,770,771,772,773,774,
    775,776,777,778,779,780,781,782,783,784,
    785,786,787,788,789,790,791,792,793,794,
    795,796,797,798,799,800,801,802,803,804,
    805,806,807,808,809,810,811,812,813,814,
    815,816,817,818,819,820,821,822,823,824,
    825,826,827,828,829,830,831,832,833,834,
    835,1605,1606,1607,1608,1609,1610,1611,1612,1613,
    1614,1615,1616,1617,1618,1619,1620,1621,1622,1623,
    1624,1625,1626,1629
<223> OTHER INFORMATION: n = A,T,C or G

<400> SEQUENCE: 285

```
ggaaaattca tgaagagggg actgaaatcc acaactcaat cagcatagag cagaagtaag      60
ggggaagtgg taagaggtgc actatgaatg agctggagaa tttaaaggga ggctgaactc     120
agagtcgaag tgaccttgag aagataaacc ctctggaaat tctcagaatc tcaggatggg     180
ccccagagta tctaaagatg ctacagttca agggattgag ccaattgtat ataaatctta     240
atggataggt tgacctcagc ataaaacttg ggtggaaatt ttaaacaggt ttctttattt     300
cagcacttct cagagccact cattgtataa ggtactttgt gaatatccag atagtattct     360
tcaaactctc ttttatttcc caggggggca tcccatagga caagaagcat tctttgtgac     420
actctgtggg aagagctggt ttaaaggggt acctgtctgg gcaacactgt cccacagggg     480
cccccatgac caaactaact ctgcttctac ccagaaaggg tgcagagtag ccactagact     540
tttatgtggc aaatgggatg ttatgcccca gcctgaagcc aagatgccct ttctggttgc     600
cttgatttgt gtttaacagc tccaaatgct taatgaggca gtaagagacg tctctcttgg     660
gcagtacttc ccaactaggg gtgagtttgc caccccttacc cccatcccag tgaatatttg     720
caattcctaa agacgtgttt tgattgtcac actgnnnnnn nnnnnnnnnn nnnnnnnnnn     780
nnnnnnnnnn nnnnnnnnnn nnnnnnnnnn nnnnnnnnnn nnnnnnnnnn nnnnnacaaa     840
agagaattat ctagccccaa atgtccataa cactgctgtt gagaaaacct accgcaggat     900
cttactgggc ttcataggta agcttgccct tgttctggc ttctgtagat atataaaata     960
aagacactgc ccagtccctc cctcaacgtc ccgagccagg gctcaaggca aattccaata    1020
acagtagaat gaacactaaa tattgatttc aaaatctcag caactagaag aatgaccaac    1080
catcctggtt ggcctgggac tgtcctagtt ttagcattga aagtttcagg ttccaggaaa    1140
gccctcaggc ctgggctgct ggtcacccta gcagctgagg gactcttcaa tacagaatta    1200
gtctttgcgc actggagatg aatatacttt aatttgtaac atgtgaaaac atctataaac    1260
atctactgga agcctgttct gtctgcaccg acattttcat tgaagtacgg attcttcctg    1320
acctagatga cagctggctg ctgacaactt tgcgagggct cggtatataa actgagcttt    1380
gtacctattt ttaataatta catgatatag tatataactt ggattaaccc agtattcggg    1440
tatttttcaat ttccttgggg agcttagagg acggacaaa taaaaagat tatttcaaca    1500
ttcaaatata tgccattggt ttacatatga agataaccac atatatgtat aaattcaccg    1560
ttactttta gcaatactat aaaatccaac agaaaaaaat agcannnnnn nnnnnnnnnn    1620
nnnnnngant tagtctttgt gggtttgggg caagcaactg cccttctcag ttaggatggg    1680
ggagttctgg acatttctag ctaaagccca ggggtcaagg gaatgataaa ctcctcggtc    1740
```

<210> SEQ ID NO 286
<211> LENGTH: 116
<212> TYPE: PRT
<213> ORGANISM: Homo sapiens

<400> SEQUENCE: 286

Met Phe Ile Asp Val Phe Thr Cys Tyr Lys Leu Lys Tyr Ile His Leu
1               5                   10                  15

Gln Cys Ala Lys Thr Asn Ser Val Leu Lys Ser Pro Ser Ala Ala Arg
            20                  25                  30

Val Thr Ser Ser Pro Gly Leu Arg Ala Phe Leu Glu Pro Glu Thr Phe
        35                  40                  45

Asn Ala Lys Thr Arg Thr Val Pro Gly Gln Pro Gly Trp Leu Val Ile
    50                  55                  60

Leu Leu Val Ala Glu Ile Leu Lys Ser Ile Phe Ser Val His Ser Thr
65                  70                  75                  80

Val Ile Gly Ile Cys Leu Glu Pro Trp Leu Gly Thr Leu Arg Glu Gly
                85                  90                  95

Leu Gly Ser Val Phe Ile Leu Tyr Ile Tyr Arg Ser Gln Asn Lys Gly
            100                 105                 110

Gln Ala Tyr Leu
        115

<210> SEQ ID NO 287
<211> LENGTH: 32
<212> TYPE: DNA
<213> ORGANISM: Artificial Sequence
<220> FEATURE:
<223> OTHER INFORMATION: PCR primer

<400> SEQUENCE: 287
cacttcttgc ttccaggctt tgcgctgcaa at                                 32

<210> SEQ ID NO 288
<211> LENGTH: 29
<212> TYPE: DNA
<213> ORGANISM: Artificial Sequence
<220> FEATURE:
<223> OTHER INFORMATION: PCR primer

<400> SEQUENCE: 288
actagctcga gtcagcagtg tgccgagaa                                     29

<210> SEQ ID NO 289
<211> LENGTH: 114
<212> TYPE: PRT
<213> ORGANISM: Homo sapiens

<400> SEQUENCE: 289

Met Trp Val Leu Gly Ile Ala Ala Thr Phe Cys Gly Leu Phe Leu Leu
1               5                   10                  15

Pro Gly Phe Ala Leu Gln Ile Gln Cys Tyr Gln Cys Glu Glu Phe Gln
            20                  25                  30

Leu Asn Asn Asp Cys Ser Ser Pro Glu Phe Ile Val Asn Cys Thr Val
        35                  40                  45

Asn Val Gln Asp Met Cys Gln Lys Glu Val Met Glu Gln Ser Ala Gly
    50                  55                  60

Ile Met Tyr Arg Lys Ser Cys Ala Ser Ala Ala Cys Leu Ile Ala
65                  70                  75                  80

Ser Ala Gly Tyr Gln Ser Phe Cys Ser Pro Gly Lys Leu Asn Ser Val
                85                  90                  95

```
Cys Ile Ser Cys Cys Asn Thr Pro Leu Cys Asn Gly Pro Arg Pro Lys
            100                 105                 110

Lys Arg

<210> SEQ ID NO 290
<211> LENGTH: 115
<212> TYPE: PRT
<213> ORGANISM: Homo sapiens

<400> SEQUENCE: 290

Met Trp Val Leu Gly Ile Ala Ala Thr Phe Cys Gly Leu Phe Leu Leu
  1               5                  10                  15

Pro Gly Phe Ala Leu Gln Ile Gln Cys Tyr Gln Cys Glu Glu Phe Gln
             20                  25                  30

Leu Asn Asn Asp Cys Ser Ser Pro Glu Phe Ile Val Asn Cys Thr Val
         35                  40                  45

Asn Val Gln Asp Met Cys Gln Lys Glu Val Met Glu Gln Ser Ala Gly
     50                  55                  60

Ile Met Tyr Arg Lys Ser Cys Ala Ser Ser Ala Ala Cys Leu Ile Ala
 65                  70                  75                  80

Ser Ala Gly Tyr Gln Ser Phe Cys Ser Pro Gly Lys Leu Asn Ser Val
                 85                  90                  95

Cys Ile Ser Cys Cys Asn Thr Pro Leu Cys Asn Gly Pro Arg Pro Lys
            100                 105                 110

Lys Arg Gly
        115

<210> SEQ ID NO 291
<211> LENGTH: 30
<212> TYPE: PRT
<213> ORGANISM: Artificial Sequence
<220> FEATURE:
<223> OTHER INFORMATION: Synthetic peptide used for generation of rabbit
      polyclonal anti-sera against O591s.

<400> SEQUENCE: 291

Tyr Gln Cys Glu Glu Phe Gln Leu Asn Asn Asp Cys Ser Ser Pro Glu
  1               5                  10                  15

Phe Ile Val Asn Cys Thr Val Asn Val Gln Asp Met Cys Gln
             20                  25                  30

<210> SEQ ID NO 292
<211> LENGTH: 25
<212> TYPE: PRT
<213> ORGANISM: Artificial Sequence
<220> FEATURE:
<223> OTHER INFORMATION: Synthetic peptide used for generation of rabbit
      polyclonal anti-sera against O591s.

<400> SEQUENCE: 292

Cys Gln Lys Glu Val Met Glu Gln Ser Ala Gly Ile Met Tyr Arg Lys
  1               5                  10                  15

Ser Cys Ala Ser Ser Ala Ala Cys Leu
             20                  25

<210> SEQ ID NO 293
<211> LENGTH: 30
<212> TYPE: PRT
<213> ORGANISM: Artificial Sequence
<220> FEATURE:
<223> OTHER INFORMATION: Synthetic peptide used for generation of rabbit
      polyclonal anti-sera against O591s.
```

```
<400> SEQUENCE: 293

Thr Pro Leu Cys Asn Gly Pro Arg Pro Lys Lys Arg Gly Ser Ser Ala
1               5                   10                  15

Ser Ala Leu Arg Pro Gly Leu Arg Thr Thr Ile Gly Cys Gly
            20                  25                  30
```